United States Patent
Chaikof et al.

(10) Patent No.: US 12,152,016 B2
(45) Date of Patent: Nov. 26, 2024

(54) ARYL HYDROCARBON RECEPTOR MODULATORS AND USES THEREOF

(71) Applicant: Beth Israel Deaconess Medical Center, Inc., Boston, MA (US)

(72) Inventors: Elliot Chaikof, Newton, MA (US); Lijun Sun, Harvard, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 18/181,099

(22) Filed: Mar. 9, 2023

(65) Prior Publication Data

US 2023/0278986 A1 Sep. 7, 2023

Related U.S. Application Data

(63) Continuation of application No. 17/045,116, filed as application No. PCT/US2019/025993 on Apr. 5, 2019, now Pat. No. 11,634,408.

(60) Provisional application No. 62/653,257, filed on Apr. 5, 2018.

(51) Int. Cl.
| | |
|---|---|
| C07D 403/06 | (2006.01) |
| A61P 29/00 | (2006.01) |
| C07D 209/12 | (2006.01) |
| C07D 401/06 | (2006.01) |
| C07D 409/06 | (2006.01) |
| C07D 471/04 | (2006.01) |

(52) U.S. Cl.
CPC ......... *C07D 403/06* (2013.01); *C07D 401/06* (2013.01); *C07D 409/06* (2013.01); *C07D 471/04* (2013.01)

(58) Field of Classification Search
CPC .. C07D 403/06; C07D 401/06; C07D 409/06; C07D 471/04; C07D 209/12; A61P 29/00
See application file for complete search history.

(56) References Cited

U.S. PATENT DOCUMENTS 11,634,408 B2  4/2023  Chaikof et al.

FOREIGN PATENT DOCUMENTS

| EP | 0080814 A1 | 6/1983 |
|---|---|---|
| EP | 0458207 A2 | 11/1991 |
| JP | 2008-050353 A | 3/2008 |
| WO | WO 95/16687 A1 | 6/1995 |
| WO | WO 2005/062795 A2 | 7/2005 |
| WO | WO 2007/002325 A1 | 1/2007 |
| WO | WO 2008/019357 A2 | 2/2008 |
| WO | WO 2008/157740 A2 | 12/2008 |
| WO | WO 2018/039310 A1 | 3/2018 |
| WO | WO 2018/121434 A1 | 7/2018 |

OTHER PUBLICATIONS

Girer et al., 2024, file:///C:/Users/sloewe/Documents/e-Red%20Folder/18181099/Girer-et-al.pdf.*
Safe et al., 2024, file:///C:/Users/sloewe/Documents/e-Red%20Folder/18181099/Safe-et-al.pdf.*
Barroso et al., 2024, file:///C:/Users/sloewe/Documents/e-Red%20Folder/18181099/Barroso-et-al.pdf.*
Cancer-Prevention, 2024, https://www.cdc.gov/cancer/dcpc/prevention/index.htm#print.*
Coliitis-Prevention, 2024, https://www.healthdirect.gov.au/ulcerative-colitis#:~: text=While%20you%20can%E2%80%99t%20prevent%20ulcerative%20colitis%2C%20you%20can,taking%20your%20medicines%20and%20maintaining%20a%20healthy%20lifestyle.*
U.S. Appl. No. 17/045,116, filed Oct. 2, 2020, Chaikof et al.
PCT/US2019/025993, Jun. 4, 2019, International Search Report and Written Opinion.
PCT/US2019/025993, Oct. 15, 2020, International Preliminary Report on Patentability.
International Search Report and Written Opinion for PCT/US2019/025993 mailed Jun. 4, 2019.
International Preliminary Report on Patentability for PCT/US2019/025993 mailed Oct. 15, 2020.
[No Author Listed], Benzoic acid. Registry Database Compound 6243-59-0. Nov. 16, 1984. 1 page.
[No Author Listed], Methanone. Registry Database Compound 37122-80-8. Nov. 16, 1984. 1 page.
Beischlag et al., The aryl hydrocarbon receptor complex and the control of gene expression. Crit Rev Eukaryot Gene Expr. 2008;18(3):207-50. doi: 10.1615/critreveukargeneexpr.v18.i3.20.

(Continued)

*Primary Examiner* — Sun Jae Yoo
(74) *Attorney, Agent, or Firm* — Wolf, Greenfield & Sacks, P.C.

(57) ABSTRACT

Provided are compounds of Formula (I), and pharmaceutically acceptable salts, solvates, hydrates, stereoisomers, tautomers, isotopically labeled derivatives, polymorphs, and prodrugs thereof, wherein $X^1$-$X^4$, $R^X$, $R^C$, $R^B$, n, and Ring A are as defined herein. The compounds may be aryl hydrocarbon receptor agonists or partial aryl hydrocarbon receptor agonists. Also provided are pharmaceutical compositions comprising a compound of Formula (I) and methods of using such compounds for treating diseases and conditions related to the activity of an aryl hydrocarbon receptor, such as, for example, inflammatory diseases, autoimmune diseases, metabolic disorders, and proliferative diseases.

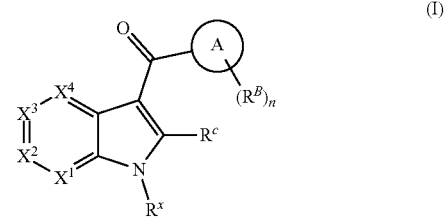

(I)

24 Claims, 15 Drawing Sheets

(56) References Cited

OTHER PUBLICATIONS

Cheng et al., Tryptophan derivatives regulate the transcription of Oct4 in stem-like cancer cells. Nat Commun. Jun. 10, 2015;6:7209. doi: 10.1038/ncomms8209.

Curtin et al., Discovery and evaluation of a series of 3-acylindole imidazopyridine platelet-activating factor antagonists. J Med Chem. Jan. 1, 1998;41(1):74-95.

Dolciami et al., Binding Mode and Structure-Activity Relationships of ITE as an Aryl Hydrocarbon Receptor (AhR) Agonist. ChemMedChem. Feb. 6, 2018;13(3):270-279. doi: 10.1002/cmdc.201700669. Epub Jan. 23, 2018.

Goettel et al., AHR Activation Is Protective against Colitis Driven by T Cells in Humanized Mice. Cell Rep. Oct. 25, 2016;17(5):1318-1329. doi: 10.1016/j.celrep.2016.09.082.

Guchhait et al., Intramolecular oxidative coupling of 3-indolylarylketones with Pd(II)-catalysis under air: convenient access to indenoindolones. Tetrahedron Letters. Jul. 25, 2012;53(30):3919-3922.

Huang et al., 3,3'-Diindolylmethane alleviates oxazolone-induced colitis through Th2/Th17 suppression and Treg induction. Mol Immunol. Apr. 2013;53(4):335-44. doi: 10.1016/j.molimm.2012.09.007. Epub Oct. 17, 2012.

Hui et al., Therapeutic potential of aryl hydrocarbon receptor ligands derived from natural products in rheumatoid arthritis. Basic Clin Pharmacol Toxicol. Jun. 2020;126(6):469-474. doi: 10.1111/bcpt.13372. Epub Dec. 19, 2019.

Kawai et al., Indigo Naturalis ameliorates murine dextran sodium sulfate-induced colitis via aryl hydrocarbon receptor activation. J Gastroenterol. Aug. 2017;52(8):904-919. doi: 10.1007/s00535-016-1292-z. Epub Nov. 29, 2016.

Kim et al., 3,3'-diindolylmethane attenuates colonic inflammation and tumorigenesis in mice. Inflamm Bowel Dis. Aug. 2009;15(8):1164-73. doi: 10.1002/ibd.20917.

Kim et al., Aryl Hydrocarbon Receptors: Evidence of Therapeutic Targets in Chronic Inflammatory Skin Diseases. Biomedicines. May 7, 2022;10(5):1087. doi: 10.3390/biomedicines10051087.

McCoull et al., Identification and optimisation of 7-azaindole PAK1 inhibitors with improved potency and kinase selectivity. Med Chem Commun. 2014;5;1533-1539.

Nebert et al., Role of the aromatic hydrocarbon receptor and [Ah] gene battery in the oxidative stress response, cell cycle control, and apoptosis. Biochem Pharmacol. Jan. 1, 2000;59(1):65-85. doi: 10.1016/s0006-2952(99)00310-x.

Nguyen et al., The search for endogenous activators of the aryl hydrocarbon receptor. Chem Res Toxicol. Jan. 2008;21(1):102-16. doi: 10.1021/tx7001965. Epub Dec. 13, 2007.

Nugent et al., ITE, a novel endogenous nontoxic aryl hydrocarbon receptor ligand, efficiently suppresses EAU and T-cell-mediated immunity. Invest Ophthalmol Vis Sci. Nov. 13, 2013;54(12):7463-9. doi: 10.1167/iovs.12-11479.

Puga et al., The aryl hydrocarbon receptor cross-talks with multiple signal transduction pathways. Biochem Pharmacol. Feb. 15, 2009;77(4):713-22. doi: 10.1016/j.bcp.2008.08.031. Epub Sep. 5, 2008.

Quintana et al., An endogenous aryl hydrocarbon receptor ligand acts on dendritic cells and T cells to suppress experimental autoimmune encephalomyelitis. Proc Natl Acad Sci U S A. Nov. 30, 2010;107(48):20768-73. doi: 10.1073/pnas.1009201107. Epub Nov. 10, 2010.

Quintana et al., Control of T(reg) and T(H)17 cell differentiation by the aryl hydrocarbon receptor. Nature. May 1, 2008;453(7191):65-71. doi: 10.1038/nature06880. Epub Mar. 23, 2008.

Rannug et al., Certain photooxidized derivatives of tryptophan bind with very high affinity to the Ah receptor and are likely to be endogenous signal substances. J Biol Chem. Nov. 15, 1987;262(32):15422-7.

Rannug et al., Structure elucidation of two tryptophan-derived, high affinity Ah receptor ligands. Chem Biol. Dec. 1995;2(12):841-5. doi: 10.1016/1074-5521(95)90090-x.

Safe et al., The Aryl Hydrocarbon Receptor (AhR) as a Drug Target for Cancer Chemotherapy. Curr Opin Toxicol. Feb. 2017;2:24-29. doi: 10.1016/j.cotox.2017.01.012. Epub Feb. 1, 2017.

Smith et al., Hepatic toxicity and uroporphyrinogen decarboxylase activity following a single dose of 2,3,7,8-tetrachlorodibenzo-p-dioxin to mice. Biochem Pharmacol. Oct. 1981;30(20):2825-30. doi: 10.1016/0006-2952(81)90421-4.

Song et al., A ligand for the aryl hydrocarbon receptor isolated from lung. Proc Natl Acad Sci USA. Nov. 12, 2002;99(23):14694-9. doi: 10.1073/pnas.232562899. Epub Oct. 30, 2002.

Sugimoto et al., Indole compounds may be promising medicines for ulcerative colitis. J Gastroenterol. Sep. 2016;51(9):853-61. doi: 10.1007/s00535-016-1220-2. Epub May 9, 2016.

Wincent et al., The suggested physiologic aryl hydrocarbon receptor activator and cytochrome P4501 substrate 6-formylindolo[3,2-b]carbazole is present in humans. J Biol Chem. Jan. 30, 2009;284(5):2690-6. doi: 10.1074/jbc.M808321200. Epub Dec. 2, 2008.

Wynne et al., 3-Acylindoles via a One-Pot, Regioselective Friedel-Crafts Reaction. Synthesis. 2004(14):2277-2282.

Zelante et al., Tryptophan catabolites from microbiota engage aryl hydrocarbon receptor and balance mucosal reactivity via interleukin-22. Immunity. Aug. 22, 2013;39(2):372-85. doi: 10.1016/j.immuni.2013.08.003.

Zhang et al., Total synthesis and bioactivity of the marine alkaloid pityriacitrin and some of its derivatives. Eur J Med Chem. Dec. 2011;46(12):6089-97. doi: 10.1016/j.ejmech.2011.10.036. Epub Oct. 25, 2011.

* cited by examiner

ARYL HYDROCARBON RECEPTOR MODULATORS AND USES THEREOF

RELATED APPLICATIONS

This application is a continuation of U.S. Ser. No. 17/045,116, filed Oct. 2, 2020, which is a national stage filing under 35 U.S.C. § 371 of International PCT Application PCT/US2019/025993, filed Apr. 5, 2019, which claims priority under 35 U.S.C. § 119(e) to U.S. Provisional Patent Application, U.S. Ser. No. 62/653,257, filed Apr. 5, 2018, the entire contents of each of which is incorporated herein by reference.

BACKGROUND OF THE INVENTION

Inflammatory bowel disease (IBD) is an umbrella term used to describe disorders that involve chronic inflammation of the digestive tract, and as such can be considered a metabolic disorder, an immune disorder, and an inflammatory disease. Inflammatory bowel disease is the consequence of a sustained inflammatory response to commensal microorganisms in a genetically susceptible host with excessive production of proinflammatory cytokines, such as TNFα and IL-1β (1, 2). As a consequence, interventions designed to induce and maintain remission of active disease have largely focused on the use of T cell suppressive agents, such as corticosteroids, azathioprine, and 6-mercaptopurine, among others; all of which have been limited by toxicity (3-10). Most recently, biologics targeting specific cytokines, such as TNFα, or the α4β7 receptor have been introduced as disease-modifying drugs (11-17). While higher rates of remission and mucosal healing have been observed, these agents have been limited by an increased risk of infection, malignancy, reduced efficacy due to the development of anti-drug antibodies, and high cost (15, 18, 19). All told, one-third of patients with IBD do not respond appropriately to existing therapies (20, 21). Recent evidence now suggests that the exacerbated inflammatory response observed in IBD is initiated and maintained by loss of gut epithelial integrity manifest by increased barrier permeability, impaired mucin production, and reduced secretion of antimicrobial peptides with an ensuing dysbiosis and accompanying bacterial translocation and invasion (22-30). However, current therapies for IBD are often ineffective despite the use of immunosuppressive agents and recently developed biologic drugs.

The aryl hydrocarbon receptor (AHR) is a member of the basic-helix-loop-helix (bHLH)/Per-Arnt-Sim (PAS) family of transcription factors, which is bound to several co-chaperones and present in an inactive form in the cytosol (84). Upon ligand binding, AHR dissociates from its chaperones and translocates to the nucleus, where it dimerizes with the aryl hydrocarbon receptor nuclear translocator (ARNT) to induce gene transcription. AHR is an essential regulator of the gut innate immune system and mediates processes responsible for microbial homeostasis, enabling commensal bacteria to outcompete pathogenic bacteria, as well as those events that support gut tissue integrity and promote epithelial repair (59, 79, 81, 84-87). In large measure, AHR accomplishes these outcomes by regulating the expression of IL-22 (58, 59, 80-82). IL-22 is produced in mice and humans by ILC3 cells (36, 37, 47, 77, 82, 88, 89) and γδ T cells (31, 33, 50) but can also be produced in the gut by Th17 cells (90, 91), all in response to AHR activation (58, 59, 80-82). AHR-deficient mice display reduced expression of IL-22, dysbiosis, and an increased risk of bacterial infection and colitis (78, 79, 81, 82) and genome-wide association studies have also identified AHR as a susceptibility locus for IBD (92, 93). These effects can be reproduced by diets deficient in AHR ligands or by constitutive expression of CYP1A1 in intestinal epithelial cells, which increases the metabolism of AHR ligands with increased susceptibility to enteric infection (78, 79, 87). In turn, genetic deletion of CYP1 enzymes delays ligand metabolism with increased protection against intestinal infection (78, 79, 87). Sources of AHR ligands include dietary compounds (94, 95), microbial virulence factors (96), and metabolites derived through microbiota- or host-mediated tryptophan metabolism (58, 69, 97, 98). Indeed, CARD9-deficient mice exhibit impaired metabolism of tryptophan into AHR ligands, decreased production of IL-22, and increased susceptibility to colitis (69). Impaired microbial production of AHR ligands has also been observed in patients with IBD and correlates with an IBD-associated genetic polymorphism within CARD9 (69). In a recent clinical trial, serum levels of tryptophan were inversely correlated with serum levels of IL-22 and the severity of IBD in patients with Crohn's disease and ulcerative colitis (65).

Endogenous AHR agonists are derived from a variety of dietary metabolites, including tryptophan, flavonoids, stilbenes, carotenoids, and indoles through microbial- or host-mediated metabolism (58, 69, 99-101). Indeed, the beneficial effect of *Lactobacillus* species as a commensal organism is likely achieved by metabolic production of AHR ligands (69). For example, *L. reuteri* and *L. johnsonii* can generate indole-3-aldehyde, which activates AHR, increases IL-22 production in ILC3 cells, and inhibits dextran sulfate sodium (DSS) induced colitis (58, 102). Although the metabolic route for many indole related AHR ligands has not been well defined, 6-formylindolo[3,2-b]carbazole (FICZ), 3,3'-diindolylmethane (DIM), and 2-(1'H-indole-3'-carbonyl)-thiazole-4-carboxylic acid methyl ester (ITE) ameliorate 2,4,6-trinitrobenzene sulfonic acid- (TNBS-), DSS-, and T cell transfer-induced colitis (97, 103-107). These compounds increase IL-22 production with beneficial effects abrogated by treatment with an IL-22 blocking antibody or an AHR antagonist (69, 80, 83, 103, 108). Adsorbed indole can also be metabolized by the gut microbiota to indirubin, a 3,2'-bisindole isomer, which is the active metabolite in indigo naturalis, a group of Old World plants that have been used in traditional Chinese medicine as a treatment for IBD (109). As a ligand for AHR, indirubin increases expression of IL-22 and reduces disease severity in TNBS and DSS models of colitis, which is not observed in AHR-deficient mice (110). In a recent study, administration of indigo naturalis to 20 patients with UC was associated with 61% mucosal healing and a 72% response rate (109). These reports demonstrate the therapeutic potential of endogenous, indole based, AHR agonists. Nonetheless, the effectiveness of these metabolites and related first generation synthetic derivatives have been limited by a number of factors, including low activity, an undesirable pharmacokinetic profile due to rapid metabolism and short compound half-life, as well as poor biodistribution and off target effects (III-116).

SUMMARY OF THE INVENTION

The present invention is based on the development of compounds that can bind to and act as aryl hydrocarbon receptor agonists. These compounds can non-covalently bind to aryl hydrocarbon receptors and induce aryl hydrocarbon receptor activity. In contrast to all currently reported small molecule aryl hydrocarbon receptor agonists, these compounds are not as rapidly metabolized as endogenous AHR agonists, allowing for an improved pharmacokinetic profile and sustained AHR activation in vivo. Importantly, these compounds do not appear to be toxic, indicating improved specificity over currently available metabolites and first generation synthetic derivatives.

Compounds described herein are generally represented by Formula (I):

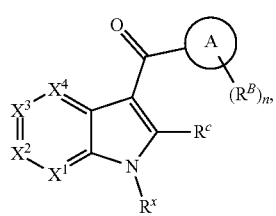

(I)

or a pharmaceutically acceptable salt, solvate, hydrate, stereoisomer, tautomer, isotopically labeled derivative, polymorph, or prodrug thereof; wherein $X^1$-$X^4$, $R^X$, $R^C$, $R^B$, n, and Ring A are as defined herein.

In some embodiments, at least one of $X^1$, $X^2$, $X^3$, and $X^4$ is N. In some embodiments, $X^1$ is N. In some embodiments, $X^1$ is N and $X^2$, $X^3$, and $X^4$ are each independently $CR^A$, wherein $R^A$ is as defined herein. In some embodiments, $X^1$, $X^2$, $X^3$, and $X^4$ are each independently $CR^A$, wherein $R^A$ is as defined herein.

In certain embodiments, Ring A is substituted or unsubstituted phenyl. In certain embodiments, Ring A is a substituted or unsubstituted, 5- to 6-membered heteroaryl ring.

In certain embodiments, the compound of Formula (I) is a compound of Formula (II):

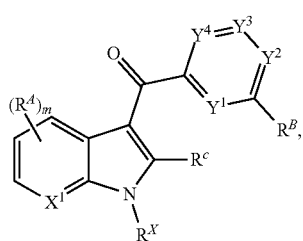

(II)

or a pharmaceutically acceptable salt, solvate, hydrate, stereoisomer, tautomer, isotopically labeled derivative, polymorph, or prodrug thereof; wherein $X^1$, $R^A$, m, $R^X$, $R^C$, $R^B$, and $Y^1$-$Y^4$ are as defined herein.

In certain embodiments, the compound of Formula (I) is a compound of Formula (III):

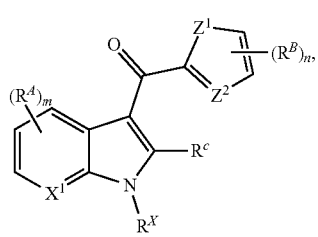

(III)

or a pharmaceutically acceptable salt, solvate, hydrate, stereoisomer, tautomer, isotopically labeled derivative, polymorph, or prodrug thereof; wherein $X^1$, $R^A$, m, $R^X$, $R^C$, $R^B$, n, $Z^1$, and $Z^2$ are as defined herein.

In another aspect, provided are pharmaceutical compositions comprising a compound of Formula (I), or a pharmaceutically acceptable salt, solvate, hydrate, stereoisomer, tautomer, isotopically labeled derivative, polymorph, or prodrug thereof, and optionally a pharmaceutically acceptable excipient. The pharmaceutical composition may be useful in treating a disease or condition associated with the activity of an aryl hydrocarbon receptor, such as, for example, an inflammatory disease, an autoimmune disease, a metabolic disorder, or a proliferative disease. In some embodiments, the compound of Formula (I), or pharmaceutically acceptable salt, solvate, hydrate, stereoisomer, tautomer, isotopically labeled derivative, polymorph, prodrug, or pharmaceutical composition thereof, is formulated for oral administration to a subject in need thereof.

In another aspect, provided herein are methods of modulating an aryl hydrocarbon receptor of a cell, the method comprising contacting a cell with a compound of Formula (I), or pharmaceutically acceptable salt, solvate, hydrate, stereoisomer, tautomer, isotopically labeled derivative, polymorph, prodrug, or pharmaceutical composition thereof. In some embodiments, the activity of the aryl hydrocarbon receptor of the cell increases in the presence of the compound.

In yet another aspect, provided are methods of treating a disease or condition associated with the activity of an aryl hydrocarbon receptor in a subject in need thereof, the method comprising administering a compound of Formula (I), or a pharmaceutically acceptable salt, solvate, hydrate, stereoisomer, tautomer, isotopically labeled derivative, polymorph, prodrug, or pharmaceutical composition thereof, to a subject in need thereof in an amount sufficient to modulate aryl hydrocarbon receptor activity. In certain embodiments, the compound is an aryl hydrocarbon receptor agonist. In certain embodiments, the compound is a partial aryl hydrocarbon receptor agonist. In certain embodiments, the compound increases the activity of the aryl hydrocarbon receptor. In certain embodiments, the disease or condition being treated is an inflammatory disease, an autoimmune disease, a metabolic disorder, or a proliferative disease.

In a further aspect, the present invention provides use of compounds of Formula (I), or pharmaceutically acceptable salt, solvate, hydrate, stereoisomer, tautomer, isotopically labeled derivative, polymorph, prodrug, or pharmaceutical composition thereof, to treat a disease or condition associated with the activity of an aryl hydrocarbon receptor. In certain embodiments, the disease or condition being treated is an inflammatory disease, an autoimmune disease, a metabolic disorder, or a proliferative disease.

Also provided herein are kits comprising a compound of Formula (I), or a pharmaceutically acceptable salt, solvate, hydrate, stereoisomer, tautomer, isotopically labeled derivative, polymorph, prodrug, or pharmaceutical composition thereof. In some embodiments, the kit optionally includes one or more additional therapeutically active agents.

In a further aspect, provided herein are kits for use in carrying out any of the methods described herein. The kits may include instructions for using the kit, safety, information, dosage information, and the like.

The details of one or more embodiments of the invention are set forth in the accompanying Figures, the Detailed Description, and the Examples. Other features, objects, and advantages of the invention will be apparent from the description and from the claims.

BRIEF DESCRIPTION OF THE DRAWINGS

FIG. 1A shows an AHR XRE luciferase assay in human hepG2 cells used to identify potent AHR agonists from a diverse library of novel (1H-indole-3-carbonyl)benzenes, 1H-indole-3-carbonyl) pyridines, (1H-indole-3-carbonyl)pyrimidines. FIG. 1B shows representative compounds from the screening library that showed remarkable structural requirements for activity with $EC_{50}$ ranging from 3.2 nM for the pyridine compound (#10) to >10,000 nM for e.g. the benzene compound (#202). FIG. 1C shows the AHR homology model built from long time scale MD simulation in the presence of compound #10. Key amino acids that form the ligand binding domain are labeled and their side chains are presented as sticks. The molecular surface area of compound #10 is displayed in blue. FIG. 1D shows that active compounds (top) adopt low energy conformers that are distinctive from inactive analogs (bottom). FIG. 1E shows plasma microsomal stability of AHR agonists quantified by LCMS/MS analysis. FIG. 1F shows liver microsomal stability of AHR agonists quantified by LCMS/MS analysis. FIG. 1G shows structures and activity data of representative analogs replacing the label ester moiety. The plasma and liver microsomal stability of compound #108, #109, and #113 are shown in FIG. 1E and FIG. 1F, respectively.

FIGS. 2A and 2B show that nuclear translocation of AhR is induced by ITE and compounds 108 and 109. Mouse Hepa-1c1c7 cells (FIG. 2A) or human HepG2 (FIG. 2B) were treated with vehicle control (DMSO) or 10 μM of ITE, compound 108, or compound 109 for 90 minutes. AhR (green), actin (red) and nucleus (blue) were stained and examined by confocal microscopy. AhR is distributed in cytoplasm of vehicle control treated cells and localized in the nucleus of cells treated with ITE, compound 108, and compound 109. Top row AhR (green), bottom row merge. FIG. 2C shows compounds 108 and 109 induced AhR-dependent cyp1a1 expression in mouse Hepa-1c1c7 cells. Cells were treated with vehicle control (DMSO) or 10 nM-10 μM ITE, compound 108, or compound 109 for 8 hours, qPCR was performed against cyp1a1 with 18S as internal reference. Compound 109 was chosen for further pharmacokinetic/pharmacodynamic studies in the mouse. Vehicle control or 109 (0.1 ug-1 mg) were administered to mice via oral gavage, 12 h later, organs and blood were harvested for qPCR analysis of cyp1a1 induction with 18S as internal reference gene. FIG. 2D shows that compound 109 induced dose-dependent cyp1a1 in liver and colon tissue. FIG. 2E shows limited cyp1a1 induction was observed in spleen and induction in circulating WBC was only observed at highest administered dose. mean±s.e.m., $*p<0.05$ versus control, $\#p<0.05$ versus ITE.

FIG. 3D shows colon lengths measured on day 11. FIG. 3E shows representative haematoxylin and eosin (H&E) staining (100×) and FIG. 3F shows histological score at day 11. FIG. 3G shows colon goblet cells stained by periodic acid-Schiff and alcian blue and quantified at day 11, results are reported as goblet cell number per mm colon length (FIG. 3H). Colon IL-22 was significantly upregulated in 109-treated mice at day 7 and 11 as characterized by qPCR (FIG. 3I) and flow cytometry staining (FIGS. 3J and 3K) of explant lamina propria mononuclear cells (LPMC). IL-22+ effecter cell types were determined using intracellular staining of IL-22 in combination with T helper staining (CD3+CD4+) or ILC3 staining (CD3−RORrt+) after 8 hours of ex vivo cytokine stimulation with Golgi inhibitor. FIGS. 3L and 3M show IL-22 responsive antimicrobial peptide mRNA expression was characterized in the colon epithelial fraction at day 0, 7, and 11. Data represent mean±s.e.m., $*p<0.05$ versus control.

FIG. 5A shows AhR-responsive gene cyp1A1 was significantly induced in compound 109 treated mice at day 7 and 1,1 while no significant difference between AhR expression (FIG. 5B) was noted between groups. FIGS. 5C-5F show that no compound 109-dependent expression of inflammatory mediators characterized in whole colon was observed at day 7 and 11: TNF-α (FIG. 5C), IFN-γ (FIG. 5D), IL-10 (FIG. 5E), and Foxp3 (FIG. 5F). FIGS. 5G-5I show that moderate differences in expression were observed in markers of epithelial barrier function, characterized in colon epithelial fraction at day 7 and 11: Muc1 (FIG. 5G), Muc3 (FIG. 5H), Bcl21 (FIG. 5I). Data represent mean±s.e.m., n=5/group, $*p<0.05$ versus control.

Figure 7A:
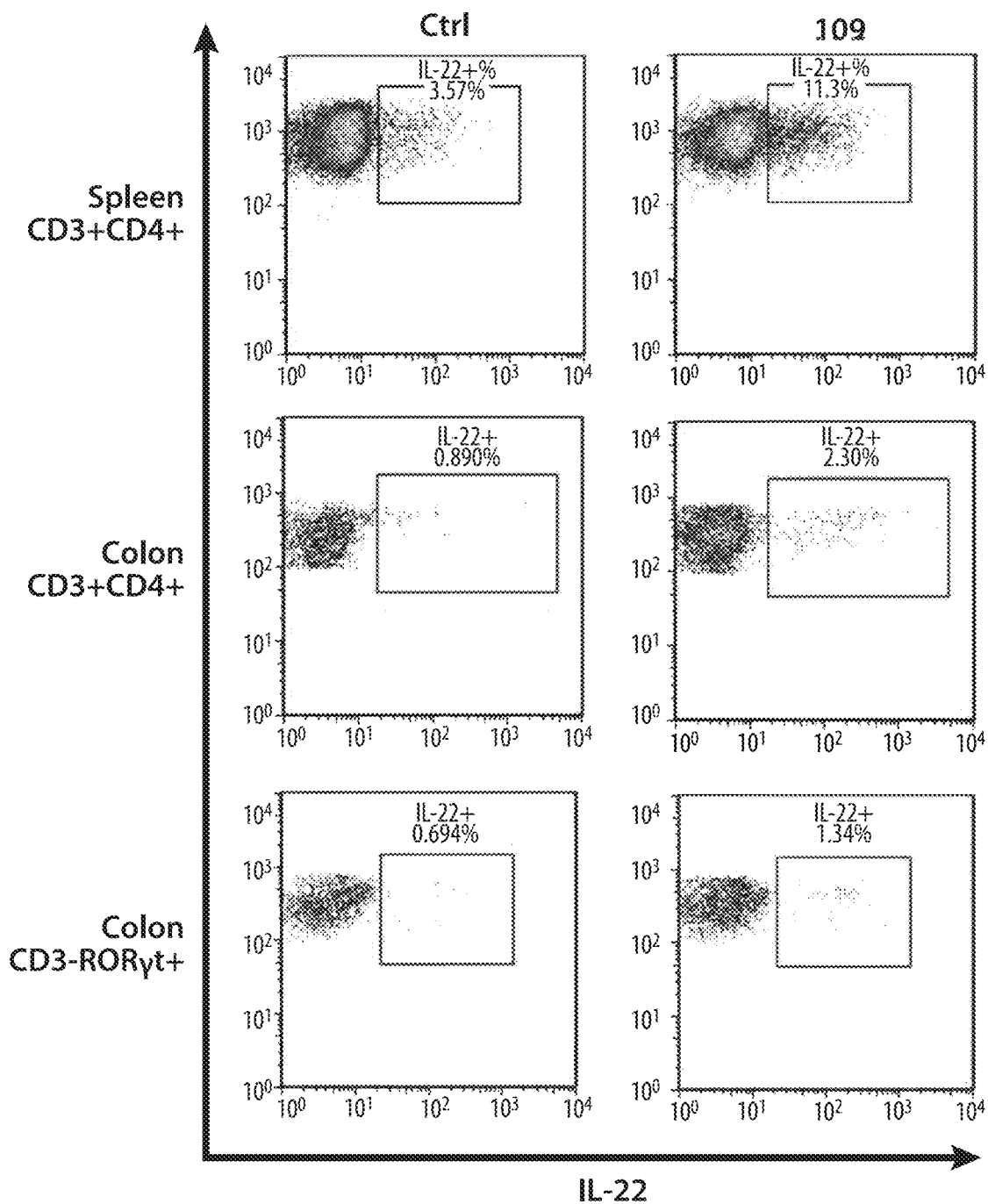
FIGS. 7A-7D show in vitro induction of IL-22 by compound 109. CD4+T helper cells were purified from mouse spleen, activated by CD3/CD28 ligation in Th-17 polarization medium and treated with vehicle or 1 μM of ITE for 3 days.
Figure 7B:
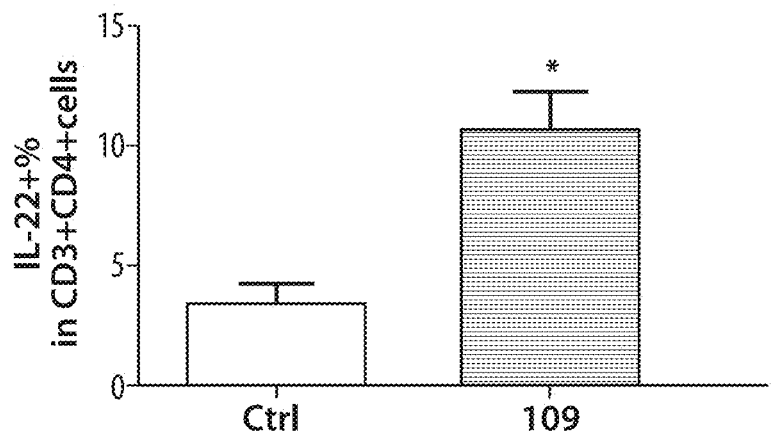
Figure 7C:
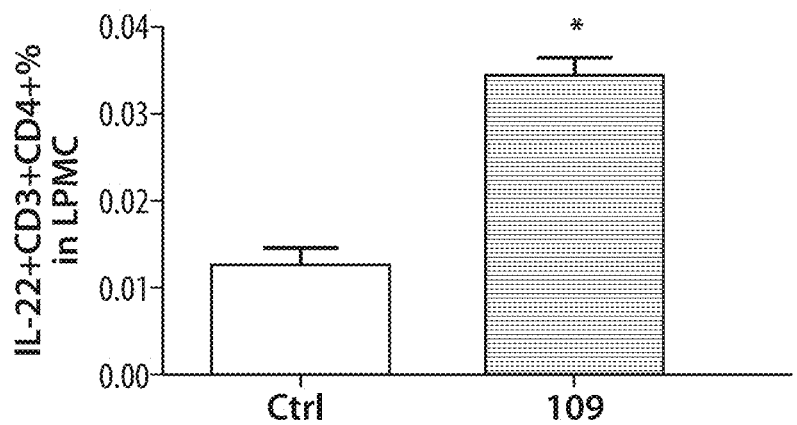
Figure 7D:
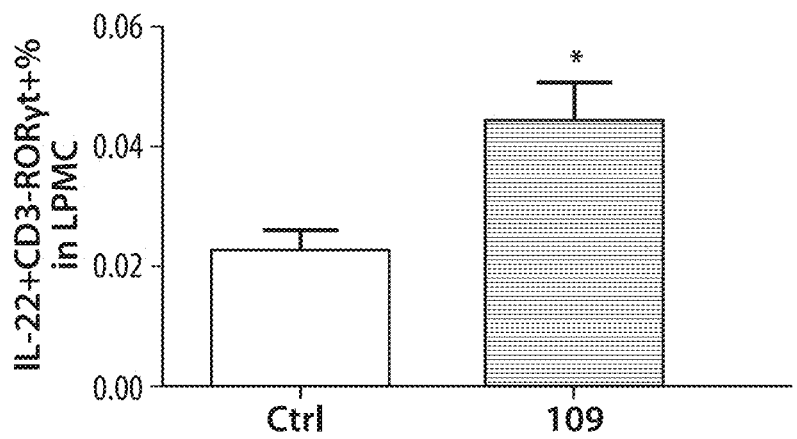

FIGS. 7A and 7B show intracellular IL-22 staining performed together with T helper markers (CD3+CD4+). Lamina propria cells were isolated from mouse colons and treated with vehicle or 1 μM of ITE and IL-1+IL-23 for 3 days. FIGS. 7A, 7C, and 7D show Intracellular IL-22 staining performed together with T helper markers (CD3+ CD4+) (FIG. 7C) or ILC markers (CD3−RORrt+) (FIG. 7D). Data represent mean±s.e.m., n=5/group, *p<0.05 versus control.

DEFINITIONS

Chemical Definitions

Definitions of specific functional groups and chemical terms are described in more detail below. The chemical elements are identified in accordance with the Periodic Table of the Elements, CAS version, *Handbook of Chemistry and Physics,* 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. "Racemic" refers to a compound in which the percent by weight of one enantiomer is equal to the percent by weight of the other enantiomer.

The terms "enantiomerically enriched," "enantiomerically pure," and "non-racemic," as used interchangeably herein, refer to a compound in which the percent by weight of one enantiomer is greater than the amount of that one enantiomer compared to a control mixture of the racemic composition (e.g., greater than 1:1 by weight). For example, an enantiomerically enriched enantiomer, means a compound having greater than 50% by weight of one enantiomer relative to the other enantiomer, e.g., at least 75% by weight, or at least 80% by weight. In some embodiments, the enrichment can be much greater than 80% by weight, providing a "substantially enantiomerically enriched," "substantially enantiomerically pure" or a "substantially non-racemic" compound, which refers to a compound with at least 85% by weight of one enantiomer relative to other enantiomer, e.g., at least 90% by weight, or at least 95% by weight.

Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, IN 1972).

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1, 2, 3, or 4 heteroatoms within the parent chain ("$heteroC_{1-10}$ alkyl"). In some embodiments, a heteroalkyl group is a saturated group having 1 to 9 carbon atoms and 1, 2, 3, or 4 heteroatoms within the parent chain ("$heteroC_{1-9}$ alkyl"). In some embodiments, a heteroalkyl group is a saturated group having 1 to 8 carbon atoms and 1, 2, 3, or 4 heteroatoms within the parent chain ("$heteroC_{1-8}$ alkyl"). In some embodiments, a heteroalkyl group is a saturated group having 1 to 7 carbon atoms and 1, 2, 3, or 4 heteroatoms within the parent chain ("$heteroC_{1-7}$ alkyl").

In some embodiments, a heteroalkyl group is a saturated group having 1 to 6 carbon atoms and 1, 2, or 3 heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

As used herein, "alkenyl" refers to a radical of a straight-chain or branched hydrocarbon group having from 2 to 10 carbon atoms and one or more double bonds (e.g., 1, 2, 3, or 4 double bonds) and no triple bonds. In some embodiments, an alkenyl group has 2 to 9 carbon atoms ("C$_{2-9}$ alkenyl"). In some embodiments, an alkenyl group has 2 to 8 carbon atoms ("C$_{2-9}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_3$), pentadienyl (C$_3$), hexenyl (C$_6$), and the like. Additional examples of alkenyl include heptenyl (C$_7$), octenyl (C$_3$), octatrienyl (C$_3$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1, 2, 3, or 4 heteroatoms within the parent chain ("heteroC$_{2-10}$ alkenyl"). In some embodiments, a heteroalkenyl group has 2 to 9 carbon atoms at least one double bond, and 1, 2, 3, or 4 heteroatoms within the parent chain ("heteroC$_{2-9}$ alkenyl"). In some embodiments, a heteroalkenyl group has 2 to 8 carbon atoms, at least one double bond, and 1, 2, 3, or 4 heteroatoms within the parent chain ("heteroC$_{2-9}$ alkenyl"). In some embodiments, a heteroalkenyl group has 2 to 7 carbon atoms, at least one double bond, and 1, 2, 3, or 4 heteroatoms within the parent chain ("heteroC$_{2-7}$ alkenyl"). In some embodiments, a heteroalkenyl group has 2 to 6 carbon atoms, at least one double bond, and 1, 2, or 3 heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-9}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

As used herein, "alkynyl" refers to a radical of a straight-chain or branched hydrocarbon group having from 2 to 10 carbon atoms and one or more triple bonds (e.g., 1, 2, 3, or 4 triple bonds) and optionally one or more double bonds (e.g., 1, 2, 3, or 4 double bonds) ("C$_{2-10}$ alkynyl"). An alkynyl group that has one or more triple bonds and one or more double bonds is also referred to as an "ene-yene" group. In some embodiments, an alkynyl group has 2 to 9 carbon atoms ("C$_{2-9}$ alkynyl"). In some embodiments, an alkynyl group has 2 to 8 carbon atoms ("C$_{2-9}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_3$), hexynyl (C$_6$), and the like. Additional examples of alkynyl include heptynyl (C$_7$), octynyl (C$_3$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1, 2, 3, or 4 heteroatoms within the parent chain ("heteroC$_{2-10}$ alkynyl"). In some embodiments, a heteroalkynyl group has 2 to 9 carbon atoms, at least one triple bond, and 1, 2, 3, or 4 heteroatoms within the parent chain ("heteroC$_{2-9}$ alkynyl"). In some embodiments, a heteroalkynyl group has 2 to 8 carbon atoms, at least one triple bond, and 1, 2, 3, or 4 heteroatoms within the parent chain ("heteroC$_{2-8}$ alkynyl"). In some embodiments, a heteroalkynyl group has 2 to 7 carbon atoms, at least one triple bond, and 1, 2, 3, or 4 heteroatoms within the parent chain ("heteroC$_{2-7}$ alkynyl"). In some embodiments, a heteroalkynyl group has 2 to 6 carbon atoms, at least one triple bond, and 1, 2, or 3 heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "acyl" refers to a group having the general formula —C(=O)R$^a$, —C(=O)OR$^a$, —C(=O)—O—C(=O)R$^a$, —C(=O)SR$^a$, —C(=O)N(R$^a$)$_2$, —C(=S)R$^a$, —C(=S)N(R$^a$)$_2$, and —C(=S)S(R$^a$), —C(=NR$^a$)R$^a$, —C(=NR$^a$)OR$^a$, —C(=NR$^a$)SR$^a$, and —C(=NR$^a$)N(R$^a$)$_2$, wherein R$^a$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^a$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 9 ring carbon atoms ("C$_{3-9}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. In certain embodiments, the carbocyclyl group is either monocyclic ("monocyclic carbocyclyl") or polycyclic (e.g., containing a fused, bridged or spiro-fused ring system such as a bicyclic system ("bicyclic carbocyclyl") or tricyclic system ("tricyclic carbocyclyl")) and can be saturated or can contain one or more carbon-carbon double or triple bonds. Exemplary fused bicyclic systems include, but are not limited to, decalin (cis or trans decalin). Exemplary fused tricyclic systems include, but are not limited to, fluorenyl. Exemplary spiro-fused bicyclic systems include, but are not limited to, spiropentane. Exemplary bridged bicyclic systems include, but are not limited to, norbornane, norbornene, bicyclo[2.2.2]octane, bicyclo[2.2.2]oct-2-ene, bicyclo[3.2.1]octane, and bicyclo[2.2.1]heptan-2-one. Exemplary bridged tricyclic systems include, but are not limited to adamantane. "Carbocyclyl" includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

"Carbocyclylalkyl" is a subset of "alkyl" and refers to an alkyl group, as defined herein, substituted by an carbocyclyl group, as defined herein, wherein the point of attachment is on the alkyl moiety.

As used herein, "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. In certain embodiments, the heterocyclyl group is either monocyclic ("monocyclic heterocyclyl") or polycyclic (e.g., containing a fused, bridged or spiro-fused ring system such as a bicyclic system ("bicyclic heterocyclyl") or tricyclic system ("tricyclic heterocyclyl")) and can be saturated or can contain one or more carbon-carbon double or triple bonds. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl, and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

"Heterocyclylalkyl" is a subset of "alkyl" and refers to an alkyl group, as defined herein, substituted by an heterocyclyl group, as defined herein, wherein the point of attachment is on the alkyl moiety.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracenyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, acyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^a$, —SC(=S)SR$^a$, —SC(=O)SR$^a$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-14}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^a$, =NNR$^{bb}$C(=O)OR$^{aa}$, =NNR$^{bb}$S(=O)$_2$R$^a$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$heteroalkenyl, C$_{2-10}$ heteroalkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$heteroalkenyl, C$_{2-10}$ heteroalkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{cc}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$heteroalkenyl, C$_{2-6}$heteroalkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal Rd substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$heteroalkenyl, C$_{2-6}$heteroalkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$heteroalkenyl, C$_{2-6}$heteroalkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)+X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, —C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{1-6}$heteroalkyl, C$_{2-6}$ heteroalkenyl, C$_{2-6}$heteroalkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quaternary amine in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^a$, —OSi(R$^{aa}$)$_3$, —OP(R$^{cc}$)$_2$, —OP(R$^{cc}$)$_3$, —OP(=O)$_2$R$^{aa}$, —OP(=O)(R$^a$)$_2$, —OP(=O)(OR$^{cc}$)$_2$, —OP(=O)$_2$N(R$^{bb}$)$_2$, and —OP(=O)(NR$^{bb}$)$_2$, wherein R$^a$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$. The term "substituted amino," by extension, refers to a monosubstituted amino, a disubstituted amino, or a trisubstituted amino, as defined herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$—NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$ X$^-$, wherein R$^{bb}$ and X$^-$ are as defined herein.

As used herein, the term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^a$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^a$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)] methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl) methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-10 doethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pme), methanesulfonamide (Ms), (3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N' dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N (R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, —SO$_2$R$^{a}$, —Si(R$^{aa}$)$_3$, —P(R$^{cc}$)$_2$, —P(R$^{cc}$)$_3$, —P(=O)$_2$R$^{aa}$, —P(=O)(R$^{a}$)$_2$, —P(=O) (OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-10 dibenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate, Ms), benzylsulfonate, benzenesulfonate (besylate, Bs), and toluenesulfonate (tosylate, Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and claims. The invention is not intended to be limited in any manner by the above exemplary listing of substituents.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Non-limiting examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include, for example, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates.

Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5 $H_2O$)), and polyhydrates (x is a number greater than 1, e.g., dihydrates (R·2 $H_2O$) and hexahydrates (R·6 $H_2O$)).

The term "tautomer" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. C1-C8 alkyl, C2-C8 alkenyl, C2-C8 alkynyl, aryl, C7-C12 substituted aryl, and C7-C12 arylalkyl esters of the compounds described herein may be preferred.

As used herein, a "leaving group" is an art-understood term referring to a molecular fragment that departs with a pair of electrons in heterolytic bond cleavage, wherein the molecular fragment is an anion or neutral molecule. See, for example, Smith, March *Advanced Organic Chemistry* 6th ed. (501-502). Exemplary leaving groups include, but are not limited to, halo (e.g., chloro, bromo, iodo) and sulfonyl substituted hydroxyl groups (e.g., tosyl, mesyl, besyl).

Other Definitions

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal. In certain embodiments, the subject is a human.

A "condition," "disease," and "disorder" are used interchangeably herein.

As used herein, and unless otherwise specified, the terms "treat," "treating," and "treatment" contemplate an action that occurs while a subject is suffering from the specified disease or condition, which reduces the severity of the disease or condition, or retards or slows the progression of the disease or condition ("therapeutic treatment"), and also contemplates an action that occurs before a subject begins to suffer from the specified disease or condition ("prophylactic treatment"). In some embodiments, a compound of Formula (I), or a pharmaceutically acceptable salt, solvate, hydrate, stereoisomer, tautomer, isotopically labeled derivate, polymorph, prodrug, or pharmaceutical composition thereof, is used to treat an inflammatory disease, an autoimmune disease, a metabolic disorder, or a proliferative disease.

In general, the "effective amount" of a compound refers to an amount sufficient to elicit the desired biological response.

As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease or condition, or to delay or minimize one or more symptoms associated with the disease or condition. A therapeutically effective amount of a compound means an amount of therapeutic agent, alone or in combination with other therapies, which provides a therapeutic benefit in the treatment of the disease or condition. The term "therapeutically effective amount" can encompass an amount that improves overall therapy, reduces or avoids symptoms or causes of disease or condition, or enhances the therapeutic efficacy of another therapeutic agent. In the context of treatment of conditions associated with reduced aryl hydrocarbon receptor activity, in certain embodiments, a therapeutically effective amount is an amount sufficient to increase aryl hydrocarbon receptor activity.

As used herein, and unless otherwise specified, a "prophylactically effective amount" of a compound is an amount sufficient to prevent a disease or condition, or one or more symptoms associated with the disease or condition, or prevent its recurrence. A prophylactically effective amount of a compound means an amount of a therapeutic agent, alone or in combination with other agents, which provides a prophylactic benefit in the prevention of the disease or condition. The term "prophylactically effective amount" can encompass an amount that improves overall prophylaxis or enhances the prophylactic efficacy of another prophylactic agent.

As used herein an "agonist" refers to a compound that can increase or induce the activity of an aryl hydrocarbon receptor relative to vehicle. In some embodiments, the cell is in vivo. In general, an agonist binds to a receptor (e.g., an aryl hydrocarbon receptor) to induce a biological response. Without wishing to be bound by any particular theory, activation of the acyl hydrocarbon receptor (e.g., by binding to an agonist) results in changes in gene expression, leading to modulation of expression of proteins (e.g., cytokines) to influence inflammatory, metabolic, and other biological responses. Modulation of biological responses by aryl hydrocarbon receptors is discussed in, e.g., Bieschlag T V et al. (2008) The aryl hydrocarbon receptor complex and the control of gene expression. *Crit Rev Eukaryot Gene Expr* 18, 207-250; Nebert D W et al. (2000) Role of the aromatic hydrocarbon receptor and [Ah] gene battery in the oxidative stress response, cell cycle control, and apoptosis. *Biochemical Pharmacology* 59, 65-85; Quintana F J et al. (2008) Control of $T_{reg}$ and $T_H17$ cell differentiation by the aryl hydrocarbon receptor. *Nature* 453, 65-71; and Puga A et al. (2009) The aryl hydrocarbon receptor cross-talks with multiple signal transduction pathways. *Biochemical Pharmacology* 77, 713-722; each of which is incorporated herein by reference in its entirety. In some embodiments, the agonist is a full agonist. A "full agonist" refers to an agonist that binds to a receptor (e.g., an aryl hydrocarbon receptor) and induces the maximum biological response that an agonist can elicit at the receptor. In some embodiments, the agonist is a partial agonist. A "partial agonist" refers to an agonist that binds to a receptor (e.g., an aryl hydrocarbon receptor) but only induces a partial biological response compared to the biological response that a full agonist can induce, even at maximum receptor occupancy.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

Figure 2:
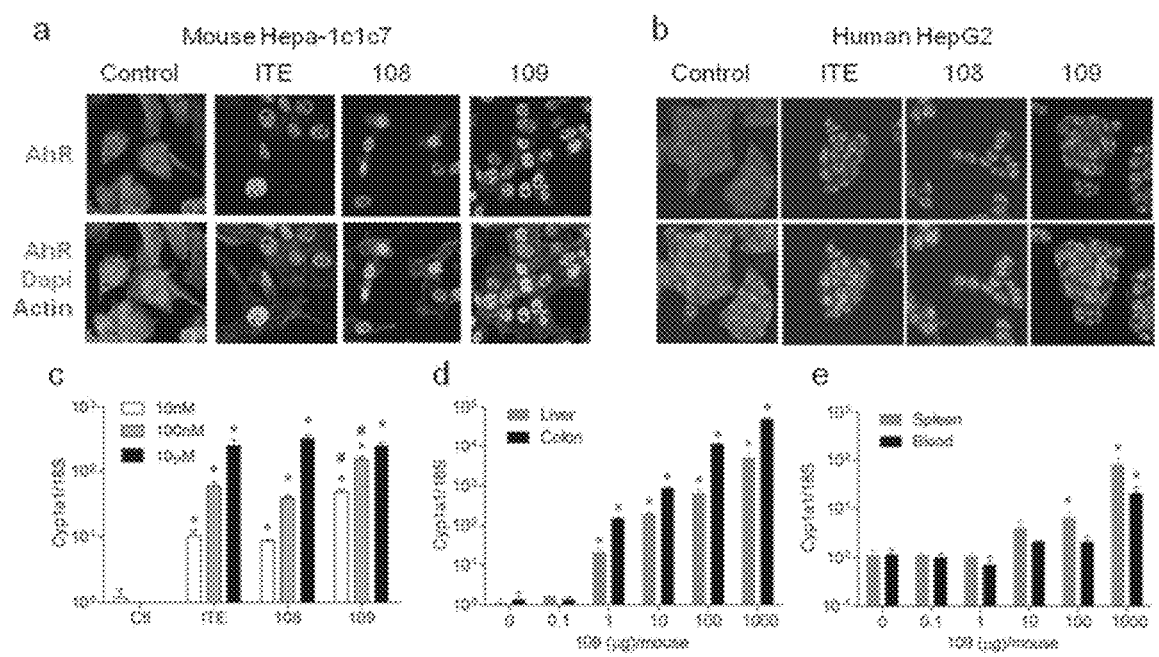
FIG. 2A-2E shows biological characterization of lead compounds in vitro and after oral administration.

"Aryl hydrocarbon receptor." An aryl hydrocarbon receptor (AhR, AHR, ahr, or ahR) is a ligand-activated transcription factor involved in the regulation of biological responses induced by planar aromatic (i.e., aryl) hydrocarbons. In humans, the aryl hydrocarbon receptor is encoded by the AHR gene. The aryl hydrocarbon receptor is a member of the family of basic helix-loop-helix transcription factors. AhR is a cytosolic transcription factor that is normally inactive, bound to several co-chaperones. Without wishing to be bound by any particular theory, upon ligand binding, the chaperones dissociate resulting in AhR translocating into the nucleus and dimerizing with ARNT (AhR nuclear translocator), leading to changes in gene transcription (see, e.g., Bieschlag T V et al. (2008) The aryl hydrocarbon receptor complex and the control of gene expression. *Crit Rev Eukaryot Gene Expr* 18, 207-250; which is incorporated herein by reference in its entirety). In some embodiments, the gene is CYP1A1. Cypa1a protein expression may be induced in an AHR-dependent manner in the presence of compounds of Formula (I) described herein (FIG. 2). In some embodiments, the gene is Muc1, Muc3, or Bcl21 (FIGS. 5C-5F).

"Modulate," as used herein, means to decrease (e.g., inhibit, reduce, suppress) or increase (e.g., stimulate, activate, enhance) a level, response, property, activity, pathway, or process. A "modulator" is an agent capable of modulating a level, response, property, activity, pathway, or process. A modulator may be an inhibitor, antagonist, activator, or agonist. In some embodiments modulation may refer to an alteration, e.g., inhibition or increase, of the relevant level, response, property, activity, pathway, or process by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

Detailed Description of Certain Embodiments of the Invention

As generally described herein, the present invention is based on the development of compounds that can bind to and modulate the aryl hydrocarbon receptor. These compounds can non-covalently bind to the aryl hydrocarbon receptor.

Compounds described herein may be generally represented by Formula (I):

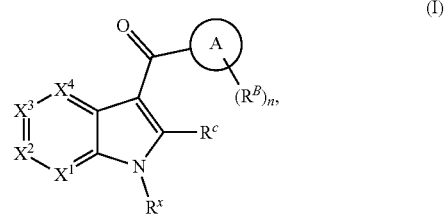

or a pharmaceutically acceptable salt, solvate, hydrate, stereoisomer, tautomer, isotopically labeled derivative, polymorph, or prodrug thereof; wherein:

Ring A is substituted or unsubstituted aryl, or substituted or unsubstituted heteroaryl;

$X^1$, $X^2$, $X^3$, and $X^4$ are each independently N or $CR^A$;

$R^X$ is independently hydrogen, substituted or unsubstituted alkyl, substituted or unsubstituted alkenyl, substituted or unsubstituted alkynyl, substituted or unsubstituted acyl, or a nitrogen protecting group;

each instance of $R^A$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{A1}$, $-N(R^{A1})_2$, $-SR^{A1}$, $-CN$, $-C(R^{A1})_3$, $-SCN$, $-C(=NR^{A1})R^{A1}$, $-C(=NR^{A1})OR^{A1}$, $-C(=NR^{A1})N(R^{A1})_2$, $-C(=O)R^{A1}$, $-C(=O)OR^{A1}$, $-C(=O)N(R^{A1})_2$, $-NO_2$, $-NR^{A1}C(=O)R^{A1}$, $-NR^{A1}C(=O)OR^{A1}$, $-NR^{A1}C(=O)N(R^{A1})_2$, $-OC(=O)R^{A1}$, $-OC(=O)OR^{A1}$, $-OC(=O)N(R^{A1})_2$, or two $R^A$ groups are joined to form a substituted or unsubstituted carbocyclic, substituted or unsubstituted heterocyclic, substituted or unsubstituted aryl, or substituted or unsubstituted heteroaryl ring;

each instance of $R^B$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{B1}$, $-N(R^{B1})_2$, $-SR^{B1}$, $-CN$, $-C(R^{B1})_3$, $-SCN$, $-C(=NR^{B1})R^{B1}$, $-C(=NR^{B1})OR^{B1}$, $-C(=NR^{B1})N(R^{B1})_2$, $-C(=O)R^{B1}$, $-C(=O)OR^{B1}$, $-C(=O)N(R^{B1})_2$, $-NO_2$, $-NR^{B1}C(=O)R^{B1}$, $-NR^{B1}C(=O)OR^{B1}$, $-NR^{B1}C(=O)N(R^{B1})_2$, $-OC(=O)R^{B1}$, $-OC(=O)OR^{B1}$, $-OC(=O)N(R^{B1})_2$, or two $R^B$ groups are joined to form a substituted or unsubstituted carbocyclic, substituted or unsubstituted heterocyclic, substituted or unsubstituted aryl, or substituted or unsubstituted heteroaryl ring;

$R^C$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{C1}$, $-N(R^{C1})_2$, $-SR^{C1}$, $-CN$, $-C(R^{C1})_3$, $-SCN$, $-C(=NR^{C1})R^{C1}$, $-C(=NR^{C1})OR^{C1}$, $-C(=NR^{C1})N(R^{C1})_2$, $-C(=O)R^{C1}$, $-C(=O)OR^{C1}$, $-C(=O)N(R^{C1})_2$, $-NO_2$, $-NR^{C1}C(=O)R^{C1}$, $-NR^{C1}C(=O)OR^{C1}$, $-NR^{C1}C(=O)N(R^{C1})_2$, $-OC(=O)R^{C1}$, $-OC(=O)OR^{C1}$, $-OC(=O)N(R^{C1})_2$, or $R^C$ and $R^X$ are joined to form a substituted or unsubstituted heterocyclic, or substituted or unsubstituted heteroaryl ring;

each instance of $R^{A1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form a substituted or unsubstituted carbocyclic, substituted or unsubstituted heterocyclic, substituted or unsubstituted aryl, or substituted or unsubstituted heteroaryl ring;

each instance of $R^{B1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{B1}$ groups are joined to form a substituted or unsubstituted carbocyclic, substituted or unsubstituted heterocyclic, substituted or unsubstituted aryl, or substituted or unsubstituted heteroaryl ring;

each instance of $R^{C1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{C1}$ groups are joined to form a substituted or unsubstituted carbocyclic, substituted or unsubstituted heterocyclic, substituted or unsubstituted aryl, or substituted or unsubstituted heteroaryl ring; and n is 0, 1, 2, 3, 4, or 5.

In some embodiments, $X^1$, $X^2$, $X^3$, and $X^4$ are $CR^A$. In some embodiments, none of $X^1$, $X^2$, $X^3$, and $X^4$ are N.

In some embodiments, at least one of $X^1$, $X^2$, $X^3$, and $X^4$ is N.

In some embodiments, only one of $X^1$, $X^2$, $X^3$, and $X^4$ is N. In some embodiments, $X^1$ is N or $CR^A$. In some embodiments, $X^1$ is N, and $X^2$, $X^3$, and $X^4$ are each independently $CR^A$.

In some embodiments, $X^2$ is N, and $X^1$, $X^3$, and $X^4$ are each independently $CR^A$. In some embodiments, $X^3$ is N, and $X^1$, $X^2$, and $X^4$ are each independently $CR^A$. In some embodiments, $X^4$ is N, and $X^1$, $X^2$, and $X^3$ are each independently $CR^A$.

In some embodiments, any two of $X^1$, $X^2$, $X^3$, and $X^4$ are N. In some embodiments, $X^1$ and $X^2$ are N, and $X^3$ and $X^4$ are each independently $CR^A$. In some embodiments, $X^1$ and $X^3$ are N, and $X^2$ and $X^4$ are each independently $CR^A$. In some embodiments, $X^1$ and $X^4$ are N, and $X^2$ and $X^3$ are each independently $CR^A$. In some embodiments, $X^2$ and $X^3$ are N, and $X^1$ and $X^4$ are each independently $CR^A$. In some embodiments, $X^3$ and $X^4$ are N, and $X^1$ and $X^2$ are each independently $CR^A$. In some embodiments, $X^2$ and $X^4$ are N, and $X^1$ and $X^3$ are each independently $CR^A$.

In some embodiments, any three of $X^1$, $X^2$, $X^3$, and $X^4$ are N. In some embodiments, $X^1$, $X^2$, and $X^3$ are N, and $X^4$ is $CR^A$. In some embodiments, $X^2$, $X^3$, and $X^4$ are N, and $X^1$ is $CR^A$. In some embodiments, $X^1$, $X^3$, and $X^4$ are N, and $X^2$ is $CR^A$. In some embodiments, $X^1$, $X^2$, and $X^4$ are N, and $X^3$ is $CR^A$.

In some embodiments, all of $X^1$, $X^2$, $X^3$, and $X^4$ are N.

In some embodiments, a compound of Formula (I) is an aryl hydrocarbon receptor agonist. In some embodiments, a compound of Formula (I) is a partial aryl hydrocarbon receptor agonist.

In some embodiments, the compound of Formula (I) is a pharmaceutically acceptable salt thereof. In some embodiments, the compound of Formula (I) is a solvate thereof. In some embodiments, the compound of Formula (I) is a hydrate thereof. In some embodiments, the compound of Formula (I) is a stereoisomer thereof. In some embodiments, the compound of Formula (I) is a tautomer thereof. In some embodiments, the compound of Formula (I) is a isotopically labeled derivative thereof. In some embodiments, the compound of Formula (I) is a polymorph thereof. In some embodiments, the compound of Formula (I) is a prodrug thereof.

Indole Core comprising $X^1$, $X^2$, $X^3$, $X^4$, $R^A$, $R^C$, and $R^X$

As generally described herein, in some embodiments, $X^1$ is N or $CR^A$, and $X^2$, $X^3$, and $X^4$ are each independently $CR^A$ to provide a compound of Formula (I-a):

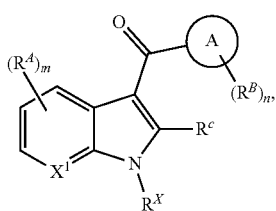

(I-a)

or a pharmaceutically acceptable salt, solvate, hydrate, stereoisomer, tautomer, isotopically labeled derivative, polymorph, or prodrug thereof, wherein m is 0, 1, 2, or 3.

In some aspects, the indole core ring system corresponding to the group:

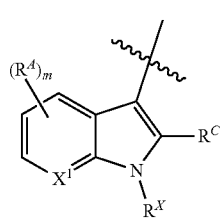

is of one of the following formulae:

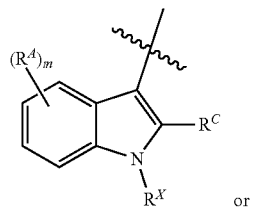

(i)

or

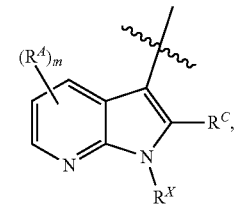

(ii)

wherein:

$R^X$ is independently hydrogen, substituted or unsubstituted alkyl, substituted or unsubstituted alkenyl, substituted or unsubstituted alkynyl, substituted or unsubstituted acyl, or a nitrogen protecting group;

each instance of $R^A$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —CN, —$C(R^{A1})_3$, —SCN, —$C(=NR^{A1})R^{A1}$, —$C(=NR^{A1})OR^{A1}$, —$C(=NR^{A1})N(R^{A1})_2$, —$C(=O)R^{A1}$, —$C(=O)OR^{A1}$, —$C(=O)N(R^{A1})_2$, —$NO_2$, —$NR^{A1}C(=O)R^{A1}$, —$NR^{A1}C(=O)OR^{A1}$, —$NR^{A1}C(=O)N(R^{A1})_2$, —$OC(=O)R^{A1}$, —$OC(=O)OR^{A1}$, —$OC(=O)N(R^{A1})_2$, or two $R^A$ groups are joined to form a substituted or unsubstituted carbocyclic, substituted or unsubstituted heterocyclic, substituted or unsubstituted aryl, or substituted or unsubstituted heteroaryl ring;

$R^C$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —$OR^{C1}$, —$N(R^{C1})_2$, —$SR^{C1}$, —CN, —$C(R^{C1})_3$, —SCN, —$C(=NR^{C1})R^{C1}$, —$C(=NR^{C1})OR^{C1}$, —$C(=NR^{C1})N(R^{C1})_2$, —$C(=O)R^{C1}$, —$C(=O)OR^{C1}$, —$C(=O)N(R^{C1})_2$, —$NO_2$, —$NR^{C1}C(=O)R^{C1}$, —$NR^{C1}C(=O)OR^{C1}$, —$NR^{C1}C(=O)N(R^{C1})_2$, —$OC(=O)R^{C1}$, —$OC(=O)OR^{C1}$, —$OC(=O)N(R^{C1})_2$, or $R^C$ and $R^X$ are joined to form a substituted or unsubstituted heterocyclic, or substituted or unsubstituted heteroaryl ring;

each instance of $R^{A1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form a substituted or unsubstituted carbocyclic, substituted or unsubstituted heterocyclic, substituted or unsubstituted aryl, or substituted or unsubstituted heteroaryl ring;

each instance of $R^{C1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{C1}$ groups are joined to form a substituted or unsubstituted carbocyclic, substituted or unsubstituted heterocyclic, substituted or unsubstituted aryl, or substituted or unsubstituted heteroaryl ring; and m is 0, 1, 2, 3, or 4.

Group $R^A$ and m

As generally described herein, $R^A$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{A1}$, $-N(R^{A1})_2$, $-SR^{A1}$, $-CN$, $-C(R^{A1})_3$, $-SCN$, $-C(=NR^{A1})R^{A1}$, $-C(=NR^{A1})OR^{A1}$, $-C(=NR^{A1})N(R^{A1})_2$, $-C(=O)R^{A1}$, $-C(=O)OR^{A1}$, $-C(=O)N(R^{A1})_2$, $-NO_2$, $-NR^{A1}C(=O)R^{A1}$, $-NR^{A1}C(=O)OR^{A1}$, $-NR^{A1}C(=O)N(R^{A1})_2$, $-OC(=O)R^{A1}$, $-OC(=O)OR^{A1}$, $-OC(=O)N(R^{A1})_2$, or two $R^A$ groups are joined to form a substituted or unsubstituted carbocyclic, substituted or unsubstituted heterocyclic, substituted or unsubstituted aryl, or substituted or unsubstituted heteroaryl ring, wherein each instance of $R^{A1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form a substituted or unsubstituted carbocyclic, substituted or unsubstituted heterocyclic, substituted or unsubstituted aryl, or substituted or unsubstituted heteroaryl ring, and m is 0, 1, 2, 3, or 4.

In some embodiments of Formula (I), m is 0; and $R^A$ is absent. In some embodiments of Formula (I), m is 1. In some embodiments of Formula (I), m is 2; and each $R^A$ is independently a group as described herein. In some embodiments of Formula (I), m is 3; and each $R^A$ is independently a group as described herein. In some embodiments of Formula (I), m is 4; and each $R^A$ is independently a group as described herein.

In certain embodiments of Formula (I), m is 1, 2, 3, or 4; and at least one instance of $R^A$ is hydrogen. In certain embodiments of Formula (I), m is 1; and $R^A$ is hydrogen. In certain embodiments of Formula (I), m is 2; and both instances of $R^A$ are hydrogen. In certain embodiments of Formula (I), m is 3; and all three instances of $R^A$ are hydrogen.

In some embodiments of Formula (I), each instance of $R^A$ is hydrogen to provide a ring system of formula:

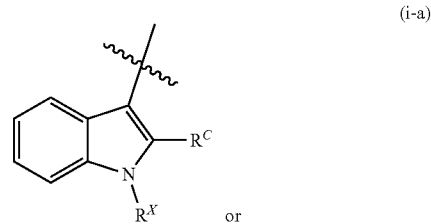

(i-a)

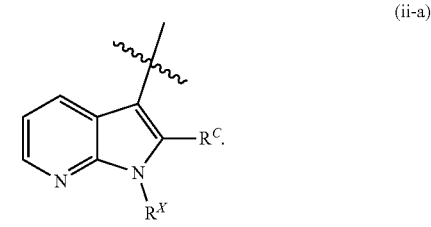

(ii-a)

In certain embodiments of Formula (I), m is 1 to provide a ring system of the formula:

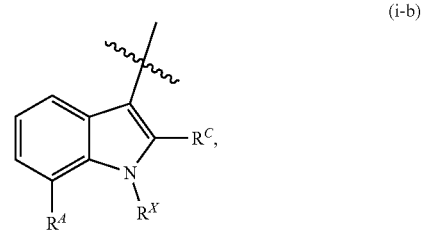

(i-b)

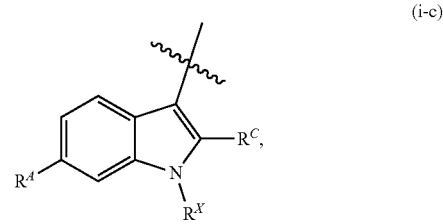

(i-c)

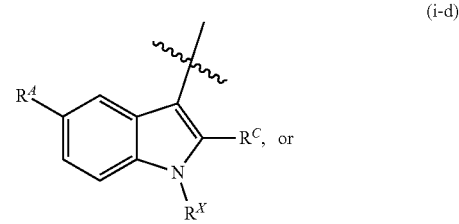

(i-d)

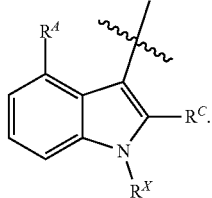

(i-e)

In certain embodiments of Formula (I), m is 1 to provide a ring system of the formula:

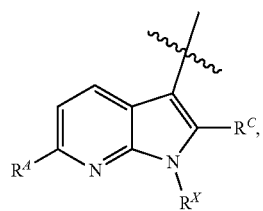

(ii-b)

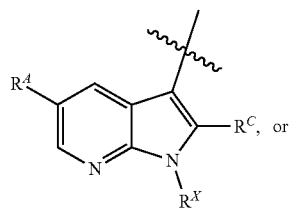

(ii-c)

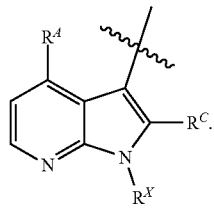

(ii-d)

In certain embodiments of Formula (I), m is 1, 2, 3, or 4; and at least one instance of $R^A$ is halogen. In certain embodiments of Formula (I), m is 1, 2, 3, or 4; and at least one instance of $R^A$ is F. In certain embodiments of Formula (I), m is 1, 2, 3, or 4; and at least one instance of $R^A$ is Cl. In certain embodiments of Formula (I), m is 1, 2, 3, or 4; and at least one instance of $R^A$ is Br. In certain embodiments of Formula (I), m is 1, 2, 3, or 4; and at least one instance of $R^A$ is I (iodine). In certain embodiments of Formula (I), m is 1; and $R^A$ is halogen. In some embodiments of Formula (I), m is 1; and $R^A$ is Cl (chlorine). In some embodiments of Formula (I), m is 1; and $R^A$ is Br (bromine). In some embodiments of Formula (I), m is 1; and $R^A$ is I (iodine).

In some embodiments of Formula (I), m is 1; and $R^A$ is halogen ("Hal") to provide a ring system of formula:

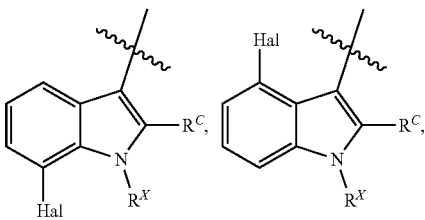

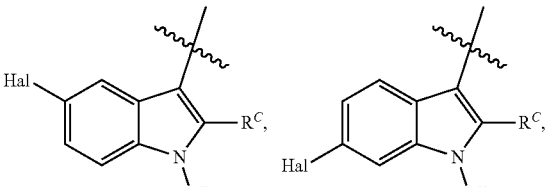

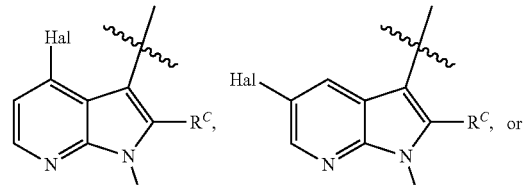

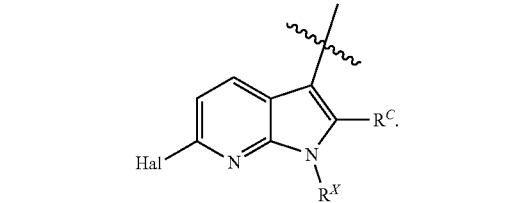

In certain embodiments of Formula (I), m is 1, 2, 3 or 4; and at least one instance of $R^A$ is substituted alkyl. In certain embodiments of Formula (I), m is 1, 2, 3 or 4; and at least one instance of $R^A$ is unsubstituted alkyl. In certain embodiments of Formula (I), m is 1, 2, 3 or 4; and at least one instance of $R^A$ is unsubstituted $C_{1-6}$ alkyl. In certain embodiments of Formula (I), m is 1, 2, 3 or 4; and at least one instance of $R^A$ is substituted $C_{1-6}$ alkyl. In certain embodiments of Formula (I), m is 1, 2, 3 or 4; and at least one instance of $R^A$ is $C_{1-6}$ alkyl substituted with at least one halogen. In certain embodiments of Formula (I), m is 1, 2, 3 or 4; and at least one instance of $R^A$ is —$CH_3$. In certain embodiments of Formula (I), m is 1, 2, 3, or 4; and at least one instance of $R^A$ is substituted methyl. In certain embodiments of Formula (I), m is 1, 2, 3 or 4; and at least one instance of $R^A$ is —$CF_3$. In certain embodiments of Formula (I), m is 1, 2, 3 or 4; and at least one instance of $R^A$ is substituted or unsubstituted ethyl. In certain embodiments of Formula (I), m is 1, 2, 3 or 4; and at least one instance of $R^A$ is substituted or unsubstituted propyl. In certain embodiments of Formula (I), m is 1, 2, 3 or 4; and at least one instance of $R^A$ is substituted or unsubstituted butyl. In certain embodiments of Formula (I), m is 1, 2, 3 or 4; and at least one instance of $R^A$ is substituted or unsubstituted pentyl. In certain embodiments of Formula (I), m is 1, 2, 3 or 4; and at least one instance of $R^A$ is substituted or unsubstituted hexyl.

In certain embodiments of Formula (I), m is 1, 2, 3 or 4; and at least one instance of $R^A$ is substituted heteroalkyl, wherein at least one atom in the alkyl chain is selected from the group consisting of nitrogen, oxygen, and sulfur. In certain embodiments of Formula (I), m is 1, 2, 3 or 4; and at least one instance of $R^A$ is unsubstituted heteroalkyl, wherein at least one atom in the alkyl chain is selected from the group consisting of nitrogen, oxygen, and sulfur.

In certain embodiments of Formula (I), m is 1, 2, 3 or 4; and at least one instance of $R^4$ is unsubstituted $C_{1-6}$ heteroalkyl, wherein at least one atom in the $C_{1-6}$ alkyl chain is selected from the group consisting of nitrogen, oxygen, and sulfur.

In certain embodiments of Formula (I), m is 1, 2, 3 or 4; and at least one instance of $R^4$ is substituted or unsubstituted alkenyl, e.g., substituted or unsubstituted $C_{2-6}$alkenyl, substituted or unsubstituted $C_{2-5}$alkenyl, substituted or unsubstituted $C_{2-4}$alkenyl, or substituted or unsubstituted $C_{2-3}$alkenyl. In certain embodiments of Formula (I), m is 1, 2, 3 or 4; and at least one instance of $R^4$ is unsubstituted alkenyl.

In certain embodiments of Formula (I), m is 1, 2, 3 or 4; and at least one instance of $R^4$ is substituted or unsubstituted heteroalkenyl, e.g., substituted or unsubstituted $C_{2-6}$heteroalkenyl, substituted or unsubstituted $C_{2-5}$heteroalkenyl, substituted or unsubstituted $C_{2-4}$heteroalkenyl, or substituted or unsubstituted $C_{2-3}$heteroalkenyl, wherein at least one atom in the alkenyl chain is selected from the group consisting of nitrogen, oxygen, and sulfur. In certain embodiments of Formula (I), m is 1, 2, 3 or 4; and at least one instance of $R^4$ is unsubstituted heteroalkenyl, wherein at least one atom in the alkenyl chain is selected from the group consisting of nitrogen, oxygen, and sulfur.

In certain embodiments of Formula (I), m is 1, 2, 3 or 4; and at least one instance of $R^4$ is substituted alkynyl, e.g., substituted or unsubstituted $C_{2-6}$alkynyl, substituted or unsubstituted $C_{2-5}$alkynyl, substituted or unsubstituted $C_{2-4}$alkynyl, or substituted or unsubstituted $C_{2-3}$alkynyl. In certain embodiments of Formula (I), m is 1, 2, 3 or 4; and at least one instance of $R^4$ is unsubstituted alkynyl.

In certain embodiments of Formula (I), m is 1, 2, 3 or 4; and at least one instance of $R^4$ is substituted heteroalkynyl, e.g., substituted or unsubstituted $C_{2-6}$heteroalkynyl, substituted or unsubstituted $C_{2-5}$heteroalkynyl, substituted or unsubstituted $C_{2-4}$heteroalkynyl, or substituted or unsubstituted $C_{2-3}$heteroalkynyl, wherein at least one atom in the alkynyl chain is selected from the group consisting of nitrogen, oxygen, and sulfur. In certain embodiments of Formula (I), m is 1, 2, 3 or 4; and at least one instance of $R^4$ is unsubstituted heteroalkynyl, wherein at least one atom in the alkynyl chain is selected from the group consisting of nitrogen, oxygen, and sulfur.

In certain embodiments of Formula (I), m is 1, 2, 3, or 4; and at least one instance of $R^4$ is —$OR^{41}$, wherein $R^{41}$ is hydrogen (i.e., to provide —OH). In certain embodiments of Formula (I), m is 1, 2, 3, or 4; and at least one instance of $R^4$ is —$OR^{41}$, wherein $R^{41}$ is a non-hydrogen group. In certain embodiments of Formula (I), m is 1, 2, 3, or 4; and at least one instance of $R^4$ is —$OR^{41}$, wherein $R^{41}$ is a substituted or unsubstituted alkyl. In certain embodiments of Formula (I), m is 1, 2, 3, or 4 and at least one instance of $R^4$ is —$OR^{41}$, wherein $R^{41}$ is a substituted or unsubstituted $C_{1-6}$ alkyl. For example, in certain embodiments of Formula (I), m is 1, 2, 3, or 4; and at least one instance of $R^4$ is —$OR^{41}$, wherein $R^{41}$ is —$CH_3$ (i.e., to provide —$OCH_3$). In some embodiments of Formula (I), $R^4$ is —$OR^{41}$ to provide a ring system of formula:

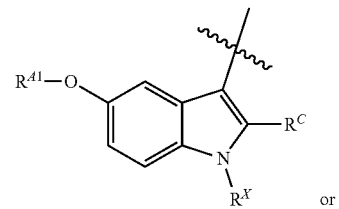

(i-f)

or

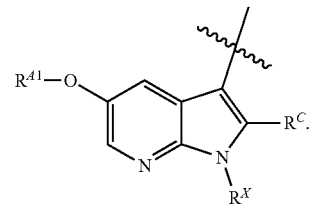

(ii-e)

In certain embodiments of Formula (I), m is 1, 2, 3, or 4; and at least one instance of $R^4$ is —$SR^{41}$, wherein $R^{41}$ is hydrogen (i.e., to provide —SH), or a non-hydrogen group.

In certain embodiments of Formula (I), m is 1, 2, 3, or 4; and at least one instance of $R^4$ is —$N(R^{41})_2$, wherein at least one $R^{41}$ is hydrogen (e.g., to provide —$NH_2$ or $NHR^{41}$), each $R^{41}$ is a non-hydrogen group, or wherein two $R^{41}$ groups are joined to form a substituted or unsubstituted heterocyclic or heteroaryl ring.

In certain embodiments of Formula (I), m is 1, 2, 3, or 4; and at least one instance of $R^4$ is —CN.

In certain embodiments of Formula (I), m is 1, 2, 3, or 4; and at least one instance of $R^4$ is —$NO_2$.

In certain embodiments of Formula (I), m is 1, 2, 3, or 4; and at least one instance of $R^4$ is —C(=$NR^{41}$)$R^{41}$, wherein $R^{41}$ is hydrogen (i.e., to provide —C(=NH)H), or a non-hydrogen group.

In certain embodiments of Formula (I), m is 1, 2, 3, or 4; and at least one instance of $R^4$ is —C(=$NR^{41}$)$OR^{41}$, wherein $R^{41}$ is hydrogen (i.e., to provide —C(=NH)OH), or a non-hydrogen group.

In certain embodiments of Formula (I), m is 1, 2, 3, or 4; and at least one instance of $R^4$ is —C(=$NR^{41}$)N($R^{41}$)$_2$, wherein $R^{41}$ is hydrogen (i.e., to provide —C(=NH)$NH_2$), or a non-hydrogen group.

In certain embodiments of Formula (I), m is 1, 2, 3, or 4; and at least one instance of $R^4$ is —C(=O)$R^{41}$, wherein $R^{41}$ is hydrogen (i.e., to provide —C(=O)H), or a non-hydrogen group.

In certain embodiments of Formula (I), m is 1, 2, 3, or 4; and at least one instance of $R^4$ is —C(=O)$OR^{41}$, wherein $R^{41}$ is hydrogen (i.e., to provide —C(=O)OH), or a non-hydrogen group.

In certain embodiments of Formula (I), m is 1, 2, 3, or 4; and at least one instance of $R^4$ is —C(=O)N($R^{41}$)$_2$, wherein $R^{41}$ is hydrogen (i.e., to provide —C(=O)$NH_2$), or a non-hydrogen group.

In certain embodiments of Formula (I), m is 1, 2, 3, or 4; and at least one instance of $R^4$ is —$NR^{41}$C(=O)$R^{41}$, wherein $R^{41}$ is hydrogen (i.e., to provide —NHC(=O)H), or a non-hydrogen group.

In certain embodiments of Formula (I), m is 1, 2, 3, or 4; and at least one instance of $R^4$ is —$NR^{41}$C(=O)$OR^{41}$, wherein $R^{41}$ is hydrogen (i.e., to provide —NHC(=O)OH), or a non-hydrogen group.

In certain embodiments of Formula (I), m is 1, 2, 3, or 4; and at least one instance of $R^4$ is —$NR^{41}$C(=O)N($R^{41}$)$_2$, wherein $R^{A1}$ is hydrogen (i.e., to provide —NHC(=O)NH$_2$), or a non-hydrogen group.

In certain embodiments of Formula (I), m is 1, 2, 3, or 4; and at least one instance of $R^A$ is —OC(=O)$R^{A1}$, wherein $R^{A1}$ is hydrogen (i.e., to provide —OC(=O)H), or a non-hydrogen group.

In certain embodiments of Formula (I), m is 1, 2, 3, or 4; and at least one instance of $R^A$ is —OC(=O)O$R^{A1}$, wherein $R^{A1}$ is hydrogen (i.e., to provide —OC(=O)OH), or a non-hydrogen group.

In certain embodiments of Formula (I), m is 1, 2, 3, or 4; and at least one instance of $R^A$ is —OC(=O)N($R^{A1}$)$_2$, wherein $R^{A1}$ is hydrogen (i.e., to provide —OC(=O)NH$_2$), or a non-hydrogen group.

In certain embodiments of Formula (I), m is 1, 2, 3, or 4; and at least one instance of $R^A$ is substituted or unsubstituted carbocyclyl. In certain embodiments of Formula (I), m is 1, 2, 3, or 4; and at least one instance of $R^A$ is saturated carbocyclyl. In certain embodiments of Formula (I), m is 1, 2, 3, or 4; and at least one instance of $R^A$ is unsaturated carbocyclyl. In certain embodiments of Formula (I), m is 1, 2, 3, or 4; and at least one instance of $R^A$ is monocyclic $C_{3-7}$ carbocyclyl.

In certain embodiments of Formula (I), m is 1, 2, 3, or 4; and at least one instance of $R^A$ is substituted or unsubstituted heterocyclyl. In certain embodiments of Formula (I), m is 1, 2, 3, or 4; and at least one instance of $R^A$ is saturated heterocyclyl. In certain embodiments of Formula (I), m is 1, 2, 3, or 4; and at least one instance of $R^A$ is unsaturated heterocyclyl. In certain embodiments of Formula (I), m is 1, 2, 3, or 4; and at least one instance of $R^A$ is heterocyclyl, wherein one, two, or three atoms in the heterocyclic ring system are independently selected from the group consisting of nitrogen, oxygen, and sulfur. In certain embodiments of Formula (I), m is 1, 2, 3, or 4; and at least one instance of $R^A$ is 3- to 7-membered, monocyclic heterocyclyl.

In certain embodiments of Formula (I), m is 1, 2, 3, or 4 and at least one instance of $R^A$ is substituted or unsubstituted aryl. In certain embodiments of Formula (I), m is 1, 2, 3, or 4 and at least one instance of $R^A$ is $C_{6-10}$ aryl. In certain embodiments of Formula (I), m is 1, 2, 3, or 4 and at least one instance of $R^A$ is monocyclic aryl. In certain embodiments of Formula (I), m is 1, 2, 3, or 4 and at least one instance of $R^A$ is substituted phenyl. In certain embodiments of Formula (I), m is 1, 2, 3, or 4 and at least one instance of $R^A$ is unsubstituted phenyl. In certain embodiments of Formula (I), m is 1, 2, 3, or 4 and at least one instance of $R^A$ is bicyclic aryl.

In certain embodiments of Formula (I), m is 1, 2, 3, or 4 and at least one instance of $R^A$ is substituted or unsubstituted heteroaryl. In certain embodiments of Formula (I), m is 1, 2, 3, or 4 and at least one instance of $R^A$ is heteroaryl, wherein one, two, three, or four atoms in the heteroaryl ring system are independently selected from the group consisting of nitrogen, oxygen, and sulfur. In certain embodiments of Formula (I), m is 1, 2, 3, or 4 and at least one instance of $R^A$ is monocyclic heteroaryl. In certain embodiments of Formula (I), m is 1, 2, 3, or 4 and at least one instance of $R^A$ is 5- or 6-membered, monocyclic heteroaryl. In certain embodiments of Formula (I), m is 1, 2, 3, or 4 and at least one instance of $R^A$ is bicyclic heteroaryl, wherein the point of attachment may be on any atom of the bicyclic heteroaryl ring system, as valency permits.

Furthermore, as generally described herein, in any of the above described embodiments of group $R^A$ comprising a group $R^{A1}$, each instance of $R^{A1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form a substituted or unsubstituted carbocyclic, substituted or unsubstituted heterocyclic, substituted or unsubstituted aryl, or substituted or unsubstituted heteroaryl ring In any of the above described embodiments of $R^A$ comprising a group $R^{A1}$, at least one instance of $R^{A1}$ is substituted or unsubstituted alkyl, e.g., substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl.

In any of the above described embodiments of $R^A$ comprising a group $R^{A1}$, at least one instance of $R^{A1}$ is substituted or unsubstituted $C_{2-6}$alkenyl, e.g., substituted or unsubstituted $C_2$alkenyl, substituted or unsubstituted $C_3$alkenyl, substituted or unsubstituted $C_4$alkenyl, substituted or unsubstituted $C_5$alkenyl, or substituted or unsubstituted $C_6$alkenyl.

In any of the above described embodiments of $R^A$ comprising a group $R^{A1}$, at least one instance of $R^{A1}$ is substituted or unsubstituted $C_{2-6}$alkynyl, e.g., substituted or unsubstituted $C_2$alkynyl, substituted or unsubstituted $C_3$alkynyl, substituted or unsubstituted $C_4$alkynyl, substituted or unsubstituted $C_5$alkynyl, or substituted or unsubstituted $C_6$alkynyl.

In certain embodiments of Formula (I), e.g., wherein $R^A$ is —N($R^{A1}$)$_2$, —C(=N$R^{A1}$)N($R^{A1}$)$_2$, —C(=O)N($R^{A1}$)$_2$, —N$R^{A1}$C(=O)N($R^{A1}$)$_2$, or —OC(=O)N($R^{A1}$)$_2$, two instances of $R^{A1}$, e.g., attached to the same nitrogen (N) atom, are joined to form a substituted or unsubstituted heterocyclic ring. In certain embodiments of Formula (I), two instances of $R^{A1}$ are joined to form a saturated heterocyclic ring. In certain embodiments of Formula (I), two instances of $R^{A1}$ are joined to form an unsaturated heterocyclic ring. In certain embodiments of Formula (I), two instances of $R^{A1}$ are joined to form a heterocyclic ring, wherein one, two, or three atoms in the heterocyclic ring system are independently selected from the group consisting of nitrogen, oxygen, and sulfur. In certain embodiments of Formula (I), two instances of $R^{A1}$ are joined to form a 3- to 7-membered, monocyclic heterocyclic ring.

In certain embodiments of Formula (I), e.g., wherein $R^A$ is —N($R^{A1}$)$_2$, —C(=N$R^{A1}$)N($R^{A1}$)$_2$, —C(=O)N($R^{A1}$)$_2$, —N$R^{A1}$C(=O)N($R^{A1}$)$_2$, or —OC(=O)N($R^{A1}$)$_2$, two instances of $R^{A1}$, e.g., attached to the same nitrogen (N) atom, are joined to form a substituted or unsubstituted heteroaryl ring. In certain embodiments of Formula (I), two instances of $R^A$ are joined to form a substituted or unsubstituted, 5- to 6-membered, monocyclic heteroaryl ring, wherein one, two, three, or four atoms in the heteroaryl ring system are independently nitrogen, oxygen, or sulfur. In certain embodiments of Formula (I), two instances of $R^{A1}$ are joined to form a substituted or unsubstituted, 9- to 10-membered, monocyclic heteroaryl ring, wherein one, two, three, or four atoms in the heteroaryl ring system are independently nitrogen, oxygen, or sulfur.

In some embodiments, various tricyclic ring systems are contemplated.

For example, in some embodiments of Formula (I), alternatively, two $R^A$ groups are joined to form a substituted or unsubstituted aryl, a substituted or unsubstituted heteroaryl, a substituted or unsubstituted carbocyclyl, or a substituted or unsubstituted heterocarbocyclyl. In some embodiments, two $R^A$ groups are joined to form a substituted or unsubstituted 6-membered aryl. For example, in some embodiments, when two $R^A$ groups are joined to form a substituted or unsubstituted, 6-membered aryl ring, provided is a group of formula:

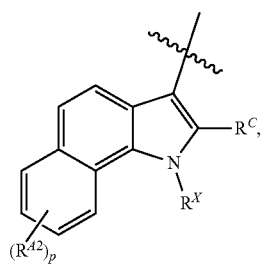

(i-g)

wherein:
each instance of $R^{A2}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, —$OR^{A3}$, —$N(R^{A3})_2$, —$SR^{A3}$, —CN, —$C(R^{A3})_3$, —SCN, —$C(=NR^{A3})R^{A3}$, —$C(=NR^{A3})OR^{A3}$, —$C(=NR^{A3})N(R^{A3})_2$, —$C(=O)R^{A3}$, —$C(=O)OR^{A3}$, —$C(=O)N(R^{A3})_2$, —$NO_2$, —$NR^{A3}C(=O)R^{A3}$, —$NR^{A3}C(=O)OR^{A3}$, —$NR^{A3}C(=O)N(R^{A3})_2$, —$OC(=O)R^{A3}$, —$OC(=O)OR^{A3}$, —$OC(=O)N(R^{A3})_2$;

each instance of $R^{A3}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, or substituted or unsubstituted heteroaryl, or two $R^{B1}$ groups are joined to form a substituted or unsubstituted carbocyclic, substituted or unsubstituted heterocyclic, substituted or unsubstituted aryl, or substituted or unsubstituted heteroaryl ring; and p is 0, 1,2,3,or 4.

In some embodiments, p is 0; and $R^{A2}$ is absent.

Alternatively, in some embodiments, two $R^A$ groups are joined to form a substituted or unsubstituted 5- to 6-membered carbocyclic ring. For example, in some embodiments, wherein two $R^A$ groups are joined to form a substituted or unsubstituted carbocyclic ring, provided is a group of formula:

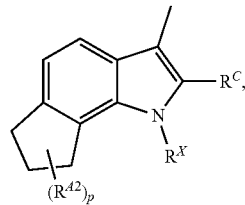

(i-h)

wherein:
each instance of $R^{A2}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, —$OR^{A3}$, —$N(R^{A3})_2$, —$SR^{A3}$, —CN, —$C(R^{A3})_3$, —SCN, —$C(=NR^{A3})R^{A3}$, —$C(=NR^{A3})OR^{A3}$, —$C(=NR^{A3})N(R^{A3})_2$, —$C(=O)R^{A3}$, —$C(=O)OR^{A3}$, —$C(=O)N(R^{A3})_2$, —$NO_2$, —$NR^{A3}C(=O)R^{A3}$, —$NR^{A3}C(=O)OR^{A3}$, —$NR^{A3}C(=O)N(R^{A3})_2$, —$OC(=O)R^{A3}$, —$OC(=O)OR^{A3}$, —$OC(=O)N(R^{A3})_2$ each instance of $R^{A3}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, or substituted or unsubstituted heteroaryl, or two $R^{B1}$ groups are joined to form a substituted or unsubstituted carbocyclic, substituted or unsubstituted heterocyclic, substituted or unsubstituted aryl, or substituted or unsubstituted heteroaryl ring; and p is 0, 1, 2, 3, 4, 5, or 6.

In some embodiments, p is 0; and $R^{A2}$ is absent. In some embodiments, p is 0, 1, 2, or 3.

Group $R^X$

As generally described herein, $R^X$ is independently hydrogen, substituted or unsubstituted alkyl, substituted or unsubstituted alkenyl, substituted or unsubstituted alkynyl, substituted or unsubstituted acyl, or a nitrogen protecting group. In some embodiments of Formula (I), $R^X$ is hydrogen, e.g., to provide a ring system of formula:

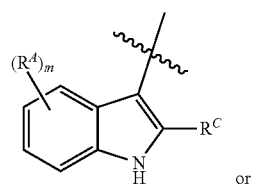

(i-j)

or

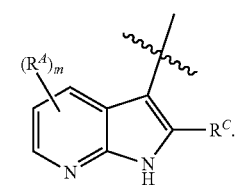

(ii-j)

In certain embodiments of Formula (I), $R^X$ is substituted alkyl. In certain embodiments of Formula (I), $R^X$ is unsubstituted alkyl. In certain embodiments of Formula (I), $R^X$ is unsubstituted $C_{1-6}$ alkyl. In certain embodiments of Formula (I), $R^X$ is substituted $C_{1-6}$ alkyl. In certain embodiments of Formula (I), $R^X$ is —$CH_3$. In certain embodiments of Formula (I), $R^X$ is $C_{1-6}$ alkyl substituted with at least one halogen. In certain embodiments of Formula (I), $R^X$ is substituted methyl. In certain embodiments of Formula (I), $R^X$ is unsubstituted methyl. In certain embodiments of Formula (I), $R^X$ is —$CF_3$. In certain embodiments of Formula (I), $R^X$ is substituted or unsubstituted ethyl. In certain embodiments of Formula (I), $R^X$ is substituted or unsubstituted propyl. In certain embodiments of Formula (I), $R^X$ is substituted or unsubstituted butyl. In certain embodiments of Formula (I), $R^X$ is substituted or unsubstituted pentyl. In certain embodiments of Formula (I), $R^X$ is substituted or unsubstituted hexyl.

In certain embodiments of Formula (I), $R^X$ is substituted or unsubstituted alkenyl, e.g., substituted or unsubstituted $C_{2-6}$alkenyl, substituted or unsubstituted $C_{2-5}$alkenyl, substituted or unsubstituted $C_{2-4}$alkenyl, or substituted or unsubstituted $C_{2-3}$alkenyl. In certain embodiments of Formula (I), $R^X$ is unsubstituted alkenyl.

In certain embodiments of Formula (I), $R^X$ is substituted alkynyl, e.g., substituted or unsubstituted $C_{2-6}$alkynyl, substituted or unsubstituted $C_{2-5}$alkynyl, substituted or unsubstituted $C_{2-4}$alkynyl, or substituted or unsubstituted $C_{2-3}$alkynyl. In certain embodiments of Formula (I), $R^X$ is unsubstituted alkynyl.

In certain embodiments of Formula (I), $R^X$ is substituted or unsubstituted acyl. In certain embodiments of Formula (I), $R^X$ is substituted acyl. In certain embodiments of Formula (I), $R^X$ is unsubstituted acyl.

In certain embodiments of Formula (I), $R^X$ is a nitrogen protecting group. In certain embodiments of Formula (I), $R^X$ is Bn, Boc, Cbz, Fmoc, trifluoroacetyl, triphenylmethyl, acetyl, or Ts.

Group $R^C$

As generally described herein, $R^C$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —$OR^{C1}$, —$N(R^{C1})_2$, —$SR^{C1}$, —CN, —$C(R^{C1})_3$, —SCN, —$C(=NR^{C1})R^{C1}$, —$C(=NR^{C1})OR^{C1}$, —$C(=NR^{C1})N(R^{C1})_2$, —$C(=O)R^{C1}$, —$C(=O)OR^{C1}$, —$C(=O)N(R^{C1})_2$, —$NO_2$, —$NR^{C1}C(=O)R^{C1}$, —$NR^{C1}C(=O)OR^{C1}$, —$NR^{C1}C(=O)N(R^{C1})_2$, —$OC(=O)R^{C1}$, —$OC(=O)OR^{C1}$, —$OC(=O)N(R^{C1})_2$, or $R^C$ and $R^X$ are joined to form a, substituted or unsubstituted heterocyclic, or substituted or unsubstituted heteroaryl ring, wherein each instance of $R^{C1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{C1}$ groups are joined to form a substituted or unsubstituted carbocyclic, substituted or unsubstituted heterocyclic, substituted or unsubstituted aryl, or substituted or unsubstituted heteroaryl ring.

In some embodiments of Formula (I), $R^C$ is hydrogen, e.g., to provide a ring system of formula:

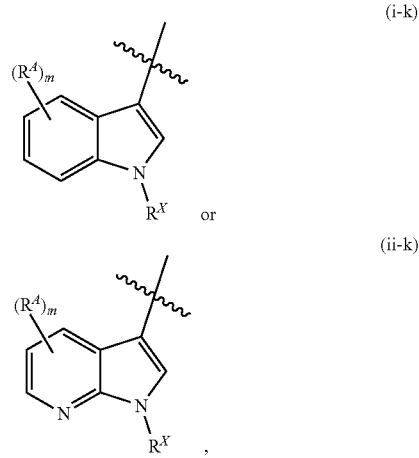

or a pharmaceutically acceptable salt, solvate, hydrate, stereoisomer, tautomer, isotopically labeled derivative, polymorph, or prodrug thereof.

In certain embodiments of Formula (I), $R^C$ is halogen. In certain embodiments of Formula (I), $R^C$ is F. In certain embodiments of Formula (I), $R^C$ is Cl. In certain embodiments of Formula (I), $R^C$ is Br. In certain embodiments of Formula (I), $R^C$ is I (iodine).

In certain embodiments of Formula (I), $R^C$ is substituted alkyl. In certain embodiments of Formula (I), $R^C$ is unsubstituted alkyl. In certain embodiments of Formula (I), $R^C$ is unsubstituted $C_{1-6}$ alkyl. In certain embodiments of Formula (I), $R^C$ is substituted $C_{1-6}$ alkyl. In certain embodiments of Formula (I), $R^C$ is —$CH_3$. In certain embodiments of Formula (I), $R^C$ is $C_{1-6}$ alkyl substituted with at least one halogen. In certain embodiments of Formula (I), $R^C$ is substituted methyl. In certain embodiments of Formula (I), $R^X$ is unsubstituted methyl. In certain embodiments of Formula (I), $R^C$ is —$CF_3$. In certain embodiments of Formula (I), $R^C$ is substituted or unsubstituted ethyl. In certain embodiments of Formula (I), $R^C$ is substituted or unsubstituted propyl. In certain embodiments of Formula (I), $R^C$ is substituted or unsubstituted butyl. In certain embodiments of Formula (I), $R^C$ is substituted or unsubstituted pentyl. In certain embodiments of Formula (I), $R^C$ is substituted or unsubstituted hexyl.

In certain embodiments of Formula (I), $R^C$ is substituted heteroalkyl, wherein at least one atom in the alkyl chain is selected from the group consisting of nitrogen, oxygen, and sulfur. In certain embodiments of Formula (I), $R^C$ is unsubstituted heteroalkyl, wherein at least one atom in the alkyl chain is selected from the group consisting of nitrogen, oxygen, and sulfur. In certain embodiments of Formula (I), $R^C$ is unsubstituted $C_{1-5}$ heteroalkyl, wherein at least one atom in the $C_{1-6}$ alkyl chain is selected from the group consisting of nitrogen, oxygen, and sulfur.

In certain embodiments of Formula (I), $R^C$ is substituted or unsubstituted alkenyl, e.g., substituted or unsubstituted $C_{2-6}$alkenyl, substituted or unsubstituted $C_{2-5}$alkenyl, substituted or unsubstituted $C_{2-4}$alkenyl, or substituted or unsubstituted $C_{2-3}$alkenyl. In certain embodiments of Formula (I), $R^C$ is unsubstituted alkenyl.

In certain embodiments of Formula (I), $R^C$ is substituted or unsubstituted heteroalkenyl, e.g., substituted or unsubstituted $C_{2-6}$heteroalkenyl, substituted or unsubstituted $C_{2-5}$heteroalkenyl, substituted or unsubstituted $C_{2-4}$heteroalkenyl, or substituted or unsubstituted $C_{2-3}$heteroalkenyl, wherein at least one atom in the alkenyl chain is selected from the group consisting of nitrogen, oxygen, and sulfur. In certain embodiments of Formula (I), $R^C$ is unsubstituted heteroalkenyl, wherein at least one atom in the alkenyl chain is selected from the group consisting of nitrogen, oxygen, and sulfur.

In certain embodiments of Formula (I), $R^C$ is substituted alkynyl, e.g., substituted or unsubstituted $C_{2-6}$alkynyl, substituted or unsubstituted $C_{2-5}$alkynyl, substituted or unsubstituted $C_{2-4}$alkynyl, or substituted or unsubstituted $C_{2-3}$alkynyl. In certain embodiments of Formula (I), $R^C$ is unsubstituted alkynyl.

In certain embodiments of Formula (I), $R^C$ is substituted heteroalkynyl, e.g., substituted or unsubstituted $C_{2-6}$heteroalkynyl, substituted or unsubstituted $C_{2-5}$heteroalkynyl, substituted or unsubstituted $C_{2-4}$heteroalkynyl, or substituted or unsubstituted $C_{2-3}$ heteroalkynyl, wherein at least one atom in the alkynyl chain is selected from the group consisting of nitrogen, oxygen, and sulfur. In certain embodiments of Formula (I), $R^C$ is unsubstituted heteroalkynyl, wherein at least one atom in the alkynyl chain is selected from the group consisting of nitrogen, oxygen, and sulfur.

In certain embodiments of Formula (I), $R^C$ is —$OR^{C1}$, wherein $R^{C1}$ is hydrogen (i.e., to provide —OH). In certain embodiments of Formula (I), $R^C$ is —$OR^{C1}$, wherein $R^{C1}$ is a non-hydrogen group. In certain embodiments of Formula (I), $R^C$ is —$OR^{C1}$, wherein $R^{C1}$ is a substituted or unsubstituted alkyl. In certain embodiments of Formula (I), Rd is —$OR^{C1}$, wherein $R^{C1}$ is a substituted or unsubstituted $C_{1-5}$ alkyl. For example, in certain embodiments of Formula (I), $R^C$ is —$OR^{C1}$, wherein $R^{C1}$ is —$CH_3$ (i.e., to provide —$OCH_3$).

In certain embodiments of Formula (I), $R^C$ is —$SR^{C1}$, wherein $R^{C1}$ is hydrogen (i.e., to provide —SH), or a non-hydrogen group.

In certain embodiments of Formula (I), $R^C$ is —$N(R^{C1})_2$, wherein at least one $R^C$ is hydrogen (e.g., to provide —$NH_2$ or $NHR^{C1}$), each $R^{C1}$ is a non-hydrogen group, or wherein two $R^{C1}$ groups are joined to form a substituted or unsubstituted heterocyclic or heteroaryl ring.

In certain embodiments of Formula (I), $R^C$ is —CN.

In certain embodiments of Formula (I) or (II), $R^C$ is —$NO_2$.

In certain embodiments of Formula (I), $R^C$ is —$C(=NR^{C1})R^{C1}$, wherein $R^{C1}$ is hydrogen (i.e., to provide —C(=NH)H), or a non-hydrogen group.

In certain embodiments of Formula (I), $R^C$ is —$C(=NR^{C1})OR^{C1}$, wherein $R^{C1}$ is hydrogen (i.e., to provide —C(=NH)OH), or a non-hydrogen group.

In certain embodiments of Formula (I), $R^C$ is —$C(=NR^{C1})N(R^{C1})_2$, wherein $R^{C1}$ is hydrogen (i.e., to provide —C(=NH)$NH_2$), or a non-hydrogen group.

In certain embodiments of Formula (I), $R^C$ is —C(=O)$R^{C1}$, wherein $R^{C1}$ is hydrogen (i.e., to provide —C(=O)H), or a non-hydrogen group.

In certain embodiments of Formula (I), $R^C$ is —C(=O)$OR^{C1}$, wherein $R^{C1}$ is hydrogen (i.e., to provide —C(=O)OH), or a non-hydrogen group.

In certain embodiments of Formula (I), $R^C$ is —C(=O)$N(R^{C1})_2$, wherein $R^{C1}$ is hydrogen (i.e., to provide —C(=O)$NH_2$), or a non-hydrogen group.

In certain embodiments of Formula (I), $R^C$ is —$NR^{C1}$C(=O)$R^{C1}$, wherein $R^{C1}$ is hydrogen (i.e., to provide —NHC(=O)H), or a non-hydrogen group.

In certain embodiments of Formula (I), $R^C$ is —$NR^{C1}$C(=O)$OR^{C1}$, wherein $R^{C1}$ is hydrogen (i.e., to provide —NHC(=O)OH), or a non-hydrogen group.

In certain embodiments of Formula (I), $R^C$ is —$NR^{C1}$C(=O)$N(R^{C1})_2$, wherein $R^{C1}$ is hydrogen (i.e., to provide —NHC(=O)$NH_2$), or a non-hydrogen group.

In certain embodiments of Formula (I), $R^C$ is —OC(=O)$R^{C1}$, wherein $R^{C1}$ is hydrogen (i.e., to provide —OC(=O)H), or a non-hydrogen group.

In certain embodiments of Formula (I), $R^C$ is —OC(=O)$OR^{C1}$, wherein $R^{C1}$ is hydrogen (i.e., to provide —OC(=O)OH), or a non-hydrogen group.

In certain embodiments of Formula (I), $R^C$ is —OC(=O)$N(R^{C1})_2$, wherein $R^{C1}$ is hydrogen (i.e., to provide —OC(=O)$NH_2$), or a non-hydrogen group.

In certain embodiments of Formula (I), $R^C$ is substituted or unsubstituted carbocyclyl. In certain embodiments of Formula (I), $R^C$ is saturated carbocyclyl. In certain embodiments of Formula (I), $R^C$ is unsaturated carbocyclyl. In certain embodiments of Formula (I), $R^C$ is monocyclic $C_{3-7}$ carbocyclyl.

In certain embodiments of Formula (I), $R^C$ is substituted or unsubstituted heterocyclyl. In certain embodiments of Formula (I), $R^C$ is saturated heterocyclyl. In certain embodiments of Formula (I), $R^C$ is unsaturated heterocyclyl. In certain embodiments of Formula (I), $R^C$ is heterocyclyl, wherein one, two, or three atoms in the heterocyclic ring system are independently selected from the group consisting of nitrogen, oxygen, and sulfur. In certain embodiments of Formula (I), $R^C$ is 3- to 7-membered, monocyclic heterocyclyl.

In certain embodiments of Formula (I), $R^C$ is substituted or unsubstituted aryl. In certain embodiments of Formula (I), $R^C$ is $C_{6-10}$ aryl. In certain embodiments of Formula (I), $R^C$ is monocyclic aryl. In certain embodiments of Formula (I), $R^C$ is substituted phenyl. In certain embodiments of Formula (I), $R^C$ is unsubstituted phenyl. In certain embodiments of Formula (I), $R^C$ is bicyclic aryl.

In certain embodiments of Formula (I), $R^C$ is substituted or unsubstituted heteroaryl. In certain embodiments of Formula (I), $R^C$ is heteroaryl, wherein one, two, three, or four atoms in the heteroaryl ring system are independently selected from the group consisting of nitrogen, oxygen, and sulfur. In certain embodiments of Formula (I), $R^C$ is monocyclic heteroaryl. In certain embodiments of Formula (I), $R^C$ is 5- or 6-membered, monocyclic heteroaryl. In certain embodiments of Formula (I), $R^C$ is bicyclic heteroaryl, wherein the point of attachment may be on any atom of the bicyclic heteroaryl ring system, as valency permits.

Furthermore, as generally described herein, in any of the above described embodiments of group $R^C$ comprising a group $R^{C1}$, each instance of $R^{C1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or $R^C$ and $R^X$ are joined to form a substituted or unsubstituted heterocyclic, or substituted or unsubstituted heteroaryl ring.

In any of the above described embodiments of $R^C$ comprising a group $R^C$, at least one instance of $R^C$ is substituted or unsubstituted alkyl, e.g., substituted or unsubstituted $C_{1-6}$alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl.

In any of the above described embodiments of $R^C$ comprising a group $R^{C1}$, at least one instance of $R^{C1}$ is substituted or unsubstituted $C_{2-6}$alkenyl, e.g., substituted or unsubstituted $C_2$alkenyl, substituted or unsubstituted $C_3$alkenyl, substituted or unsubstituted $C_4$alkenyl, substituted or unsubstituted $C_5$alkenyl, or substituted or unsubstituted $C_6$alkenyl.

In any of the above described embodiments of $R^C$ comprising a group $R^{C1}$, at least one instance of $R^{C1}$ is substituted or unsubstituted $C_{2-6}$alkynyl, e.g., substituted or unsubstituted $C_2$alkynyl, substituted or unsubstituted $C_3$alkynyl, substituted or unsubstituted $C_4$alkynyl, substituted or unsubstituted $C_5$alkynyl, or substituted or unsubstituted $C_6$alkynyl.

In certain embodiments of Formula (I), e.g., wherein Rd is —N($R^{C1}$), —C(=N$R^{C1}$)N($R^{C1}$)$_2$, —C(=O)N($R^{C1}$), —N$R^{C1}$C(=O)N($R^{C1}$)$_2$, or —OC(=O)N($R^{C1}$)$_2$, two instances of $R^{C1}$, e.g., attached to the same nitrogen (N) atom, are joined to form a substituted or unsubstituted heterocyclic ring. In certain embodiments of Formula (I), two instances of $R^{C1}$ are joined to form a saturated heterocyclic ring. In certain embodiments of Formula (I), two instances of $R^{C1}$ are joined to form an unsaturated heterocyclic ring. In certain embodiments of Formula (I), two instances of $R^{C1}$ are joined to form a heterocyclic ring, wherein one, two, or three atoms in the heterocyclic ring system are independently selected from the group consisting of nitrogen, oxygen, and sulfur. In certain embodiments of Formula (I), two instances of $R^{C1}$ are joined to form a 3- to 7-membered, monocyclic heterocyclic ring. In certain embodiments of Formula (I), two instances of $R^{C1}$ are joined to form a 5- to 6-membered heterocyclic ring.

In certain embodiments of Formula (I), e.g., wherein Rd is substituted or unsubstituted alkyl, substituted or unsubstituted heteroalkyl, substituted or unsubstituted alkenyl, substituted or unsubstituted heteroalkenyl, substituted or unsubstituted alkynyl, or substituted or unsubstituted heteroalkynyl, $R^C$ and $R^X$ are joined to form a substituted or unsubstituted heterocyclic ring. In certain embodiments of Formula (I), $R^C$ and $R^X$ are joined to form a saturated heterocyclic ring. In certain embodiments of Formula (I), $R^C$ and $R^X$ are joined to form an unsaturated heterocyclic ring. In certain embodiments of Formula (I), $R^C$ and $R^X$ are joined to form a heterocyclic ring, wherein one, two, or three atoms in the heterocyclic ring system are independently selected from the group consisting of nitrogen, oxygen, and sulfur. In certain embodiments of Formula (I), $R^C$ and $R^X$ are joined to form a heterocyclic ring, wherein one, atom in the heterocyclic ring system is nitrogen. In certain embodiments of Formula (I), $R^C$ and $R^X$ are joined to form a 3- to 7-membered, monocyclic heterocyclic ring. In certain embodiments of Formula (I), $R^C$ and $R^X$ are joined to form a 5- to 6-membered heterocyclic ring.

In certain embodiments of Formula (I), e.g., wherein $R^{C1}$ is —N($R^{C1}$), —C(=N$R^{C1}$)N($R^{C1}$)$_2$, —C(=O)N($R^{C1}$), —N$R^{C1}$C(=O)N($R^{C1}$)$_2$, or —OC(=O)N($R^{C1}$)$_2$, two instances of $R^{C1}$, e.g., attached to the same nitrogen (N) atom, are joined to form a substituted or unsubstituted heteroaryl ring. In certain embodiments of Formula (I), two instances of $R^{C1}$ are joined to form a substituted or unsubstituted, 5- to 6-membered, monocyclic heteroaryl ring, wherein one, two, three, or four atoms in the heteroaryl ring system are independently nitrogen, oxygen, or sulfur. In certain embodiments of Formula (I), two instances of $R^{C1}$ are joined to form a substituted or unsubstituted, 9- to 10-membered, monocyclic heteroaryl ring, wherein one, two, three, or four atoms in the heteroaryl ring system are independently nitrogen, oxygen, or sulfur.

In certain embodiments of Formula (I), e.g., $R^C$ is substituted or unsubstituted alkyl, substituted or unsubstituted heteroalkyl, substituted or unsubstituted alkenyl, substituted or unsubstituted heteroalkenyl, substituted or unsubstituted alkynyl, or substituted or unsubstituted heteroalkynyl, $R^C$ and $R^X$ are joined to form a substituted or unsubstituted heteroaryl ring. In certain embodiments of Formula (I), $R^C$ and $R^X$ are joined to form a substituted or unsubstituted, 5- to 6-membered, monocyclic heteroaryl ring, wherein one, two, three, or four atoms in the heteroaryl ring system are independently nitrogen, oxygen, or sulfur. In certain embodiments of Formula (I), $R^C$ and $R^X$ are joined to form a substituted or unsubstituted, 9- to 10-membered, monocyclic heteroaryl ring, wherein one, two, three, or four atoms in the heteroaryl ring system are independently nitrogen, oxygen, or sulfur.

Ring A

As generally described herein, Ring A is substituted or unsubstituted aryl, or substituted or unsubstituted heteroaryl. In some embodiments, Ring A is a substituted aryl. In some embodiments, Ring A is a substituted phenyl. In some embodiments, Ring A is an unsubstituted aryl. In some embodiments, Ring A is an unsubstituted phenyl. In some embodiments, Ring A is a substituted heteroaryl. In some embodiments, Ring A is a substituted 5- to 6-membered heteroaryl ring. In some embodiments, Ring A is an unsubstituted heteroaryl. In some embodiments, Ring A is an unsubstituted 5- to 6-membered heteroaryl ring.

In some embodiments of Formula (I), Ring A is of the formula:

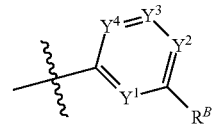

wherein, $Y^1$, $Y^2$, $Y^3$, and $Y^4$ are each independently N or $CR^Z$;

each instance of $R^Z$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —O$R^{Z1}$, —N($R^{Z1}$), —S$R^{Z1}$, —CN, —C($R^{Z1}$)$_3$, —SCN, —C(=N$R^{Z1}$)$R^{Z1}$, —C(=N$R^{Z1}$)O$R^{Z1}$, —C(=N$R^{Z1}$)N($R^{Z1}$)$_2$, —C(=O)$R^{Z1}$, —C(=O)O$R^{Z1}$, —C(=O)N($R^{Z1}$)$_2$, —NO$_2$, —N$R^{Z1}$C(=O)$R^{Z1}$, —N$R^{Z1}$C(=O)O$R^{Z1}$, —N$R^{Z1}$C(=O)N($R^{Z1}$)$_2$, —OC(=O)$R^{Z1}$, —OC(=O)O$R^{Z1}$, —OC(=O)N($R^{Z1}$)$_2$, or two $R^Z$ groups are joined to form a substituted or unsubstituted carbocyclic, substituted or unsubstituted heterocyclic, substituted or unsubstituted aryl, or substituted or unsubstituted heteroaryl ring; and each instance of $R^{Z1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{Z1}$ groups are joined to form a substituted or unsubstituted carbocyclic, substituted or unsubstituted heterocyclic, substituted or unsubstituted aryl, or substituted or unsubstituted heteroaryl ring.

In some embodiments of Formula (I), Ring A is of the formula:

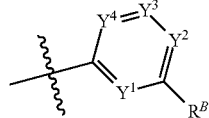

to provide a compound of Formula (II):

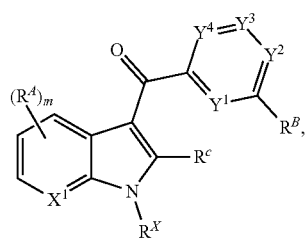

(II)

or a pharmaceutically acceptable salt, solvate, hydrate, stereoisomer, tautomer, isotopically labeled derivative, polymorph, or prodrug thereof.

In some embodiments, $Y^1$, $Y^2$, $Y^3$, and $Y^4$ are each independently $CR^Z$. In some embodiments, $Y^1$, $Y^2$, $Y^3$, and $Y^4$ are not N.

In some embodiments, at least one of $Y^1$, $Y^2$, $Y^3$, and $Y^4$ is N.

In some embodiments, only one of $Y^1$, $Y^2$, $Y^3$, and $Y^4$ is N. In some embodiments, $Y^1$ is N or $CR^Z$. In some embodiments, $Y^1$ is N, and $Y^2$, $Y^3$, and $Y^4$ are each independently $CR^Z$. In some embodiments, $Y^2$ is N, and $Y^1$, $Y^3$, and $Y^4$ are each independently $CR^Z$. In some embodiments, $Y^3$ is N, and $Y^1$, $Y^2$, and $Y^4$ are each independently $CR^Z$. In some embodiments, $Y^4$ is N, and $Y^1$, $Y^2$, and $Y^3$ are each independently $CR^Z$.

In some embodiments, any two of $Y^1$, $Y^2$, $Y^3$, and $Y^4$ are N. In some embodiments, $Y^1$ and $Y^2$ are N, and $Y^3$ and $Y^4$ are each independently $CR^Z$. In some embodiments, $Y^1$ and $Y^3$ are N, and $Y^2$ and $Y^4$ are each independently $CR^Z$. In some embodiments, $Y^1$ and $Y^4$ are N, and $Y^2$ and $Y^3$ are each independently $CR^Z$. In some embodiments, $Y^2$ and $Y^3$ are N, and $Y^1$ and $Y^4$ are each independently $CR^Z$. In some embodiments, $Y^3$ and $Y^4$ are N, and $Y^1$ and $Y^2$ are each independently $CR^Z$. In some embodiments, $Y^2$ and $Y^4$ are N, and $Y^1$ and $Y^3$ are each independently $CR^Z$.

In some embodiments, any three of $Y^1$, $Y^2$, $Y^3$, and $Y^4$ are N. In some embodiments, $Y^1$, $Y^2$, and $Y^3$ are N, and $Y^4$ is $CR^Z$. In some embodiments, $Y^2$, $Y^3$, and $Y^4$ are N, and $Y^1$ is $CR^Z$. In some embodiments, $Y^1$, $Y^3$, and $Y^4$ are N, and $Y^2$ is $CR^Z$. In some embodiments, $Y^1$, $Y^2$, and $Y^4$ are N, and $Y^3$ is $CR^Z$.

In some embodiments, all of $Y^1$, $Y^2$, $Y^3$, and $Y^4$ are N.

As generally described herein, Formula (II) comprises a group of formula:

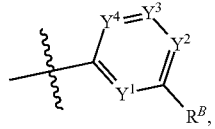

which in certain embodiments is selected from the group consisting of:

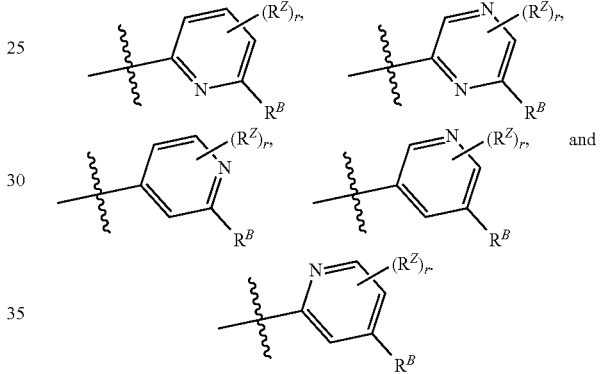

In some embodiments of Formula (II),

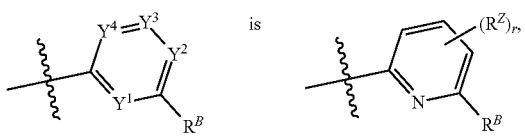

to provide a compound of Formula (II-a)

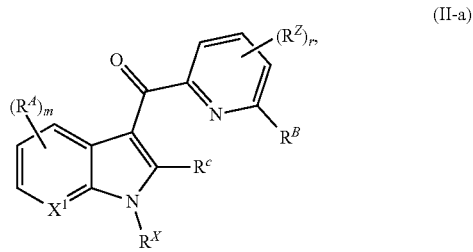

(II-a)

or a pharmaceutically acceptable salt, solvate, hydrate, stereoisomer, tautomer, isotopically labeled derivative, polymorph, or prodrug thereof, wherein:

$X^1$ is N or $CR^A$;

$R^X$ is independently hydrogen, substituted or unsubstituted alkyl, substituted or unsubstituted alkenyl, substituted or unsubstituted alkynyl, substituted or unsubstituted acyl, or a nitrogen protecting group;

each instance of $R^A$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —CN, —$C(R^{A1})_3$, —SCN, —$C(=NR^{A1})R^{A1}$ $C(=NR^{A1})OR^{A1}$, —$C(=NR^{A1})N(R^{A1})_2$, —$C(=O)R^{A1}$, —$C(=O)OR^{A1}$, —$C(=O)N(R^{A1})_2$, —$NO_2$, —$NR^{A1}C(=O)R^{A1}$, —$NR^{A1}C(=O)OR^{A1}$, —$NR^{A1}C(=O)N(R^{A1})_2$, —$OC(=O)R^{A1}$, —$OC(=O)OR^{A1}$, —$OC(=O)N(R^{A1})_2$, or two $R^A$ groups are joined to form a substituted or unsubstituted carbocyclic, substituted or unsubstituted heterocyclic, substituted or unsubstituted aryl, or substituted or unsubstituted heteroaryl ring;

each instance of $R^B$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —$OR^{B1}$, —$N(R^{B1})_2$, —$SR^{B1}$, —CN, —$C(R^{B1})_3$, —SCN, —$C(=NR^{B1})R^{B1}$, —$C(=NR^{B1})OR^{B1}$, —$C(=NR^{B1})N(R^{B1})_2$, —$C(=O)R^{B1}$, —$C(=O)OR^{B1}$, —$C(=O)N(R^{B1})_2$, —$NO_2$, —$NR^{B1}C(=O)R^{B1}$, —$NR^{B1}C(=O)OR^{B1}$, —$NR^{B1}C(=O)N(R^{B1})_2$, —$OC(=O)R^{B1}$, —$OC(=O)OR^{B1}$, —$OC(=O)N(R^{B1})_2$, or two $R^B$ groups are joined to form a substituted or unsubstituted carbocyclic, substituted or unsubstituted heterocyclic, substituted or unsubstituted aryl, or substituted or unsubstituted heteroaryl ring;

$R^C$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —$OR^{C1}$, —$N(R^{C1})_2$, —$SR^{C1}$, —CN, —$C(R^{C1})_3$, —SCN, —$C(=NR^{C1})R^{C1}$, —$C(=NR^{C1})OR^{C1}$, —$C(=NR^{C1})N(R^{C1})_2$, —$C(=O)R^{C1}$, —$C(=O)OR^{C1}$, —$C(=O)N(R^{C1})_2$, —$NO_2$, —$NR^{C1}C(=O)R^{C1}$, —$NR^{C1}C(=O)OR^{C1}$, —$NR^{C1}C(=O)N(R^{C1})_2$, —$OC(=O)R^{C1}$, —$OC(=O)OR^{C1}$, —$OC(=O)N(R^{C1})_2$, or $R^C$ and $R^X$ are joined to form a substituted or unsubstituted heterocyclic, or substituted or unsubstituted heteroaryl ring;

each instance of $R^{A1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form a substituted or unsubstituted carbocyclic, substituted or unsubstituted heterocyclic, substituted or unsubstituted aryl, or substituted or unsubstituted heteroaryl ring;

each instance of $R^{B1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{B1}$ groups are joined to form a substituted or unsubstituted carbocyclic, substituted or unsubstituted heterocyclic, substituted or unsubstituted aryl, or substituted or unsubstituted heteroaryl ring;

each instance of $R^{C1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{C1}$ groups are joined to form a substituted or unsubstituted carbocyclic, substituted or unsubstituted heterocyclic, substituted or unsubstituted aryl, or substituted or unsubstituted heteroaryl ring;

each instance of $R^Z$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —$OR^{Z1}$, —$N(R^{Z1})_2$, —$SR^{Z1}$, —CN, —$C(R^{Z1})_3$, —SCN, —$C(=NR^{Z1})R^{Z1}$, —$C(=NR^{Z1})OR^{Z1}$, —$C(=NR^{Z1})N(R^{Z1})_2$, —$C(=O)R^{Z1}$, —$C(=O)OR^{Z1}$, —$C(=O)N(R^{Z1})_2$, —$NO_2$, —$NR^{Z1}C(=O)R^{Z1}$, —$NR^{Z1}C(=O)OR^{Z1}$, —$NR^{Z1}C(=O)N(R^{Z1})_2$, —$OC(=O)R^{Z1}$, —$OC(=O)OR^{Z1}$, —$OC(=O)N(R^{Z1})_2$, or two $R^Z$ groups are joined to form a substituted or unsubstituted carbocyclic, substituted or unsubstituted heterocyclic, substituted or unsubstituted aryl, or substituted or unsubstituted heteroaryl ring;

each instance of $R^{Z1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{Z1}$ groups are joined to form a substituted or unsubstituted carbocyclic, substituted or unsubstituted heterocyclic, substituted or unsubstituted aryl, or substituted or unsubstituted heteroaryl ring;

m is 0, 1, 2, or 3; and r is 0, 1, 2, or 3.

In some embodiments of Formula (II-a), the group of formula

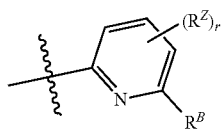

selected from the group consisting of

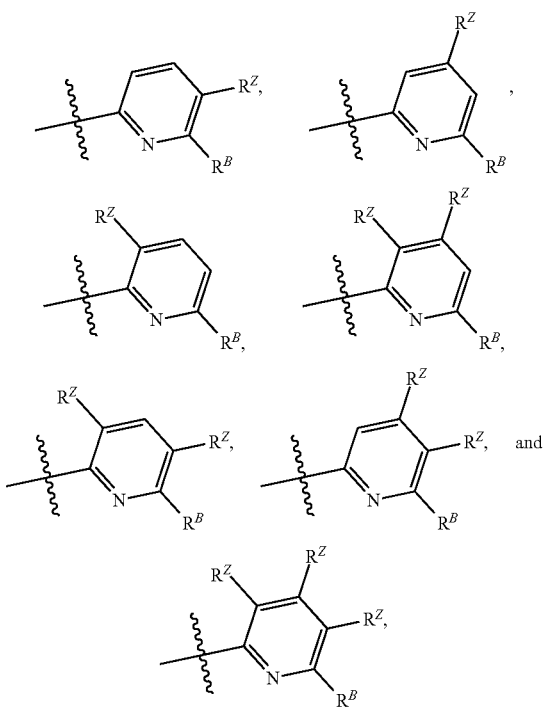

wherein $R^B$ and each instance of $R^Z$ are independently a group as described herein.

In some embodiments of Formula (II-a),

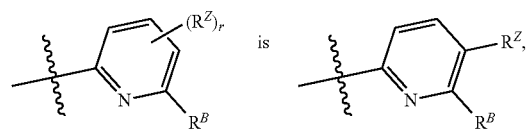

to provide a compound of Formula (II-ai):

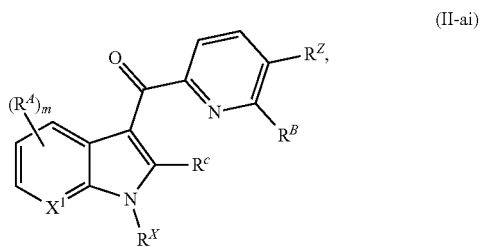

or a pharmaceutically acceptable salt, solvate, hydrate, stereoisomer, tautomer, isotopically labeled derivative, polymorph, or prodrug thereof, wherein:

$X^1$ is N or $CR^A$;

$R^X$ is independently hydrogen, substituted or unsubstituted alkyl, substituted or unsubstituted alkenyl, substituted or unsubstituted alkynyl, substituted or unsubstituted acyl, or a nitrogen protecting group;

each instance of $R^A$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{A1}$, $-N(R^{A1})_2$, $-SR^{A1}$, $-CN$, $-C(R^{A1})_3$, $-SCN$, $-C(=NR^{A1})R^{A1}$, $-C(=NR^{A1})OR^{A1}$, $-C(=NR^{A1})N(R^{A1})_2$, $-C(=O)R^{A1}$, $-C(=O)OR^{A1}$, $-C(=O)N(R^{A1})_2$, $-NO_2$, $-NR^{A1}C(=O)R^{A1}$, $-NR^{A1}C(=O)OR^{A1}$, $-NR^{A1}C(=O)N(R^{A1})_2$, $-OC(=O)R^{A1}$, $-OC(=O)OR^{A1}$, $-OC(=O)N(R^{A1})_2$, or two $R^A$ groups are joined to form a substituted or unsubstituted carbocyclic, substituted or unsubstituted heterocyclic, substituted or unsubstituted aryl, or substituted or unsubstituted heteroaryl ring;

each instance of $R^B$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{B1}$, $-N(R^{B1})_2$, $-SR^{B1}$, $-CN$, $-C(R^{B1})_3$, $-SCN$, $-C(=NR^{B1})R^{B1}$, $-C(=NR^{B1})OR^{B1}$, $-C(=NR^{B1})N(R^{B1})_2$, $-C(=O)R^{B1}$, $-C(=O)OR^{B1}$, $-C(=O)N(R^{B1})_2$, $-NO_2$, $-NR^{B1}C(=O)R^{B1}$, $-NR^{B1}C(=O)OR^{B1}$, $-NR^{B1}C(=O)N(R^{B1})_2$, $-OC(=O)R^{B1}$, $-OC(=O)OR^{B1}$, $-OC(=O)N(R^{B1})_2$, or two $R^B$ groups are joined to form a substituted or unsubstituted carbocyclic, substituted or unsubstituted heterocyclic, substituted or unsubstituted aryl, or substituted or unsubstituted heteroaryl ring;

$R^C$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{C1}$, $-N(R^{C1})_2$, $-SR^{C1}$, $-CN$, —C(R$^{C1}$)$_3$, —SCN, —C(=NR$^{C1}$)R$^{C1}$, —C(=NR$^{C1}$)OR$^{C1}$, —C(=NR$^{C1}$)N(R$^{C1}$)$_2$, —C(=O)R$^{C1}$, —C(=O)OR$^{C1}$, —C(=O)N(R$^{C1}$)$_2$, —NO$_2$, —NR$^{C1}$C(=O)R$^{C1}$, —NR$^{C1}$C(=O)OR$^{C1}$, —NR$^{C1}$C(=O)N(R$^{C1}$)$_2$, —OC(=O)R$^{C1}$, —OC(=O)OR$^{C1}$, —OC(=O)N(R$^{C1}$)$_2$, or R$^C$ and R$^X$ are joined to form a substituted or unsubstituted heterocyclic, or substituted or unsubstituted heteroaryl ring;

each instance of R$^{A1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{A1}$ groups are joined to form a substituted or unsubstituted carbocyclic, substituted or unsubstituted heterocyclic, substituted or unsubstituted aryl, or substituted or unsubstituted heteroaryl ring;

each instance of R$^{B1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{B1}$ groups are joined to form a substituted or unsubstituted carbocyclic, substituted or unsubstituted heterocyclic, substituted or unsubstituted aryl, or substituted or unsubstituted heteroaryl ring;

each instance of R$^{C1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{C1}$ groups are joined to form a substituted or unsubstituted carbocyclic, substituted or unsubstituted heterocyclic, substituted or unsubstituted aryl, or substituted or unsubstituted heteroaryl ring;

each instance of R$^Z$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —OR$^{Z1}$, —N(R$^{Z1}$), —SR$^{Z1}$, —CN, —C(R$^{Z1}$)$_3$, —SCN, —C(=NR$^{Z1}$)R$^{Z1}$, —C(=NR$^{Z1}$)OR$^{Z1}$, —C(=NR$^{Z1}$)N(R$^{Z1}$), —C(=O)R$^{Z1}$, —C(=O)OR$^{Z1}$, —C(=O)N(R$^{Z1}$), —NO$_2$, —NR$^{Z1}$C(=O)R$^{Z1}$, —NR$^{Z1}$C(=O)OR$^{Z1}$, —NR$^{Z1}$C(=O)N(R$^{Z1}$)$_2$, —OC(=O)R$^{Z1}$, —OC(=O)OR$^{Z1}$, —OC(=O)N(R$^{Z1}$)$_2$, or two R$^Z$ groups are joined to form a substituted or unsubstituted carbocyclic, substituted or unsubstituted heterocyclic, substituted or unsubstituted aryl, or substituted or unsubstituted heteroaryl ring;

each instance of R$^{Z1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{Z1}$ groups are joined to form a substituted or unsubstituted carbocyclic, substituted or unsubstituted heterocyclic, substituted or unsubstituted aryl, or substituted or unsubstituted heteroaryl ring; and m is 0, 1, 2, or 3.

In some embodiments of Formula (II-a), wherein r is 0; and R$^Z$ is absent, provided is a compound of Formula (II-aii):

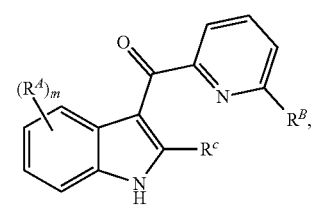

(II-aii)

or a pharmaceutically acceptable salt, solvate, hydrate, stereoisomer, tautomer, isotopically labeled derivative, polymorph, or prodrug thereof.

In some embodiments of Formula (II-a), wherein r is 0; and R$^Z$ is absent, provided is a compound of Formula (II-aiii):

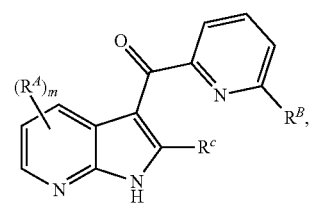

(II-aiii)

or a pharmaceutically acceptable salt, solvate, hydrate, stereoisomer, tautomer, isotopically labeled derivative, polymorph, or prodrug thereof.

In some embodiments of Formula (II),

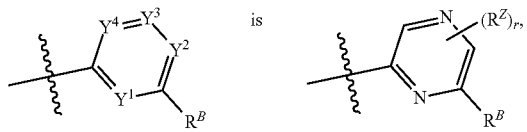

to provide a compound of Formula (II-b):

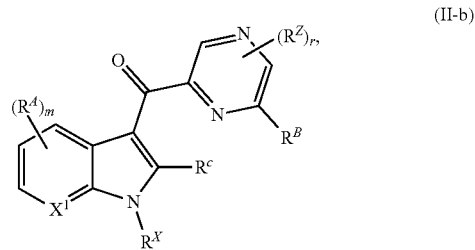

or a pharmaceutically acceptable salt, solvate, hydrate, stereoisomer, tautomer, isotopically labeled derivative, polymorph, or prodrug thereof, wherein:

$X^1$ is N or $CR^A$;

$R^X$ is independently hydrogen, substituted or unsubstituted alkyl, substituted or unsubstituted alkenyl, substituted or unsubstituted alkynyl, substituted or unsubstituted acyl, or a nitrogen protecting group;

each instance of $R^A$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{A1}$, $-N(R^{A1})_2$, $-SR^{A1}$, $-CN$, $-C(R^{A1})_3$, $-SCN$, $-C(=NR^{A1})R^{A1}$ $C(=NR^{A1})OR^{A1}$, $-C(=NR^{A1})N(R^{A1})_2$, $-C(=O)R^{A1}$, $-C(=O)OR^{A1}$, $-C(=O)N(R^{A1})_2$, $-NO_2$, $-NR^{A1}C(=O)R^{A1}$, $-NR^{A1}C(=O)OR^{A1}$, $-NR^{A1}C(=O)N(R^{A1})_2$, $-OC(=O)R^{A1}$, $-OC(=O)OR^{A1}$, $-OC(=O)N(R^{A1})_2$, or two $R^A$ groups are joined to form a substituted or unsubstituted carbocyclic, substituted or unsubstituted heterocyclic, substituted or unsubstituted aryl, or substituted or unsubstituted heteroaryl ring;

each instance of $R^B$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{B1}$, $-N(R^{B1})_2$, $-SR^{B1}$, $-CN$, $-C(R^{B1})_3$, $-SCN$, $-C(=NR^{B1})R^{B1}$, $-C(=NR^{B1})OR^{B1}$, $-C(=NR^{B1})N(R^{B1})_2$, $-C(=O)R^{B1}$, $-C(=O)OR^{B1}$, $-C(=O)N(R^{B1})_2$, $-NO_2$, $-NR^{B1}C(=O)R^{B1}$, $-NR^{B1}C(=O)OR^{B1}$, $-NR^{B1}C(=O)N(R^{B1})_2$, $-OC(=O)R^{B1}$, $-OC(=O)OR^{B1}$, $-OC(=O)N(R^{B1})_2$, or two $R^B$ groups are joined to form a substituted or unsubstituted carbocyclic, substituted or unsubstituted heterocyclic, substituted or unsubstituted aryl, or substituted or unsubstituted heteroaryl ring;

$R^C$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{C1}$, $-N(R^{C1})_2$, $-SR^{C1}$, $-CN$, $-C(R^{C1})_3$, $-SCN$, $-C(=NR^{C1})R^{C1}$, $-C(=NR^{C1})OR^{C1}$, $-C(=NR^{C1})N(R^{C1})_2$, $-C(=O)R^{C1}$, $-C(=O)OR^{C1}$, $-C(=O)N(R^{C1})_2$, $-NO_2$, $-NR^{C1}C(=O)R^{C1}$, $-NR^{C1}C(=O)OR^{C1}$, $-NR^{C1}C(=O)N(R^{C1})_2$, $-OC(=O)R^{C1}$, $-OC(=O)OR^{C1}$, $-OC(=O)N(R^{C1})_2$, or $R^C$ and $R^X$ are joined to form a substituted or unsubstituted heterocyclic, or substituted or unsubstituted heteroaryl ring;

each instance of $R^{A1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form a substituted or unsubstituted carbocyclic, substituted or unsubstituted heterocyclic, substituted or unsubstituted aryl, or substituted or unsubstituted heteroaryl ring;

each instance of $R^{B1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{B1}$ groups are joined to form a substituted or unsubstituted carbocyclic, substituted or unsubstituted heterocyclic, substituted or unsubstituted aryl, or substituted or unsubstituted heteroaryl ring;

each instance of $R^{C1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{C1}$ groups are joined to form a substituted or unsubstituted carbocyclic, substituted or unsubstituted heterocyclic, substituted or unsubstituted aryl, or substituted or unsubstituted heteroaryl ring;

each instance of $R^Z$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{Z1}$, $-N(R^{Z1})$, $-SR^{Z1}$, $-CN$, $-C(R^{Z1})_3$, $-SCN$, $-C(=NR^{Z1})R^{Z1}$, $-C(=NR^{Z1})OR^{Z1}$, $-C(=NR^{Z1})N(R^{Z1})_2$, $-C(=O)R^{Z1}$, $-C(=O)OR^{Z1}$, $-C(=O)N(R^{Z1})_2$, $-NO_2$, $-NR^{Z1}C(=O)R^{Z1}$, $-NR^{Z1}C(=O)OR^{Z1}$, $-NR^{Z1}C(=O)N(R^{Z1})_2$, $-OC(=O)R^{Z1}$, $-OC(=O)OR^{Z1}$, $-OC(=O)N(R^{Z1})_2$, or two $R^Z$ groups are joined to form a substituted or unsubstituted carbocyclic, substituted or unsubstituted heterocyclic, substituted or unsubstituted aryl, or substituted or unsubstituted heteroaryl ring;

each instance of $R^{Z1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{Z1}$ groups are joined to form a substituted or unsubstituted carbocyclic, substituted or unsubstituted heterocyclic, substituted or unsubstituted aryl, or substituted or unsubstituted heteroaryl ring;

m is 0, 1, 2, or 3; and
r is 0, 1, or 2.

In some embodiments of Formula (II-b), the group of formula

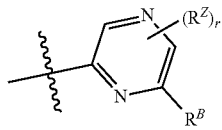

is selected from the group consisting of:

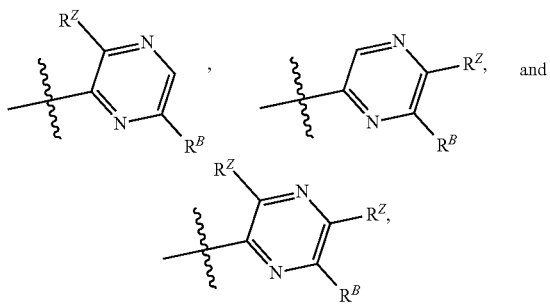

wherein $R^B$ and each instance of $R^Z$ are independently a group as described herein.

In some embodiments of Formula (II-b),

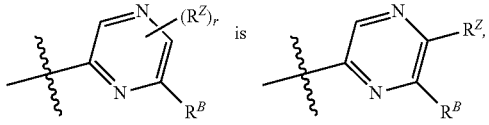

to provide a compound of Formula (II-bi):

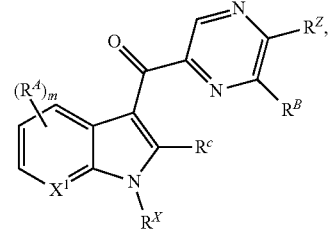

(II-bi)

or a pharmaceutically acceptable salt, solvate, hydrate, stereoisomer, tautomer, isotopically labeled derivative, polymorph, or prodrug thereof.

In some embodiments of Formula (II),

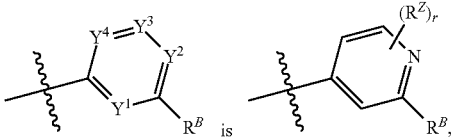

to provide a compound of Formula (II-c):

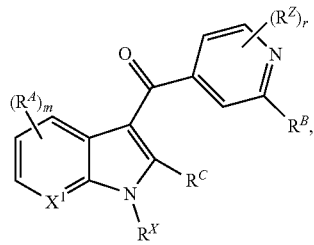

(II-c)

or a pharmaceutically acceptable salt, solvate, hydrate, stereoisomer, tautomer, isotopically labeled derivative, polymorph, or prodrug thereof, wherein:

$X^1$ is N or $CR^A$;

$R^X$ is independently hydrogen, substituted or unsubstituted alkyl, substituted or unsubstituted alkenyl, substituted or unsubstituted alkynyl, substituted or unsubstituted acyl, or a nitrogen protecting group;

each instance of $R^A$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —OR$^{A1}$, —N(R$^{A1}$)$_2$, —SR$^{A1}$, —CN, —C(R$^{A1}$)$_3$, —SCN, —C(=NR$^{A1}$)R$^{A1}$, —C(=NR$^{A1}$)OR$^{A1}$, —C(=NR$^{A1}$)N(R$^{A1}$)$_2$, —C(=O) R$^{A1}$, —C(=O)OR$^{A1}$, —C(=O)N(R$^{A1}$)$_2$, —NO$_2$, —NR$^{A1}$C(=O)R$^{A1}$, —NR$^{A1}$C(=O)OR$^{A1}$, —NR$^{A1}$C(=O)N(R$^{A1}$)$_2$, —OC(=O)R$^{A1}$, —OC(=O)OR$^{A1}$, —OC(=O)N(R$^{A1}$)$_2$, or two R$^A$ groups are joined to form a substituted or unsubstituted carbocyclic, substituted or unsubstituted heterocyclic, substituted or unsubstituted aryl, or substituted or unsubstituted heteroaryl ring;

each instance of R$^B$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —OR$^{B1}$, —N(R$^{B1}$)$_2$, —SR$^{B1}$, —CN, —C(R$^{B1}$)$_3$, —SCN, —C(=NR$^{B1}$)R$^{B1}$, —C(=NR$^{B1}$)OR$^{B1}$, —C(=NR$^{B1}$)N(R$^{B1}$)$_2$, —C(=O) R$^{B1}$, —C(=O)OR$^{B1}$, —C(=O)N(R$^{B1}$)$_2$, —NO$_2$, —NR$^{B1}$C(=O)R$^{B1}$, —NR$^{B1}$C(=O)OR$^{B1}$, —NR$^{B1}$C(=O)N(R$^{B1}$)$_2$, —OC(=O)R$^{B1}$, —OC(=O)OR$^{B1}$, —OC(=O)N(R$^{B1}$)$_2$, or two R$^B$ groups are joined to form a substituted or unsubstituted carbocyclic, substituted or unsubstituted heterocyclic, substituted or unsubstituted aryl, or substituted or unsubstituted heteroaryl ring;

R$^C$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —OR$^{C1}$, —N(R$^{C1}$)$_2$, —SR$^{C1}$, —CN, —C(R$^{C1}$)$_3$, —SCN, —C(=NR$^{C1}$)R$^{C1}$, —C(=NR$^{C1}$) OR$^{C1}$, —C(=NR$^{C1}$)N(R$^{C1}$)$_2$, —C(=O)R$^{C1}$, —C(=O)OR$^{C1}$, —C(=O)N(R$^{C1}$)$_2$, —NO$_2$, —NR$^{C1}$C(=O)R$^{C1}$, —NR$^{C1}$C(=O)OR$^{C1}$, —NR$^{C1}$C(=O)N(R$^{C1}$)$_2$, —OC(=O)R$^{C1}$, —OC(=O)OR$^{C1}$, —OC(=O)N(R$^{C1}$)$_2$, or R$^C$ and R$^X$ are joined to form a substituted or unsubstituted heterocyclic, or substituted or unsubstituted heteroaryl ring;

each instance of R$^{A1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{A1}$ groups are joined to form a substituted or unsubstituted carbocyclic, substituted or unsubstituted heterocyclic, substituted or unsubstituted aryl, or substituted or unsubstituted heteroaryl ring;

each instance of R$^{B1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{B1}$ groups are joined to form a substituted or unsubstituted carbocyclic, substituted or unsubstituted heterocyclic, substituted or unsubstituted aryl, or substituted or unsubstituted heteroaryl ring;

each instance of R$^C$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{C1}$ groups are joined to form a substituted or unsubstituted carbocyclic, substituted or unsubstituted heterocyclic, substituted or unsubstituted aryl, or substituted or unsubstituted heteroaryl ring;

each instance of R$^Z$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —OR$^{Z1}$, —N(R$^{Z1}$)$_2$, —SR$^{Z1}$, —CN, —C(R$^{Z1}$)$_3$, —SCN, —C(=NR$^{Z1}$)R$^{Z1}$, —C(=NR$^{Z1}$)OR$^{Z1}$, —C(=NR$^{Z1}$)N(R$^{Z1}$)$_2$, —C(=O) R$^{Z1}$, —C(=O)OR$^{Z1}$, —C(=O)N(R$^{Z1}$)$_2$, —NO$_2$, —NR$^{Z1}$C(=O)R$^{Z1}$, —NR$^{Z1}$C(=O)OR$^{Z1}$, —NR$^{Z1}$C(=O)N(R$^{Z1}$)$_2$, —OC(=O)R$^{Z1}$, —OC(=O)OR$^{Z1}$, —OC(=O)N(R$^{Z1}$)$_2$, or two R$^Z$ groups are joined to form a substituted or unsubstituted carbocyclic, substituted or unsubstituted heterocyclic, substituted or unsubstituted aryl, or substituted or unsubstituted heteroaryl ring;

each instance of R$^{Z1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{Z1}$ groups are joined to form a substituted or unsubstituted carbocyclic, substituted or unsubstituted heterocyclic, substituted or unsubstituted aryl, or substituted or unsubstituted heteroaryl ring;

m is 0, 1, 2, or 3; and r is 0, 1, 2, or 3.

In some embodiments of Formula (II-c), the group of formula

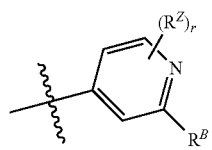

is selected from the group consisting of

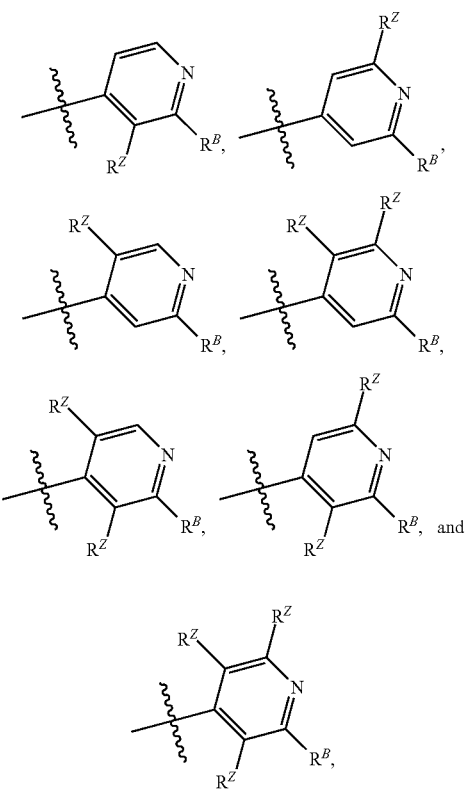

wherein $R^B$ and each instance of $R^Z$ are independently a group as described herein.

In some embodiments of Formula (II-c),

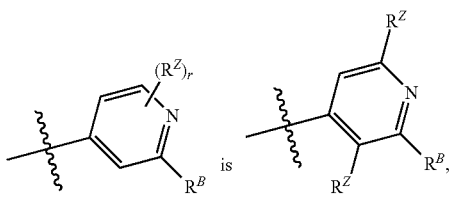

to provide a compound of Formula (II-ci):

(II-ci)

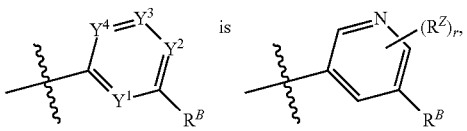

or a pharmaceutically acceptable salt, solvate, hydrate, stereoisomer, tautomer, isotopically labeled derivative, polymorph, or prodrug thereof. In some embodiments of Formula (II), $$\text{is}$$

to provide a compound of Formula (II-d):

(II-d)

or a pharmaceutically acceptable salt, solvate, hydrate, stereoisomer, tautomer, isotopically labeled derivative, polymorph, or prodrug thereof, wherein:

$X^1$ is N or $CR^A$;

$R^X$ is independently hydrogen, substituted or unsubstituted alkyl, substituted or unsubstituted alkenyl, substituted or unsubstituted alkynyl, substituted or unsubstituted acyl, or a nitrogen protecting group;

each instance of $R^A$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{A1}$, $-N(R^{A1})_2$, $-SR^A$, $-CN$, $-C(R^{A1})_3$, $-SCN$, $-C(=NR^{A1})R^{A1}$, $-C(=NR^{A1})OR^{A1}$, $-C(=NR^{A1})N(R^{A1})_2$, $-C(=O)R^{A1}$, $-C(=O)OR^{A1}$, $-C(=O)N(R^{A1})_2$, $-NO_2$, $-NR^{A1}C(=O)R^{A1}$, $-NR^{A1}C(=O)OR^{A1}$, $-NR^{A1}C(=O)N(R^{A1})_2$, $-OC(=O)R^{A1}$, $-OC(=O)OR^{A1}$, $-OC(=O)N(R^{A1})_2$, or two $R^A$ groups are joined to form a substituted or unsubstituted carbocyclic, substituted or unsubstituted heterocyclic, substituted or unsubstituted aryl, or substituted or unsubstituted heteroaryl ring;

each instance of $R^B$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —$OR^{B1}$, —$N(R^{B1})_2$, —$SR^{B1}$, —CN, —$C(R^{B1})_3$, —SCN, —$C(=NR^{B1})R^{B1}$, —$C(=NR^{B1})OR^{B1}$, —$C(=NR^{B1})N(R^{B1})_2$, —$C(=O)R^{B1}$, —$C(=O)OR^{B1}$, —$C(=O)N(R^{B1})_2$, —$NO_2$, —$NR^{B1}C(=O)R^{B1}$, —$NR^{B1}C(=O)OR^{B1}$, —$NR^{B1}C(=O)N(R^{B1})_2$, —$OC(=O)R^{B1}$, —$OC(=O)OR^{B1}$, —$OC(=O)N(R^{B1})_2$, or two $R^B$ groups are joined to form a substituted or unsubstituted carbocyclic, substituted or unsubstituted heterocyclic, substituted or unsubstituted aryl, or substituted or unsubstituted heteroaryl ring;

$R^C$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —$OR^{C1}$, —$N(R^{C1})_2$, —$SR^{C1}$, —CN, —$C(R^{C1})_3$, —SCN, —$C(=NR^{C1})R^{C1}$, —$C(=NR^{C1})OR^{C1}$, —$C(=NR^{C1})N(R^{C1})_2$, —$C(=O)R^{C1}$, —$C(=O)OR^{C1}$, —$C(=O)N(R^{C1})_2$, —$NO_2$, —$NR^{C1}C(=O)R^{C1}$, —$NR^{C1}C(=O)OR^{C1}$, —$NR^{C1}C(=O)N(R^{C1})_2$, —$OC(=O)R^{C1}$, —$OC(=O)OR^{C1}$, —$OC(=O)N(R^{C1})_2$, or $R^C$ and $R^X$ are joined to form a substituted or unsubstituted heterocyclic, or substituted or unsubstituted heteroaryl ring;

each instance of $R^{A1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form a substituted or unsubstituted carbocyclic, substituted or unsubstituted heterocyclic, substituted or unsubstituted aryl, or substituted or unsubstituted heteroaryl ring;

each instance of $R^{B1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{B1}$ groups are joined to form a substituted or unsubstituted carbocyclic, substituted or unsubstituted heterocyclic, substituted or unsubstituted aryl, or substituted or unsubstituted heteroaryl ring;

each instance of $R^{C1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{C1}$ groups are joined to form a substituted or unsubstituted carbocyclic, substituted or unsubstituted heterocyclic, substituted or unsubstituted aryl, or substituted or unsubstituted heteroaryl ring;

each instance of $R^Z$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —$OR^{Z1}$, —$N(R^{Z1})$, —$SR^{Z1}$, —CN, —$C(R^{Z1})_3$, —SCN, —$C(=NR^{Z1})R^{Z1}$, —$C(=NR^{Z1})OR^{Z1}$, —$C(=NR^{Z1})N(R^{Z1})$, —$C(=O)R^{Z1}$, —$C(=O)OR^{Z1}$, —$C(=O)N(R^{Z1})$, —$NO_2$, —$NR^{Z1}C(=O)R^{Z1}$, —$NR^{Z1}C(=O)OR^{Z1}$, —$NR^{Z1}C(=O)N(R^{Z1})_2$, —$OC(=O)R^{Z1}$, —$OC(=O)OR^{Z1}$, —$OC(=O)N(R^{Z1})_2$, or two $R^Z$ groups are joined to form a substituted or unsubstituted carbocyclic, substituted or unsubstituted heterocyclic, substituted or unsubstituted aryl, or substituted or unsubstituted heteroaryl ring;

each instance of $R^{Z1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{Z1}$ groups are joined to form a substituted or unsubstituted carbocyclic, substituted or unsubstituted heterocyclic, substituted or unsubstituted aryl, or substituted or unsubstituted heteroaryl ring;

m is 0, 1, 2, or 3; and r is 0, 1, 2, or 3.

In some embodiments of Formula (II-d), the group of formula

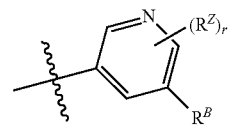

is selected from the group consisting of

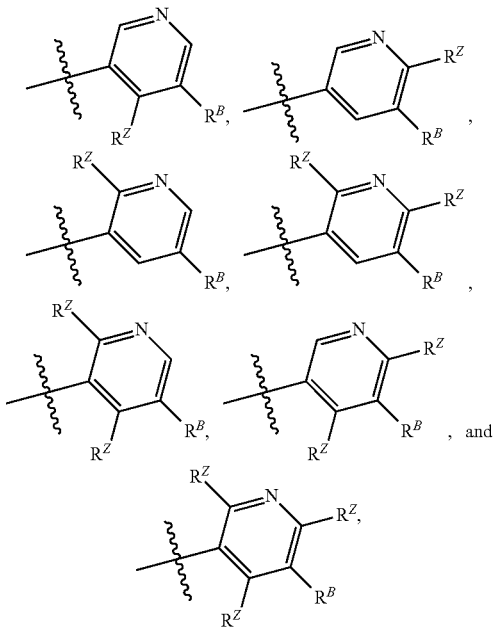

wherein $R^B$ and each instance of $R^Z$ are independently a group as described herein.

In some embodiments of Formula (II-d),

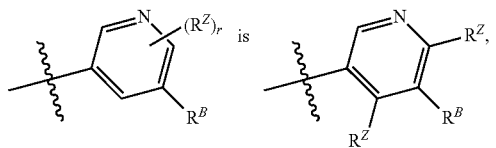

to provide a compound of Formula (II-di):

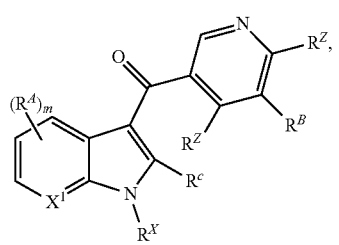

or a pharmaceutically acceptable salt, solvate, hydrate, stereoisomer, tautomer, isotopically labeled derivative, polymorph, or prodrug thereof.

In some embodiments of Formula (II),

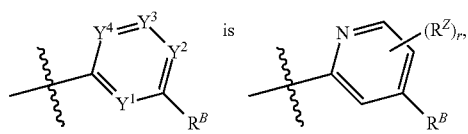

to provide a compound of Formula (II-e):

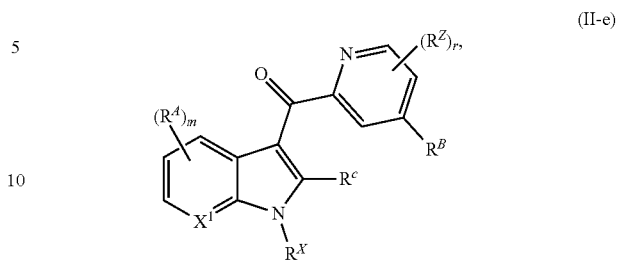

or a pharmaceutically acceptable salt, solvate, hydrate, stereoisomer, tautomer, isotopically labeled derivative, polymorph, or prodrug thereof, wherein:

$X^1$ is N or $CR^A$;

$R^X$ is independently hydrogen, substituted or unsubstituted alkyl, substituted or unsubstituted alkenyl, substituted or unsubstituted alkynyl, substituted or unsubstituted acyl, or a nitrogen protecting group;

each instance of $R^A$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{A1}$, $-N(R^{A1})_2$, $-SR^{A1}$, $-CN$, $-C(R^{A1})_3$, $-SCN$, $-C(=NR^{A1})R^{A1}C(=NR^{A1})OR^{A1}$, $-C(=NR^{A1})N(R^{A1})_2$, $-C(=O)R^{A1}$, $-C(=O)OR^{A1}$, $-C(=O)N(R^{A1})_2$, $-NO_2$, $-NR^{A1}C(=O)R^{A1}$, $-NR^{A1}C(=O)OR^{A1}$, $-NR^{A1}C(=O)N(R^{A1})_2$, $-OC(=O)R^{A1}$, $-OC(=O)OR^{A1}$, $-OC(=O)N(R^{A1})_2$, or two $R^A$ groups are joined to form a substituted or unsubstituted carbocyclic, substituted or unsubstituted heterocyclic, substituted or unsubstituted aryl, or substituted or unsubstituted heteroaryl ring;

each instance of $R^B$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{B1}$, $-N(R^{B1})_2$, $-SR^{B1}$, $-CN$, $-C(R^{B1})_3$, $-SCN$, $-C(=NR^{B1})R^{B1}$, $-C(=NR^{B1})OR^{B1}$, $-C(=NR^{B1})N(R^{B1})_2$, $-C(=O)R^{B1}$, $-C(=O)OR^{B1}$, $-C(=O)N(R^{B1})_2$, $-NO_2$, $-NR^{B1}C(=O)R^{B1}$, $-NR^{B1}C(=O)OR^{B1}$, $-NR^{B1}C(=O)N(R^{B1})_2$, $-OC(=O)R^{B1}$, $-OC(=O)OR^{B1}$, $-OC(=O)N(R^{B1})_2$, or two $R^B$ groups are joined to form a substituted or unsubstituted carbocyclic, substituted or unsubstituted heterocyclic, substituted or unsubstituted aryl, or substituted or unsubstituted heteroaryl ring;

$R^C$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{C1}$, $-N(R^{C1})_2$, $-SR^{C1}$, $-CN$, —C(R$^{C1}$)$_3$, —SCN, —C(=NR$^{C1}$)R$^{C1}$, —C(=NR$^{C1}$)OR$^{C1}$, —C(=NR$^{C1}$)N(R$^{C1}$)$_2$, —C(=O)R$^{C1}$, —C(=O)OR$^{C1}$, —C(=O)N(R$^{C1}$)$_2$, —NO$_2$, —NR$^{C1}$C(=O)R$^{C1}$, —NR$^{C1}$C(=O)OR$^{C1}$, —NR$^{C1}$C(=O)N(R$^{C1}$)$_2$, —OC(=O)R$^{C1}$, —OC(=O)OR$^{C1}$, —OC(=O)N(R$^{C1}$)$_2$, or R$^C$ and R$^X$ are joined to form a substituted or unsubstituted heterocyclic, or substituted or unsubstituted heteroaryl ring;

each instance of R$^{A1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{A1}$ groups are joined to form a substituted or unsubstituted carbocyclic, substituted or unsubstituted heterocyclic, substituted or unsubstituted aryl, or substituted or unsubstituted heteroaryl ring;

each instance of R$^{B1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{B1}$ groups are joined to form a substituted or unsubstituted carbocyclic, substituted or unsubstituted heterocyclic, substituted or unsubstituted aryl, or substituted or unsubstituted heteroaryl ring;

each instance of R$^C$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{C1}$ groups are joined to form a substituted or unsubstituted carbocyclic, substituted or unsubstituted heterocyclic, substituted or unsubstituted aryl, or substituted or unsubstituted heteroaryl ring;

each instance of R$^Z$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —OR$^{Z1}$, —N(R$^{Z1}$), —SR$^{Z1}$, —CN, —C(R$^{Z1}$)$_3$, —SCN, —C(=NR$^{Z1}$)R$^{Z1}$, —C(=NR$^{Z1}$)OR$^{Z1}$, —C(=NR$^{Z1}$)N(R$^{Z1}$)$_2$, —C(=O)R$^{Z1}$, —C(=O)OR$^{Z1}$, —C(=O)N(R$^{Z1}$)$_2$, —NO$_2$, —NR$^{Z1}$C(=O)R$^{Z1}$, —NR$^{Z1}$C(=O)OR$^{Z1}$, —NR$^{Z1}$C(=O)N(R$^{Z1}$)$_2$, —OC(=O)R$^{Z1}$, —OC(=O)OR$^{Z1}$, —OC(=O)N(R$^{Z1}$)$_2$, or two R$^{Z1}$ groups are joined to form a substituted or unsubstituted carbocyclic, substituted or unsubstituted heterocyclic, substituted or unsubstituted aryl, or substituted or unsubstituted heteroaryl ring;

each instance of R$^{Z1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{Z1}$ groups are joined to form a substituted or unsubstituted carbocyclic, substituted or unsubstituted heterocyclic, substituted or unsubstituted aryl, or substituted or unsubstituted heteroaryl ring;

m is 0, 1, 2, or 3; and r is 0, 1, 2, or 3.

In some embodiments of Formula (II-e), the group of formula

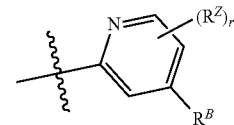

is selected from the group consisting of

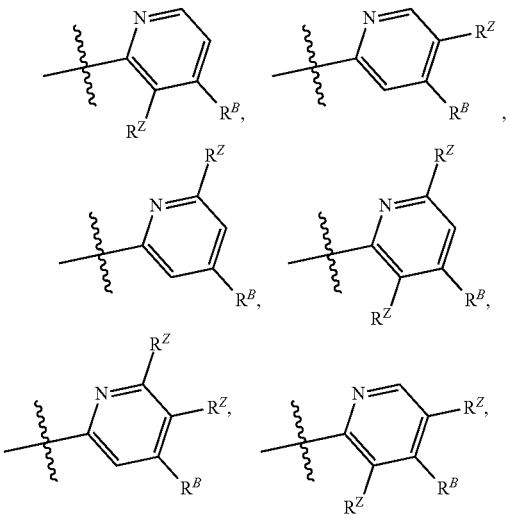

-continued

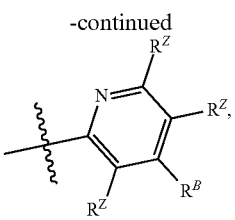

wherein $R^B$ and each instance of $R^Z$ are independently a group as described herein.

In some embodiments, $X^1$ is N and $R^X$ is hydrogen. In some embodiments, $X^1$ is $CR^A$ and $R^X$ is hydrogen. In some embodiments, $X^1$ is CH and $R^X$ is hydrogen. In some embodiments, $X^1$ is N and $R^X$ is substituted or unsubstituted methyl. In some embodiments, $X^1$ is $CR^A$ and $R^X$ is substituted or unsubstituted methyl. In some embodiments, $X^1$ is CH and $R^X$ is hydrogen. In some embodiments, $X^1$ is N, $R^X$ is hydrogen, and $R^C$ is hydrogen. In some embodiments, $X^1$ is $CR^A$, $R^X$ is hydrogen, and $R^C$ is hydrogen. In some embodiments, $X^1$ is CH, $R^X$ is hydrogen, and $R^C$ is hydrogen. In some embodiments, $X^1$ is N, $R^X$ is hydrogen, and $R^C$ is substituted or unsubstituted methyl. In some embodiments, $X^1$ is $CR^A$, $R^X$ is hydrogen, and $R^C$ is substituted or unsubstituted methyl. In some embodiments, $X^1$ is CH, $R^X$ is hydrogen, and $R^C$ is substituted or unsubstituted methyl.

In some embodiments, m is 0. In some embodiments, m is 1. In some embodiments, $R^A$ is halogen. In some embodiments, $R^A$ is —$OR^{A1}$.

In some embodiments, $R^B$ is a substituted or unsubstituted phenyl. In some embodiments, $R^B$ is a substituted or unsubstituted 5- to 6-membered heteroaryl ring. In some embodiments, $R^B$ is a substituted or unsubstituted 5- to 6-membered aryl ring. In some embodiments, $R^B$ is a substituted or unsubstituted 3- to 8-membered heterocyclic ring. In some embodiments, $R^B$ is a 6-membered heterocyclic ring. In some embodiments, $R^B$ is morpholinyl. In some embodiments, $R^B$ is a substituted or unsubstituted 3- to 8-membered carbocyclic ring. In some embodiments, $R^B$ is —$OR^{B1}$. In some embodiments, $R^B$ is —C(=O)$OR^{B1}$. In some embodiments, $R^B$ is —OC(=O)$R^{B1}$. In some embodiments, $R^{B1}$ is hydrogen. In some embodiments, $R^{B1}$ is $C_{1-6}$ alkyl. In some embodiments, $R^{B1}$ is —$CH_3$. In some embodiments, $R^B$ is —CN. In some embodiments, $R^B$ is —C($R^{B1}$)$_3$, wherein each instance of $R^{B1}$ is independently a halogen. In some embodiments, $R^B$ is —$CF_3$. In some embodiments, $R^B$ is not hydrogen.

In some embodiments, r is 0. In some embodiments, r is 1. In some embodiments, $R^Z$ is H. In some embodiments, $R^Z$ is a substituted or unsubstituted phenyl. In some embodiments, $R^Z$ is a substituted or unsubstituted 5- to 6-membered heteroaryl ring. In some embodiments, $R^Z$ is a substituted or unsubstituted 5- to 6-membered aryl ring. In some embodiments, $R^Z$ is a substituted or unsubstituted 3- to 8-membered heterocyclic ring. In some embodiments, $R^Z$ is a 6-membered heterocyclic ring. In some embodiments, $R^Z$ is morpholinyl. In some embodiments, $R^Z$ is a substituted or unsubstituted 3- to 8-membered carbocyclic ring. In some embodiments, $R^Z$ is —$OR^{Z1}$. In some embodiments, $R^Z$ is —C(=O)$OR^{Z1}$. In some embodiments, $R^Z$ is —OC(=O)$R^{Z1}$. In some embodiments, $R^{Z1}$ is hydrogen. In some embodiments, $R^{Z1}$ is $C_{1-6}$ alkyl. In some embodiments, $R^{Z1}$ is —$CH_3$. In some embodiments, $R^Z$ is —CN. In some embodiments, $R^Z$ is —C($R^{Z1}$)$_3$, wherein each instance of $R^{Z1}$ is independently a halogen. In some embodiments, $R^Z$ is —$CF_3$.

In some embodiments of Formula (I), Ring A is of the formula:

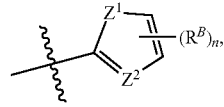

wherein:

$Z^1$ is $NR^W$, $C(R^W)_2$, O, or S;

$Z^2$ is N or $CR^W$;

each instance of $R^W$ is independently hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group, two $R^W$ groups are joined to form a substituted or unsubstituted carbocyclic, substituted or unsubstituted heterocyclic, substituted or unsubstituted aryl, or substituted or unsubstituted heteroaryl ring, or $R^B$ and $R^W$ are joined to form a substituted or unsubstituted carbocyclic, substituted or unsubstituted heterocyclic, substituted or unsubstituted aryl, or substituted or unsubstituted heteroaryl ring;

each instance of $R^B$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —$OR^{B1}$, —N($R^{B1}$)$_2$, —$SR^{B1}$, —CN, —C($R^{B1}$)$_3$, —SCN, —C(=$NR^{B1}$)$R^{B1}$, —C(=$NR^{B1}$)$OR^{B1}$, —C(=$NR^{B1}$)N($R^{B1}$)$_2$, —C(=O)$R^{B1}$, —C(=O)$OR^{B1}$, —C(=O)N($R^{B1}$)$_2$, —$NO_2$, —$NR^{B1}$C(=O)$R^{B1}$, —$NR^{B1}$C(=O)$OR^{B1}$, —$NR^{B1}$C(=O)N($R^{B1}$)$_2$, —OC(=O)$R^{B1}$, —OC(=O)$OR^{B1}$, —OC(=O)N($R^{B1}$)$_2$, or two $R^B$ groups are joined to form a substituted or unsubstituted carbocyclic, substituted or unsubstituted heterocyclic, substituted or unsubstituted aryl, or substituted or unsubstituted heteroaryl ring;

each instance of $R^{B1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{B1}$ groups are joined to form a substituted or unsubstituted carbocyclic, substituted or unsubstituted heterocyclic, substituted or unsubstituted aryl, or substituted or unsubstituted heteroaryl ring; and n is 0, 1, or 2.

In some embodiments of Formula (I), Ring A is of the formula:

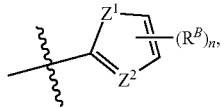

to provide a compound of Formula (III):

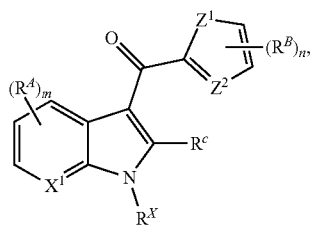

(III)

or a pharmaceutically acceptable salt, solvate, hydrate, stereoisomer, tautomer, isotopically labeled derivative, polymorph, or prodrug thereof. In some embodiments, $Z^2$ is N. In some embodiments, $Z^2$ is $CR^W$. In some embodiments, $Z^2$ is CH. In some embodiments, $Z^1$ is S.

In some embodiments of Formula (III), $Z^2$ is CH, provided herein is a compound of Formula (III-a):

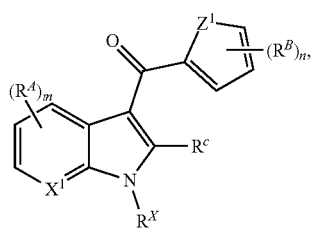

(III-a)

or a pharmaceutically acceptable salt, solvate, hydrate, stereoisomer, tautomer, isotopically labeled derivative, polymorph, or prodrug thereof. In some embodiments, $Z^2$ is N. In some embodiments, $Z^2$ is $CR^W$. In some embodiments, $Z^2$ is CH. In some embodiments, $Z^1$ is S.

In some embodiments of Formula (III-a), the group of formula

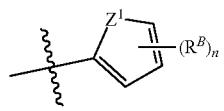

is selected from the group consisting of

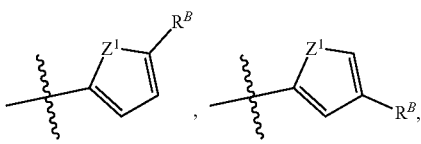

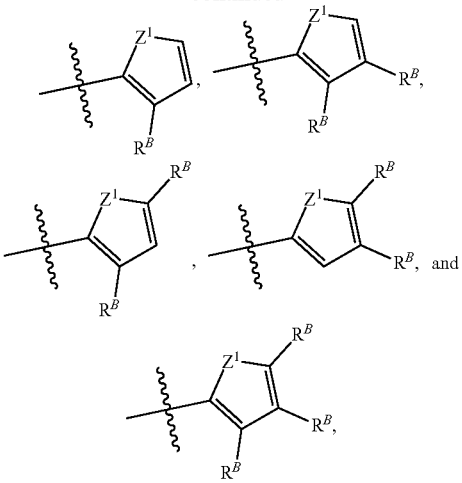

wherein $R^B$ and each instance of $R^Z$ are independently a group as described herein.

In some embodiments of Formula (III-a) wherein n is 1,

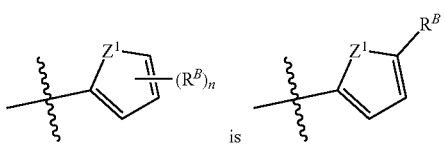

is to provide a compound of Formula (III-ai):

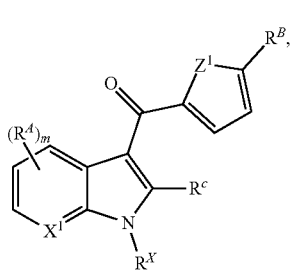

(III-ai)

or a pharmaceutically acceptable salt, solvate, hydrate, stereoisomer, tautomer, isotopically labeled derivative, polymorph, or prodrug thereof. In some embodiments, $Z^2$ is N. In some embodiments, $Z^2$ is $CR^W$. In some embodiments, $Z^2$ is CH. In some embodiments, $Z^1$ is S.

Group $R^B$ and n

As generally described herein, $R^B$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{B1}$, $-N(R^{B1})_2$, $-SR^{B1}$, $-CN$, $-C(R^{B1})_3$, $-SCN$, $-C(=NR^{B1})R^{B1}$, $-C(=NR^{B1})OR^{B1}$, $-C(=NR^{B1})N(R^{B1})_2$, $-C(=O)R^{B1}$, $-C(=O)OR^{B1}$, $-C(=O)N(R^{B1})_2$, $-NO_2$, $-NR^{A1}C(=O)R^{B1}$, $-NR^{B1}C(=O)OR^{B1}$, $-NR^{B1}C(=O)N(R^{B1})_2$, $-OC(=O)R^{B1}$, $-OC(=O)OR^{B1}$, $-OC(=O)N(R^{B1})_2$, or two $R^B$ groups are joined to form a substituted or unsubstituted carbocyclic, substituted or unsubstituted heterocyclic, substituted or unsubstituted aryl, or substituted or unsubstituted heteroaryl ring, wherein each instance of $R^{B1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{B1}$ groups are joined to form a substituted or unsubstituted carbocyclic, substituted or unsubstituted heterocyclic, substituted or unsubstituted aryl, or substituted or unsubstituted heteroaryl ring, and n is 0, 1, 2, 3, 4, or 5.

In some embodiments of Formula (I), n is 0 and $R^B$ is absent.

In some embodiments of Formula (I), n is 1, and $R^B$ is attached ortho to the point of attachment of —C(=O)—. In some embodiments of Formula (I), n is 1, and $R^B$ is attached meta to the point of attachment of —C(=O)—. In some embodiments of Formula (I), n is 1, and $R^B$ is attached para to the point of attachment of —C(=O)—.

In some embodiments of Formula (I), n is 2. In some embodiments of Formula (I), n is 2; and each $R^B$ is independently a group as described herein, wherein one $R^B$ group is attached ortho and one $R^B$ group is attached meta to the point of attachment of —C(=O)—. In some embodiments of Formula (I), n is 2; and each $R^B$ is independently a group as described herein, wherein one $R^B$ group is attached ortho and one $R^B$ group is attached para to the point of attachment of —C(=O)—. In some embodiments of Formula (I), n is 2; and each $R^B$ is independently a group as described herein, wherein one $R^B$ group is attached para and one $R^B$ group is attached meta to the point of attachment of —C(=O)—.

In some embodiments of Formula (I), n is 3; and each $R^B$ is independently a group as described herein. In some embodiments of Formula (I), n is 4; and each $R^B$ is independently a group as described herein. In some embodiments of Formula (I), n is 5; and each $R^B$ is independently a group as described herein.

In certain embodiments of Formula (I), n is 1, 2, 3, 4, or 5; and at least one instance of $R^B$ is hydrogen. In certain embodiments of Formula (I), n is 1; and $R^B$ is hydrogen. In certain embodiments of Formula (I), n is 2; and both instances of $R^B$ are hydrogen. In certain embodiments of Formula (I), n is 3; and all three instances of $R^B$ are hydrogen. In certain embodiments of Formula (I), n is 4; and all four instances of $R^B$ are hydrogen.

In certain embodiments of Formula (I), n is 1, 2, 3, 4, or 5; and at least one instance of $R^B$ is not hydrogen. In certain embodiments of Formula (I), n is 1; and $R^B$ is not hydrogen. In certain embodiments of Formula (I), n is 2 and at least one of $R^B$ is not hydrogen. In certain embodiments of Formula (I), n is 3 and at least one of $R^B$ is not hydrogen. In certain embodiments of Formula (I), n is 4 and at least one of $R^B$ is not hydrogen. In certain embodiments of Formula (I), n is 5 and at least one of $R^B$ is not hydrogen.

In certain embodiments of Formula (I), n is 1, 2, 3, 4, or 5 and at least one instance of $R^B$ is halogen. In certain embodiments of Formula (I), n is 1, 2, 3, 4, or 5; and at least one instance of $R^B$ is F. In certain embodiments of Formula (I), n is 1, 2, 3, 4, or 5 and at least one instance of $R^B$ is Cl. In certain embodiments of Formula (I), n is 1, 2, 3, 4, or 5; and at least one instance of $R^B$ is Br. In certain embodiments of Formula (I), n is 1, 2, 3, 4, or 5; and at least one instance of $R^B$ is I (iodine). In certain embodiments of Formula (I), n is 1; and $R^B$ is halogen. In some embodiments of Formula (I), n is 1; and $R^B$ is Cl (chlorine). In some embodiments of Formula (I), n is 1; and $R^B$ is Br (bromine). In some embodiments of Formula (I), n is 1 and $R^B$ is I (iodine).

In certain embodiments of Formula (I), n is 1, 2, 3, 4, or 5 and at least one instance of $R^B$ is substituted alkyl. In certain embodiments of Formula (I), n is 1, 2, 3, 4, or 5; and at least one instance of $R^B$ is unsubstituted alkyl. In certain embodiments of Formula (I), n is 1, 2, 3, 4, or 5 and at least one instance of $R^B$ is unsubstituted $C_{1-6}$ alkyl. In certain embodiments of Formula (I), n is 1, 2, 3, 4, or 5 and at least one instance of $R^B$ is substituted $C_{1-6}$ alkyl. In certain embodiments of Formula (I), n is 1, 2, 3, 4, or 5 and at least one instance of $R^B$ is —CH$_3$. In certain embodiments of Formula (I), n is 1, 2, 3, 4, or 5; and at least one instance of $R^B$ is $C_{1-6}$ alkyl substituted with at least one halogen. In certain embodiments of Formula (I), n is 1, 2, 3, 4, or 5; and at least one instance of $R^B$ is substituted methyl. In certain embodiments of Formula (I), n is 1, 2, 3, 4, or 5 and at least one instance of $R^B$ is —CH$_2$F. In certain embodiments of Formula (I), n is 1, 2, 3, 4, or 5 and at least one instance of $R^B$ is —CHF$_2$. In certain embodiments of Formula (I), n is 1, 2, 3, 4, or 5 and at least one instance of $R^B$ is —CF$_3$. In certain embodiments of Formula (I), n is 1, 2, 3, 4, or 5 and at least one instance of $R^B$ is substituted or unsubstituted ethyl. In certain embodiments of Formula (I), n is 1, 2, 3, 4, or 5 and at least one instance of $R^B$ is substituted or unsubstituted propyl. In certain embodiments of Formula (I), n is 1, 2, 3, 4, or 5; and at least one instance of $R^B$ is substituted or unsubstituted butyl. In certain embodiments of Formula (I), n is 1, 2, 3, 4, or 5; and at least one instance of $R^B$ is substituted or unsubstituted pentyl. In certain embodiments of Formula (I), n is 1, 2, 3, 4, or 5; and at least one instance of $R^B$ is substituted or unsubstituted hexyl.

In certain embodiments of Formula (I), n is 1, 2, 3, 4, or 5; and at least one instance of $R^B$ is substituted heteroalkyl, wherein at least one atom in the alkyl chain is selected from the group consisting of nitrogen, oxygen, and sulfur. In certain embodiments of Formula (I), n is 1, 2, 3, 4, or 5; and at least one instance of $R^B$ is unsubstituted heteroalkyl, wherein at least one atom in the alkyl chain is selected from the group consisting of nitrogen, oxygen, and sulfur. In certain embodiments of Formula (I), n is 1, 2, 3, 4, or 5 and at least one instance of $R^B$ is unsubstituted $C_{1-6}$ heteroalkyl, wherein at least one atom in the $C_{1-6}$ alkyl chain is selected from the group consisting of nitrogen, oxygen, and sulfur.

In certain embodiments of Formula (I), n is 1, 2, 3, 4, or 5 and at least one instance of $R^B$ is substituted or unsubstituted alkenyl, e.g., substituted or unsubstituted $C_{2-6}$alkenyl, substituted or unsubstituted $C_{2-5}$alkenyl, substituted or unsubstituted $C_{2-4}$alkenyl, or substituted or unsubstituted $C_{2-3}$alkenyl. In certain embodiments of Formula (I), n is 1, 2, 3, 4, or 5 and at least one instance of $R^B$ is unsubstituted alkenyl.

In certain embodiments of Formula (I), n is 1, 2, 3, 4, or 5 and at least one instance of $R^B$ is substituted or unsubstituted heteroalkenyl, e.g., substituted or unsubstituted $C_{2-6}$heteroalkenyl, substituted or unsubstituted $C_{2-5}$heteroalkenyl, substituted or unsubstituted $C_{2-4}$heteroalkenyl, or substituted or unsubstituted $C_{2-3}$heteroalkenyl, wherein at least one atom in the alkenyl chain is selected from the group consisting of nitrogen, oxygen, and sulfur. In certain embodiments of Formula (I), n is 1, 2, 3, 4, or 5 and at least one instance of $R^B$ is unsubstituted heteroalkenyl, wherein at least one atom in the alkenyl chain is selected from the group consisting of nitrogen, oxygen, and sulfur.

In certain embodiments of Formula (I), n is 1, 2, 3, 4, or 5 and at least one instance of $R^B$ is substituted alkynyl, e.g., substituted or unsubstituted $C_{2-6}$alkynyl, substituted or unsubstituted $C_{2-5}$alkynyl, substituted or unsubstituted $C_{2-4}$alkynyl, or substituted or unsubstituted $C_{2-3}$alkynyl. In certain embodiments of Formula (I), n is 1, 2, 3, 4, or 5 and at least one instance of $R^B$ is unsubstituted alkynyl.

In certain embodiments of Formula (I), n is 1, 2, 3, 4, or 5 and at least one instance of $R^B$ is substituted heteroalkynyl, e.g., substituted or unsubstituted $C_{2-6}$heteroalkynyl, substituted or unsubstituted $C_{2-5}$heteroalkynyl, substituted or unsubstituted $C_{2-4}$heteroalkynyl, or substituted or unsubstituted $C_{2-3}$heteroalkynyl, wherein at least one atom in the alkynyl chain is selected from the group consisting of nitrogen, oxygen, and sulfur. In certain embodiments of Formula (I), n is 1, 2, 3, 4, or 5 and at least one instance of $R^B$ is unsubstituted heteroalkynyl, wherein at least one atom in the alkynyl chain is selected from the group consisting of nitrogen, oxygen, and sulfur.

In certain embodiments of Formula (I), n is 1, 2, 3, 4, or 5 and at least one instance of $R^B$ is —$OR^{B1}$, wherein $R^{B1}$ is hydrogen (i.e., to provide —OH). In certain embodiments of Formula (I), n is 1, 2, 3, 4, or 5 and at least one instance of $R^B$ is —$OR^{B1}$, wherein $R^{B1}$ is a non-hydrogen group. In certain embodiments of Formula (I), n is 1, 2, 3, 4, or 5 and at least one instance of $R^B$ is —$OR^{B1}$, wherein $R^{B1}$ is a substituted or unsubstituted alkyl. In certain embodiments of Formula (I), n is 1, 2, 3, 4, or 5 and at least one instance of $R^B$ is —$OR^{B1}$, wherein $R^{B1}$ is a substituted or unsubstituted $C_{1-6}$ alkyl. For example, in certain embodiments of Formula (I), n is 1, 2, 3, 4, or 5 and at least one instance of $R^B$ is —$OR^{B1}$, wherein $R^{B1}$ is —$CH_3$ (i.e., to provide —$OCH_3$).

In certain embodiments of Formula (I), n is 1, 2, 3, 4, or 5 and at least one instance of $R^B$ is —$SR^{B1}$, wherein $R^{B1}$ is hydrogen (i.e., to provide —SH), or a non-hydrogen group.

In certain embodiments of Formula (I), n is 1, 2, 3, 4, or 5 and at least one instance of $R^B$ is —$N(R^{B1})_2$, wherein at least one $R^{B1}$ is hydrogen (e.g., to provide —$NH_2$ or $NHR^{B1}$), each $R^{B1}$ is a non-hydrogen group, or wherein two $R^{B1}$ groups are joined to form a substituted or unsubstituted heterocyclic or heteroaryl ring.

In certain embodiments of Formula (I), n is 1, 2, 3, 4, or 5; and at least one instance of $R^B$ is —CN.

In certain embodiments of Formula (I), n is 1, 2, 3, 4, or 5 and at least one instance of $R^B$ is —$NO_2$.

In certain embodiments of Formula (I), n is 1, 2, 3, 4, or 5 and at least one instance of $R^B$ is —$C(=NR^{B1})R^{B1}$, wherein $R^{B1}$ is hydrogen (i.e., to provide —C(=NH)H), or a non-hydrogen group.

In certain embodiments of Formula (I), n is 1, 2, 3, 4, or 5 and at least one instance of $R^B$ is —$C(=NR^{B1})OR^{B1}$, wherein $R^{B1}$ is hydrogen (i.e., to provide —C(=NH)OH), or a non-hydrogen group.

In certain embodiments of Formula (I), n is 1, 2, 3, 4, or 5 and at least one instance of $R^B$ is —$C(=NR^{B1})N(R^{B1})_2$, wherein $R^{B1}$ is hydrogen (i.e., to provide —C(=NH)$NH_2$), or a non-hydrogen group.

In certain embodiments of Formula (I), n is 1, 2, 3, 4, or 5 and at least one instance of $R^B$ is —$C(=O)R^{B1}$, wherein $R^{B1}$ is hydrogen (i.e., to provide —C(=O)H), or a non-hydrogen group.

In certain embodiments of Formula (I), n is 1, 2, 3, 4, or 5 and at least one instance of $R^B$ is —$C(=O)OR^{B1}$, wherein $R^{B1}$ is hydrogen (i.e., to provide —C(=O)OH), or a non-hydrogen group.

In certain embodiments of Formula (I), n is 1, 2, 3, 4, or 5 and at least one instance of $R^B$ is —$C(=O)N(R^{B1})_2$, wherein $R^{B1}$ is hydrogen (i.e., to provide —C(=O)$NH_2$), or a non-hydrogen group.

In certain embodiments of Formula (I), n is 1, 2, 3, 4, or 5 and at least one instance of $R^B$ is —$NR^{B1}C(=O)R^{B1}$, wherein $R^{B1}$ is hydrogen (i.e., to provide —NHC(=O)H), or a non-hydrogen group.

In certain embodiments of Formula (I), n is 1, 2, 3, 4, or 5 and at least one instance of $R^B$ is —$NR^{B1}C(=O)OR^{B1}$, wherein $R^{B1}$ is hydrogen (i.e., to provide —NHC(=O)OH), or a non-hydrogen group.

In certain embodiments of Formula (I), n is 1, 2, 3, 4, or 5 and at least one instance of $R^B$ is —$NR^{B1}C(=O)N(R^{B1})_2$, wherein $R^{B1}$ is hydrogen (i.e., to provide —NHC(=O)$NH_2$), or a non-hydrogen group.

In certain embodiments of Formula (I), n is 1, 2, 3, 4, or 5 and at least one instance of $R^B$ is —$OC(=O)R^{B1}$, wherein $R^{B1}$ is hydrogen (i.e., to provide —OC(=O)H), or a non-hydrogen group.

In certain embodiments of Formula (I), n is 1, 2, 3, 4, or 5 and at least one instance of $R^B$ is —$OC(=O)OR^{B1}$, wherein $R^{B1}$ is hydrogen (i.e., to provide —OC(=O)OH), or a non-hydrogen group.

In certain embodiments of Formula (I), n is 1, 2, 3, 4, or 5 and at least one instance of $R^B$ is —$OC(=O)N(R^{B1})_2$, wherein $R^{B1}$ is hydrogen (i.e., to provide —OC(=O)$NH_2$), or a non-hydrogen group.

In certain embodiments of Formula (I), n is 1, 2, 3, 4, or 5 at least one instance of $R^B$ is substituted or unsubstituted carbocyclyl. In certain embodiments of Formula (I), n is 1, 2, 3, 4, or 5 and at least one instance of $R^B$ is saturated carbocyclyl. In certain embodiments of Formula (I), n is 1, 2, 3, 4, or 5 and at least one instance of $R^B$ is unsaturated carbocyclyl. In certain embodiments of Formula (I), n is 1, 2, 3, 4, or 5 and at least one instance of $R^B$ is monocyclic $C_{3-7}$ carbocyclyl.

In certain embodiments of Formula (I), n is 1, 2, 3, 4, or 5 and at least one instance of $R^B$ is substituted or unsubstituted heterocyclyl. In certain embodiments of Formula (I), n is 1, 2, 3, 4, or 5 and at least one instance of $R^B$ is saturated heterocyclyl. In certain embodiments of Formula (I), n is 1, 2, 3, 4, or 5 and at least one instance of $R^B$ is unsaturated heterocyclyl. In certain embodiments of Formula (I), n is 1, 2, 3, 4, or 5 and at least one instance of $R^B$ is heterocyclyl, wherein one, two, or three atoms in the heterocyclic ring system are independently selected from the group consisting of nitrogen, oxygen, and sulfur.

In certain embodiments of Formula (I), n is 1, 2, 3, 4, or 5 and at least one instance of $R^B$ is 3- to 8-membered heterocyclyl. In certain embodiments of Formula (I), n is 1, 2, 3, 4, or 5 and at least one instance of $R^B$ is 5- to 6-membered heterocyclyl.

In certain embodiments of Formula (I), n is 1, 2, 3, 4, or 5 and at least one instance of $R^B$ is substituted or unsubstituted aryl. In certain embodiments of Formula (I), n is 1, 2, 3, 4, or 5 and at least one instance of $R^B$ is $C_{6-10}$ aryl. In certain embodiments of Formula (I), n is 1, 2, 3, 4, or 5 is at least one instance of $R^B$ is monocyclic aryl. In certain embodiments of Formula (I), n is 1, 2, 3, 4, or 5 and at least one instance of $R^B$ is substituted phenyl. In certain embodiments of Formula (I), n is 1, 2, 3, 4, or 5 and at least one instance of $R^B$ is unsubstituted phenyl. In certain embodiments of Formula (I), n is 1, 2, 3, 4, or 5 and at least one instance of $R^B$ is bicyclic aryl.

In certain embodiments of Formula (I), n is 1, 2, 3, 4, or 5 and at least one instance of $R^B$ is substituted or unsubstituted heteroaryl. In certain embodiments of Formula (I), n is 1, 2, 3, 4, or 5 and at least one instance of $R^B$ is heteroaryl, wherein one, two, three, or four atoms in the heteroaryl ring system are independently selected from the group consisting of nitrogen, oxygen, and sulfur. In certain embodiments of Formula (I), n is 1, 2, 3, 4, or 5 and at least one instance of $R^B$ is monocyclic heteroaryl. In certain embodiments of Formula (I), n is 1, 2, 3, 4, or 5 and at least one instance of $R^B$ is 5- or 6-membered, monocyclic heteroaryl. In certain embodiments of Formula (I), n is 1, 2, 3, 4, or 5 and at least one instance of $R^B$ is bicyclic heteroaryl, wherein the point of attachment may be on any atom of the bicyclic heteroaryl ring system, as valency permits.

Furthermore, as generally described herein, in any of the above described embodiments of group $R^B$ comprising a group $R^{B1}$, each instance of $R^{B1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{B1}$ groups are joined to form a substituted or unsubstituted carbocyclic, substituted or unsubstituted heterocyclic, substituted or unsubstituted aryl, or substituted or unsubstituted heteroaryl ring.

In any of the above described embodiments of $R^B$ comprising a group $R^{B1}$, at least one instance of $R^{B1}$ is substituted or unsubstituted alkyl, e.g., substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In some embodiments, $R^{B1}$ is $C_1$alkyl (e.g., methyl). In some embodiments, $R^{B1}$ is $C_2$ alkyl (e.g., ethyl). In some embodiments, $R^{B1}$ is $C_3$ alkyl (e.g., isopropyl, propyl).

In any of the above described embodiments of $R^B$ comprising a group $R^{B1}$, at least one instance of $R^{B1}$ is substituted or unsubstituted $C_{2-6}$alkenyl, e.g., substituted or unsubstituted $C_2$alkenyl, substituted or unsubstituted $C_3$alkenyl, substituted or unsubstituted $C_4$alkenyl, substituted or unsubstituted $C_5$alkenyl, or substituted or unsubstituted $C_6$alkenyl.

In any of the above described embodiments of $R^B$ comprising a group $R^{B1}$, at least one instance of $R^{B1}$ is substituted or unsubstituted $C_{2-6}$alkynyl, e.g., substituted or unsubstituted $C_2$alkynyl, substituted or unsubstituted $C_3$alkynyl, substituted or unsubstituted $C_4$alkynyl, substituted or unsubstituted $C_5$alkynyl, or substituted or unsubstituted $C_6$alkynyl.

In certain embodiments of Formula (I), e.g., wherein $R^B$ is —N($R^{B1}$)$_2$, —C(=N$R^{B1}$)N($R^{B1}$)$_2$, —C(=O)N($R^{B1}$)$_2$, —N$R^{B1}$C(=O)N($R^{B1}$)$_2$, or —OC(=O)N($R^{B1}$)$_2$, two instances of $R^{B1}$, e.g., attached to the same nitrogen (N) atom, are joined to form a substituted or unsubstituted heterocyclic ring. In certain embodiments of Formula (I), two instances of $R^{B1}$ are joined to form a saturated heterocyclic ring. In certain embodiments of Formula (I), two instances of $R^{B1}$ are joined to form an unsaturated heterocyclic ring. In certain embodiments of Formula (I), two instances of $R^{B1}$ are joined to form a heterocyclic ring, wherein one, two, or three atoms in the heterocyclic ring system are independently selected from the group consisting of nitrogen, oxygen, and sulfur. In certain embodiments of Formula (I), two instances of $R^{B1}$ are joined to form a 3- to 7-membered, monocyclic heterocyclic ring.

In certain embodiments of Formula (I), e.g., wherein $R^B$ is —N($R^{B1}$)$_2$, —C(=N$R^{B1}$)N($R^{B1}$)$_2$, —C(=O)N($R^{B1}$)$_2$, —N$R^{B1}$C(=O)N($R^{B1}$)$_2$, or —OC(=O)N($R^{B1}$)$_2$, two instances of $R^{B1}$, e.g., attached to the same nitrogen (N) atom, are joined to form a substituted or unsubstituted heteroaryl ring. In certain embodiments of Formula (I), two instances of $R^{B1}$ are joined to form a substituted or unsubstituted, 5- to 6-membered, monocyclic heteroaryl ring, wherein one, two, three, or four atoms in the heteroaryl ring system are independently nitrogen, oxygen, or sulfur. In certain embodiments of Formula (I), two instances of $R^{B1}$ are joined to form a substituted or unsubstituted, 9- to 10-membered, monocyclic heteroaryl ring, wherein one, two, three, or four atoms in the heteroaryl ring system are independently nitrogen, oxygen, or sulfur.

Group $R^Z$ and r

As generally described herein, $R^Z$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —O$R^{Z1}$, —N($R^{Z1}$)$_2$, —S$R^{Z1}$, —CN, —C($R^{Z1}$)$_3$, —SCN, —C(=N$R^{Z1}$)$R^{Z1}$, —C(=N$R^{Z1}$)O$R^{Z1}$, —C(=N$R^{Z1}$)N($R^{Z1}$)$_2$, —C(=O)$R^{Z1}$, —C(=O)O$R^{Z1}$, —C(=O)N($R^{Z1}$)$_2$, —NO$_2$, —N$R^{Z1}$C(=O)$R^{Z1}$, —N$R^{Z1}$C(=O)O$R^{Z1}$, —N$R^{Z1}$C(=O)N($R^{Z1}$)$_2$, —OC(=O)$R^{Z1}$, —OC(=O)O$R^{Z1}$, or —OC(=O)N($R^{Z1}$)$_2$, or two $R^Z$ groups are joined to form a substituted or unsubstituted carbocyclic, substituted or unsubstituted heterocyclic, substituted or unsubstituted aryl, or substituted or unsubstituted heteroaryl ring, wherein each instance of $R^{Z1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{Z1}$ groups are joined to form a substituted or unsubstituted carbocyclic, substituted or unsubstituted heterocyclic, substituted or unsubstituted aryl, or substituted or unsubstituted heteroaryl ring, and r is 0, 1, 2, or 3.

In some embodiments of Formula (I), r is 0; and $R^Z$ is absent.

In some embodiments of Formula (I), r is 1, and $R^Z$ is attached ortho to the point of attachment of —C(=O)—. In some embodiments of Formula (I), r is 1; and $R^Z$ is attached meta to the point of attachment of —C(=O)—. In some embodiments of Formula (I), r is 1, and $R^Z$ is attached para to the point of attachment of —C(=O)—.

In some embodiments of Formula (I), r is 2. In some embodiments of Formula (I), r is 2 and each $R^Z$ is independently a group as described herein, wherein one $R^Z$ group is attached ortho and one $R^Z$ group is attached meta to the point of attachment of —C(=O)—. In some embodiments of Formula (I), r is 2 and each $R^Z$ is independently a group as described herein, wherein one $R^Z$ group is attached ortho and one $R^Z$ group is attached para to the point of attachment of —C(=O)—. In some embodiments of Formula (I), r is 2 and each $R^Z$ is independently a group as described herein, wherein one $R^Z$ group is attached para and one $R^Z$ group is attached meta to the point of attachment of —C(=O)—.

In some embodiments of Formula (I), r is 3 and each $R^Z$ is independently a group as described herein. In certain embodiments of Formula (I), r is 1, 2, or 3 and at least one instance of $R^Z$ is hydrogen. In certain embodiments of Formula (I), r is 1 and $R^Z$ is hydrogen. In certain embodiments of Formula (I), r is 2 and both instances of $R^Z$ are hydrogen. In certain embodiments of Formula (I), r is 3; and all three instances of $R^Z$ are hydrogen.

In certain embodiments of Formula (I), r is 1, 2, or 3; and at least one instance of $R^Z$ is halogen. In certain embodiments of Formula (I), r is 1, 2, or 3 and at least one instance of $R^Z$ is F. In certain embodiments of Formula (I), r is 1, 2, or 3 and at least one instance of $R^Z$ is Cl. In certain embodiments of Formula (I), r is 1, 2, or 3 and at least one instance of $R^Z$ is Br. In certain embodiments of Formula (I), r is 1, 2, or 3 and at least one instance of $R^Z$ is I (iodine). In certain embodiments of Formula (I), r is 1 and $R^Z$ is halogen. In some embodiments of Formula (I), r is 1 and $R^Z$ is Cl (chlorine). In some embodiments of Formula (I), r is 1 and $R^Z$ is Br (bromine). In some embodiments of Formula (I), r is 1 and $R^Z$ is I (iodine).

In certain embodiments of Formula (I), r is 1, 2, or 3 and at least one instance of $R^Z$ is substituted alkyl. In certain embodiments of Formula (I), r is 1, 2, or 3 and at least one instance of $R^Z$ is unsubstituted alkyl. In certain embodiments of Formula (I), r is 1, 2, or 3 and at least one instance of $R^Z$ is unsubstituted $C_{1-6}$ alkyl. In certain embodiments of Formula (I), r is 1, 2, or 3 and at least one instance of $R^Z$ is substituted $C_{1-6}$ alkyl. In certain embodiments of Formula (I), r is 1, 2, or 3 and at least one instance of $R^Z$ is —CH$_3$. In certain embodiments of Formula (I), r is 1, 2, or 3 and at least one instance of $R^Z$ is $C_{1-6}$ alkyl substituted with at least one halogen. In certain embodiments of Formula (I), r is 1, 2, or 3 and at least one instance of $R^Z$ is substituted methyl. In certain embodiments of Formula (I), r is 1, 2, or 3 and at least one instance of $R^Z$ is —CH$_2$F. In certain embodiments of Formula (I), r is 1, 2, or 3 and at least one instance of $R^Z$ is —CHF$_2$. In certain embodiments of Formula (I), r is 1, 2, or 3 and at least one instance of $R^Z$ is —CF$_3$. In certain embodiments of Formula (I), r is 1, 2, or 3 and at least one instance of $R^Z$ is substituted or unsubstituted ethyl. In certain embodiments of Formula (I), r is 1, 2, or 3 and at least one instance of $R^Z$ is substituted or unsubstituted propyl. In certain embodiments of Formula (I), r is 1, 2, or 3 and at least one instance of $R^Z$ is substituted or unsubstituted butyl. In certain embodiments of Formula (I), r is 1, 2, or 3 and at least one instance of $R^Z$ is substituted or unsubstituted pentyl. In certain embodiments of Formula (I), r is 1, 2, or 3 and at least one instance of $R^Z$ is substituted or unsubstituted hexyl.

In certain embodiments of Formula (I), r is 1, 2, or 3 and at least one instance of $R^Z$ is substituted heteroalkyl, wherein at least one atom in the alkyl chain is selected from the group consisting of nitrogen, oxygen, and sulfur. In certain embodiments of Formula (I), r is 1, 2, or 3 and at least one instance of $R^Z$ is unsubstituted heteroalkyl, wherein at least one atom in the alkyl chain is selected from the group consisting of nitrogen, oxygen, and sulfur.

In certain embodiments of Formula (I), r is 1, 2, or 3 and at least one instance of $R^Z$ is unsubstituted $C_{1-6}$ heteroalkyl, wherein at least one atom in the $C_{1-6}$ alkyl chain is selected from the group consisting of nitrogen, oxygen, and sulfur.

In certain embodiments of Formula (I), r is 1, 2, or 3 and at least one instance of $R^Z$ is substituted or unsubstituted alkenyl, e.g., substituted or unsubstituted $C_{2-6}$alkenyl, substituted or unsubstituted $C_{2-5}$alkenyl, substituted or unsubstituted $C_{2-4}$alkenyl, or substituted or unsubstituted $C_{2-3}$alkenyl. In certain embodiments of Formula (I), r is 1, 2, or 3 and at least one instance of $R^Z$ is unsubstituted alkenyl.

In certain embodiments of Formula (I), r is 1, 2, or 3 and at least one instance of $R^Z$ is substituted or unsubstituted heteroalkenyl, e.g., substituted or unsubstituted $C_{2-6}$heteroalkenyl, substituted or unsubstituted $C_{2-5}$heteroalkenyl, substituted or unsubstituted $C_{2-4}$ heteroalkenyl, or substituted or unsubstituted $C_{2-3}$heteroalkenyl, wherein at least one atom in the alkenyl chain is selected from the group consisting of nitrogen, oxygen, and sulfur. In certain embodiments of Formula (I), r is 1, 2, or 3 and at least one instance of $R^Z$ is unsubstituted heteroalkenyl, wherein at least one atom in the alkenyl chain is selected from the group consisting of nitrogen, oxygen, and sulfur.

In certain embodiments of Formula (I), r is 1, 2, or 3 and at least one instance of $R^Z$ is substituted alkynyl, e.g., substituted or unsubstituted $C_{2-6}$alkynyl, substituted or unsubstituted $C_{2-5}$alkynyl, substituted or unsubstituted $C_{2-4}$alkynyl, or substituted or unsubstituted $C_{2-3}$alkynyl. In certain embodiments of Formula (I), r is 1, 2, or 3 and at least one instance of $R^Z$ is unsubstituted alkynyl.

In certain embodiments of Formula (I), r is 1, 2, or 3 and at least one instance of $R^Z$ is substituted heteroalkynyl, e.g., substituted or unsubstituted $C_{2-6}$heteroalkynyl, substituted or unsubstituted $C_{2-5}$heteroalkynyl, substituted or unsubstituted $C_{2-4}$heteroalkynyl, or substituted or unsubstituted $C_{2-3}$heteroalkynyl, wherein at least one atom in the alkynyl chain is selected from the group consisting of nitrogen, oxygen, and sulfur. In certain embodiments of Formula (I), r is 1, 2, or 3 and at least one instance of $R^Z$ is unsubstituted heteroalkynyl, wherein at least one atom in the alkynyl chain is selected from the group consisting of nitrogen, oxygen, and sulfur.

In certain embodiments of Formula (I), r is 1, 2, or 3 and at least one instance of $R^Z$ is —OR$^{Z1}$, wherein $R^{Z1}$ is hydrogen (i.e., to provide —OH). In certain embodiments of Formula (I), r is 1, 2, or 3 and at least one instance of $R^Z$ is —OR$^{Z1}$, wherein $R^{Z1}$ is a non-hydrogen group. In certain embodiments of Formula (I), r is 1, 2, or 3 and at least one instance of $R^Z$ is —OR$^{Z1}$, wherein $R^{Z1}$ is a substituted or unsubstituted alkyl. In certain embodiments of Formula (I), r is 1, 2, or 3 and at least one instance of $R^Z$ is —OR$^{Z1}$, wherein $R^{Z1}$ is a substituted or unsubstituted $C_{1-6}$ alkyl. For example, in certain embodiments of Formula (I), r is 1, 2, or 3 and at least one instance of $R^Z$ is —OR$^{Z1}$, wherein $R^{Z1}$ is —CH$_3$ (i.e., to provide —OCH$_3$).

In certain embodiments of Formula (I), r is 1, 2, or 3 and at least one instance of $R^Z$ is —SR$^{Z1}$, wherein $R^{Z1}$ is hydrogen (i.e., to provide —SH), or a non-hydrogen group.

In certain embodiments of Formula (I), r is 1, 2, or 3 and at least one instance of $R^Z$ is —N(R$^{Z1}$)$_2$, wherein at least one $R^{Z1}$ is hydrogen (e.g., to provide —NH$_2$ or NHR$^{Z1}$), each $R^{Z1}$ is a non-hydrogen group, or wherein two $R^{B1}$ groups are joined to form a substituted or unsubstituted heterocyclic or heteroaryl ring.

In certain embodiments of Formula (I), r is 1, 2, or 3 and at least one instance of $R^Z$ is —CN.

In certain embodiments of Formula (I), r is 1, 2, or 3 and at least one instance of $R^Z$ is —NO$_2$.

In certain embodiments of Formula (I), r is 1, 2, or 3 and at least one instance of $R^Z$ is —C(=NR$^{11}$)R$^1$, wherein $R^{Z1}$ is hydrogen (i.e., to provide —C(=NH)H), or a non-hydrogen group.

In certain embodiments of Formula (I), r is 1, 2, or 3 and at least one instance of $R^Z$ is —C(=NR$^{Z1}$)OR$^{Z1}$, wherein $R^{Z1}$ is hydrogen (i.e., to provide —C(=NH)OH), or a non-hydrogen group.

In certain embodiments of Formula (I), r is 1, 2, or 3 and at least one instance of $R^Z$ is —C(=NR$^{Z1}$)N(R$^{Z1}$)$_2$, wherein $R^{Z1}$ is hydrogen (i.e., to provide —C(=NH)NH$_2$), or a non-hydrogen group.

In certain embodiments of Formula (I), r is 1, 2, or 3 and at least one instance of $R^Z$ is —C(=O)R$^{Z1}$, wherein $R^{Z1}$ is hydrogen (i.e., to provide —C(=O)H), or a non-hydrogen group.

In certain embodiments of Formula (I), r is 1, 2, or 3 and at least one instance of $R^Z$ is —C(=O)OR$^{Z1}$, wherein $R^{Z1}$ is hydrogen (i.e., to provide —C(=O)OH), or a non-hydrogen group.

In certain embodiments of Formula (I), r is 1, 2, or 3 and at least one instance of $R^Z$ is —C(=O)N(R$^{Z1}$)$_2$, wherein $R^{Z1}$ is hydrogen (i.e., to provide —C(=O)NH$_2$), or a non-hydrogen group.

In certain embodiments of Formula (I), r is 1, 2, or 3 and at least one instance of $R^Z$ is —NR$^{Z1}$C(=O)R$^{Z1}$, wherein $R^{Z1}$ is hydrogen (i.e., to provide —NHC(=O)H), or a non-hydrogen group.

In certain embodiments of Formula (I), r is 1, 2, or 3 and at least one instance of $R^Z$ is —NR$^{Z1}$C(=O)OR$^{Z1}$, wherein $R^{Z1}$ is hydrogen (i.e., to provide —NHC(=O)OH), or a non-hydrogen group.

In certain embodiments of Formula (I), r is 1, 2, or 3 and at least one instance of $R^Z$ is —NR$^{Z1}$C(=O)N(R$^{Z1}$)$_2$, wherein $R^{Z1}$ is hydrogen (i.e., to provide —NHC(=O)NH$_2$), or a non-hydrogen group.

In certain embodiments of Formula (I), r is 1, 2, or 3 and at least one instance of $R^Z$ is —OC(=O)R$^{Z1}$, wherein $R^{Z1}$ is hydrogen (i.e., to provide —OC(=O)H), or a non-hydrogen group.

In certain embodiments of Formula (I), r is 1, 2, or 3 and at least one instance of $R^Z$ is —OC(=O)OR$^{Z1}$, wherein $R^{Z1}$ is hydrogen (i.e., to provide —OC(=O)OH), or a non-hydrogen group.

In certain embodiments of Formula (I), r is 1, 2, or 3 and at least one instance of $R^Z$ is —OC(=O)N(R$^{Z1}$)$_2$, wherein $R^{Z1}$ is hydrogen (i.e., to provide —OC(=O)NH$_2$), or a non-hydrogen group.

In certain embodiments of Formula (I), r is 1, 2, or 3 at least one instance of $R^Z$ is substituted or unsubstituted carbocyclyl. In certain embodiments of Formula (I), r is 1, 2, or 3 and at least one instance of $R^Z$ is saturated carbocyclyl. In certain embodiments of Formula (I), r is 1, 2, or 3 and at least one instance of $R^Z$ is unsaturated carbocyclyl. In certain embodiments of Formula (I), r is 1, 2, or 3 and at least one instance of $R^Z$ is monocyclic $C_{3-7}$ carbocyclyl.

In certain embodiments of Formula (I), r is 1, 2, or 3 and at least one instance of $R^Z$ is substituted or unsubstituted heterocyclyl. In certain embodiments of Formula (I), r is 1, 2, or 3 and at least one instance of $R^Z$ is saturated heterocyclyl. In certain embodiments of Formula (I), r is 1, 2, or 3 and at least one instance of $R^Z$ is unsaturated heterocyclyl. In certain embodiments of Formula (I), r is 1, 2, or 3 and at least one instance of $R^Z$ is heterocyclyl, wherein one, two, or three atoms in the heterocyclic ring system are independently selected from the group consisting of nitrogen, oxygen, and sulfur. In certain embodiments of Formula (I), r is 1, 2, or 3 and at least one instance of $R^Z$ is 3- to 8-membered heterocyclyl. In certain embodiments of Formula (I), r is 1, 2, or 3 and at least one instance of $R^Z$ is 5- to 6-membered heterocyclyl.

In certain embodiments of Formula (I), r is 1, 2, or 3 and at least one instance of $R^Z$ is substituted or unsubstituted aryl. In certain embodiments of Formula (I), r is 1, 2, or 3 and at least one instance of $R^Z$ is $C_{6-10}$ aryl. In certain embodiments of Formula (I), r is 1, 2, or 3 is at least one instance of $R^Z$ is monocyclic aryl. In certain embodiments of Formula (I), r is 1, 2, or 3 and at least one instance of $R^Z$ is substituted phenyl. In certain embodiments of Formula (I), r is 1, 2, or 3 and at least one instance of $R^Z$ is unsubstituted phenyl. In certain embodiments of Formula (I), r is 1, 2, or 3 and at least one instance of $R^Z$ is bicyclic aryl.

In certain embodiments of Formula (I), r is 1, 2, or 3 and at least one instance of $R^Z$ is substituted or unsubstituted heteroaryl. In certain embodiments of Formula (I), r is 1, 2, or 3 and at least one instance of $R^Z$ is heteroaryl, wherein one, two, three, or four atoms in the heteroaryl ring system are independently selected from the group consisting of nitrogen, oxygen, and sulfur. In certain embodiments of Formula (I), r is 1, 2, or 3 and at least one instance of $R^Z$ is monocyclic heteroaryl. In certain embodiments of Formula (I), r is 1, 2, or 3 and at least one instance of $R^Z$ is 5- or 6-membered, monocyclic heteroaryl. In certain embodiments of Formula (I), r is 1, 2, or 3 and at least one instance of $R^Z$ is bicyclic heteroaryl, wherein the point of attachment may be on any atom of the bicyclic heteroaryl ring system, as valency permits.

Furthermore, as generally described herein, in any of the above described embodiments of group $R^Z$ comprising a group $R^{Z1}$, each instance of $R^{Z1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{Z1}$ groups are joined to form a substituted or unsubstituted carbocyclic, substituted or unsubstituted heterocyclic, substituted or unsubstituted aryl, or substituted or unsubstituted heteroaryl ring.

In any of the above described embodiments of $R^Z$ comprising a group $R^{Z1}$, at least one instance of $R^{Z1}$ is substituted or unsubstituted alkyl, e.g., substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In some embodiments, $R^{Z1}$ is $C_1$alkyl (e.g., methyl). In some embodiments, $R^{Z1}$ is $C_2$ alkyl (e.g., ethyl). In some embodiments, $R^{Z1}$ is $C_3$ alkyl (e.g., isopropyl, propyl).

In any of the above described embodiments of $R^Z$ comprising a group $R^{Z1}$, at least one instance of $R^{B1}$ is substituted or unsubstituted $C_{2-6}$alkenyl, e.g., substituted or unsubstituted $C_2$alkenyl, substituted or unsubstituted $C_3$alkenyl, substituted or unsubstituted $C_4$alkenyl, substituted or unsubstituted $C_5$alkenyl, or substituted or unsubstituted $C_6$alkenyl.

In any of the above described embodiments of $R^Z$ comprising a group $R^{Z1}$, at least one instance of $R^{Z1}$ is substituted or unsubstituted $C_{2-6}$alkynyl, e.g., substituted or unsubstituted $C_2$alkynyl, substituted or unsubstituted $C_3$alkynyl, substituted or unsubstituted $C_4$alkynyl, substituted or unsubstituted $C_5$alkynyl, or substituted or unsubstituted $C_6$alkynyl.

In certain embodiments of Formula (I), e.g., wherein $R^Z$ is —N($R^{Z1}$)$_2$, —C(=N$R^{Z1}$)N($R^{Z1}$)$_2$, —C(=O)N($R^{Z1}$)$_2$, —N$R^{Z1}$C(=O)N($R^{Z1}$)$_2$, or —OC(=O)N($R^{Z1}$)$_2$, two instances of $R^{Z1}$, e.g., attached to the same nitrogen (N) atom, are joined to form a substituted or unsubstituted heterocyclic ring. In certain embodiments of Formula (I), two instances of $R^{Z1}$ are joined to form a saturated heterocyclic ring. In certain embodiments of Formula (I), two instances of $R^{Z1}$ are joined to form an unsaturated heterocyclic ring. In certain embodiments of Formula (I), two instances of $R^{Z1}$ are joined to form a heterocyclic ring, wherein one, two, or three atoms in the heterocyclic ring system are independently selected from the group consisting of nitrogen, oxygen, and sulfur. In certain embodiments of Formula (I), two instances of $R^{Z1}$ are joined to form a 3- to 7-membered, monocyclic heterocyclic ring.

In certain embodiments of Formula (I), e.g., wherein $R^Z$ is —N($R^{Z1}$)$_2$, —C(=N$R^{Z1}$)N($R^{Z1}$)$_2$, —C(=O)N($R^{Z1}$)$_2$, —N$R^{Z1}$C(=O)N($R^{Z1}$)$_2$, or —OC(=O)N($R^{Z1}$)$_2$, two instances of $R^{Z1}$, e.g., attached to the same nitrogen (N) atom, are joined to form a substituted or unsubstituted heteroaryl ring. In certain embodiments of Formula (I), two instances of $R^Z$ are joined to form a substituted or unsubstituted, 5- to 6-membered, monocyclic heteroaryl ring, wherein one, two, three, or four atoms in the heteroaryl ring system are independently nitrogen, oxygen, or sulfur. In certain embodiments of Formula (I), two instances of $R^{Z1}$ are joined to form a substituted or unsubstituted, 9- to 10-membered, monocyclic heteroaryl ring, wherein one, two, three, or four atoms in the heteroaryl ring system are independently nitrogen, oxygen, or sulfur.

Group $R^W$

As generally described herein, each $R^W$ is independently hydrogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to nitrogen, two $R^W$ groups are joined to form a substituted or unsubstituted carbocyclic, substituted or unsubstituted heterocyclic, substituted or unsubstituted aryl, or substituted or unsubstituted heteroaryl ring, or $R^B$ and $R^W$ are joined to form a substituted or unsubstituted carbocyclic, substituted or unsubstituted heterocyclic, substituted or unsubstituted aryl, or substituted or unsubstituted heteroaryl ring.

In certain embodiments of Formula (I), $R^W$ is hydrogen. In certain embodiments of Formula (I), $R^W$ is halogen. In certain embodiments of Formula (I), $R^W$ is F. In certain embodiments of Formula (I), $R^W$ is Cl. In certain embodiments of Formula (I), $R^W$ is Br. In certain embodiments of Formula (I), $R^W$ is I (iodine).

In certain embodiments of Formula (I), $R^W$ is substituted alkyl. In certain embodiments of Formula (I), $R^W$ is unsubstituted alkyl. In certain embodiments of Formula (I), $R^W$ is unsubstituted $C_{1-6}$ alkyl. In certain embodiments of Formula (I), $R^W$ is substituted $C_{1-6}$ alkyl. In certain embodiments of Formula (I), $R^W$ is —CH$_3$. In certain embodiments of Formula (I), $R^W$ is $C_{1-6}$ alkyl substituted with at least one halogen. In certain embodiments of Formula (I), $R^W$ is substituted methyl. In certain embodiments of Formula (I), $R^W$ is —CH$_2$F.

In certain embodiments of Formula (I), $R^W$ is —CHF$_2$. In certain embodiments of Formula (I), $R^W$ is —CF$_3$. In certain embodiments of Formula (I), $R^W$ is substituted or unsubstituted ethyl.

In certain embodiments of Formula (I), $R^W$ is substituted or unsubstituted propyl. In certain embodiments of Formula (I), $R^W$ is substituted or unsubstituted butyl. In certain embodiments of Formula (I), $R^W$ is substituted or unsubstituted pentyl. In certain embodiments of Formula (I), $R^W$ is substituted or unsubstituted hexyl.

In certain embodiments of Formula (I), $R^W$ is substituted heteroalkyl, wherein at least one atom in the alkyl chain is selected from the group consisting of nitrogen, oxygen, and sulfur. In certain embodiments of Formula (I), $R^W$ is unsubstituted heteroalkyl, wherein at least one atom in the alkyl chain is selected from the group consisting of nitrogen, oxygen, and sulfur. In certain embodiments of Formula (I), $R^W$ is unsubstituted $C_{1-6}$ heteroalkyl, wherein at least one atom in the $C_{1-6}$ alkyl chain is selected from the group consisting of nitrogen, oxygen, and sulfur.

In certain embodiments of Formula (I), $R^W$ is substituted or unsubstituted alkenyl, e.g., substituted or unsubstituted $C_{2-6}$alkenyl, substituted or unsubstituted $C_{2-5}$alkenyl, substituted or unsubstituted $C_{2-4}$alkenyl, or substituted or unsubstituted $C_{2-3}$alkenyl. In certain embodiments of Formula (I), $R^W$ is unsubstituted alkenyl.

In certain embodiments of Formula (I), $R^W$ is substituted or unsubstituted heteroalkenyl, e.g., substituted or unsubstituted $C_{2-6}$heteroalkenyl, substituted or unsubstituted $C_{2-5}$heteroalkenyl, substituted or unsubstituted $C_{2-4}$heteroalkenyl, or substituted or unsubstituted $C_{2-3}$heteroalkenyl, wherein at least one atom in the alkenyl chain is selected from the group consisting of nitrogen, oxygen, and sulfur. In certain embodiments of Formula (I), $R^W$ is unsubstituted heteroalkenyl, wherein at least one atom in the alkenyl chain is selected from the group consisting of nitrogen, oxygen, and sulfur.

In certain embodiments of Formula (I), $R^W$ is substituted alkynyl, e.g., substituted or unsubstituted $C_{2-6}$alkynyl, substituted or unsubstituted $C_{2-5}$alkynyl, substituted or unsubstituted $C_{2-4}$alkynyl, or substituted or unsubstituted $C_{2-3}$alkynyl. In certain embodiments of Formula (I), $R^W$ is unsubstituted alkynyl.

In certain embodiments of Formula (I), $R^W$ is substituted heteroalkynyl, e.g., substituted or unsubstituted $C_{2-6}$heteroalkynyl, substituted or unsubstituted $C_{2-5}$heteroalkynyl, substituted or unsubstituted $C_{2-4}$heteroalkynyl, or substituted or unsubstituted $C_{2-3}$ heteroalkynyl, wherein at least one atom in the alkynyl chain is selected from the group consisting of nitrogen, oxygen, and sulfur. In certain embodiments of Formula (I), $R^W$ is unsubstituted heteroalkynyl, wherein at least one atom in the alkynyl chain is selected from the group consisting of nitrogen, oxygen, and sulfur.

In certain embodiments of Formula (I), $R^W$ is a nitrogen protecting group when attached to a nitrogen atom. In certain embodiments of Formula (I), at least one instance of $R^W$ is Bn, Boc, Cbz, Fmoc, trifluoroacetyl, triphenylmethyl, acetyl, or Ts when attached to a nitrogen atom.

In certain embodiments of Formula (I), $R^W$ is substituted or unsubstituted carbocyclyl. In certain embodiments of Formula (I), $R^W$ is saturated carbocyclyl. In certain embodiments of Formula (I), $R^W$ is unsaturated carbocyclyl. In certain embodiments of Formula (I), $R^W$ is monocyclic $C_{3-7}$ carbocyclyl.

In certain embodiments of Formula (I), $R^W$ is substituted or unsubstituted heterocyclyl. In certain embodiments of Formula (I), $R^W$ is saturated heterocyclyl. In certain embodiments of Formula (I), $R^W$ is unsaturated heterocyclyl. In certain embodiments of Formula (I), $R^W$ is heterocyclyl, wherein one, two, or three atoms in the heterocyclic ring system are independently selected from the group consisting of nitrogen, oxygen, and sulfur.

In certain embodiments of Formula (I), $R^W$ is 3- to 8-membered heterocyclyl. In certain embodiments of Formula (I), $R^W$ is 5- to 6-membered heterocyclyl.

In certain embodiments of Formula (I), $R^W$ is substituted or unsubstituted aryl. In certain embodiments of Formula (I), $R^W$ is $C_{6-10}$ aryl. In certain embodiments of Formula (I), $R^W$ is monocyclic aryl. In certain embodiments of Formula (I), $R^W$ is substituted phenyl. In certain embodiments of Formula (I), $R^W$ is unsubstituted phenyl. In certain embodiments of Formula (I), $R^W$ is bicyclic aryl.

In certain embodiments of Formula (I), $R^W$ is substituted or unsubstituted heteroaryl. In certain embodiments of Formula (I), $R^W$ is heteroaryl, wherein one, two, three, or four atoms in the heteroaryl ring system are independently selected from the group consisting of nitrogen, oxygen, and sulfur. In certain embodiments of Formula (I), $R^W$ is monocyclic heteroaryl. In certain embodiments of Formula (I), $R^W$ is 5- or 6-membered, monocyclic heteroaryl. In certain embodiments of Formula (I), $R^W$ is bicyclic heteroaryl, wherein the point of attachment may be on any atom of the bicyclic heteroaryl ring system, as valency permits.

In some embodiments of Formula (I), $R^W$ is substituted or unsubstituted acyl. In some embodiments of Formula (I), $R^W$ is substituted acyl. In some embodiments of Formula (I), $R^W$ is unsubstituted acyl.

In certain embodiments of Formula (I), e.g., wherein $R^W$ is substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, or substituted or unsubstituted acyl, $R^W$ and $R^B$ are joined to form a substituted or unsubstituted heterocyclic ring. In certain embodiments of Formula (I), $R^W$ and $R^B$ are joined to form a saturated heterocyclic ring. In certain embodiments of Formula (I), $R^W$ and $R^B$ are joined to form an unsaturated heterocyclic ring. In certain embodiments of Formula (I), $R^W$ and $R^B$ are joined to form a heterocyclic ring, wherein one, two, or three atoms in the heterocyclic ring system are independently selected from the group consisting of nitrogen, oxygen, and sulfur. In certain embodiments of Formula (I), $R^W$ and $R^B$ are joined to form a 3- to 7-membered, monocyclic heterocyclic ring. In certain embodiments of Formula (I), $R^C$ and $R^X$ are joined to form a 5- to 6-membered heterocyclic ring.

In certain embodiments of Formula (I), e.g., $R^C$ is substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, or substituted or unsubstituted acyl, $R^W$ and $R^B$ are joined to form a substituted or unsubstituted heteroaryl ring. In certain embodiments of Formula (I), $R^B$ and $R^W$ are joined to form a substituted or unsubstituted, 5- to 6-membered, monocyclic heteroaryl ring, wherein one, two, three, or four atoms in the heteroaryl ring system are independently nitrogen, oxygen, or sulfur. In certain embodiments of Formula (I), $R^B$ and $R^W$ are joined to form a substituted or unsubstituted, 9- to 10-membered, monocyclic heteroaryl ring, wherein one, two, three, or four atoms in the heteroaryl ring system are independently nitrogen, oxygen, or sulfur.

In some embodiments, the compound of Formula (I) is a compound of the formula:

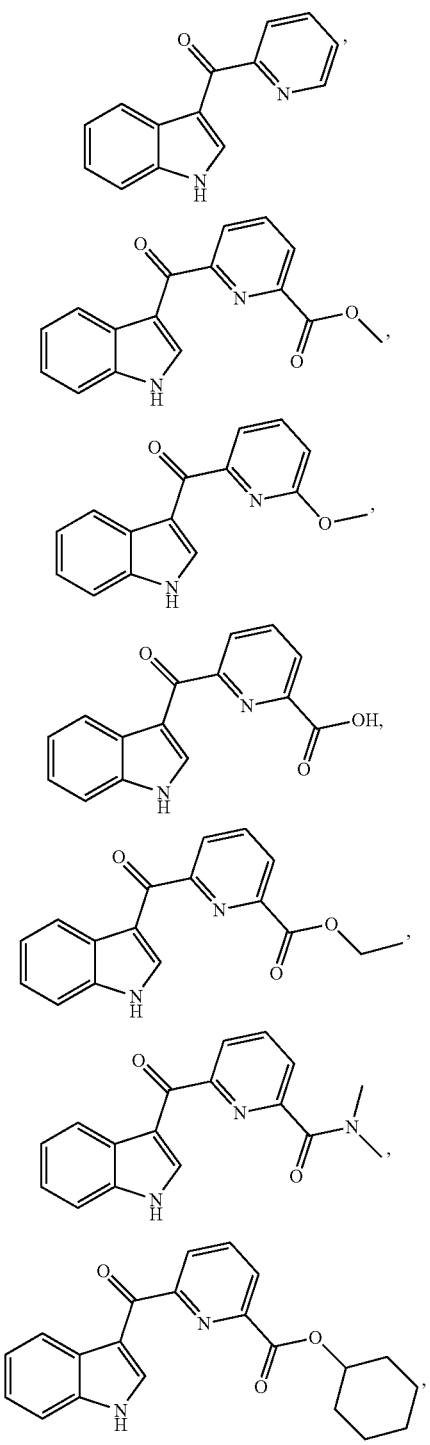

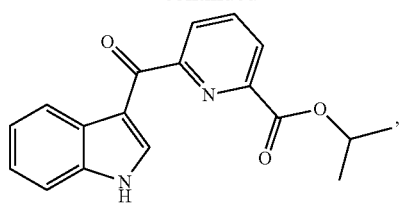
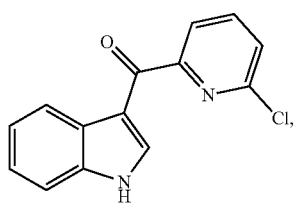
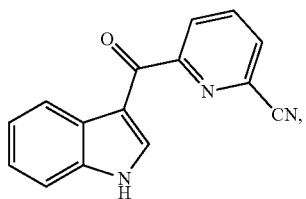
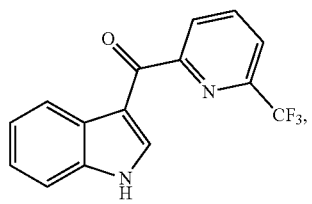
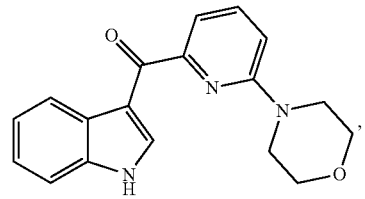
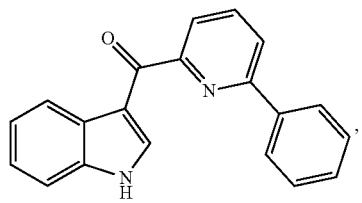
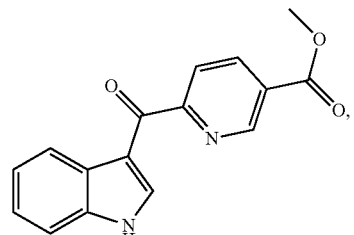
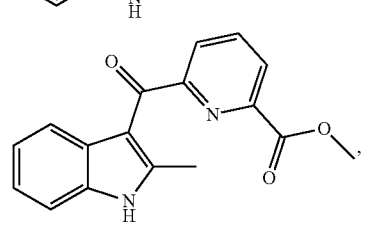
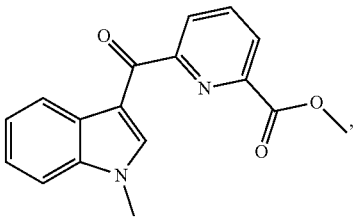
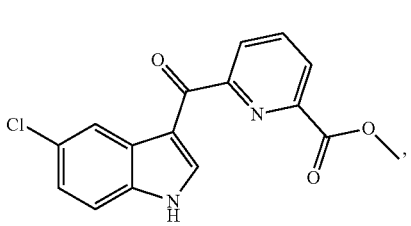
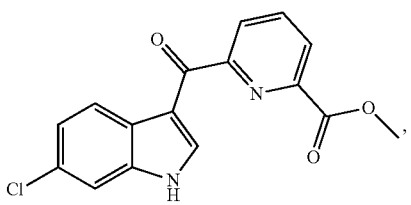
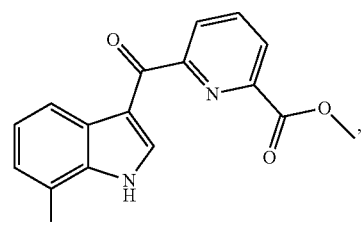
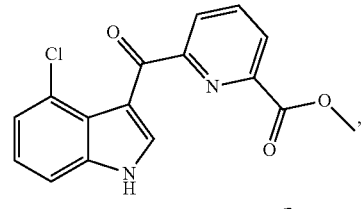
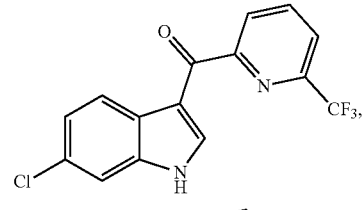
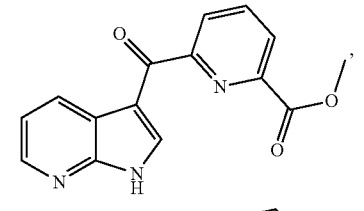
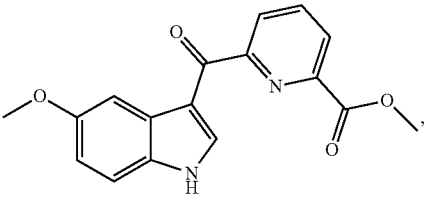

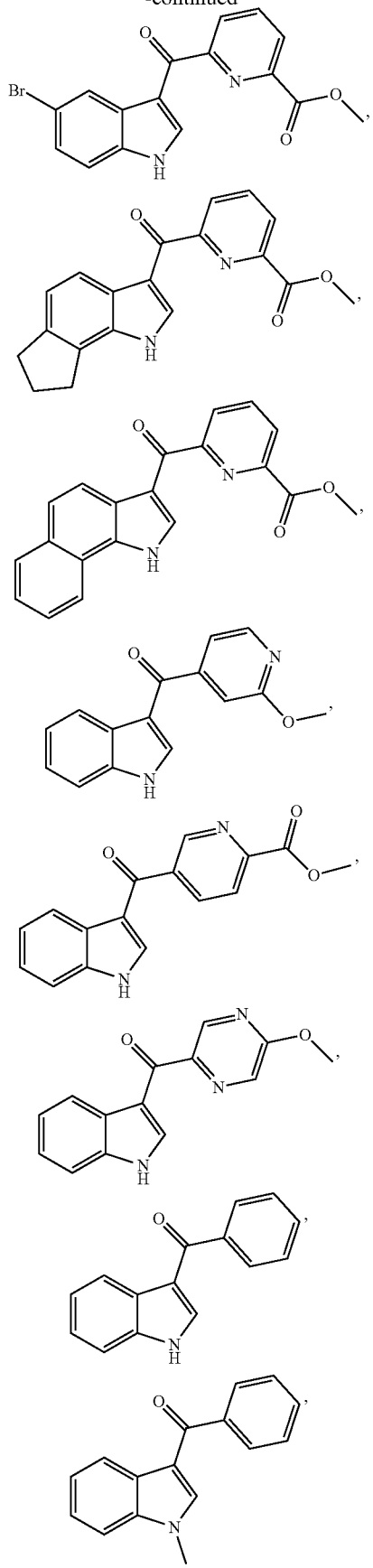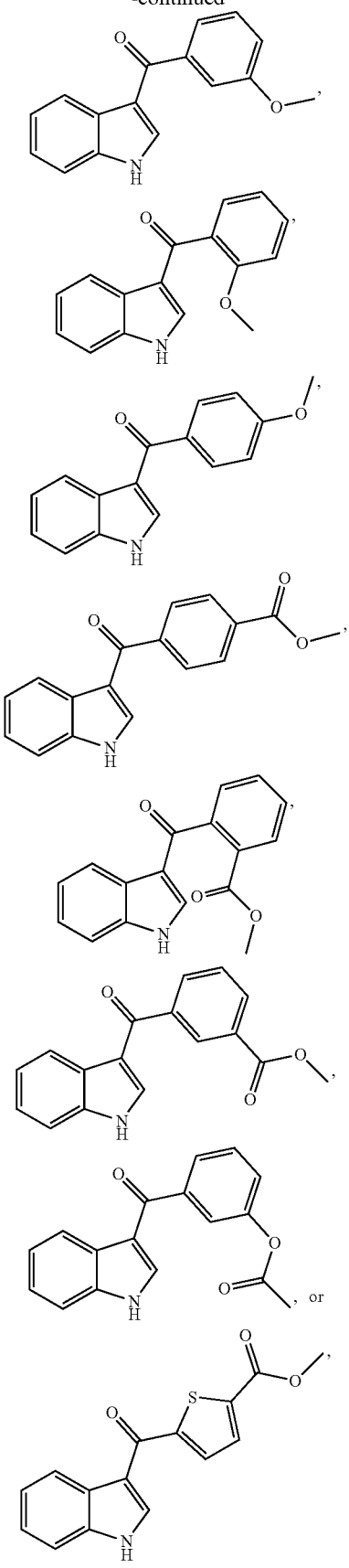

or a pharmaceutically acceptable salt, hydrate, solvate, stereoisomer, tautomer, isotopically labeled derivative, polymorph, or prodrug thereof.

Aryl Hydrocarbon Receptor Modulators

In certain embodiments, a compound of Formula (I) provided herein modulates an aryl hydrocarbon receptor. In some embodiments, the compound is an aryl hydrocarbon receptor agonist. In some embodiments, the compound is a partial aryl hydrocarbon agonist. The compounds provided herein may bind to and increase the activity of the aryl hydrocarbon receptor. Without wishing to be bound by any particular theory, Without wishing to be bound by any particular theory, activation of the acyl hydrocarbon receptor (e.g., by binding to an agonist) results in changes in gene expression, leading to modulation of expression of proteins (e.g., cytokines) to influence inflammatory, metabolic, and other biological responses. Modulation of biological responses by aryl hydrocarbon receptors is discussed in, e.g., Bieschlag T V et al. (2008) The aryl hydrocarbon receptor complex and the control of gene expression. *Crit Rev Eukaryot Gene Expr* 18, 207-250; Nebert D W et al. (2000) Role of the aromatic hydrocarbon receptor and [Ah] gene battery in the oxidative stress response, cell cycle control, and apoptosis. *Biochemical Pharmacology* 59, 65-85; Quintana F J et al. (2008) Control of $T_{reg}$ and $T_H17$ cell differentiation by the aryl hydrocarbon receptor. *Nature* 453, 65-71; and Puga A et al. (2009) The aryl hydrocarbon receptor cross-talks with multiple signal transduction pathways. *Biochemical Pharmacology* 77, 713-722; each of which is incorporated herein by reference in its entirety.

An aryl hydrocarbon receptor (AhR, AHR, ahr, or ahR) is a ligand-activated transcription factor involved in the regulation of biological responses induced by planar aromatic (i.e., aryl) hydrocarbons. AhR is a cytosolic transcription factor that is normally inactive, bound to several co-chaperones. Without wishing to be bound by any particular theory, upon ligand binding, the chaperones dissociate resulting in AhR translocating into the nucleus and dimerizing with ARNT (AhR nuclear translocator), leading to changes in gene transcription. In some embodiments, the gene is CYP1A1. Cypa1a protein expression may be induced in an AHR-dependent manner in the presence of compounds of Formula (I) described herein (FIG. 2). In some embodiments, the gene is CYP1A1, CYP1A2, CYP1B1, ALDH3A1, NQO1, or UGT1A1. In some embodiments, the gene is Muc1, Muc3, or Bcl21 (FIGS. 5C-5F). In some embodiments, the transcription of these genes is increased in the presence of AHR agonists (i.e., compounds of Formula (I)).

Figure 1:
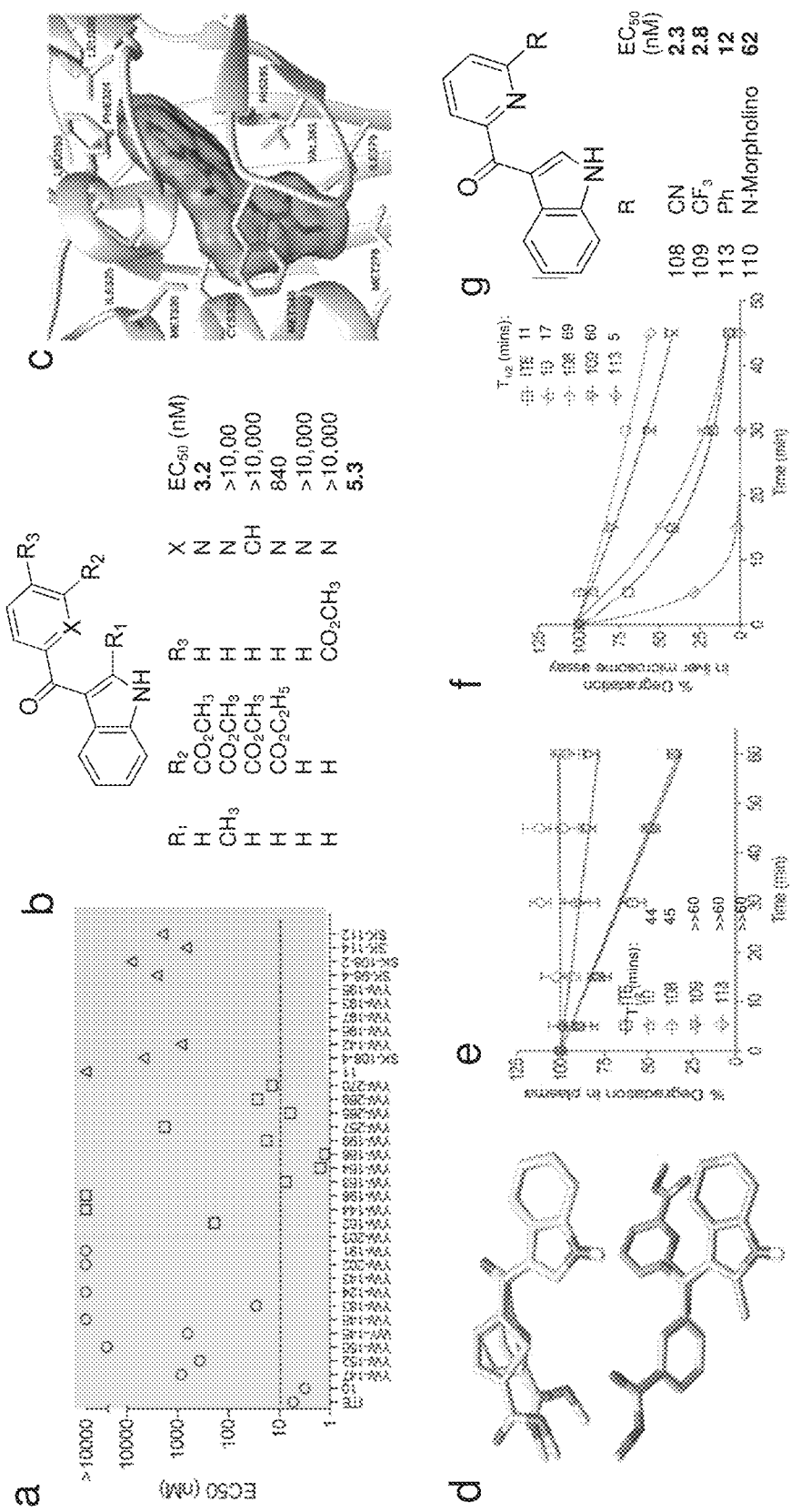
FIGS. 1A-1G show representative experiments performed for aryl hydrocarbon receptor modulators.

To identify starting points for developing compounds that modulate the aryl hydrocarbon receptor, the inventors synthesized a focused library of 3-aryl- and 3-heteroaryl-indoles and analyzed their ability to activate AHR in a XRE luciferase assay (FIG. 1A). From the activity screen, methyl 6-(1H-indole-3-carbonyl)pyridine-2-carboxylate (compound #10) was identified as a novel synthetic AHR agonist with identical potency ($EC_{50}$: 3.2 nM) as 2-(1H-indol-3-ylcarbonyl)-4-thiazolecarboxylic acid methyl ester (ITE), an endogenous agonist of the AHR (FIG. 1B). Synthetic derivatization of the 3-aryl- and 3-heteroaryl-indoles (e.g., compounds of Formula (I)) is shown in the Examples section.

Non-limiting examples of compounds of Formula (I), and pharmaceutically acceptable salts, hydrates, solvates, stereoisomers, tautomers, isotopically labeled derivatives, polymorphs, and prodrugs thereof are provided below in Table 1.

TABLE 1

Exemplary Compounds of Formula (I)

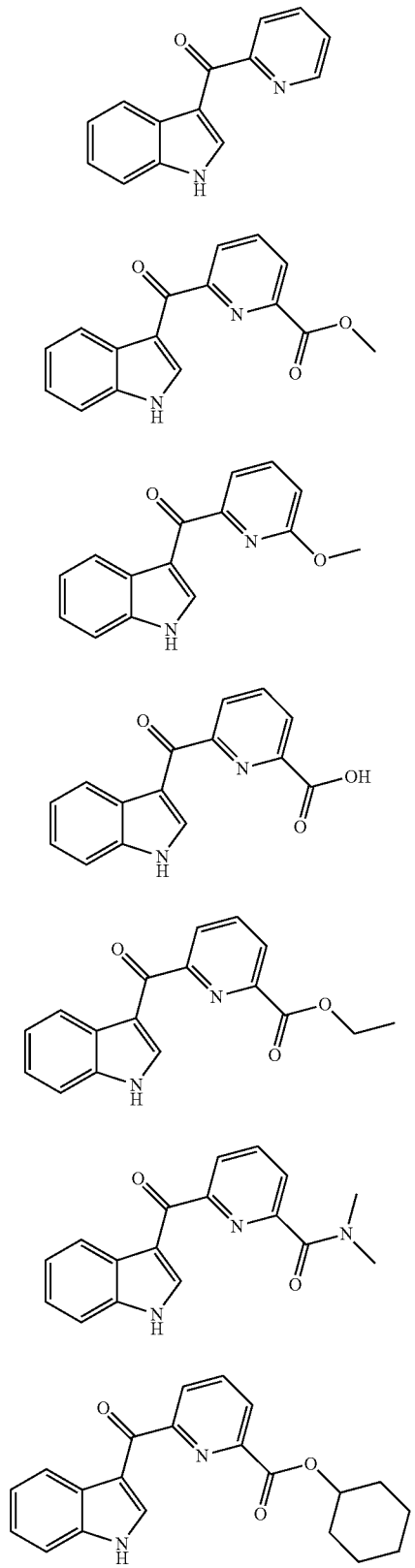

TABLE 1-continued

Exemplary Compounds of Formula (I)

TABLE 1-continued

Exemplary Compounds of Formula (I)

TABLE 1-continued

Exemplary Compounds of Formula (I)

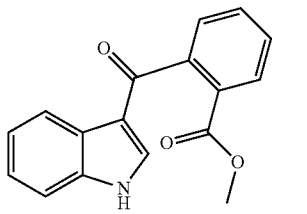 [SMILES: COC(=O)c1ccccc1C(=O)c1c[nH]c2ccccc12]

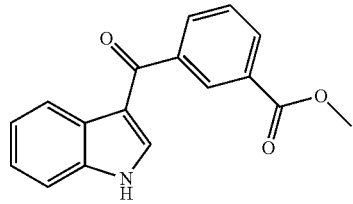

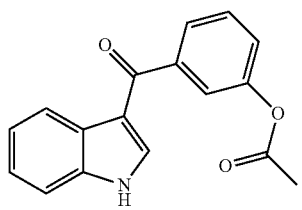 [SMILES: CC(=O)Oc1cccc(C(=O)c2c[nH]c3ccccc23)c1]

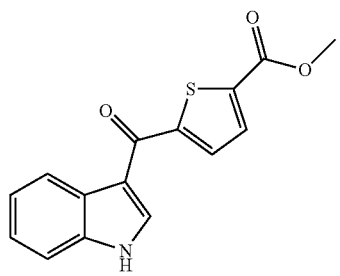 [SMILES: COC(=O)c1ccc(C(=O)c2c[nH]c3ccccc23)s1]

Pharmaceutical Compositions

In certain embodiments, the present invention provides a pharmaceutical composition comprising a compound of Formula (I), or a pharmaceutically acceptable salt, solvate, hydrate, stereoisomer, tautomer, isotopically labeled derivative, polymorph, or prodrug thereof and, optionally, a pharmaceutically acceptable excipient. In certain embodiments, the compound is present in an effective amount, e.g., a therapeutically effective amount or a prophylactically effective amount. In some embodiments, the compound is administered orally to a subject in need thereof. In some embodiments, the compound is administered topically to a subject in need thereof. In some embodiments, the compound is administered via inhalation (e.g., pulmonary) to a subject in need thereof. In some embodiments, the compound is formulated for nasal or ophthalmologic administration to subject in need thereof.

Pharmaceutically acceptable excipients include any and all solvents, diluents, or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutical compositions agents can be found, for example, in Remington's Pharmaceutical Sciences, Sixteenth Edition, E. W. Martin (Mack Publishing Co., Easton, Pa., 1980), and Remington: The Science and Practice of Pharmacy, 21$^{st}$ Edition (Lippincott Williams & Wilkins, 2005).

Pharmaceutical compositions described herein can be prepared by any method known in the art of pharmacology. In general, such preparatory methods include the steps of bringing the compound of Formula (I), or a pharmaceutically acceptable salt, solvate, hydrate, stereoisomer, tautomer, isotopically labeled derivative, polymorph, or prodrug thereof, (the "active ingredient") into association with the excipient and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions.

Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension.

Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner.

Examples of embedding compositions which can be used include polymeric substances and waxes.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* $21^{st}$ ed., Lippincott Williams & Wilkins, 2005.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins, etc.

Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

Still further encompassed by the invention are pharmaceutical packs and/or kits. Pharmaceutical packs and/or kits provided may comprise a provided composition and a container (e.g., a vial, ampoule, bottle, syringe, and/or dispenser package, or other suitable container). In some embodiments, provided kits may optionally further include a second container comprising a suitable aqueous carrier for dilution or suspension of the provided composition for preparation of administration to a subject. In some embodiments, contents of provided formulation container and solvent container combine to form at least one unit dosage form.

Optionally, a single container may comprise one or more compartments for containing a provided composition, and/or appropriate aqueous carrier for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A pharmaceutical pack or kit may thus comprise such multi-compartment containers including a provided composition and appropriate solvent and/or appropriate aqueous carrier for suspension.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with additional therapy.

Methods

The present invention also provides methods of using the compounds of Formula (I) as described herein to modulate the function of an aryl hydrocarbon receptor.

For example, in one aspect, provided is a method of modulating an aryl hydrocarbon receptor, the method comprising contacting a cell with a compound of Formula (I), or pharmaceutical composition thereof. In some embodiments, the activity of the aryl hydrocarbon receptor increases in the presence of the compound.

In another aspect, provided herein is a method of increasing expression of a gene in a cell. The expression of genes that are operably linked to aryl hydrocarbon response elements (e.g., XRE) can be induced once the aryl hydrocarbon receptor is activated (e.g., by a compound of Formula (I)). In some embodiments, the method comprising contacting the cell with a compound of a compound of Formula (I), or pharmaceutical composition thereof. In some embodiments, the expression of the gene is activated in the present of an activated aryl hydrocarbon receptor. In some embodiments, the gene is CYP1A1, CYP1A2, CYP1B1, ALDH3A1, NQO1, or UGT1A1. In some embodiments, the gene is CYP1A1. In some embodiments, the gene is Muc1, Muc3, or Bcl21.

In another aspect, provided is a method of regulating the expression of an cytokine in a cell, the method comprising contacting the cell with a compound of Formula (I), or pharmaceutical composition thereof. In some embodiments, the expression of the cytokine is increased. In some embodiments, the expression of the cytokine is decreased. In some embodiments, the cell is in vitro. In some embodiments, the cell is in vivo. In some embodiments, the cytokine is a chemokine, interferon, interleukin, lymphokine, or tumor necrosis factor. In some embodiments, the cytokine is an interleukin.

In another aspect, provided is a method of regulating the expression of an interleukin in a cell, the method comprising contacting the cell with a compound of Formula (I), or pharmaceutical composition thereof. In some embodiments, the expression of the interleukin is increased. In some embodiments, the expression of the interleukin is decreased. In some embodiments, the cell is in vitro. In some embodiments, the cell is in vivo. In some embodiments, the interleukin is interleukin 22 (IL-22), interleukin 6 (IL-6), interleukin 10 (IL-10), or interleukin 17 (IL-17). In some embodiments, the interleukin is interleukin 22 (IL-22). In some embodiments, the interleukin is interleukin 6 (IL-6). In some embodiments, the interleukin is interleukin 10 (IL-10). In some embodiments, the interleukin is interleukin 17 (IL-17). In some embodiments, the expression of interleukin 22 (IL-22) is increased. In some embodiments, the expression of interleukin 22 (IL-22) is decreased. In some embodiments, the expression of interleukin 6 (IL-6) is increased. In some embodiments, the expression of interleukin 6 (IL-6) is decreased. In some embodiments, the expression of interleukin 10 (IL-10) is increased. In some embodiments, the expression of interleukin 10 (IL-10) is decreased. In some embodiments, the expression of interleukin 17 (IL-17) is increased. In some embodiments, the expression of interleukin 17 (IL-17) is decreased.

In another aspect, provided is a method of regulating secretion of an interleukin from a cell, the method comprising contacting the cell with a compound of Formula (I), or pharmaceutical composition thereof. In some embodiments, secretion of the interleukin is increased. In some embodiments, secretion of the interleukin is decreased. In some embodiments, the cell is in vitro. In some embodiments, the cell is in vivo. In some embodiments, the interleukin is interleukin 22 (IL-22), interleukin 6 (IL-6), interleukin 10 (IL-10), or interleukin 17 (IL-17). In some embodiments, the interleukin is interleukin 22 (IL-22). In some embodiments, the interleukin is interleukin 6 (IL-6). In some embodiments, the interleukin is interleukin 10 (IL-10). In some embodiments, the interleukin is interleukin 17 (IL-17). In some embodiments, secretion of interleukin 22 (IL-22) is increased. In some embodiments, secretion of interleukin 22 (IL-22) is decreased. In some embodiments, secretion of interleukin 6 (IL-6) is increased. In some embodiments, secretion of interleukin 6 (IL-6) is decreased. In some embodiments, secretion of interleukin 10 (IL-10) is increased. In some embodiments, secretion of interleukin 10 (IL-10) is decreased. In some embodiments, secretion of interleukin 17 (IL-17) is increased. In some embodiments, secretion of interleukin 17 (IL-17) is decreased.

In yet another aspect, provided is a method of modulating the function of an immune cell, the method comprising contacting the immune cell with a compound of Formula (I), or pharmaceutical composition thereof. In some embodiments, the activity of the immune cell is increased upon contacting the cell with the compound. In some embodiments, the activity of the immune cell is decreased upon contacting the cell with the compound. In some embodiments, the immune cell is a T cell, a mast cell, a natural killer cell, a B cell, or an innate lymphoid cell. In some embodiments, the T cell is a regulatory T ($T_{reg}$) cell. In some embodiments, the T cell is a helper T ($T_H$) cell. In some embodiments, the helper T ($T_H$) cell is a $T_H17$ cell. In some embodiments, the helper T ($T_H$) cell is a $T_H22$ cell.

In yet another aspect, provided is a method of treating a disease or condition associated with the activity of an aryl hydrocarbon receptor, the method comprising administering a compound of Formula (I), or pharmaceutical composition thereof, to a subject in need thereof in an amount sufficient to modulate the aryl hydrocarbon receptor. Such methods include therapeutic as well as prophylactic (preventative) methods. In some embodiments, the disease or condition is associated with reduced activity of an aryl hydrocarbon receptor. In some embodiments, the disease or condition is associated with reduced activity of an aryl hydrocarbon receptor compared to the activity of the aryl hydrocarbon receptor in a normal (i.e., non-disease) cell.

Also provided herein are compounds, or pharmaceutical compositions thereof, for use for modulating the activity of an aryl hydrocarbon receptor in a cell. The compounds, or pharmaceutical compositions thereof, may be used to treat diseases or conditions associated with the reduced activity of an aryl hydrocarbon receptor in a cell. Thus, provided herein are compounds, or pharmaceutical compositions thereof, for use in treating a proliferative disease, inflammatory disease, autoimmune disease, or metabolic disorder in a subject in need thereof.

In some embodiments, the compound is an aryl hydrocarbon receptor agonist. In some embodiments, the compound is a partial aryl hydrocarbon receptor agonist. In some embodiments, the compound modulates the aryl hydrocarbon receptor by increasing the activity of the aryl hydrocarbon receptor. In some embodiments, increased activity of the aryl hydrocarbon receptor leads to an increase in gene expression in the cell. In some embodiments, the cell is in vitro. In some embodiments, the cell is in vivo.

Exemplary diseases associated with the activity of an aryl hydrocarbon receptor include, but are not limited to, proliferative diseases, inflammatory diseases, autoimmune diseases, and metabolic disorders.

In certain embodiments, the disease or condition associated with activity of an aryl hydrocarbon receptor is a proliferative disorder. Exemplary proliferative diseases include, but are not limited to, tumors, begnin neoplasms, pre-malignant neoplasms (carcinoma in situ), and malignant neoplasms (cancers). In some embodiments, the proliferative disease is cancer Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic adenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In some embodiments, the cancer is stomach cancer. In some embodiments, the cancer is breast cancer. In some embodiments, the cancer is skin cancer. In some embodiments, the cancer is ovarian cancer. In some embodiments, the cancer is pancreatic cancer. In some embodiments, the cancer is liver cancer. In some embodiments, the cancer is hematopoietic cancer. In some embodiments, the hematopoietic cancer is leukemia.

In certain embodiments, the disease or condition associated with activity of an aryl hydrocarbon receptor is an inflammatory disorder. The term "inflammatory disorder" refers to those diseases or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory disorders include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, colitis (e.g., ulcerative colitis), conjunctivitis, Chagas disease, chronic obstructive pulmonary disease (COPD), cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, insulitis, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), graft versus host disease, inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), pancreatitis, prostatitis, chronic inflammation associated with cranial radiation injury, pelvic inflammatory disease, reperfusion injury, regional enteritis, rheumatic fever, systemic lupus erythematosus, schleroderma, scleredoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis.

In certain embodiments, the inflammatory disorder is colitis. In certain embodiments, the inflammatory disorder is inflammatory bowel disease. In certain embodiments, the inflammatory disorder is Crohn's disease. In certain embodiments, the inflammatory disorder is rheumatoid arthritis. In certain embodiments, the inflammatory disorder is multiple sclerosis. In certain embodiments, the inflammatory disorder is psoriasis. In certain embodiments, the inflammatory disorder is dermatitis. In certain embodiments, the inflammatory disorder is pancreatitis. In certain embodiments, the inflammatory disorder is insulitis. In certain embodiments, the inflammatory disorder is atherosclerosis.

In certain embodiments, the disease or condition associated with activity of an aryl hydrocarbon receptor is an autoimmune disorder. Exemplary autoimmune disorders include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In certain embodiments, the disease or condition associated with activity of an aryl hydrocarbon receptor is a metabolic disorder. The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, steatosis (e.g., fatty liver disease), and obesity.

In some embodiments, the metabolic disorder is type I diabetes. In some embodiments, the metabolic disorder is steatosis.

In some embodiments, the metabolic disorder is metabolic syndrome. "Metabolic syndrome" refers to a cluster of conditions that can occur together to increase the risk of heart disease, stroke, and/or diabetes in a patient. Exemplary conditions that can be present in a subject with metabolic syndrome include, but are not limited to, increased blood pressure, high blood sugar, excess body fat around the waist (e.g., obesity), abnormal cholesterol levels, and abnormal triglyceride levels. Metabolic syndrome can be linked to obesity, inactivity, and/or insulin resistance.

Compounds of Formula (I) may be formulated in dosage unit form for ease of administration and uniformity of dosage. It will be understood, however, that the total daily usage of the compositions comprising a compound of Formula (I) will be decided by the attending physician within the scope of sound medical judgment. The specific therapeutically effective dose level for any particular subject or organism will depend upon a variety of factors including the disease or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, intradermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration. In general the most appropriate route of administration will depend upon a variety of factors including the nature of the agent (e.g., its stability in the environment of the gastrointestinal tract), the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder (for example, a compound can be administered in combination with an anti-inflammatory agent, anti-cancer agent, etc.), and/or it may achieve different effects (e.g., control of adverse side-effects, e.g., emesis controlled by an anti-emetic).

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually. Additional therapeutically active agents include, but are not limited to, small organic molecules such as drug compounds (e.g., compounds approved by the Food and Drugs Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells. In certain embodiments, the additional therapeutically agent is a cancer agent (e.g., a biotherapeutic or chemotherapeutic cancer agent). In other embodiments, the additional therapeutically active agent is an anti-inflammatory agent.

EXAMPLES

In order that the invention described herein may be more fully understood, the following examples are set forth. It should be understood that these examples are for illustrative purposes only and are not to be construed as limiting this invention in any manner.

Example 1—Aryl Hydrocarbon Receptor Modulators

Therapy for IBD is Often Ineffective Despite the Use of Immunosuppressive Agents and New Biologic Drugs Inflammatory bowel disease (IBD) is the consequence of a sustained inflammatory response to commensal microorganisms in a genetically susceptible host with excessive production of proinflammatory cytokines, such as TNFα and IL-1β (1, 2). As a consequence, interventions designed to induce and maintain remission of active disease have largely focused on the use of T cell suppressive agents, such as corticosteroids, azathioprine, and 6-mercaptopurine, among others; all of which have been limited by toxicity (3-10). Most recently, biologics targeting specific cytokines, such as TNFα, or the α4β7 receptor have been introduced as disease-modifying drugs (11-17). While higher rates of remission and mucosal healing have been observed, these agents have been limited by an increased risk of infection, malignancy, reduced efficacy due to the development of anti-drug antibodies, and high cost (15, 18, 19). All told, one-third of patients with IBD do not respond appropriately to existing therapies (20, 21). Recent evidence now suggests that the exacerbated inflammatory response observed in IBD is initiated and maintained by loss of gut epithelial integrity manifest by increased barrier permeability, impaired mucin production, and reduced secretion of antimicrobial peptides with an ensuing dysbiosis and accompanying bacterial translocation and invasion (22-30). Crucial to the maintenance of epithelial barrier integrity, as well as gut microbial homeostasis and protection from pathogenic microorganisms is the mucosal innate immune system.

Intestinal Barrier Integrity and Microbial Homeostasis is Dependent Upon the Mucosal Innate Immune System Among the cellular components of the gut innate immune system, both intraepithelial lymphocytes (IEL) and innate lymphoid cells (ILC) are critically important for the preservation of epithelial barrier integrity and intestinal homeostasis (26, 29, 31-33). In particular, Group 3 innate lymphoid cells (ILC3) promote mucosal wound healing by regulating intestinal stem cell regeneration, inducing epithelial and goblet cell proliferation (34-40), and enhancing the expression of mucins (41-43). Microbial homeostasis is supported by the capacity of ILC3 cells to enhance epithelial expression of fucose, which is catabolized by commensal bacteria (44), as well as the secretion of a variety of antimicrobial peptides that prevent dissemination of pathogenic bacteria (45-49). Intraepithelial lymphocytes and specifically, tissue-resident γδ T cells, promote tissue repair, dampen proinflammatory responses, and inhibit cytotoxic effector functions of αβ T cells (31, 33, 50). Recent evidence demonstrates that δS T cells and ILC3 cells mediate these effects by production of IL-22 (36, 40, 44, 45, 51-59). Indeed, disease responses in murine models of colitis are dramatically exacerbated by genetic deletion of IL-22 or by administration of an IL-22 blocking antibody (60, 61). In contrast, treatment with IL-22 promotes goblet and epithelial cell restitution, expression of mucins and antimicrobial peptides, and accelerates mucosal healing with attenuation of local inflammation (40, 54, 59, 62, 63). Studies in patients with Crohn's disease demonstrate decreased IL-22-secreting ILCs in the lamina propria (64) and serum levels of IL-22 is associated with disease activity in both UC and Crohn's disease (65). CARD9 is an adaptor protein that integrates signals from innate immune receptors to selectively activate the IL-22 pathway (66-68). CARD9 deficient mice exhibit impaired production of IL-22, microbial dysbiosis, and increased susceptibility to colitis (69). Significantly, genome-wide association studies have identified genetic polymorphisms of CARD9 that confer IBD risk or protection (70-76). A key regulator of the gut innate immune system, including the role of innate immune cells in IL-22 expression, intestinal barrier surveillance, microbial homeostasis, and mucosal repair is the aryl hydrocarbon receptor (AHR) (58, 59, 77-83).

AHR is a Critical Regulator of the Gut Innate Immune System, IL-22 Expression, and Intestinal Integrity and Repair The aryl hydrocarbon receptor is a member of the basic-helix-loop-helix (bHLH)/Per-Arnt-Sim (PAS) family of transcription factors, which is bound to several co-chaperones and present in an inactive form in the cytosol (84). Upon ligand binding, AHR dissociates from its chaperones and translocates to the nucleus, where it dimerizes with the aryl hydrocarbon receptor nuclear translocator (ARNT) to induce gene transcription. AHR is an essential regulator of the gut innate immune system and mediates processes responsible for microbial homeostasis, enabling commensal bacteria to outcompete pathogenic bacteria, as well as those events that support gut tissue integrity and promote epithelial repair (59, 79, 81, 84-87). In large measure, AHR accomplishes these outcomes by regulating the expression of IL-22 (58, 59, 80-82). IL-22 is produced in mice and humans by ILC3 cells (36, 37, 47, 77, 82, 88, 89) and γδ T cells (31, 33, 50), but can also be produced in the gut by Th17 cells (90, 91), all in response to AHR activation (58, 59, 80-82). AHR-deficient mice display reduced expression of IL-22, dysbiosis, and an increased risk of bacterial infection and colitis (78, 79, 81, 82) and genome-wide association studies have also identified AHR as a susceptibility locus for IBD (92, 93). These effects can be reproduced by diets deficient in AHR ligands or by constitutive expression of CYP1A1 in intestinal epithelial cells, which increases the metabolism of AHR ligands with increased susceptibility to enteric infection (78, 79, 87). In turn, genetic deletion of CYP1 enzymes delays ligand metabolism with increased protection against intestinal infection (78, 79, 87). Sources of AHR ligands include dietary compounds (94, 95), microbial virulence factors (96), and metabolites derived through microbiota- or host-mediated tryptophan metabolism (58, 69, 97, 98). Indeed, CARD9 deficient mice exhibit impaired metabolism of tryptophan into AHR ligands, decreased production of IL-22, and increased susceptibility to colitis (69). Impaired microbial production of AHR ligands has also been observed in patients with IBD and correlates with an IBD-associated geneic polymorphism within CARD9 (69). In a recent clinical trial, serum levels of tryptophan were inversely correlated with serum levels of IL-22 and the severity of IBD in patients with Crohn's disease and ulcerative colitis (65).

Dietary Metabolites Afford AHR Agonists that Modulate Innate Immune Responses and Promote Mucosal Repair Endogenous AHR agonists are derived from a variety of dietary metabolites including tryptophan, flavonoids, stilbenes, carotenoids, and indoles through microbial- or host-mediated metabolism (58, 69, 99-101). Indeed, the beneficial effect of *Lactobacillus* species as a commensal organism is likely achieved by metabolic production of AHR ligands (69). For example, *L. reuteri* and *L. johnsonii* can generate indole-3-aldehyde, which activates AHR, increases IL-22 production in ILC3 cells, and inhibits DSS induced colitis (58, 102). Although the metabolic route for many indole related AHR ligands has not been well defined, 6-formylindolo[3,2-b]carbazole (FICZ), 3,3'-diindolylmethane (DIM) and 2-(1'H-indole-3'-carbonyl)-thiazole-4-carboxylic acid methyl ester (ITE) ameliorate TNBS-, DSS-, and T cell transfer-induced colitis (97, 103-107). These compounds increase IL-22 production with beneficial effects abrogated by treatment with an IL-22 blocking antibody or an AHR antagonist (69, 80, 83, 103, 108). Adsorbed indole can also be metabolized by the gut microbiota to indirubin, a 3,2'-bisindole isomer, which is the active metabolite in indigo naturalis, a group of Old World plants that have been used in traditional Chinese medicine as a treatment for IBD (109). As a ligand for AHR, indirubin increases expression of IL-22 and reduces disease severity in TNBS and DSS models of colitis, which is not observed in AHR deficient mice (110). In a recent study, administration of indigo naturalis to 20 patients with UC was associated with 61% mucosal healing and a 72% response rate (109). These reports demonstrate the therapeutic potential of endogenous, indole based, AHR agonists.

REFERENCES

1. Ananthakrishnan A N. Epidemiology and risk factors for IBD. Nat Rev Gastroenterol Hepatol 2015; 12:205-217.
2. Kaser A, Zeissig S, Blumberg R S. Inflammatory bowel disease. Annu Rev Immunol 2010; 28:573-621.
3. Baumgart D C, Sandborn W J. Crohn's disease. Lancet 2012; 380:1590-1605.
4. Feagan B G, Fedorak R N, Irvine E J, Wild G, Sutherland L, Steinhart A H, Greenberg G R, Koval J, Wong C J, Hopkins M, Hanauer S B, McDonald J W. A comparison of methotrexate with placebo for the maintenance of remission in Crohn's disease. North American Crohn's Study Group Investigators. N Engl J Med 2000; 342:1627-1632.
5. Fellermann K, Ludwig D, Stahl M, David-Walek T, Stange E F. Steroid-unresponsive acute attacks of inflammatory bowel disease: Immunomodulation by tacrolimus (FK506). Am J Gastroenterol 1998; 93:1860-1866.
6. Flammer J R, Rogatsky L. Glucocorticoids in autoimmunity: Unexpected targets and mechanisms. Mol Endocrinol 2011; 25:1075-1086.
7. Kornbluth A., Present D H, Lichtiger S. Hanauer S. Cyclosporin for severe ulcerative colitis: A user's guide. Am J Gastroenterol 1997; 92:1424-1428.
8. Sandborn W J. A review of immune modifier therapy for inflammatory bowel disease: Azathioprine, 6-mercaptopurine, cyclosporine, and methotrexate. Am J Gastroenterol 1996: 91:423-433.
9. Truelove S C, Witts L J. Cortisone in ulcerative colitis; preliminary report on a therapeutic trial. Br Med J 1954; 2:375-378.
10. Ungaro R. Mehandru S. Allen P B, Peyrin-Biroulet L, Colombel J F. Ulcerative colitis. Lancet 2017; 389:1756-1770.
11. Rutgeerts P, Sandborn W J, Feagan B C, Reinisch W, Olson A, Johanns J, Travers S, Rachmilewitz D, Hanauer S B, Lichtenstein C R, de Villiers W J, Present D, Sands B E, Colombel J F. Infliximab for induction and maintenance therapy for ulcerative colitis. N Engl J Med 2005; 353:2462-2476.
12. Colombel J F, Sandborn W J, Reinisch W. Mantzaris G, Kornbluth A, Rachmilewitz D, Lichtiger S, D'Haens G, Diamond R H, Broussard D L, Tang K L, van der Woude C J, Rutgeerts P, Group S S. Infliximab, azathioprine, or combination therapy for Crohn's disease. N Engl J Med 2010; 362:1383-1395.
13. Feagan B G, Rutgeerts P, Sands B E, Hanauer S, Colombel J F, Sandborn W J, Van Assche G, Axler J, Kim H J, Danese S, Fox 1, Milch C, Sankoh S, Wyant T, Xu J, Parikh A, Group G S. Vedolizumab as induction and maintenance therapy for ulcerative colitis. N Engl J Med 2013; 369:699-710.
14. Sandborn W J, Feagan B G, Rutgeerts P, Hanauer S. Colombel J F, Sands B E, Lukas M. Fedorak R N, Lee S, Bressler B, Fox I, Rosario M, Sankoh S, Xu J, Stephens K, Milch C, Parikh A, Group G S. Vedolizumab as induction and maintenance therapy for Crohn's disease. N Engl J Med 2013; 369:711-721.
15. Danese S, Vuitton L. Peyrin-Biroulet L. Biologic agents for IBD: Practical insights. Nat Rev Gastroenterol Hepatol 2015; 12:537-545.
16. Feagan B G. Sandborn W J, Gasink C, Jacobstein D, Lang Y, Friedman J R, Blank M A, Johanns J, Gao L L, Miao Y, Adedokun O J, Sands B E, Hanauer S B, Vermeire S, Targan S, Ghosh S, de Villiers W I, Colombel J F, Tulassay Z, Seidler U, Salzberg B A, Desreumaux P, Lee S D, Loftus E V, Jr., Dieleman L A, Katz S, Rutgeerts P, Group U-I-US. Ustekinumab as induction and maintenance therapy for Crohn's disease. N Engl J Med 2016; 375:1946-1960.
17. Neurath M. Current and emerging therapeutic targets for IBD. Nat Rev Gastroenterol Hepatol 2017; 14:688.
18. de Silva S, Devlin S, Panaccione R. Optimizing the safety of biologic therapy for IBD. Nat Rev Gastroenterol Hepatol 2010; 7:93-101.
19. Beaugerie L, Itzkowitz S H. Cancers complicating inflammatory bowel disease. N Engl J Med 2015; 372: 1441-1452.
20. Yanai H. Hanauer S B. Assessing response and loss of response to biological therapies in IBD). Am J Gastroenterol 2011; 106:685-698.
21. Roda C, Jharap B, Neeraj N. Colombel J F. Loss of response to anti-TNFs: Definition, epidemiology, and management. Clin Trans Castroenterol 2016; 7:e135.
22. de Souza H S, Fiocehi C. Immunopathogenesis of IBD: Current state of the art. Nat Rev Gastroenterol Hepatol 2016; 13:13-27.
23. Kamada N. Seo S U, Chen G Y, Nunez G. Role of the gut microbiota in immunity and inflammatory disease. Nat Rev Immunol 2013; 13:321-335.
24. Lvnch S V. Pedersen O. The human intestinal microbiome in health and disease. N Engl J Med 2016; 375:2369-2379.
25. Okamoto R, Watanabe M. Role of epithelial cells in the pathogenesis and treatment of inflammatory bowel disease. J Gastroenterol 2016; 51:11-21.
26. Peterson L W, Artis D. Intestinal epithelial cells: Regulators of barrier function and immune homeostasis. Nat Rev Immunol 2014; 14:141-153.
27. Salim S Y, Soderhoim J D. Importance of disrupted intestinal barrier in antiinflammatory bowel diseases. Inflamm Bowel Dis 2011; 17:362-381.
28. Sartor R B. Mechanisms of disease: Pathogenesis of Crohn's disease and ulcerative colitis. Nat Clin Pract Gastroenterol Hepatol 2006; 3:390-407.
29. Thaiss C A, Zmora N, Levy M, Elinav E. The microbiome and innate immunity. Nature 2016; 535:65-74.
30. Wallace K L, Zheng L B. Kanazawa Y, Shih D Q. Immunopathology of inflammatory bowel disease. World J Gastroenterol 2014; 20:6-21.
31. Fan X. Rudensky A Y. Hallmarks of tissue-resident lymphocytes. Cell 2016; 164:1198-1211.
32. Faria A M C, Reis B S, Mucida 1). Tissue adaptation: Implications for gut immunity and tolerance. J Exp Med 2017; 214:1211-1226.
33. Nielsen M M, Witherden D A, Havran W L. gammadelta T cells in homeostasis and host defence of epithelial barrier tissues. Nat Rev Immunol 2017; 17:733-745.
34. Sawa S, Cherrier M, Lochner M, Satoh-Takayarna N, Fehling H J, Langa F, Di Santo J P, Eberl G. Lineage relationship analysis of RORgammat+ innate lymphoid cells. Science 2010; 330:665-669.
35. Reynders A, Yessaad N, Vu Manh T P, Dalod M, Fenis A, Aubry C, Nikitas G, Escaliere B, Renauld J C, Dussurget O, Cossart P, Lecuit M. Vivier E, Tomasello E. Identity, regulation and in vivo function of gut NKp46+ RORgammat+ and NKp46+ RORgammat-lymphoid cells. EMBO J 2011; 30:2934-2947.
36. Sawa S, Lochner M, Satoh-Takayama N, Dulauroy S, Berard M, Kleinschek M, Cua D, Di Santo J P, Eberl G. RORgammat+ innate lymphoid cells regulate intestinal homeostasis by integrating negative signals from the symbiotic microbiota. Nat Immunol 2011; 12:320-326.
37. Spits H, Di Santo J P. The expanding family of innate lymphoid cells: Regulators and effectors of immunity and tissue remodeling. Nat Immunol 2011; 12:21-27.
38. Nlortha A, Chudnovskiy A, Hashimoto D, Bogunovic M. Spencer S P, Belkaid N Y, Merad M. Microbiota-dependent crosstalk between macrophages and ILC3 promotes intestinal homeostasis. Science 2014; 343:1249288.
39. Hepworth M R, Fung T C, Masur S H, Kelsen J R. McConnell F M. Dubrot J. Withers D R, Hugues S, Farrar M A, Reith W, Eberl C, Baldassano R N, Laufer T M, Elson C O, Sonnenberg G F. Group 3 innate lymphoid cells mediate intestinal selection of commensal bacteria-specific CD4(+) T cells. Science 2015; 348:1031-1035.
40. Lindemans C A, Calafiore M, Mertelsmann A M, O'Connor M H, Dudakov J A. Ienq R R, Velardi E, Young L F, Smith O M, Lawrence G. Ivanov J A. Fu Y Y, Takashima S. Hua G, Martin M L, O'Rourke K P, Lo Y I, Mokry M, Romera-Hernandez M. Cupedo T, Dow L. Nieuwenhuis E E, Shroyer N F. Liu C, Kolesnick R, van den Brink M R M, Hanash A M. Interleukin-22 promotes intestinal-stem-cell-mediated epithelial regeneration. Nature 2015; 528:560-564.
41. Broadhurst M J, Leung J M, Kashyap V, McCune J M, Mahadevan U, McKerrow J H, Loke P. IL-22+CD4+ T cells are associated with therapeutic *trichuris trichiura* infection in an ulcerative colitis patient. Sci Transl Med 2010: 2:60ra88.
42. Goto Y, Obata T, Kunisawa J, Sato S, Ivanov, I I, Lamichhane A, Takeyanma N, Kamioka M, Sakamoto M, Matsuki T, Setoyama H, Jmaoka A, Uematsu S, Akira S, Domino S E, Kulig P, Becher B, Renauld J C, Sasakawa C, Umesaki Y, Benno Y, Kiyono H. Innate lymphoid cells regulate intestinal epithelial cell glycosylation. Science 2014; 345:1254009.

43. Goto Y, Uematsu S, Kiyono H. Epithelial glycosylation in gut homeostasis and inflammation. Nat Immunol 2016; 17:1244-1251.
44. Pickard J M, Maurice C F, Kinnebrew M A, Abt M C, Schenten D, Golovkina T V, Bogatyrev S R, Ismagilov R E Pamer E G. Turnbaugh P J. Chervonsky A V. Rapid fucosylation of intestinal epithelium sustains host-commensal symbiosis in sickness. Nature 2014; 514:638-641.
45. Sonnenberg G F, Monticelli L A, Elloso M M, Fouser L A, Artis D. CD4(+) lymphoid tissue-inducer cells promote innate immunity in the gut. Immunity 2011; 34:122-134.
46. Manta C, Heupel E. Radulovic K, Rossini V, Garbi N. Riedel C U, Niess J H. CX(3)CR1(+) macrophages support IL-22 production by innate lymphoid cells during infection with *Citrobacter rodentium*. Mucosal Immunol 2013; 6:177-188.
47. Satoh-Takayama N, Serafini N, Verrier T. Rekiki A, Renauld J C, Frankel G, Di Santo J P. The chemokine receptor CXCR6 controls the functional topography of interleukin-22 producing intestinal innate lymphoid cells. Immunity 2014; 41:776-788.
48. Singh A K, Eken A, Fry M, Bettelli E, Oukka M. DOCK8 regulates protective immunity by controlling the function and survival of RORgammat+ ILCs. Nat Commun 2014; 5:4603.
49. Friedrich C, Mamareli P, Thiemann S, Kruse F, Wang Z, Holzmann B, Strowig T, Sparwasser T, Lochner M. MyD88 signaling in dendritic cells and the intestinal epithelium controls immunity against intestinal infection with *C. rodentium*. PLoS Pathog 2017; 13:e1006357.
50. Mielke L A, Jones S A, Raverdeau M, Higgs R, Stefanska A. Groom J R, Misiak A, Dungan L S, Sutton C E, Streubel G, Bracken A P, Mills K U. Retinoic acid expression associates with enhanced IL-22 production by gamnniadelta T cells and innate lyniphoid cells and attenuation of intestinal inflammation. J Exp Med 2013; 210:1117-1124.
51. Wolk K, Kunz S, Witte E, Friedrich M, Asadullah K, Sabat R. IL-22 increases the innate immunity of tissues. Immunity 2004; 21:241-254.
52. Nagalakshnii M L, Rascle A, Zurawski S, Menon S, de Waal Malefyt R. Interleukin-22 activates STAT3 and induces IL-10 by colon epithelial cells. Int Immunopharmacol 2004; 4:679-691.
53. Satoh-Takayama N, Vosshenrich C A, Lesjean-Pottier S, Sawa S, Lochner M, Rattis F, Mention J J, Thiam K, Cerf-Bensussan N, Mandelboim O, Eberi G, Di Santo J P. Microbial flora drives interleukin 22 production in intestinal NK_p46$^+$ cells that provide innate mucosal immune defense. Immunity 2008; 29:958-970.
54. Zheng Y, Valdez P A, Danilenko D M, Hu Y, Sa S M, Gong Q. Abbas A R, Modrusan Z, Ghilardi N, de Sauvage F J, Ouvang W. Interleukin-22 mediates early host defense against attaching and effacing bacterial pathogens. Nat Med 2008; 14:282-289.
55. Cella M, Fuchs A, Vermi W, Facchetti F, Otero K, Lennerz J K, Doherty J M, Mills J C, Colonna M. A human natural killer cell subset provides an innate source of IL-22 for mucosal immunity. Nature 2009: 457:722-725.
56. Sanos S L, Bui V L, Mortha A. Oberle K, Heners C. Johner C, Diefenbach A. RORgammat and commensal microflora are required for the differentiation of mucosal interleukin 22-producing NKp46+ cells. Nat Immunol 2009 10:83-91.
57. Takatori H, Kanno Y, Watford W T, Tato C M, Weiss G, Ivanov, I I, Littman D R, O'Shea J J. Lymphoid tissue inducer-like cells are an innate source of IL-17 and IL-22. J Exp Med 2009; 206:35-41.
58. Zelante T, lannitti R G, Cunha C, De Luca A, Giovannini G, Pieraccini G, Zecchi R, D'Angelo C. Massi-Benedetti C. Fallarino F, Carvalho A, Puccetti P. Romani L. Tryptophan catabolites from microbiota engage aryl hydrocarbon receptor and balance mucosal reactivity via interleukin-22. Immunity 2013; 39:372-385.
59. Hainzl F, Stockinger S, Rauch I, Heider S, Berry D, Lassnig C, Schwab C, Rosebrock F, Milinovich G, Schlederer M, Wagner M, Schleper C, Loy A, Urich T, Kenner L. Han X, Decker T, Strobl B, Muller M. Intestinal epithelial cell tyrosine kinase 2 transduces IL-22 signals to protect from acute colitis. J Immunol 2015; 195:5011-5024.
60. Zenewicz L A, Yancopoulos G D, Valenizuela D M, Murphy A J, Stevens S, Flavell R A. Innate and adaptive interleukin-22 protects mice from inflammatory bowel disease. Iinmuinity 2008; 29:947-957.
61. NIizoguchi A. Healing of intestinal inflammation by IL-22. Inflamm Bowel Dis 2012; 18:1777-1784.
62. Sugimoto K, Ogawa A, Mizoguchi E, Shimomura Y, Andoh A, Bhan A K, Blumberg R S, Xavier R J. Mizoguchi A. IL-22 ameliorates intestinal inflammation in a mouse model of ulcerative colitis. J Clin Invest 2008; 118:534-544.
63. Bootz F, Ziffels B. Neri D. Antibody-based targeted delivery of interleukin-22 promotes rapid clinical recovery in mice With DSS-induced colits. Inflamm Bowel Dis 2016; 22:2098-2105.
64. Takayama T, Kamada N, Chinen H, Okamoto S, Kitazume M T, Chang J, Matuzaki Y, Suzuki S, Sugita A, Koganei K, lisamatsu T, Kanai T, Flibi T. Imbalance of NKp44(+)NKp46(−) and NKp44(−)NKp46(+) natural killer cells in the intestinal mucosa of patients with Crohn's disease. Gastroenterology 2010; 139:882-892.
65. Nikolaus S, Schulte B, A1-Massad N, Thieme F, Schulte D M, Bethge J, Rehman A, Tran F, Aden K, Hasler R, Moll N, Schutze G, Schwarz M J, Waetzig G H, Rosenstiel P. Krawczak M, Szymezak S, Schreiber S. Increased tryptophan metabolism is associated with activity of inflammatory bowel diseases. Gastroenterology 2017.
66. Hsu Y M, Zhang Y, You Y, Wang D, Li H, Duramad O, Qin X F, Dong C, Lin X. The adaptor protein CARD9 is required for innate immune responses to intracellular pathogens. Nat Immunol 2007; 8:198-205.
67. Sokol H, Conway K L, Zhang M, Choi M. Morin B, Cao Z. Villablanca E J, Li C, Wijmenga C, Yun S H, Shi H N. Xavier R J. Card9 mediates intestinal epithelial cell restitution, T-helper 17 responses, and control of bacterial infection in mice. Gastroenterology 2013; 145:591-601 e593.
68. Bergmann H, Roth S, Pechloff K, Kiss E A, Kuhn S, Heikenwalder M, Diefenbach A, Greten F R, Ruland J. Card9-dependent IL-1beta regulates IL-22 production from group 3 innate lymphoid cells and promotes colitis-associated cancer. Eur J Immunol 2017; 47:1342-1353.
69. Lamas B, Richard M L, Leducq V, Pham H P, Michel M L, Da Costa G, Bridonneau C, Jegou S, Hoffmann T W, Natividad J M. Brot L, Taleb S. Couturier-Maillard A. Nion-Larmurier I, Merabtene F, Seksik P, Bourrier A, Cosnes J, Ryffel B, Beaugerie L, Launay J M, Langella P, Xavier R J, Sokol H. CARD9 impacts colitis by altering gut microbiota metabolisin of tryptophan into aryl hydrocarbon receptor ligands. Nat Med 2016; 22:598-605.
70. Zhernakova A, Festen E M, Franke L, Trynka G, van Diernen C C, Monsuur A J, Bevova M, Nijmeijer R N I, van't Slot R, Heijmans R. Boezen H M, van Heel D A, van Bodegraven A A, Stolkers P C, Wijnienga C, Crusius J B, Weersma R K. Genetic analysis of innate immunity in Crohn's disease and ulcerative colitis identifies two susceptibility loci harboring CARD9 and IL18RAP. Am J Hum Genet 2008; 82:1202-1210.
71. Franke A. McGovern D P, Barrett J C, Wang K, Radford-Smith G L, Ahmad T. Lees C W, Balschun T, Lee J, Roberts R, Anderson C A, Bis J C, Bumpstead S, Ellinghaus D, Festen E M, Georges M, Green T, Haritunians T, Jostins L, Latiano A, Mathew C G, Montgomery G W, Prescott N J, Raychaudhuri S, Rotter J I, Schurnm P, Sharma Y, Simms L A, Taylor K D, Whitenman D, Wijmenga C, Baldassano R N, Barclay M, Bayless T M, Brand S, Buning C, Cohen A. Colombel J F, Cottone M, Stronati L, Denson T, De Vos M, D'Incal R, Dubinsky M, Edwards C, Florin T, Franchimont D, Gearry R, Glas J, Van Gossum A, Guthery S L, Halfvarson J, Verspaget H W, Hugot J P, Karban A, Laukens D, Lawrance I, Lemann M, Levine A. Libioulle C, Louis E, Mowat C. Newman W, Panes J, Phillips A, Proctor D D, Regueiro M, Russell R, Rutgeerts P, Sanderson J, Sans M, Seibold F, Steinhart A H, Stokkers P C, Torkvist L, Kullak-Ublick G, Wilson D, Walters T, Targan S R. Brant S R, Rioux J D, D'mato M, Weersma R K, Kugathasan S, Griffiths A M, Mansfield J C, Vermeire S, Duerr R H, Silverberg M S, Satsangi J, Schreiber S, Cho J H, Annese V. Hakonarson H, Daly M J, Parkes M. Genome-wide meta-analysis increases to 71 the number of confirmed Crohn's disease susceptibility loci. Nat Genet 2010; 42:1118-1125.
72. McGovern D P, Gardet A, Torkvist L. Goyette P. Essers J. Taylor K D, Neale B M, Ong R T, Lagace C. Li C, Green T, Stevens C R, Beauchamp C, Fleshner P I, Carlson M, D'Amato M, Halfvarson J, Hibberd M L, Lordal M. Padyukov L, Andriulli A, Colombo E, Latiano A, Palmieri O, Bernard E J, Deslandres C, Hommes D W, de Jong D J, Stokkers P C, Weersma R K, Consortium N J G. Sharma Y, Silverberg M S. Cho J I, Wu J, Roeder K, Brant S R, Schumm L P, Duerr R H, Dubinsky M C, Glazer N L, Haritunians T, Ippoliti A, Melmed G Y, Siscovick D S, Vasiliauskas E A, Targan S R, Annese V, Wijmenga C, Pettersson S, Rotter J I, Xavier R J, Daly M J, Rioux J D, Seielstad M. Genome-wide association identifies multiple ulcerative colitis susceptibility loci. Nat Genet 2010; 42:332-337.
73. Rivas M A, Beaudoin N, Gardet A, Stevens C, Sharma Y, Zhang C K, Boucher G, Ripke S. Eilinghaus D, Burtt N, Fennell T, Kirby A. Latiano A, Coyette P, Green T, Halfvarson J, Haritunians T, Korn J M, Kuruvilla F, Lagace C, Neale B3, Lo K S, Schumm P. Torkvist L, National Institute of D, Digestive Kidney Diseases Inflammatory Bowel Disease Genetics C, United Kingdom Inflammatory Bowel Disease Genetics C, International Inflammatory Bowel Disease Genetics C, Dubinsky M C. Brant S R. Silverberg M S, Duerr R H, Altshuler D, Gabriel S. Lettre G. Franke A, D'Amato M, McGovern D P, Cho J E H, Rioux J D, Xavier R J, Daly M J. Deep resequencing of GWAS loci identifies independent rare variants associated with inflammatory bowel disease. Nat Genet 2011; 46:1066-1073.
74. Beaudoin M, Coyette P, Boucher G, Lo K S, Rivas M A, Stevens C, Alikashani A, Ladouceur M, Ellinghaus D, Torkvist L, Goel G, Lagace C, Annese V, Bitton A, Begun J, Brant S R, Bresso F, Cho J H, Duerr R H, Halfvarson J, McGovern D P, Radford-Smith C, Schreiber S, Schumm P L, Sharma Y, Silverberg M S, Weersma R K, Quebec IBDGC, Consortium N I G, International IBDGC, D'Amato M, Vermeire S, Franke A, Lettre G, Xavier R J, Daly M J, Rioux J D. Deep resequencing of CWAS loci identifies rare variants in CARD9, IL23R and RNF186 that are associated with ulcerative colitis. PLoS Genet 2013; 9:e1003723.
75. Prescott N J, Lehne B, Stone K. Lee J C. Taylor K, Knight J, Papouli E, Mirza M M, Simpson M A, Spain S L, Li G, Fraternali F, Bumpstead S J, Gray E, Amar A, Bye H, Green P, Chung-Faye G, Hayee B, Pollok R, Satsangi J. Parkes M, Barrett J C, Mansfield J C, Sanderson J, Lewis C M, Weale M E, Schlitt T, Mathew C G. Consortium UIG. Pooled sequencing of 531 genes in inflammatory bowel disease identifies an associated rare variant in BTNL2 and implicates other immune related genes. PLoS Genet 2015; 11:e1004955.
76. Huang H, Fang M, Jostins L. Umicevic Mirkov M. Boucher G, Anderson C A, Andersen V, Cleynen I, Cortes A, Crins F, D'Amato M, Deffontaine V, Dmitrieva J, Docampo E, Elansary M, Farh K K, Franke A. Gori A S, Goyette P, Halfvarson J. Hlaritunians T, Knight J, Lawrance I C, Lees C W, Louis E, Mariman R, Meuwissen T, Mni M, Momozawa Y, Parkes M, Spain S L, Theatre E, Trynka G, Satsangi J, van Sommeren S, Vermeire S, Xavier R J, International Inflammatory Bowel Disease Genetics C, Weersma R K, Duerr R H, Mathew C G, Rioux J D, McGovern D P B, Cho J H, Georges M, Daly M J, Barrett J C. Fine-mapping inflammatory bowel disease loci to single-variant resolution. Nature 2017; 547:173-178.
77. Alam M S, Mackawa Y, Kitamura A, Tanigaki K, Yoshimoto T, Kishihara K. Yasutomo K. Notch signaling drives IL-22 secretion in CD4+ T cells by stimulating the aryl hydrocarbon receptor. Proc Natl Acad Sci USA 2010; 107:5943-5948.
78. Li Y, Innocentin S, Withers D R, Roberts N A, Gallagher A R, Grigorieva E F, Wilhelm C, Veldhoen M. Exogenous stimuli maintain intraepithelial lymphocytes via aryl hydrocarbon receptor activation. Cell 2011; 147:629-640.
79. Kiss E A, Vonarbourg C, Kopfmann S, Hobeika E, Finke D, Esser C. Diefenbach A. Natural aryl hydrocarbon receptor ligands control organogenesis of intestinal lymphoid follicles. Science 2011; 334:1561-1565,
80. Monteleone 1, Rizzo A, Sarra M, Sica G, Sileri P, Biancone L, MacDonald T T, Pallone F, Monteleone G. Aryl hydrocarbon receptor-induced signals up-regulate IL-22 production and inhibit inflammation in the gastrointestinal tract. Gastroenterology 2011; 141:237-248, 248 e231.
81. Qiu J, Heller J. J, Guo X, Chen Z M, Fish K, Fu Y X, Zhou L. The aryl hydrocarbon receptor regulates gut immunity through modulation of innate lymphoid cells. Immunity 2012; 36:92-104.
82. Qiu J, Guo X, Chen Z M, He L, Sonnenberg G F, Artis D, Fu Y X, Zhou L. Group 3 innate lymphoid cells inhibit T-cell-mediated intestinal inflammation through aryl hydrocarbon receptor signaling and regulation of microflora. Immunity 2013: 39:386-399.
83. Goettel J A, Gandhi R, Kenison J E. Yeste A, Nlurugaiyan G, Sambanthamoorthy S, Griffith A E, Patel B, Shouval D S, Weiner H L, Snapper S B, Quintana F J. AHR activation Is protective against colitis driven by T cells in humanized mice. Cell Rep 2016; 17:1318-1329.
84. Stockinger B, Di Meglio P, Gialitakis M, Duarte J H. The aryl hydrocarbon receptor: Multitasking in the immune system. Annu Rev Immunol 2014; 32:403-432.

85. Cella M, Colonna M. Aryl hydrocarbon receptor: Linking environment to immunity. Semin Immunol 2015; 27:310-314.
86. Esser C, R annug A. The aryl hydrocarbon receptor in barrier organ physiology, immunology, and toxicology. Pharmacol Rev 2015; 67:259-279.
87. Schiering C. Wincent E, Metidji A. Iseppon A, Li Y, Potocnik A J, Omenetti S, Henderson C J. Wolf C R, Nebert D W, Stockinger B. Feedback control of AHR signalling regulates intestinal immunity. Nature 2017: 542:242-245.
88. Trifari S, Kaplan C D, Tran E-I, Crellin N K, Spits 11. Identification of a human helper T cell population that has abundant production of interleukin 22 and is distinct from T(H)-17, T(H)$_1$ and T(H)$_2$ cells. Nat Imrnmunol 2009; 10:864-871.
89. Tumanov A V, Koroleva E P, Guo X, Wang Y, Kruglov A, Nedospasov S, Fu Y X. Lymphotoxin controls the IL-2 protection pathway in gut innate lymphoid cells during mucosal pathogen challenge. Cell Host Microbe 2011; 10:44-53.
90. Aujla S J, Chan Y R. Zheng M. Fei M, Askew D J, Pociask D A, Reinhart T A. McAllister F, Edeal J, Gaus K. Husain S, Kreindler J L, Dubin P J. Pilewski J M, Myerburg M M, Mason C A, Iwakura Y, Kolls J K. IL-22 mediates mucosal host defense against Grant-negative bacterial pneumonia. Nat Med 2008; 14:275-281.
91. Cua D J, Tato C M. Innate IL-17-producing cells: The sentinels of the immune system. Nat Rev Immunol 2010; 10:479-489.
92. Liu J Z, van Sommeren S, 1-luang H, Ng S C, Alberts R, Takahashi A, Ripke S, Lee J C, Jostins L, Shah T, Abedian S, Cheon J H, Cho J, Dayani N E, Franke L, Fuyuno Y. Hart A, Juyal R C, Juyal G, Kim W H, Morris A P, Poustchi F L, Newman W G, Midha V, Orchard T R, Vahedi H, Sood A, Sung J Y. Malekzadeh R, Westra H J, Yamazaki K. Yang S K, International Multiple Sclerosis Genetics C, International IBDGC, Barrett J C, Alizadeh B Z, Parkes M, Bk T, Daly M J, Kubo M, Anderson C A, Weersma R K. Association analyses identify 38 susceptibility loci for inflammatory bowel disease and highlight shared genetic risk across populations. Nat Genet 2015; 47:979-986.
93. Prager M, Buttner J, Grunert P, Ellinghaus D. Buning C. A promoter variant within the aryl hydrocarbon receptor gene Is associated with an epithelial barrier defect in smokers with crohn's disease. Inflamm Bowel Dis 2016; 22:2356-2368.
94. Bjeldanes L F, Kim J Y, Grose K R. Bartholomew J C, Bradfield C A. Aromatic hydrocarbon responsiveness-receptor agonists generated from indole-3-carbinol in vitro and in vivo: Comparisons with 2,3,7,8-tetrachlorodibenzo-p-dioxin. Proc Natl Acad Sci USA 1991; 88:9543-9547.
95. Jeuken A. Keser B J. Khan E, Brouwer A, Koeman J, Denison M S. Activation of the Ah receptor by extracts of dietary herbal supplements, vegetables, and fruits. J Agric Food Chem 2003: 51:5478-5487.
96. Moura-Alves P, Fae K, Houthuys E, Dorhoi A, Kreuchwig A, Furkert J. Barison N, Diehl A, Munder A, Constant P. Skrahina T, Guhlich-Bornhof U, Klemm M. Koehler A B, Bandermann S, Goosmann C, Mollenkopf H J, Hurwitz R, Brinkmann V. Fillatreau S, Daffe M, Tunmler B, Kolbe M, Oschkinat H, Krause C, Kaufmann S H. AhR sensing of bacterial pigments regulates antibacterial defence. Nature 2014; 512:387-392.
97. Wincent E, Amini N, Luecke S. Glatt H, Bergman J, Crescenzi C, Rannug A, Rannug U. The suggested physiologic aryl hydrocarbon receptor activator and cytochrome P4501 substrate 6-formylindolo[3,2-b]carbazole is present in humans. J Biol Chem 2009; 284:2690-2696.
98. Lin L, Xu X. Indole-3-acetic acid production by endophytic *Streptomyces* sp. En-1 isolated from medicinal plants. Curr Microbiol 2013; 67:209-217.
99. Hleath-Pagliuso S, Rogers W J, Tullis K, Seidel S D, Cenijn P H, Brouwer A, Denison M S. Activation of the Ah receptor by tryptophan and tryptophan metabolites. Biochemistry 1998; 37:11508-11515.
100. Lowe M M, Mold J E. Kanwar B, Huang Y, Louie A, Pollastri M P, Wang C, Patel G, Franks D G, Schlezinger J, Sherr D H, Silverstone A E, Hahn M E, McCune J M. Identification of cinnabarinic acid as a novel endogenous aryl hydrocarbon receptor ligand that drives IL-22 production. PLoS One 2014; 9:e87877.
101. Hubbard T D, Murray I A, Perdew G H. Indole and tryptophan metabolism: Endogenous and dietary routes to Ah receptor activation. Drug Metab Dispos 2015; 43:1522-1535.
102. Cervantes-Barragan L. Chai J N, Tianero M D, Di Luccia B, Ahern P P, Nlerriman J, Cortez V S, Caparon M G, Donia M S, Gilfillan S, Cella M, Gordon J I, Hsieh C S, Colonna M. *Lactobacillus reuteri* induces gut intraepithelial CD4(+)CD8alphaalpha(+) T cells. Science 2017; 357:806-810.
103. Huang Z, Jiang Y. Yang Y, Shao J, Sun X, Chen J, Dong L. Zhang J. 3,3-Diindolyimethane alleviates oxazolone-induced colitis through Th2/Th17 suppression and Treg induction. Mol Immunol 2013; 53:335-344.
104. Nguyen L P, Bradfield C A. The search for endogenous activators of the aryl hydrocarbon receptor. Chem Res Toxicol 2008; 21:102-116.
105. Rannug A, Rannug U, Rosenkranz H S, Wingvist L, Westerholm R, Agurell E, Grafstrom A K. Certain photooxidized derivatives of tryptophan bind with very high affinity to the Ah receptor and are likely to be endogenous signal substances. J Biol Chem 1987; 262:15422-15427.
106. Rannug U, Rannug A, Sjoberg U, Li H, Westerholm R, Bergman J. Structure elucidation of two tryptophan-derived, high affinity Ah receptor ligands. Chem Biol 1995; 2:841-845.
107. Song J. Clagett-Dame M, Peterson R E, Hahn M E, Westler W M, Sicinski R R, DeLuca H F. A ligand for the aryl hydrocarbon receptor isolated from lung. Proc Natl Acad Sci USA 2002; 99:14694-14699.
108. Kim Y H, Kwon H S, Kim D H, Shin E K, Kang Y H, Park J H, Shin H K, Kim J K. 3,3'-diindolylmethane attenuates colonic inflammation and tumorigenesis in mice. Inflamm Bowel Dis 2009: 15:1164-1173.
109. Suginoto S. Naganuma M, Kanai T. Indole compounds may be promising medicines for ulcerative colitis. J Gastroenterol 2016; 51:853-861.
110. Kawai S, Iijima H, Shinzaki S, Hiyama S, Yamaguchi T, Araki M, Iwatani S, Shiraishi E, Mukai A, Inoue T, Hayashi Y, Tsujii M, Motooka D, Nakamura S, Iida T. Takehara T. Indigo naturalis ameliorates murine dextran sodium sulfate-induced colitis via aryl hydrocarbon receptor activation. J Gastroenterol 2017: 52:904-919.
111. McDougal A, Gupta M S, Morrow D, Ramamoorthy K, Lee J E, Safe S H. Methyl-substituted diindolylmethanes as inhibitors of estrogen-induced growth of T47D cells and mammary tumors in rats. Breast Cancer Res Treat 2001; 66:147-157.

112. Murray I A, Morales J L, Flaveny C A, Dinatale B C, Chiaro C, Gowdahalli K, Amin S, Perdew G H. Evidence for ligand-mediated selective modulation of aryl hydrocarbon receptor activity. Mol Pharmacol 2010; 77:247-254.
113. Winston-McPherson G N, Shu D. Tang W. Synthesis and biological evaluation of 2,3'-diindolylmethanes as agonists of aryl hydrocarbon receptor. Bioorg Med Chem Lett 2014-24:4023-4025.
114. Blazevic T, Heiss E H, Atanasov A G, Breuss J M. Dirsch V M, Uhrin P. Indirubin and indirubin derivatives for counteracting proliferative diseases. Evid Based Complement Alternat Med 2015; 2015:654098.
115. Chakraborty S, Ghosh S, Banerjee B, Santra A, Adhikary A, Misra A K, Sen P C. Phemindole, a synthetic di-indole derivative maneuvers the store operated calcium entry (SOCE) to induce potent anti-carcinogenic activity in human triple negative breast cancer cells. Front Pharmacol 2016; 7:114.
116. Gutierrez M A, Davis S S, Rosko A, Nguyen S M, Mitchell K P, Mateen S, Neves J, Garcia T Y, Mooney S, Perdew G H, Hubbard T D. Lamba D A, Ramanathan A. A novel AhR ligand. 2AI, protects the retina from environmental stress. Sci Rep 2016; 6:29025.

Example 2—First Generation AHR Agonists Lack Suitable Pharmaceutical Properties for Therapeutic Development and Need Improvement Once ligand-activated, the aryl hydrocarbon receptor (AHR) interacts with a diverse group of co-activators and co-suppressors to form a supramolecular assembly that binds to a gene response element, thereby, controlling protein expression [1-3]. The formation of the AHR regulatory complex via specific protein-protein interactions (PPI) and the consequential unique pattern of gene expression is ligand-, tissue-, and context-dependent [4-13]. Distinct, ligand-dependent responses are thought to be due to induced conformational changes in AHR, which confers selective interactions with protein binding partners. AHR activation may lead to varied biological and toxicological responses that are specific to the nature of the AHR agonist with observed toxicity presumed a consequence of tool compound off-target effects [14-16]. For example, 2,3,7,8-tetrachlorodibenzo-p-dioxin (TCDD) and 6-formylindolo[3,2-b]carbazole (FICZ) display opposing effects in the delay of disease progression in murine models of multiple sclerosis (MS) [17-19]. Treatment of human epidermal keratinocytes with TCDD, but not ITE, induces a chloracne-like phenotype [20] and unlike TCDD, ITE neither suppresses placental vascular remodeling [21] nor induces thymic atrophy in rodents [22].

A number of high affinity tool compounds have been used to delineate the multifaceted biological functions of AHR. Toxicological findings associated with these agonists and, specifically, TCDD and benzo[a]pyrene [25, 26], have raised concerns that AHR does not represent a suitable therapeutic target. However, TCDD, as a polyhalogenated aromatic, induces perpetual activation of AHR due to its extremely long half-life (2,840 days) [23]. Likewise, benzo[a]pyrene, a polycyclic aromatic, forms epoxides that can non-selectively alkylate proteins and nucleic acids [27]. Similarly, the aldehyde group of FICZ is a known toxicophore because of its chemical reactivity and capacity to form a Schiff base [28]. Naturally occurring indirubin is known to cause cytotoxicity by inhibiting the activity of cyclin-dependent kinases and glycogen synthase kinase-3 [29-31]. Further, indirubin has very low water solubility (<1 µg/mL) that limits its oral bioavailability [32-34]. Therefore, while these preliminary AHR ligands have been useful tools, they lack the properties necessary to serve as a starting point for drug development.

There is overwhelming evidence that naturally occurring and synthetic AHR agonists are capable of inducing desired pharmacological effects without the toxicity commonly associated with TCDD or benzo[a]pyrene. Most notably, ITE, an endogenous high affinity AHR agonist, has not been associated with toxicity in a number of animal studies. Daily dosing of ITE for 3 weeks in a murine EAE model showed efficacy without hepatotoxicity, common to TCDD treatment [35, 36]. Similarly, in a 14-day mouse model of experimental autoimmune uveitis, daily treatment with ITE was safe and efficacious [37]. In a mouse model of IBD, daily dosing of ITE for 5 consecutive days reduced disease severity [38]. However, an important of ITE is the instability of the ester moiety, which is rapidly metabolized leading to compound inactivation. Even in cell culture, 75% of ITE is inactivated within 8 h [39]. To overcome this limitation, a nanoparticle formulation has been used to improve exposure in animal models of multiple sclerosis and diabetes [40, 41]. Nevertheless, intraperitoneal (IP) administration has been used in all of the aforementioned animal studies, which is impractical for clinical translation.

Drug-like AHR ligands suitable for oral administration as described herein have been designed and their therapeutic potential has been validated. Specifically, we have synthesized a focused library of 3-aroyl- and 3-heteroaroyl-indoles and analyzed their ability to activate AHR in a XRE luciferase assay (FIG. 1A). From the activity screen, we identified methyl 6-(1H-indole-3-carbonyl)pyridine-2-carboxylate (compound #10) as a novel synthetic AHR agonist with identical potency ($EC_{50}$: 3.2 nM) as ITE (FIG. 1B). Significantly, during the course of both computational and experimental studies we have identified stringent structural requirements for ligand induced activation of AHR. Specifically, the addition of a methyl group at the 2-position of the indole (FIG. 1B, #144), the replacement of N in the pyridine with CH (FIG. 1B, #202), or migrating the methyl ester to the 5-position of the pyridine (FIG. 1B, #11) all resulted in inactive compounds ($EC_{50}$>10,000 nM).

Homology modeling and molecular dynamics (MD) simulations were performed to investigate the unique structural requirements for AHR activation. Although the 3D structure of the AHR ligand-binding domain (LBD) has not been resolved by protein crystallography or NMR spectroscopy, the crystal structure of a truncated AHR mutant without the PAS B ligand-binding domain has been reported [42-45]. To capture the PAS B domain, ligand-bound structures of hypoxia-inducible factor 2α (HIF-2α), which shares ~26% homology to the human AHR PAS B domain, was used for construction of homology models [46-50]. MODELLER was applied to generate homology models using the co-crystal structures of HIF-2α PAS-B domain (PDB: 3H82, 3H7W, 3F10) [51, 52]. We selected the 20 best AHR models, as scored by Discrete Optimized Protein Energy (DOPE), as receptors for docking test compounds (Autodock Vina). Using the AHR tool compound #10, 200 ligand-receptor docking poses were produced by selecting the 10 lowest energy-binding poses for each receptor, which were further refined by explicit solvent energy minimization and then subject to 10 MD simulations, each for 100 nanoseconds, for a total 1 microsecond (GROMACS). After running all ten simulations, the AHR-LBD/#10 complex with the lowest potential energy was removed from the MD trajectory (FIG. 1C).

Homology modeling informed our understanding of AHR-ligand interactions, which guided subsequent SAR (structure-activity relationship) studies and optimization of drug-like properties. First, the model indicated that hydrogen (H) bonding interactions do not contribute to the stabilization of the complex. None of the indole NH, pyridine N, or carboxylate O atoms formed H-bonds with the surrounding amino acids in the ligand-binding domain. Instead, hydrophobic interactions were observed, predominantly involving LEU308, PHE324, ILE325, and LEU353, which surround the indole moiety, and MET330, CYS333, MET348, MET340, PHE295, ALA367, ILE379, and VAL381 that enclose the pyridyl-6-carboxylate methyl ester. Second, AHR tool compound #10 adopts a low energy conformer, optimal for positioning the pyridyl-6-carboxylate methyl ester within a deep pocket confined by MET340, ALA367, ILE379, and VAL381. Significantly, MET340 and ALA379 form the bottom of the pocket and are in close proximity, 3.78 and 3.40 Å, respectively, to the methyl carbon atom of compound #10. It is likely that this tight binding pocket, deep within the protein, does not have the flexibility to undergo a ligand-induced change in conformation, providing an explanation for the much lower AHR activity (>250-fold less active) observed for a slightly bulkier ethyl ester analogue (FIG. 1B, #147, $EC_{50}$: 840 nM). Conformational analysis (PLUMED) indicates that inactive compounds #144 and #202 were unable to adopt low-energy conformers that favor the occupancy of this pocket by the ester moiety. Specifically, steric clashes were observed between the methyl group at the 2-position of the indole and the pyridine ring in compound #144 and between the hydrogen atoms at the 2-position of indole and the 2-position of the 3-benzoyl methyl ester in compound #202 (FIG. 1D). The importance of appropriate filling the AHR pocket confined by MET340, ALA367, ILE379, and VAL381 is further highlighted by the inactivity (EC50>10,000 nM) of those analogues without an ester moiety (FIG. 1B, #124) or with an ester group directed away from the pocket (FIG. 1B, #11).

Ester groups are metabolically labile and readily hydrolyzed by plasma esterases or hepatic enzymes. Indeed, we observed that ITE and compound #10 were highly unstable when incubated in plasma (FIG. 1E) or in the presence of liver microsomes (FIG. 1F). Following oral dosing of mice with compound #10, LC-MS/MS analysis of plasma samples only revealed the presence of the much less active carboxylic acid derivative (#145 IC50: 640 nM) rather than the parent compound #10.

Homology modeling supported the notion that the methyl ester group contributes to ligand-receptor stabilization primarily by space filling and not through H-bonding interactions. Therefore, we synthesized analogues in which with the methyl ester was replaced with more stable substituents (FIG. 1G). Both cyano (CN) and trifluoromethyl ($CF_3$) analogues, compounds #108 and #109, displayed low nanomolar $EC_{50}$(<10 nM). The hydrophobic and flat phenyl ring in compound #113 was associated with a marginal decrease in potency ($EC_{50}$: 12 nM), while the hydrophilic and bulky morpholino group in compound #110 was detrimental, causing a nearly 20-fold decrease in activity ($EC_{50}$: 62 nM). Collectively, SAR investigations supported the findings of molecular simulation studies, which indicated a preference for a sterically small group at the 6-position of the pyridine. Moreover, plasma and liver microsomal stability were significantly improved upon replacement of the ester group with these more stable substituents with an observed half-life ($t_{1/2}$) in the liver microsomal assay of 69 and 60 min for compounds #108 and #109, respectively (FIGS. 1E and 1F). Compound #113 was stable in plasma but was rapidly metabolized by liver enzymes presumably due to increased hydrophobicity or metabolic degradation of the phenyl ring. Cell permeability was assessed using a Caco2 monolayer equilibrium dialysis assay. Compounds #108 and #109 exhibited high cellular permeability and a low efflux ratio (Apparent permeability $P_{app}$:412 nm/s for #108, 358 nm/s for #109; efflux ratio: 0.74 for #108, 1.07 for #109). These data indicate that compounds #108 and #109 are sufficiently stable to achieve a therapeutic effect by oral dosing, with appropriate plasma clearance to avoid persistent AHR activation. Therefore, both lead compounds were used for pharmacological validation in a preclinical model of IBD.

Once activated, the AHR heterodimerizes with another factor called Arnt to form a complex that binds to xenobiotic response elements (XREs), thereby enhancing expression of genes such as CYP1A1, CYP1A2, CYP1B1, ALDH3A1, NQO1, and UGT1A1, which play a role in metabolizing and detoxifying harmful xenobiotics. The Human HepG2 cell line is a human liver cancer cell line, and provide a relevant in vitro AHR activity model. These Hep2G cells have been modified to stably express an AHR-responsive (XRE) firefly luciferase reporter gene to give Hep2G-XRE cells. The expression of luciferase should primarily reflect AHR-dependent transcription controlled by XRE. See, e.g., Ishikawa T, et al. (2014) Induction of AhR-mediated gene transcription by coffee. PLoS ONE, 9, e102152.

Mouse macrophages were also used to test AHR-dependent transcription of the CYP1A1 gene in vivo. Finally, the activity of exemplary compounds of Formula (I) described herein was tested in the human lung cell line U937. The U937 cell line is derived from a patient with diffuse histiocytic lymphoma. Tables 2-4 summarize structure-activity relationship data collected for exemplary, non-limiting compounds of Formula (I) described herein.

TABLE 2

| Cmpd # | Structure | Human HepG2 XRE luciferase | | Mouse macrophages CYP1A1 induction | |
|---|---|---|---|---|---|
| | | $EC_{50}$ (nM) | $E_{max}$ (fold) | (% of ITE ± SEM) | |
| | | | | 5 µM | 50 nM |
| 10 | | 3.2 | 57 | 88 ± 38 | 143 ± 90 |

TABLE 2-continued
| Cmpd # | Structure | Human HepG2 XRE luciferase EC$_{50}$ (nM) | E$_{max}$ (fold) | Mouse macrophages CYP1A1 induction (% of ITE ± SEM) 5 μM | 50 nM |
|---|---|---|---|---|---|
| 147 | 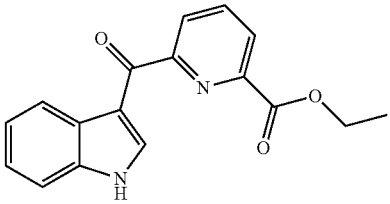 [SMILES: CCOC(=O)c1cccc(C(=O)c2c[nH]c3ccccc23)n1] | 840 | 40 | 52 ± 28 | 8 ± 2 |
| 1 | 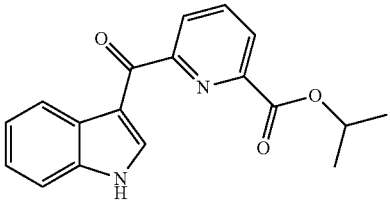 [SMILES: CC(C)OC(=O)c1cccc(C(=O)c2c[nH]c3ccccc23)n1] | 370 | 37 | 128 ± 11 | 22 ± 11 |
| 2 | 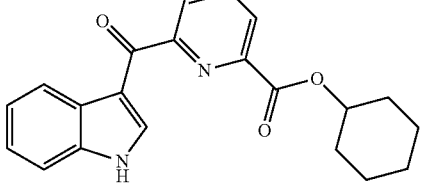 | 12000 | 55 | 95 ± 7 | 19 ± 4 |
| 3 | 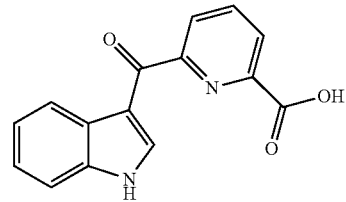 [SMILES: O=C(O)c1cccc(C(=O)c2c[nH]c3ccccc23)n1] | 640 | 47 | 97 ± 16 | 27 ± 17 |
| 4 | 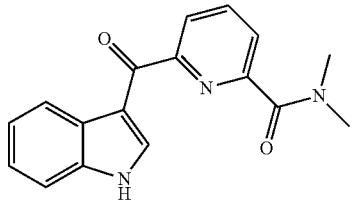 | >10,000[b] | 23 | 2.5 ± 1.4 | — |
| 5 | 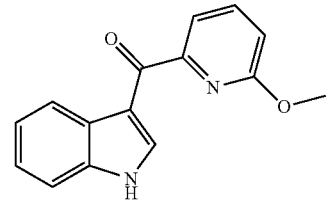 [SMILES: COc1cccc(C(=O)c2c[nH]c3ccccc23)n1] | 96 | 48 | 101 ± 33 | 168 ± 86 |

TABLE 2-continued

| Cmpd # | Structure | Human HepG2 XRE luciferase EC$_{50}$ (nM) | E$_{max}$ (fold) | Mouse macrophages CYP1A1 induction (% of ITE ± SEM) 5 μM | 50 nM |
|---|---|---|---|---|---|
| 6 | indol-3-yl (6-chloropyridin-2-yl) ketone | (29)$^a$ | (109)$^c$ | | 86 ± 47 |
| 108 | indol-3-yl (6-cyanopyridin-2-yl) ketone | 2.8 | 74 | 94 ± 24 | 33 ± 3 |
| 109 | indol-3-yl (6-trifluoromethylpyridin-2-yl) ketone | 2.3 | 66 | 90 ± 17 | 124 ± 5 |
| 113 | indol-3-yl (6-phenylpyridin-2-yl) ketone | (12.1)$^a$ | (114)$^c$ | 97 ± 9 | 91 ± 7 |
| 110 | indol-3-yl (6-morpholinopyridin-2-yl) ketone | 62 | 59 | 46 ± 4 | — |
| 124 | indol-3-yl (pyridin-2-yl) ketone | >10,000$^b$ | 20 | 15 ± 6 | — |

TABLE 2-continued

| Cmpd # | Structure | Human HepG2 XRE luciferase EC$_{50}$ (nM) | E$_{max}$ (fold) | Mouse macrophages CYP1A1 induction (% of ITE ± SEM) 5 μM | 50 nM |
|---|---|---|---|---|---|
| 7 | (3-benzoyl-1H-indole) | — | — | 0.6 ± 0.2 | — |
| 8 | (methyl 3-(1H-indole-3-carbonyl)benzoate) | >10,000[b] | (2.1)[c] | — | 3 ± 1 |
| 9 | (3-methoxyphenyl)(1H-indol-3-yl)methanone | >10,000[b] | (25)[c] | — | 9 ± 5 |
| 12 | 3-(1H-indole-3-carbonyl)phenyl acetate | — | — | — | 5 ± 3 |
| 13 | methyl 6-(1-methyl-1H-indole-3-carbonyl)picolinate | 190 | 55 | 50 ± 20 | 29 ± 10 |
| 144 | methyl 6-(2-methyl-1H-indole-3-carbonyl)picolinate | >10,000[b] | (22)[c] | 6 ± 2 | — |

TABLE 2-continued
| Cmpd # | Structure | Human HepG2 XRE luciferase | | Mouse macrophages CYP1A1 induction (% of ITE ± SEM) | |
|---|---|---|---|---|---|
| | | EC$_{50}$ (nM) | E$_{max}$ (fold) | 5 μM | 50 nM |
| 14 | 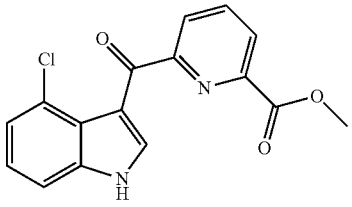 [SMILES: COC(=O)c1cccc(C(=O)c2c[nH]c3cccc(Cl)c23)n1] | >10,000[b] | (19)[c] | — | 141 ± 83 |
| 15 | 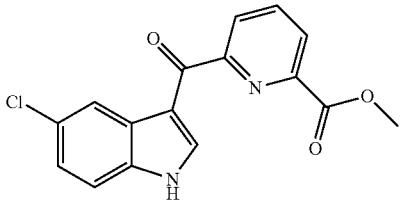 [SMILES: COC(=O)c1cccc(C(=O)c2c[nH]c3ccc(Cl)cc23)n1] | 7.6 | 62 | 89 ± 44 | 150 ± 36 |
| 16 | 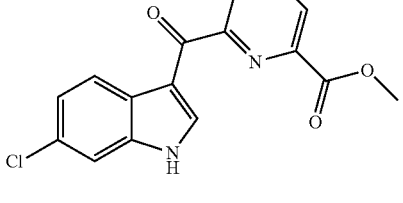 | (1.6)[a] | (141)[c] | 122 ± 48 | 169 ± 59 |
| 17 | 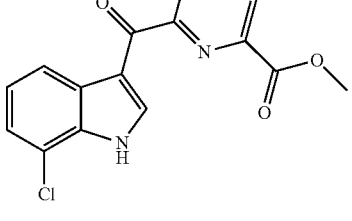 | 1.3 | 68 | — | 49 ± 19 |
| 18 | 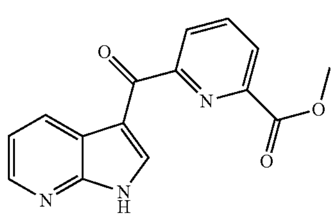 [SMILES: COC(=O)c1cccc(C(=O)c2c[nH]c3ncccc23)n1] | 18 | 42 | — | 11 ± 4 |
| 19 | 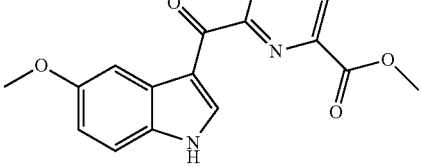 | 1800 | 131 | 120 ± 13 | 121 ± 12 |

TABLE 2-continued

| Cmpd # | Structure | Human HepG2 XRE luciferase EC$_{50}$ (nM) | E$_{max}$ (fold) | Mouse macrophages CYP1A1 induction (% of ITE ± SEM) 5 µM | 50 nM |
|---|---|---|---|---|---|
| 20 | | 6.2 | 55 | 144 ± 20 | 138 ± 8 |
| 21 | | 27 | 53 | 118 ± 5 | 129 ± 8 |
| 22 | | (14)$^a$ | (121)$^c$ | 105 ± 3 | 57 ± 5 |
| 11 | | >10,000$^b$ | (2.3)$^c$ | 26 ± 10 | 2 ± 1 |
| 23 | | 4,700 | 74 | 65 ± 9 | — |
| 24 | | 860 | 81 | 59 ± 22 | 99 ± 18 |

TABLE 2-continued

| Cmpd # | Structure | Human HepG2 XRE luciferase EC$_{50}$ (nM) | E$_{max}$ (fold) | Mouse macrophages CYP1A1 induction (% of ITE ± SEM) 5 µM | 50 nM |
|---|---|---|---|---|---|
| 25 | indol-3-yl 4-(methoxycarbonyl)phenyl ketone | — | — | — | 20 ± 16 |
| 26 | indol-3-yl 2-(methoxycarbonyl)phenyl ketone | — | — | — | 10 ± 7 |
| 27 | indol-3-yl 2-methoxyphenyl ketone | — | — | — | 6 ± 1 |
| 28 | indol-3-yl 4-methoxyphenyl ketone | — | — | — | 19 ± 8 |
| 29 | indol-3-yl 2-methoxypyridin-4-yl ketone | 2,600 | 65 | 44 ± 2 | — |
| 30 | indol-3-yl 5-methoxypyrazin-2-yl ketone | (8.1)$^a$ | (30)$^c$ | 41 ± 3 | — |

TABLE 2-continued

| Cmpd # | Structure | Human HepG2 XRE luciferase | | Mouse macrophages CYP1A1 induction (% of ITE ± SEM) | |
|---|---|---|---|---|---|
| | | $EC_{50}$ (nM) | $E_{max}$ (fold) | 5 µM | 50 nM |
| ITE (control) | 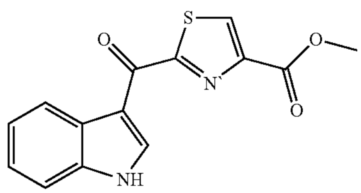 | 5.3 | 63 | 100 | 100 |

[a] For compounds, $EC_{50}$ defined as concentration induced 50% of $E_{max}$ of ITE.
[b] For compounds that do not reach 50% of $E_{max}$ of ITE at 10 µM (highest concentration tested). $EC_{50}$ described as >10 µM.
[c] $E_{max}$ defined as fold increase at highest concentration tested (10 µM)

TABLE 3

| Cmpd # | Structure | XRE luciferase Human HepG2 | | CYP1A1 induction (% of ITE ± SEM) | | | |
|---|---|---|---|---|---|---|---|
| | | | | Mouse macrophages | | Human U937 | |
| | | $EC_{50}$ (nM) | $E_{max}$ (fold) | 5 µM | 50 nM | 5 nM | 1 µM |
| 144 | 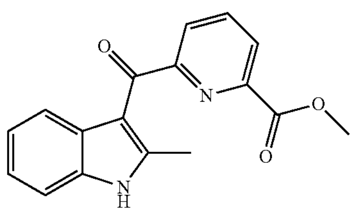 [SMILES: COC(=O)c1cccc(C(=O)c2c(C)[nH]c3ccccc23)n1] | >10,000[b] | (22)[c] | 6 ± 2 | — | — | 29 ± 14 |
| 202 | 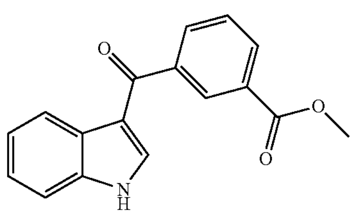 [SMILES: COC(=O)c1cccc(C(=O)c2c[nH]c3ccccc23)c1] | >10,000[b] | (2.1)[c] | — | 3 ± 1 | — | 3 ± 1 |
| 5 | 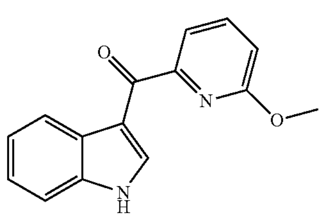 [SMILES: COc1cccc(C(=O)c2c[nH]c3ccccc23)n1] | 96 | 48 | 101 ± 33 | 168 ± 86 | 57 ± 22 | 165 ± 27 |
| 9 | 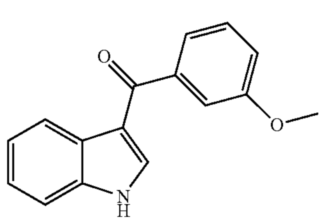 [SMILES: COc1cccc(C(=O)c2c[nH]c3ccccc23)c1] | >10,000[b] | (25)[c] | — | 9 ± 5 | — | 101 ± 12 |

TABLE 3-continued

| Cmpd # | Structure | XRE luciferase Human HepG2 | | CYP1A1 induction (% of ITE ± SEM) | | | |
|---|---|---|---|---|---|---|---|
| | | | | Mouse macrophages | | Human U937 | |
| | | $EC_{50}$ (nM) | $E_{max}$ (fold) | 5 μM | 50 nM | 5 nM | 1 μM |
| 24 | [indole-C(O)-thiophene-C(O)OMe] | 860 | 81 | 59 ± 22 | 99 ± 18 | 60 ± 13 | 244 ± 28 |
| Control | [indazole-C(O)-phenyl-C(O)OMe] | 680 | 117 | 90 ± 2 | 14 ± 4 | — | 48 ± 6 |
| Control | [indazole-C(O)-phenyl-OMe] | (2000)[a] | (87)[c] | 27 ± 3 | 1 ± 0.2 | — | 194 ± 18 |
| ITE (control) | [indole-C(O)-thiazole-C(O)OMe] | 5.3 | 63 | 100 | 100 | 100 | 100 |

[a] For compounds, $EC_{50}$ defined as concentration induced 50% of $E_{max}$ of ITE.
[b] For compounds that do not reach 50% of $E_{max}$ of ITE at 10 μM (highest concentration tested). $EC_{50}$ described as >10 μM.
[c] $E_{max}$ defined as fold increase at highest concentration tested (10 μM)

TABLE 4

| Cmpd # | Structure | XRE luciferase | | | | CYP1A1 induction (% of ITE ± SEM) | | | |
|---|---|---|---|---|---|---|---|---|---|
| | | Human HepG2 | | Mouse Hepa1c1c7 | | Mouse macrophages | | Human U937 | |
| | | $EC_{50}$ (nM) | $E_{max}$ (fold) | $EC_{50}$ (nM) | $E_{max}$ (fold) | 5 μM | 50 nM | 5 nM | 1 μM |
| 108 | [indole-C(O)-pyridine-CN] | 2.8 | 74 | 94 | 86 | 94 ± 24 | 33 ± 3 | — | — |

TABLE 4-continued

| | | XRE luciferase | | | | CYP1A1 induction (% of ITE ± SEM) | | | |
|---|---|---|---|---|---|---|---|---|---|
| | | Human HepG2 | | Mouse Hepa1c1c7 | | | | | |
| | | | | | | Mouse macrophages | | Human U937 | |
| Cmpd # | Structure | EC$_{50}$ (nM) | E$_{max}$ (fold) | EC$_{50}$ (nM) | E$_{max}$ (fold) | 5 μM | 50 nM | 5 nM | 1 μM |
| 109 | | 2.3 | 66 | 0.7 | 92 | 90 ± 17 | 124 ± 5 | — | — |
| ITE (control) | | 5.3 | 63 | 30 | 79 | 100 | 100 | 1100 | 100 |

REFERENCES

1. Stockinger, B. et al. (2014) The aryl hydrocarbon receptor: multitasking in the immune system. Annu Rev Immunol 32, 403-32.
2. Bock, K. W. (2017) From dioxin toxicity to putative physiologic functions of the human Ah receptor in homeostasis of stem/progenitor cells. Biochem Pharmacol 123, 1-7.
3. Bock, K. W. (2017) Human and rodent aryl hydrocarbon receptor (AHR): from mediator of dioxin toxicity to physiologic AHR functions and therapeutic options. Biol Chem 398 (4), 455-464.
4. Denison, M. S. et al. (2011) Exactly the same but different: promiscuity and diversity in the molecular mechanisms of action of the aryl hydrocarbon (dioxin) receptor. Toxicol Sci 124 (1), 1-22.
5. Ehrlich, A. K. et al. (2017) TCDD, FICZ, and other high affinity AhR ligands dose-dependently determine the fate of CD4+ T cell differentiation. Toxicol Sci.
6. Farmahin, R. et al. (2016) Time-dependent transcriptomic and biochemical responses of 6-formylindolo[3,2-b]carbazole (FICZ) and 2,3,7,8-tetrachlorodibenzo-p-dioxin (TCDD) are explained by AHR activation time. Biochem Pharmacol 115, 134-43.
7. Harrill, J. A. et al. (2015) Lineage-dependent effects of aryl hydrocarbon receptor agonists contribute to liver tumorigenesis. Hepatology 61 (2), 548-60.
8. Mitchell, K. A. and Elferink, C. J. (2009) Timing is everything: consequences of transient and sustained AhR activity. Biochem Pharmacol 77 (6), 947-56.
9. Wall, R. J. et al. (2012) Novel 2-amino-isoflavones exhibit aryl hydrocarbon receptor agonist or antagonist activity in a species/cell-specific context. Toxicology 297 (1-3), 26-33.
10. Wheeler, J. L. et al. (2014) Differential consequences of two distinct AhR ligands on innate and adaptive immune responses to influenza A virus. Toxicol Sci 137 (2), 324-34.
11. Guyot, E. et al. (2013) The AhR twist: ligand-dependent AhR signaling and pharmaco-toxicological implications. Drug Discov Today 18 (9-10), 479-86.
12. Zhou, L. (2016) AHR Function in Lymphocytes: Emerging Concepts. Trends Immunol 37 (1), 17-31.
13. Kawajiri, K. and Fujii-Kuriyama, Y. (2017) The aryl hydrocarbon receptor: a multifunctional chemical sensor for host defense and homeostatic maintenance. Exp Anim 66 (2), 75-89.
14. Denison, M. S. and Faber, S. C. (2017) And Now for Something Completely Different: Diversity in Ligand-Dependent Activation of Ah Receptor Responses. Curr Opin Toxicol 2, 124-131.
15. Sorg, O. (2014) AhR signalling and dioxin toxicity. Toxicol Lett 230 (2), 225-33.
16. Okey, A. B. (2007) An aryl hydrocarbon receptor odyssey to the shores of toxicology: the Deichmann Lecture, International Congress of Toxicology-XI. Toxicol Sci 98 (1), 5-38.
17. Duarte, J. H. et al. (2013) Differential influences of the aryl hydrocarbon receptor on Th17 mediated responses in vitro and in vivo. PLoS One 8 (11), e79819.
18. Quintana, F. J. et al. (2008) Control of T(reg) and T(H)17 cell differentiation by the aryl hydrocarbon receptor. Nature 453 (7191), 65-71.
19. Veldhoen, M. et al. (2008) The aryl hydrocarbon receptor links TH17-cell-mediated autoimmunity to environmental toxins. Nature 453 (7191), 106-9.
20. Forrester, A. R. et al. (2014) Induction of a chloracne phenotype in an epidermal equivalent model by 2,3,7,8-tetrachlorodibenzo-p-dioxin (TCDD) is dependent on aryl hydrocarbon receptor activation and is not reproduced by aryl hydrocarbon receptor knock down. J Dermatol Sci 73 (1), 10-22.
21. Wu, Y. et al. (2014) ITE and TCDD differentially regulate the vascular remodeling of rat placenta via the activation of AhR. PLoS One 9 (1), e86549.
22. Henry, E. C. et al. (2006) A potential endogenous ligand for the aryl hydrocarbon receptor has potent agonist activity in vitro and in vivo. Arch Biochem Biophys 450 (1), 67-77.

23. Geyer, H. J. et al. (2002) Half-lives of tetra-, penta-, hexa-, hepta-, and octachlorodibenzo-p-dioxin in rats, monkeys, and humans-a critical review. Chemosphere 48 (6), 631-44.
24. Boffetta, P. et al. (2011) TCDD and cancer: a critical review of epidemiologic studies. Crit Rev Toxicol 41 (7), 622-36.
25. Hockley, S. L. et al. (2007) AHR- and DNA-damage-mediated gene expression responses induced by benzo(a)pyrene in human cell lines. Chem Res Toxicol 20 (12), 1797-810.
26. Kerley-Hamilton, J. S. et al. (2012) Inherent and benzo[a]pyrene-induced differential aryl hydrocarbon receptor signaling greatly affects life span, atherosclerosis, cardiac gene expression, and body and heart growth in mice. Toxicol Sci 126 (2), 391-404.
27. Srivastava, A. et al. (2010) Role of reactive metabolites in drug-induced hepatotoxicity. Handb Exp Pharmacol (196), 165-94.
28. Benigni, R. et al. (2013) Nongenotoxic carcinogenicity of chemicals: mechanisms of action and early recognition through a new set of structural alerts. Chem Rev 113 (5), 2940-57.
29. Hoessel, R. et al. (1999) Indirubin, the active constituent of a Chinese antileukaemia medicine, inhibits cyclin-dependent kinases. Nat Cell Biol 1 (1), 60-7.
30. Meijer, L. et al. (2003) GSK-3-selective inhibitors derived from Tyrian purple indirubins. Chem Biol 10 (12), 1255-66.
31. Polychronopoulos, P. et al. (2004) Structural basis for the synthesis of indirubins as potent and selective inhibitors of glycogen synthase kinase-3 and cyclin-dependent kinases. J Med Chem 47 (4), 935-46.
32. Cheng, X. et al. (2017) Identification of a Water-Soluble Indirubin Derivative as Potent Inhibitor of Insulin-like Growth Factor 1 Receptor through Structural Modification of the Parent Natural Molecule. J Med Chem 60 (12), 4949-4962.
33. Chen, Z. Q. et al. (2012) Improved oral bioavailability of poorly water-soluble indirubin by a supersaturatable self-microemulsifying drug delivery system. Int J Nanomedicine 7, 1115-25.
34. Jautelat, R. et al. (2005) From the insoluble dye indirubin towards highly active, soluble CDK2-inhibitors. Chembiochem 6 (3), 531-40.
35. Quintana, F. J. et al. (2010) An endogenous aryl hydrocarbon receptor ligand acts on dendritic cells and T cells to suppress experimental autoimmune encephalomyelitis. Proc Natl Acad Sci USA 107 (48), 20768-73.
36. Smith, A. G. et al. (1981) Hepatic toxicity and uroporphyrinogen decarboxylase activity following a single dose of 2,3,7,8-tetrachlorodibenzo-p-dioxin to mice. Biochem Pharmacol 30 (20), 2825-30.
37. Nugent, L. F. et al. (2013) ITE, a novel endogenous nontoxic aryl hydrocarbon receptor ligand, efficiently suppresses EAU and T-cell-mediated immunity. Invest Ophthalmol Vis Sci 54 (12), 7463-9.
38. Goettel, J. A. et al. (2016) AHR activation is protective against colitis driven by T cells in humanized mice. Cell Rep 17 (5), 1318-29.
39. Cheng, J. et al. (2015) Tryptophan derivatives regulate the transcription of Oct4 in stem-like cancer cells. Nat Commun 6, 7209.
40. Yeste, A. et al. (2012) Nanoparticle-mediated codelivery of myelin antigen and a tolerogenic small molecule suppresses experimental autoimmune encephalomyelitis. Proc Natl Acad Sci USA 109 (28), 11270-5.
41. Yeste, A. et al. (2016) Tolerogenic nanoparticles inhibit T cell-mediated autoimmunity through SOCS2. Sci Signal 9 (433), ra61.
42. Sakurai, S. et al. (2017) The crystal structure of the AhRR-ARNT heterodimer reveals the structural basis of the repression of AhR-mediated transcription. J Biol Chem 292 (43), 17609-17616.
43. Schulte, K. W. et al. (2017) Structural Basis for Aryl Hydrocarbon Receptor-Mediated Gene Activation. Structure 25 (7), 1025-1033.e3.
44. Seok, S. H. et al. (2017) Structural hierarchy controlling dimerization and target DNA recognition in the AHR transcriptional complex. Proc Natl Acad Sci USA 114 (21), 5431-5436.
45. Wu, D. et al. (2013) Structure and dimerization properties of the aryl hydrocarbon receptor PAS-A domain. Mol Cell Biol 33 (21), 4346-56.
46. Bisson, W. H. et al. (2009) Modeling of the aryl hydrocarbon receptor (AhR) ligand binding domain and its utility in virtual ligand screening to predict new AhR ligands. J Med Chem 52 (18), 5635-41.
47. Dolciami, D. et al. (2017) Binding Mode and Structure-Activity Relationships of ITE as Aryl Hydrocarbon Receptor (AhR) Agonist. Chem Med Chem.
48. Fraccalvieri, D. et al. (2013) Comparative analysis of homology models of the AH receptor ligand binding domain: verification of structure-function predictions by site-directed mutagenesis of a nonfunctional receptor. Biochemistry 52 (4), 714-25.
49. Motto, I. et al. (2011) New aryl hydrocarbon receptor homology model targeted to improve docking reliability. J Chem Inf Model 51 (11), 2868-81.
50. Perkins, A. et al. (2014) A Structural Switch between Agonist and Antagonist Bound Conformations for a Ligand-Optimized Model of the Human Aryl Hydrocarbon Receptor Ligand Binding Domain. Biology (Basel) 3 (4), 645-69.
51. Scheuermann, T. H. et al. (2009) Artificial ligand binding within the HIF2α PAS-B domain of the HIF2 transcription factor. Proc Natl Acad Sci USA 106 (2), 450-5.
52. Key, J. et al. (2009) Principles of ligand binding within a completely buried cavity in HIF2α PAS-B. J Am Chem Soc 131 (48), 17647.

Methods of Preparation and Synthetic Procedures

All reagents and solvents were purchased from commercially available sources and used without further purification. All reactions were carried out according to the indicated procedures and conditions. Reactions were monitored by LC/MS analysis and/or thin-layer chromatography (TLC) on silica-coated glass plates (EMD silica gel 60 F254) with the indicated eluent. The compounds were visualized by UV light (254 nm). LC/MS analysis was performed on an Agilent 1200 HPLC/UV (220 nm and/or 254 nm wavelength) system coupled with a mass spectroscopic (Applied Biosystems, MDS SCIEX, Q TRAP LC/MS/MS) detector. Compounds for analysis were dissolved in 100% DMSO and separated on C18 cartridge (particle size 2.6m, dimensions: 100 mm×2.1 mm, 0.3 mL/min flow rate, 1 mL injection volume) using acetonitrile/water mobile phase with 0.1% formic acid as a modifier. The gradient started at 20% acetonitrile, held for 2 min, and linearly increased to 97% acetonitrile over 10 min, with 3 min hold at 97% acetonitrile and subsequent re-equilibration to the original conditions in a total of 17 min. All compounds reported were obtained in a purity as >95% at 254 nm wavelength. Nuclear magnetic resonance ($^1$H NMR) spectra were recorded on a Varian Mercury plus NMR spectrometer operating at 400.13 MHz frequencies for 1H, using a 5 mm ASW PFG probe capable of detecting $^{1}H$, $^{13}C$, $^{31}P$, and $^{15}N$ nuclei. The proton chemical shifts (ppm) were referenced to the tetramethylsilane internal standard (0 ppm). NMR data are reported with these descriptions: s, singlet; d, doublet; t, triplet; q, quartet; m, multiplet; br, broad peak.

A general synthetic procedure is shown in Scheme A below.

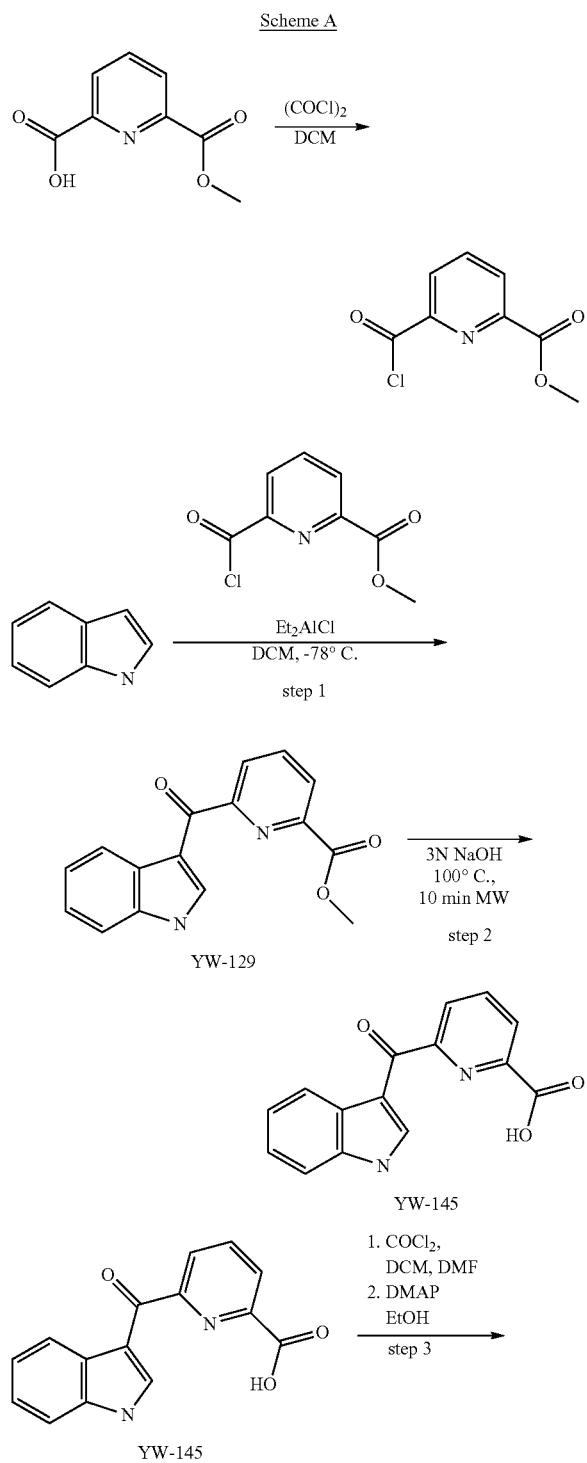

Step 1: Synthesis of methyl 6-(1H-indole-3-carbonyl) pyridine-2-carboxylate. To a solution of 2,6-Pyridinedicarboxylic acid monomethyl ester (20 mmol, 3.62 g) in 20 mL anhydrous DCM was slowly added $(COCl)_2$ (100 mmol, 14 g) and a drop of DMF. The mixture was stirred at 30° C. for 1 hour. TLC showed the disappearance of the starting material. The mixture was concentrated to get a light yellow liquid as the acid chloride. To a solution of indole (24 mmol, 2.81 g) in 15 mL anhydrous DCM, $Et_2AlCl$ (24 mmol, 24 mL, 1 M in ethanol) was slowly added at −78° C. The mixture was stirred for 15 minutes. The corresponding acid chloride, dissolved in 2 mL DCM, was added to the solution at −10° C. The mixture was stirred at room temperature for 2 hours. TLC showed the disappearance of the starting material and the formation of one major spot. The mixture was washed with water for 3 times. The mixture was concentrated to get a yellow residue. The residue was loaded on a silica gel column and flash-chromatographed with hexane/EtOAc (3:1) and the desired fractions were pooled. After evaporation of solvent the residue was dried in vacuo to afford the title compound. 1.50 g: yield 27% as a pink solid. $^{1}H$ NMR (400 MHz DMSO-d6) δ 12.19 (s, 1H), 9.11 (d, 1H, J=1.6 Hz), 8.40-8.43 (m, 1H), 8.22-8.31 (m, 3H), 7.53-7.55 (m, 1H), 7.26-7.28 (m, 2H), 3.98 (s, 3H, CH3), MS (ESI+): m/z calc. for $[C_{16}H_{12}N_2O_3]$ 280.08. Found: 281.4 $[M+H]^+$.

Step 2. Synthesis of 6-(1H-indole-3-carbonyl)pyridine-2-carboxylic acid. To a solution of 3N NaOH (5 mL) was added methyl 6-(1H-indole-3-carbonyl)pyridine-2-carboxylate (100 mg). The mixture was reacted by microwave reactor at 100° C. for 10 minutes. TLC showed the disappearance of the starting material and formation of one major spot. The solution was cooled in an ice bath, and the pH was adjusted 3 to 4 using 1 N HCl. The resulting suspension was chilled in a dry ice/acetone bath and thawed to 4° C. overnight in a refrigerator. The precipitate was filtered, washed with cold water, and dried in a desiccator under reduced pressure using $P_2O_5$ afford 1e 85 mg: yield 90% as a yellow powder. $^{1}H$ NMR (400 MHz DMSO-d6) δ 13.50 (s, 1H), 12.18 (s, 1H), 9.22 (d, 1H, J=1.6 Hz), 8.41-8.44 (m, 1H), 8.19-8.29 (m, 3H), 7.52-7.55 (m, 1H), 7.26-7.28 (m, 2H), MS (ESI+): m/z calc. for $[C_{15}H_{10}N_2O_3]_{266.07}$. Found: 266.5 $[M+H]^+$.

Step 3. Synthesis of ethyl 6-(1H-indole-3-carbonyl)pyridine-2-carboxylate. To a solution of 6-(1H-indole-3-carbonyl)pyridine-2-carboxylic acid (0.3 mmol, 80 mg) in 5 mL anhydrous DCM was slowly added $(COCl)_2$ (1.5 mmol, 0.25 g) and a drop of DMF. The mixture was stirred at room temperature for 1 hour. TLC showed the disappearance of the starting material. The mixture was concentrated to get a light yellow liquid as the acid chloride. The acid chloride was added into 10 mL EtOH and DMAP (0.03 mmol, 4 mg). The mixture was stirred at room temperature for overnight. TLC showed the disappearance of the starting material and the formation of one major spot. The mixture was concentrated to get a yellow residue. The residue was loaded on a silica gel column and flash-chromatographed with hexanes/EtOAc (3:1) and the desired fractions were pooled. After evaporation of solvent the residue was dried in vacuo to afford 80 mg: yield 91% as a pale solid. $^1$H NMR (400 MHz DMSO-d6) δ 12.22 (s, 1H), 9.21 (d, J=1.6 Hz, 1H), 8.41-8.44 (m, 1H), 8.22-8.31 (m, 3H), 7.54-7.56 (m, 1H), 7.26-7.28 (m, 2H), 1.43 (t, J=7.2 Hz, 3H), 4.44 (q, J=10.8 Hz, 2H), MS (ESI+): m/z calc. for $[C_{17}H_{14}N_2O_3]$ 294.10. Found: 295.6 $[M+H]^+$.

A second general synthetic procedure is shown in Scheme B below.

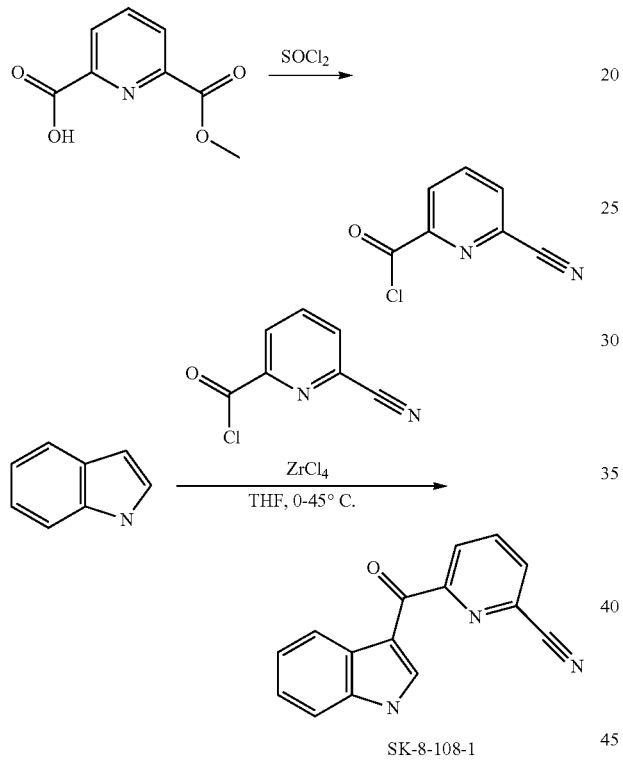

Scheme B

Preparation of 6-(1H-indole-3-carbonyl)pyridine-2-carbonitrile was carried out according to Scheme B. 6-cyanopyridine-2-carboxylic acid (350 mg, 2.4 mmol) was in 2 mL SOCl$_2$. DMF (one drop) was added. The reaction was heated to 40° C. for 3 hours. After cooling to room temperature the solvent was removed in vacuo. The resulting 6-cyanopyridine-2-carbonyl chloride was dried overnight in vacuo and used without further purification. To a solution of indole (304 mg, 2.6 mmol) in anhydrous DCE (4 mL) at 0° C. under nitrogen, 6-cyanopyridine-2-carbonyl chloride (2.4 mmol, in 3 mL DCE) was added by syringe. Zirconiumtetrachloride (699 mg, 3.0 mmol) was added under a flow of nitrogen. The reaction temperature was increased to 45° C. and kept at this temperature until completion (24-30 hours). After completion of the reaction, indicated by LCMS, the mixture was quenched with water (15 mL) and extracted with EtOAc (3×50 mL). The combined organic layer was washed with water (10 mL), dried with anhydrous Na$_2$SO$_4$, and concentrated under vacuum. Purification by HPLC (acetonitrile/water with 0.1% TFA as modifier; 30-97% acetonitrile over 25 min) yielded the title compound as beige powder. $^1$H NMR (400 MHz DMSO-d6) δ 12.16 (s, 1H), 8.65 (dJ=3.2 Hz, 1H,), 8.32-8.35 (m, 1H), 8.23-8.28 (m, 3H), 7.53-7.56 (m, 1H), 7.24-7.29 (m, 2H), MS (ESI+): m/z calc. for $[C_{15}H_9N_3O]$ 247.07. Found: 248.6 $[M+H]^+$.

A third general synthetic procedure is shown in Scheme C.

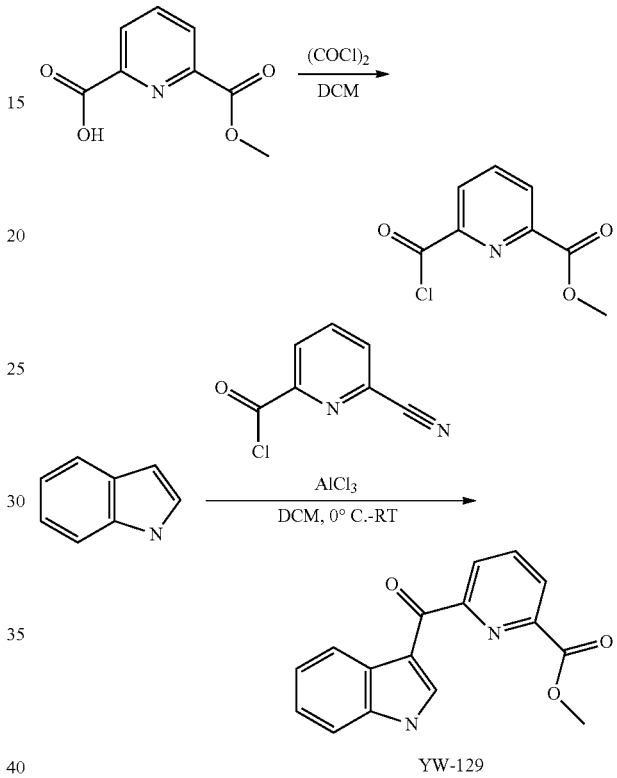

Scheme C

Synthesis of methyl 6-(1H-indole-3-carbonyl)pyridine-2-carboxylate using Scheme C. To a solution of 2,6-Pyridinedicarboxylic acid monomethyl ester (740 mg, 4 mmol) in 20 mL anhydrous DCM was slowly added (COCl)$_2$ (2.7 g, 21 mmol) and a drop of DMF. The mixture was stirred at 30° C. for 1 hour. TLC showed the disappearance of the starting material. The mixture was concentrated to get a light yellow liquid as the acid chloride. To a solution of indole (608 mg, 5.2 mmol) in 3 mL anhydrous DCM was added methyl 6-chlorocarbonylpyridine-2-carboxylate, dissolved in 2 mL DCM at 0'° C. To the mixture was added and AlCl$_3$ (800 mg, 6 mmol) at 0'° C. The mixture was stirred for 15 mins then slowly allowed to warm to room temperature. The reaction was stirred at room temperature overnight. TLC showed the disappearance of the starting material. The mixture was quenched with 2 N HCl (5 mL) washed with water (10 mL) for 3 times, dried over Na$_2$SO$_4$ and concentrated to get a yellow residue. The residue was purified by preparative HPLC (acetonitrile/water with 0.1% TFA as modifier; 30-97% acetonitrile over 25 min) to yield compound YW-129.

155

Synthesis of 1H-indol-3-yl(2-pyridyl)methanone

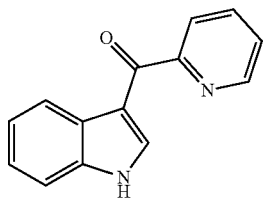 [SMILES: O=C(c1ccccn1)c1c[nH]c2ccccc12]

The title compound was synthesized according to Scheme A: yield 24% as a yellow viscose oil. $^1$H NMR (400 MHz DMSO-$d_6$): δ12.08 (s, 1H), 8.82 (d, J=1.6 Hz, 1H), 8.75 (d, J=2.4 Hz, 2H), 8.37-8.40 (m, 1H), 8.03 (d, J=3.8 Hz, 2H), 7.24-7.26 (m, 2H), 7.61-7.64 (m, 1H), 7.52-7.55 (m, 1H), MS (ESI+): m/z calc. for [$C_{14}H_{10}N_2O$] 222.08. Found: 223.6 [M+H]$^+$.

Synthesis of 1H-indol-3-yl-(6-methoxy-2-pyridyl)methanone

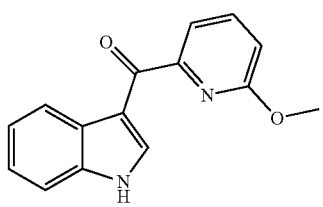

The title compound was synthesized according to Scheme A: yield 24% as a yellow viscose oil. 1H NMR (400 MHz DMSO-$d_6$) δ 12.04 (s, 1H), 8.90 (d, J=1.6 Hz, 1H), 8.37-8.39 (m, 1H), 7.91-7.95 (m, 1H), 7.83-7.86 (m, 1H), 7.63-7.67 (m, 1H), 7.52-7.54 (m, 1H), 7.24-7.26 (m, 1H), 7.02-7.09 (m, 1H), 4.01 (s, 3H, CH3), MS (ESI+): m/z calc. for [$C_{15}H_{12}N_2O_2$] 252.09. Found: 253.5 [M+H]$^+$.

Synthesis of (6-chloro-2-pyridyl)-(1H-indol-3-yl)methanone

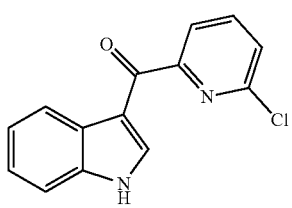 [SMILES: O=C(c1cccc(Cl)n1)c1c[nH]c2ccccc12]

The title compound was synthesized according to Scheme A: yield 33% as a yellow solid. $^1$H NMR (400 MHz DMSO-$d_6$) δ 12.14 (s, 1H), 8.70 (s, 1H), 8.34-8.37 (m, 1H), 8.11 (t, J=8.0 Hz, 1H), 8.02-8.04 (m, 1H), 7.76-7.79 (m, 1H), 7.54-7.56 (m, 1H), 7.26-7.28 (m, 2H), MS (ESI+): m/z calc. for [$C_{14}H_9ClN_2O$] 256.04. Found: 257.6 [M+H]$^+$.

156

Synthesis of 6-(1H-indole-3-carbonyl)-N,N-dimethyl-pyridine-2-carboxamide

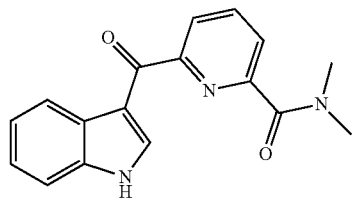 [SMILES: CN(C)C(=O)c1cccc(C(=O)c2c[nH]c3ccccc23)n1]

The title compound was synthesized according to Scheme A, step 3: yield 88% as a pale solid. $^1$H NMR (400 MHz DMSO-$d_6$) δ 12.24 (s, 1H), 9.27 (d, J=1.6 Hz, 1H), 8.42-8.44 (m, 1H), 8.30-8.32 (m, 1H), 8.22-8.26 (m, 2H), 7.54-7.56 (m, 1H), 7.26-7.28 (m, 2H), 5.22-5.28 (m, 1H), 1.44 (s, 3H, CH$_3$), 1.42 (s, 3H, CH$_3$), MS (ESI+): m/z calc. for [$C_{17}H_{15}N_3O_2$] 293.12. Found: 294.6 [M+H]$^+$.

Synthesis of hexyl 6-(1H-indole-3-carbonyl)pyridine-2-carboxylate

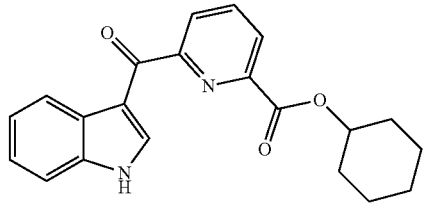 [SMILES: O=C(OC1CCCCC1)c1cccc(C(=O)c2c[nH]c3ccccc23)n1]

The title compound was synthesized according to Scheme A, step 3: yield 76% as a pale solid. $^1$H NMR (400 MHz DMSO-$d_6$) δ 12.25 (s, 1H), 9.28 (d, J=1.6 Hz, 1H), 8.42-8.45 (m, 1H), 8.30-8.33 (m, 1H), 8.21-8.28 (m, 2H), 7.54-7.56 (m, 1H), 7.26-7.28 (m, 2H), 5.04-5.08 (m, 1H), 1.44-1.80 (m, 10H), MS (ESI+): m/z calc. for [$C_{21}H_{20}N_2O_3$] 348.15. Found: 349.7 [M+H]$^+$.

Synthesis of isopropyl 6-(1H-indole-3-carbonyl)pyridine-2-carboxylate

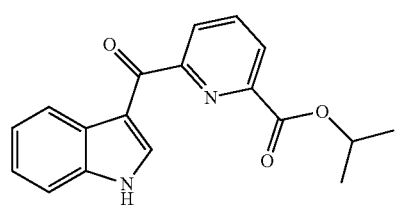 [SMILES: CC(C)OC(=O)c1cccc(C(=O)c2c[nH]c3ccccc23)n1]

The title compound was synthesized according to Scheme A, step 3: yield 45% as a pale solid. $^1$H NMR (DMSO-$d_6$) δ 3.02 (s, 3H, CH$_3$), 3.06 (s, 3H, CH$_3$), 7.25-7.32 (m, 2H), 7.53-7.56 (m, 1H), 7.76-7.81 (m, 1H), 8.08-8.17 (m, 2H), 8.36-8.40 (m, 1H), 8.67 (d, 1H, J=1.6 Hz), 12.07 (s, 1H),), MS (ESI+): m/z calc. for [$C_{18}H_{16}N_2O_3$] 308.12. Found: 309.6 [M+H]$^+$.

Synthesis of (2-methyl-1H-indol-3-yl)-phenyl-methanone

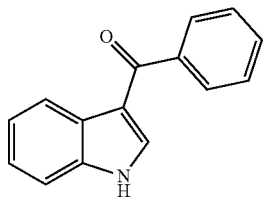 [SMILES: O=C(c1ccccc1)c1c[nH]c2ccccc12]

The title compound was synthesized according to Scheme A: yield 32% as a white solid. ¹H NMR (400 MHz DMSO-$d_6$) δ 12.19 (s, 1H), 7.57-7.61 (m, 3H), 7.49-7.52 (m, 2H), 7.38 (d, J=4.0 Hz, 1H), 7.32 (d, J=4.0 Hz, 1H),), 7.09-7.13 (m, 1H), 6.99-7.03 (m, 1H), 2.38 (s, 3H, $CH_3$), MS (ESI+): m/z calc. for [$C_{16}H_{13}NO$] 235.10. Found: 236.6 [M+H]⁺.

Synthesis of methyl 6-(2-methyl-1H-indole-3-carbonyl)pyridine-2-carboxylate

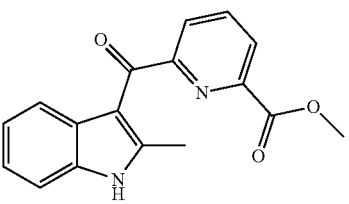 [SMILES: COC(=O)c1cccc(C(=O)c2c(C)[nH]c3ccccc23)n1]

The title compound was synthesized according to Scheme A: yield 32% as a pink solid. ¹H NMR (400 MHz DMSO-$d_6$) δ 12.19 (s, 1H), 8.21-8.23 (m, 2H), 7.92-7.94 (m, 1H), 7.56 (d, J=4.0 Hz, 1H), 7.40 (d, J=4.0 Hz, 1H), 7.14-7.18 (m, 1H), 7.06-7.10 (m, 1H), 3.87 (s, 3H, $CH_3$), 2.22 (s, 3H, $CH_3$), MS (ESI+): m/z calc. for [$C_{17}H_{14}N_2O_3$] 294.10. Found: 295.4 [M+H]⁺.

Synthesis of (1-methylindol-3-yl)-phenyl-methanone

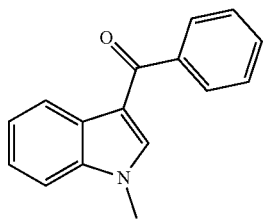 [SMILES: Cn1cc(C(=O)c2ccccc2)c2ccccc21]

The title compound was synthesized according to Scheme A: yield 35% as a yellow solid. ¹H NMR (400 MHz DMSO-$d_6$) δ 8.27 (d, J=4.0 Hz, 1H) 8.00 (s, 1H), 7.78 (d, J=4.0 Hz, 2H), 7.53-7.61 (m, 4H), 7.27-7.36 (m, 2H), 3.88 (s, 3H), MS (ESI+): m/z calc. for [$C_{16}H_{13}NO$] 235.10. Found: 236.6 [M+H]⁺.

Synthesis of methyl 6-(1-methylindole-3-carbonyl)pyridine-2-carboxylate

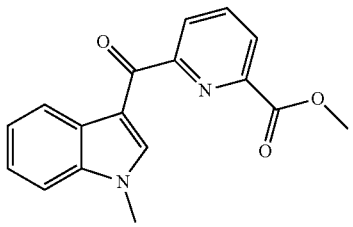 [SMILES: COC(=O)c1cccc(C(=O)c2cn(C)c3ccccc23)n1]

The title compound was synthesized according to Scheme A: yield 41% as a yellow solid. ¹H NMR (400 MHz DMSO-$d_6$) δ 9.04 (s, 1H), 8.41-8.44 (m, 1H), 8.21-8.28 (m, 3H), 7.62 (d, J=4.0, 1H), 7.30-7.37 (m, 2H), 4.00 (s, 3H), 3.93 (s, 3H), MS (ESI+): m/z calc. for [$C_{17}H_{14}N_2O_3$] 294.10. Found: 295.6 [M+H]⁺.

Synthesis of methyl 6-(4-chloro-1H-indole-3-carbonyl)pyridine-2-carboxylate

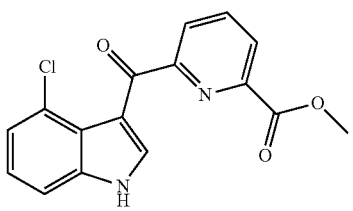 [SMILES: COC(=O)c1cccc(C(=O)c2c[nH]c3cccc(Cl)c23)n1]

The title compound was synthesized according to Scheme A, step 1; yield 28% as a brown solid. ¹H NMR (400 DMSO-$d_6$) δ 12.35 (s, 1H), 8.31 (d, J=1.6 Hz, 1H), 8.24-8.27 (m, 1H), 8.19-8.22 (m, 2H), 7.50-7.53 (m, 1H), 7.23-7.28 (m, 2H), 3.89 (s, 3H), MS (ESI+): m/z calc. for [$C_{16}H_{11}ClN_2O_3$] 314.04. Found: 315.5 [M+H]⁺.

Synthesis of methyl 6-(5-chloro-1H-indole-3-carbonyl)pyridine-2-carboxylate

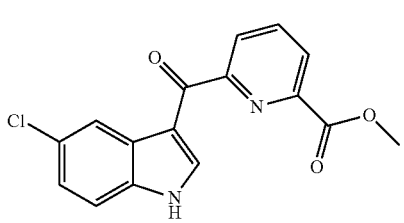 [SMILES: COC(=O)c1cccc(C(=O)c2c[nH]c3ccc(Cl)cc23)n1]

The title compound was synthesized according to Scheme A; yield 31% as a yellow solid. ¹H NMR (400 MHz DMSO-$d_6$) δ 12.37 (s, 1H),), 9.20 (d, J=1.6 Hz, 1H), 8.40 (d, J=1.2 Hz, 1H), 8.23-8.32 (m, 3H), 7.58 (d, J=4.0 Hz, 1H), 7.29-7.32 (m, 1H), 3.98 (s, 3H), MS (ESI+): m/z calc. for [$C_{16}H_{11}ClN_2O_3$] 314.04. Found: 315.5 [M+H]⁺.

Synthesis of methyl 6-(6-chloro-1H-indole-3-carbonyl)pyridine-2-carboxylate

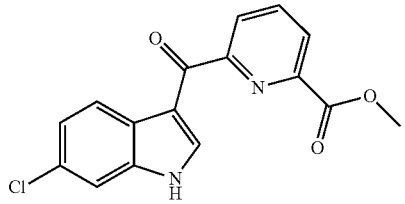 [SMILES: COC(=O)c1cccc(C(=O)c2c[nH]c3cc(Cl)ccc23)n1]

The title compound was synthesized according to Scheme A: yield 19% as a brown solid. $^1$H NMR (400 MHz DMSO-d$_6$) δ 12.28 (s, 1H), 9.15 (d, J=1.6 Hz, 1H), 8.39 (d, J=4.0 Hz, 1H), 8.24-8.29 (m, 3H), 7.61 (d, J=0.8 Hz, 1H), 7.28-7.31 (m, 1H), 3.98 (s, 3H), MS (ESI+): m/z calc. for [C$_{16}$H$_{11}$ClN$_2$O$_3$] 314.04. Found: 315.4 [M+H]$^+$.

Synthesis of methyl 6-(7-chloro-1H-indole-3-carbonyl)pyridine-2-carboxylate

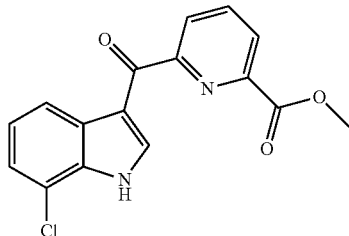 [SMILES: COC(=O)c1cccc(C(=O)c2c[nH]c3c(Cl)cccc23)n1]

The title compound was synthesized according to Scheme A; yield 44% as a brown solid. $^1$H NMR (400 MHz DMSO-d$_6$) δ 12.56 (s, 1H), 9.26 (d, J=1.6 Hz, 1H), 8.39 (d, J=4.0 Hz, 1H), 8.23-8.34 (m, 3H), 7.26-7.41 (m, 2H), 3.99 (s, 3H), MS (ESI+): m/z calc. for [C$_{16}$H$_{11}$ClN$_2$O$_3$] 314.04. Found: 315.4 [M+H]$^+$.

Synthesis of methyl 6-(1H-pyrrolo[2,3-b]pyridine-3-carbonyl)pyridine-2-carboxylate

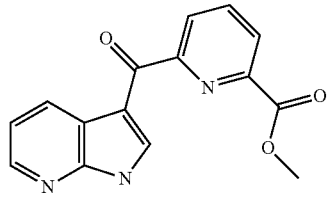 [SMILES: COC(=O)c1cccc(C(=O)c2c[nH]c3ncccc23)n1]

The title compound was synthesized according to Scheme A; yield 32% as a white solid. $^1$H NMR (400 MHz DMSO-d$_6$) δ 12.71 (s, 1H), 9.29 (d, J=1.6 Hz, 1H,), 8.68-8.71 (m, 1H), 8.37-8.39 (m, 1H), 8.24-8.33 (m, 3H), 7.32-7.35 (m, 1H), 3.99 (s, 3H), MS (ESI+): m/z calc. for [C$_{15}$H$_{11}$N$_3$O$_3$] 281.08. Found: 282.5 [M+H]$^+$.

Synthesis of methyl 6-(5-methoxy-1H-indole-3-carbonyl)pyridine-2-carboxylate

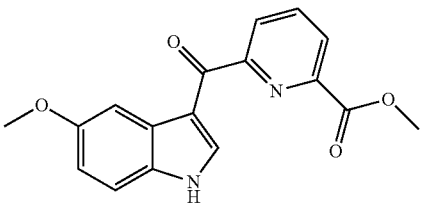

The title compound was synthesized according to Scheme A; yield 34% as a yellow solid. $^1$H NMR (400 MHz DMSO-d$_6$) δ 12.08 (s, 1H), 9.06 (d, J=1.6 Hz, 1H), 8.21-8.30 (m, 3H), 7.95 (d, J=1.2 Hz, 1H), 7.44 (d, J=4.0 Hz, 1H), 6.89-6.92 (m, 1H), 3.98 (s, 3H), 3.83 (s, 3H), MS (ESI+): m/z calc. for [C$_{17}$H$_{14}$N$_2$O$_4$] 310.10. Found: 311.6 [M+H]$^+$.

Synthesis of methyl 6-(5-bromo-1H-indole-3-carbonyl)pyridine-2-carboxylate

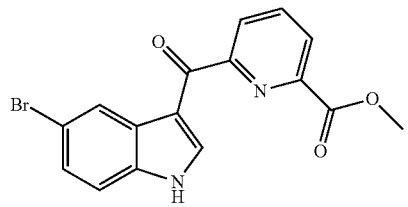

The title compound was synthesized according to Scheme A: yield 21% as a brown solid. $^1$H NMR (400 MHz DMSO-d$_6$) δ 12.38 (s, 1H), 9.18 (d, J=1.6 Hz, 1H), 8.56 (d, J=1.0 Hz, 1H), 8.23-8.32 (m, 3H), 7.53 (d, J=4.0 Hz, 1H), 7.40-7.43 (m, 1H), 3.98 (s, 3H), MS (ESI+): m/z calc. for [C$_{16}$H$_{11}$BrN$_2$O$_3$] 358.00. Found: 359.5 [M+H]$^+$.

Synthesis of methyl 6-(1,6,7,8-tetrahydrocyclopenta[g]indole-3-carbonyl)pyridine-2-carboxylate

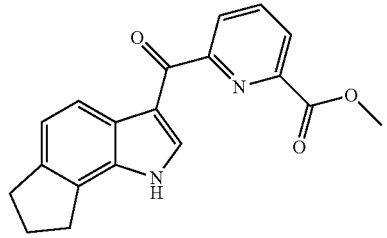 [SMILES: COC(=O)c1cccc(C(=O)c2c[nH]c3c4c(ccc23)CCC4)n1]

The title compound was synthesized according to Scheme A; yield 29% as a brown solid. $^1$H NMR (400 MHz DMSO-d$_6$) δ 12.15 (s, 1H), 9.06 (d, J=1.6 Hz, 1H), 8.20-8.29 (m, 4H), 7.16 (d, J=4.0 Hz, 1H), 3.98 (s, 3H), 2.16 (t, J=7.2 Hz, 2H), 3.09 (t, J=7.2 Hz, 2H), 2.99 (t, J=7.6 Hz, 2H), MS (ESI+): m/z calc. for [C$_{19}$H$_{16}$N$_2$O$_3$] 320.12. Found: 321.6 [M+H]$^+$.

Synthesis of methyl 6-(1H-benzo[g]indole-3-carbonyl)pyridine-2-carboxylate

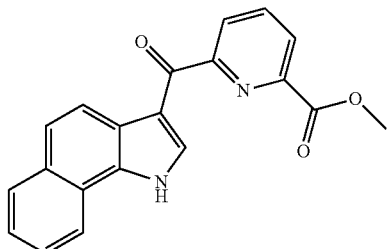

The title compound was synthesized according to Scheme A; yield 37% as a yellow solid. $^1$H NMR (400 MHz DMSO-d$_6$) δ 13.04 (s, 1H), 9.18 (d, J=1.6 Hz, 1H), 8.53 (d, J=4.4 Hz, 1H), 8.43 (d, J=4.0 Hz, 1H), 8.24-8.36 (m, 3H), 8.02 (d, J=4.0 Hz, 1H), 7.74 (d, J=4.0 Hz, 1H), 7.64 (t, J=8.0 Hz, 1H), 7.52 (t, J=8.4 Hz, 1H), 4.00 (s, 3H), MS (ESI+): m/z calc. for [C$_{20}$H$_{14}$N$_2$O$_3$] 330.10. Found: 331.6 [M+H]$^+$.

Synthesis of methyl 2-(1H-indole-3-carbonyl)benzoate

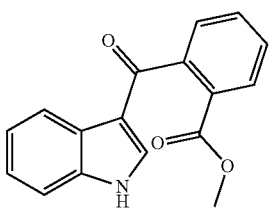 [SMILES: COC(=O)c1ccccc1C(=O)c1c[nH]c2ccccc12]

The title compound was synthesized according to Scheme A; yield 36% as a pink solid. $^1$H NMR (400 MHz DMSO-d$_6$) δ 11.97 (s, 1H), 8.13 (d, J=1.6 Hz, 1H), 7.89-7.91 (m, 1H), 7.71 (t, J=7.6 Hz, 1H), 7.64 (t, J=7.6 Hz, 1H), 7.54-7.58 (m, 2H), 7.50 (d, J=3.4 Hz, 1H), 7.20-7.28 (m, 2H), 3.58 (s, 3H), MS (ESI+): m/z calc. for [C$_{17}$H$_{13}$NO$_3$] 279.09. Found: 280.6 [M+H]$^+$

Synthesis of 1H-indol-3-yl-(2-methoxyphenyl)methanone

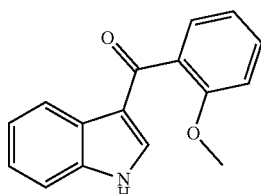

The title compound was synthesized according to Scheme A; yield 32% as a pale solid. $^1$H NMR (400 MHz DMSO-d$_6$) δ 11.93 (s, 1H), 8.14 (d, J=1.6 Hz, 1H), 7.59 (d, J=1.6 Hz, 1H), 7.45-7.50 (m, 2H), 7.29-7.32 (m, 1H), 7.21-7.24 (m, 2H), 7.15 (d, J=4.0 Hz, 1H), 7.04 (t, J=7.6 Hz, 1H), 3.72 (s, 3H, CH$_3$), MS (ESI+): m/z calc. for [C$_{16}$H$_{13}$NO$_2$] 251.09. Found: 252.6 [M+H]$^+$.

Synthesis of methyl 3-(1H-indole-3-carbonyl)benzoate

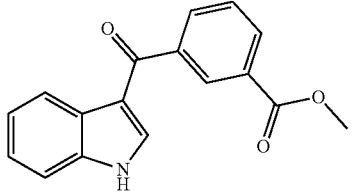 [SMILES: COC(=O)c1cccc(C(=O)c2c[nH]c3ccccc23)c1]

The title compound was synthesized according to Scheme A; yield 22% as a yellow solid. $^1$H NMR (400 MHz DMSO-d$_6$) δ 12.13 (s, 1H), 8.29 (s, 1H), 8.24-8.26 (m, 1H), 8.17 (d, J=4.0 Hz, 1H), 8.06 (d, J=3.8 Hz, 1H), 7.98 (d, J=1.6 Hz, 1H), 7.71 (t, J=7.6 Hz, 1H), 7.54 (d, J=3.6 Hz, 1H), 7.23-7.30 (m, 2H), 3.90 (s, 3H, CH$_3$), MS (ESI+): m/z calc. for [C$_{17}$H$_{13}$NO$_3$] 279.09. Found: 280.6 [M+H]$^+$.

Synthesis of 1H-indol-3-yl-(3-methoxyphenyl)methanone

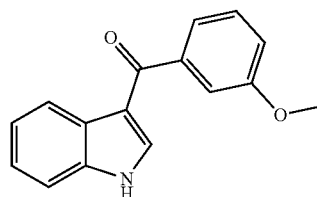

The title compound was synthesized according to Scheme A; yield 20% as a pale solid. $^1$H NMR (400 MHz DMSO-d$_6$) δ 12.04 (s, 1H), 8.23-8.25 (m, 1H), 7.96 (d, J=1.6 Hz, 1H), 7.51-7.53 (m, 1H), 7.45 (t, J=8.4 Hz, 1H), 7.35 (d, J=3.6 Hz, 1H), 7.23-7.28 (m, 3H), 7.16-7.18 (m, 1H), 3.83 (s, 3H, CH$_3$), MS (ESI+): m/z calc. for [C$_{16}$H$_{13}$NO$_2$] 251.09. Found: 252.6 [M+H]$^+$.

Synthesis of [3-(1H-indole-3-carbonyl)phenyl] acetate

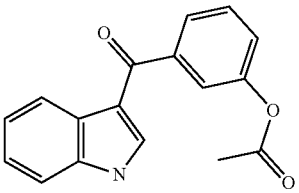 [SMILES: CC(=O)Oc1cccc(C(=O)c2c[nH]c3ccccc23)c1]

The title compound was synthesized according to Scheme A; yield 26% as a white solid. $^1$H NMR (400 MHz DMSO-d$_6$) δ 12.11 (s, 1H), 8.24-8.26 (m, 1H), 7.94 (d, J=1.6 Hz, 1H), 7.67-7.70 (m, 1H), 7.52-7.60 (m, 3H), 7.35-7.38 (m, 1H), 7.22-7.30 (m, 2H), 2.30 (s, 3H), MS (ESI+): m/z calc. for [C$_{17}$H$_{13}$NO$_3$] 279.09. Found: 280.6 [M+H]$^+$.

Synthesis of methyl 6-(1H-indole-3-carbonyl)pyridine-3-carboxylate

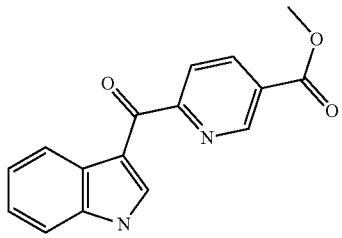 [SMILES: COC(=O)c1ccc(C(=O)c2c[nH]c3ccccc23)nc1]

To a solution of 5-methoxycarbonylpyridine-2-carboxylic acid (0.5 g, 2.76 mmol) in DCM (10 mL) was added $(COCl_2)_2$ (1.7 g, 13.8 mmol) and a drop of DMF at 0° C., the resulting mixture was stirred at room temperature (approximately 25° C.) for 1 hour, at which point TLC showed the reaction was over. The reaction mixture was concentrated to give methyl 6-chlorocarbonylpyridine-3-carboxylate. To a solution of EtMgBr (2.76 mL, 1 M in THF, 2.76 mmol) was added a solution of indol (315 mg, 2.7 mmol) in ether (anhydrous, 10 mL). The resulting two-phase system was allowed to stand for 15 min under stirring whereupon $ZnCl_2$ (370 mg, 2.7 mmol) was added with stirring. The two-phase system was allowed to stand for 30 min when compound methyl 6-chlorocarbonylpyridine-3-carboxylate (560 mg, 2.76 mmol) in anhydrous ether (5 ml) was added. The reaction mixture was stirred at room temperature (approximately 25° C.) for 2 hours, whereupon $NH_4Cl$ (15 ml) was added. The reaction mixture was diluted with water, extracted with DCM, dried over $Na_2SO_4$, concentrated and purified by SGC (PE:EA=15:1) to give the title compound, yield 24%, as a yellow syrup. 1H NMR (300 MHz, DMSO-$d_6$) 4.03 (s, 3H), 6.66 (d, J=4.0 Hz, 1H), 7.31-7.42 (m, 2H), 7.60 (d, J=7.6 Hz, 1H), 7.92 (d, J=3.6 Hz, 1H), 8.16 (d, J=8.0 Hz, 1H), 8.52-8.54 (m, 2H), 9.32 (s, 1H), MS (ESI+): m/z calc. for $[C_{16}H_{12}N_2O_3]$ 280.08. Found: 281.6 $[M+H]^+$.

Synthesis of methyl 4-(1H-indole-3-carbonyl)benzoate

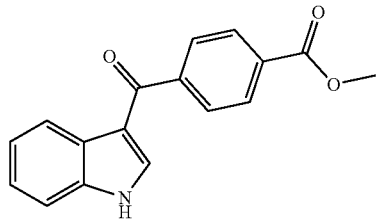 [SMILES: COC(=O)c1ccc(C(=O)c2c[nH]c3ccccc23)cc1]

The title compound was synthesized according to Scheme A; yield 18% as a pale solid. $^1$H NMR (400 MHz DMSO-$d_6$) δ 12.16 (s, 1H), 8.24-8.27 (m, 1H), 8.06-8.12 (m, 2H), 7.96 (d, J=1.6 Hz, 1H), 7.89 (d, J=4.1 Hz, 2H), 7.52-7.54 (m, 1H), 7.25-7.29 (m, 2H), 3.91 (s, 3H, $CH_3$), MS (ESI+): m/z calc. for $[C_{17}H_{13}NO_3]$ 279.09. Found: 280.6 $[M+H]^+$.

Synthesis of 1H-indol-3-yl-(4-methoxyphenyl)methanone

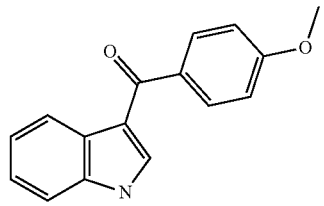 [SMILES: COc1ccc(C(=O)c2c[nH]c3ccccc23)cc1]

The title compound was synthesized according to Scheme A; yield 21% as a pale solid. $^1$H NMR (400 MHz DMSO-$d_6$) δ 11.99 (s, 1H), 8.21 (d, J=3.6 Hz, 1H), 7.94 (d, J=1.6 Hz, 1H), 7.81 (d, J=1.6 Hz, 2H), 7.51 (d, J=3.6 Hz, 1H), 7.19-7.27 (m, 2H), 7.07-7.09 (m, 2H), 3.86 (s, 3H, $CH_3$), MS (ESI+): m/z calc. for $[C_{16}H_{13}NO_2]$ 251.09. Found: 252.6 $[M+H]^+$.

Synthesis of methyl 5-(1H-indole-3-carbonyl)thiophene-2-carboxylate

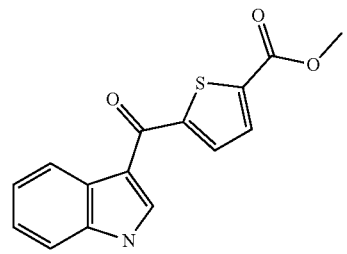 [SMILES: COC(=O)c1ccc(C(=O)c2c[nH]c3ccccc23)s1]

The title compound was synthesized according to Scheme A; yield 17% as a yellow solid. $^1$H NMR (400 MHz DMSO-$d_6$) δ 12.26 (s, 1H), 8.42 (d, J=1.6 Hz, 1H), 8.22-8.24 (m, 1H), 7.95 (d, J=2.0 Hz, 1H), 7.87 (d, J=2.0 Hz, 1H), 7.53-7.55 (m, 1H), 7.23-7.30 (m, 2H), 3.88 (s, 3H, $CH_3$), MS (ESI+): m/z calc. for $[C_{15}H_{11}NO_3S]$ 285.04. Found: 286.6 $[M+H]^+$.

Synthesis of 1H-indol-3-yl-[6-(trifluoromethyl)-2-pyridyl]methanone

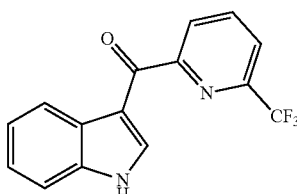

The title compound was synthesized according to Scheme B; Yield 28%. $^1$H NMR (400 MHz DMSO-$d_6$) δ 12.15 (d, J=2.8 Hz, 1H), 8.70 (d, J=3.6 Hz, 1H), 8.29-8.38 (m, 3H), 8.14 (dd, J=7.3, 2.0 Hz, 1H), 7.53-7.55 (m, 1H), 7.24-7.29 (m, 2H),). $^{13}$C NMR: δ 184.8, 156.6, 145.6 (q, J=136.8 Hz), 140.6, 138.2 (2), 136.6, 126.7, 123.8, 123.4, 122.8, 122.1, 113.9, 121.9, 112.8, MS (ESI+): m/z calc. for $[C_{15}H_9F_3N_2O]$ 290.07. Found: 291.3 [M+H]$^+$, HRMS: calc. for [C$_{15}$H$_9$F$_3$N$_2$O] 291.0745. Found: 291.0755.

Synthesis of
6-(1H-indole-3-carbonyl)pyridine-2-carbonitrile

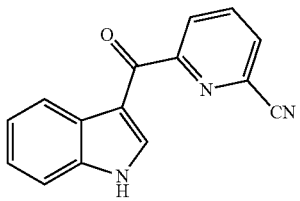 [SMILES: N#Cc1cccc(C(=O)c2c[nH]c3ccccc23)n1]

The title compound was synthesized according to Scheme B; Yield 17%. $^1$H NMR (400 MHz DMSO-d$_6$) δ 12.15 (d, J=2.8 Hz, 1H), 8.65 (d, J=3.2 Hz, 1H), 8.32-8.34 (m, 1H), 8.23-8.28 (m, 3H), 7.53-7.56 (m, 1H), 7.24-7.29 (m, 2H),). $^{13}$C NMR: δ 184.7, 157.6, 140.0, 138.7, 136.7, 131.8, 131.3, 127.1 (2), 123.8, 122.9, 122.0, 117.9, 113.8, 112.9, MS (ESI+): m/z calc. for [C$_{15}$H$_9$N$_3$O] 248.07. Found: 248.6 [M+H]$^+$, HRMS: calc. for [C$_{15}$H$_9$N$_3$O] 248.0824. Found: 248.0823.

Synthesis of
1H-indol-3-yl-(2-methoxy-4-pyridyl)methanone

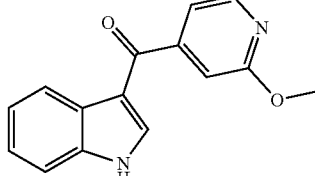

The title compound was synthesized according to Scheme C; Yield 8%. $^1$H NMR (400 MHz DMSO-d$_6$) δ 12.18 (s, 1H), 8.32 (d, J=5.2 Hz, 1H), 8.22-8.24 (m, 1H), 7.98 (d, J=2.8 Hz, 1H), 7.50-7.52 (m, 1H), 7.23-7.28 (m, 3H), 7.03 (s, 1H), 3.91 (s, 3H), MS (ESI+): m/z calc. for [C$_{15}$H$_{12}$N$_2$O$_2$] 252.09. Found: 253.4 [M+H]$^+$.

Synthesis of methyl
6-(1H-indole-3-carbonyl)pyridine-3-carboxylate

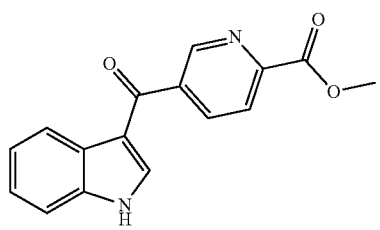 [SMILES: COC(=O)c1ccc(C(=O)c2c[nH]c3ccccc23)cn1]

The title compound was synthesized according to Scheme C; Yield 11%. $^1$H NMR (400 MHz DMSO-d$_6$) δ 12.14 (s, 1H), 8.96 (d, J=5.2 Hz, 1H), 8.83 (d, J=3.2 Hz, 1H), 8.41-8.42 (m, 1H), 8.36-8.38 (m, 1H), 8.04 (dd, J=4.8 Hz, 1.6 Hz, 1H), 7.52-7.54 (m, 1H), 7.24-7.28 (m, 2H), 3.94 (s, 3H), MS (ESI+): m/z calc. for [C$_{16}$H$_{12}$N$_2$O$_3$] 280.08. Found: 281.5 [M+H]$^+$.

Synthesis of
1H-indol-3-yl-(5-methoxypyrazin-2-yl)methanone

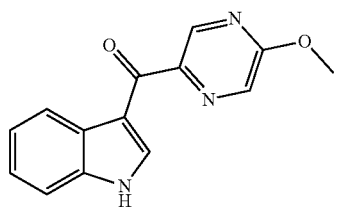 [SMILES: COc1cnc(C(=O)c2c[nH]c3ccccc23)cn1]

The title compound was synthesized according to Scheme B; Yield 26%. $^1$H NMR (400 MHz DMSO-d$_6$) δ 12.24 (s, 1H), 8.77 (d, J=3.2 Hz, 1H), 8.73 (s, 1H), 8.54 (s, 1H), 8.33-8.36 (m, 1H), 7.16-7.54 (m, 1H), 7.23-7.27 (m, 2H), 4.04 (s, 3H), MS (ESI+): m/z calc. for [C$_{14}$H$_{11}$N$_3$O$_2$] 253.08. Found: 254.5 [M+H]$^+$.

Synthesis of
1H-indol-3-yl-(6-morpholino-2-pyridyl)methanone

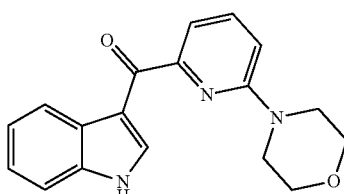

The title compound was synthesized according to Scheme B; Yield 22%. $^1$H NMR (400 MHz DMSO-d$_6$) δ 11.97 (s, 1H), 8.64 (d, J=3.2 Hz, 1H), 8.32-8.34 (m, 1H), 7.76 (dd, J=8.8 Hz, 7.6 Hz, 1H), 7.48-7.50 (m, 1H), 7.30 (d, J=7.2 Hz, 1H) 7.19-7.24 (m, 2H), 7.07 (d, J=8.8 Hz, 1H), 3.74 (dd, J=4.8 Hz, 4.8 Hz, 4H), 3.53 (dd, J=4.8 Hz, 4.8 Hz, 4H), (MS (ESI+): m/z calc. for [C$_{18}$H$_{17}$N$_3$O$_2$] 307.13. Found: 308.3 [M+H]$^+$.

Synthesis of
1H-indol-3-yl-(6-phenyl-2-pyridyl)methanone

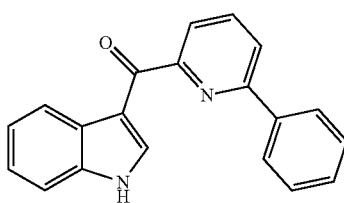 [SMILES: O=C(c1cccc(-c2ccccc2)n1)c1c[nH]c2ccccc12]

The title compound was synthesized according to Scheme B; Yield 21%. $^1$H NMR (400 MHz DMSO-d$_6$) δ 12.07 (s, 1H), 8.82 (d, J=3.2 Hz, 1H), 8.38-8.40 (m, 1H), 8.09-8.20 (m, 4H), 7.97 (dd, J=7.6 Hz, 2.0 Hz, 1H), 7.47-7.57 (m, 4H), 7.24-7.26 (m, 2H), MS (ESI+): m/z calc. for [$C_{20}H_{14}N_2O$] 298.11. Found: 299.2 [M+H]$^+$.

Synthesis of (6-chloro-1H-indol-3-yl)-[6-(trifluoromethyl)-2-pyridyl]methanone

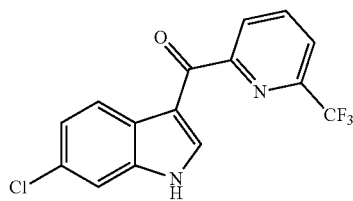 [SMILES: O=C(c1cccc(C(F)(F)F)n1)c1c[nH]c2cc(Cl)ccc12]

The title compound was synthesized according to Scheme B; Yield: 29%; $^1$H NMR (400 MHz DMSO-d$_6$) δ 12.21 (s, 1H), 8.72 (d, J=2.8 Hz, 1H), 8.30-8.35 (m, 3H), 8.14 (dd, J=6.8 Hz, 1.6 Hz, 1H), 7.61 (d, J=2.0 Hz, 1H), 7.27 (dd, J=8.8 Hz, 2.0 Hz, 1H), MS (ESI+): m/z calc. for [$C_{15}H_8ClF_3N_2O$] 324.04. Found: 325.1 [M+H]$^+$.

Example 3: Biological Characterization of Aryl Hydrocarbon Receptor Modulators

XRE-Driven Luciferase Reporter Assay

Human HepG2 or mouse Hepa-1c1c7 cells were seeded in 96 well opaque plates at 75,000 cells per well in full medium (DMEM+10% FBS) for 24 hours. Transfection was performed with 150 ng XRE-luciferase plasmid (Promega) with 4:1 Fugene to DNA ratio for 18 hours in Opti-MEM. Transfected cells were treated with AhR agonist ($10^{-5}$-$10^{-12}$) for 4.5 h in full medium. Cells were lysed and luciferase was activated using the Luciferase Assay System (Promega). Luminescence signals were measured with a FluroStar Omega microplate reader. Luminescence signals of compound treated groups were normalized to vehicle (DMSO) treated control and plotted as concentration dependent fold changes. For active compounds with saturated curves, $EC_{50}$ ($CL_{95\%}$) and $E_{max}$±SD were calculated by least square curve fitting using Graphpad. For low activity compounds that did not reach half $E_{max}$ of ITE at 10 uM (highest concentration tested), $EC_{50}$ was presented as larger than 10 uM and $E_{max}$ was defined as fold increase at highest concentration tested (10 μM).

AhR Nuclear Translocation Assay

Mouse Hepa-1c1c7 or human HepG2 cells were seeded in 8 well chamber slides followed by 24 hours incubation in tryptophan deficient media (HBSS with Ca$^{2+}$ and Mg$^{2+}$, 10% heat inactivated FBS, 1× non-essential amino acids, 1× sodium pyruvate, 4.5 g/L glucose). Cells were treated with vehicle control (DMSO) or 10 μM ITE, compound 108, or compound 109 for 90 minutes in tryptophan deficient media. Following treatment, cells were fixed in 4% formaldehyde and processed according to standard immunofluorescence staining protocol. Primary anti-AhR antibody was applied at 1:100 dilution (Enzo, BML-SA210) and Alexa488 conjugated secondary antibody was applied at 1:500 dilution (Cell Signaling, 4412S). Actin was stained using Alexa 568 conjugated Phalloidin (Fisher). Samples were mounted in antifade mounting medium supplemented with DAPI for nuclear staining and imaged with confocal microscopy (Leica SP5× MP, 63× oil lens).

DSS Induced Colitis

C57BL/6 (8-10 week, male) mice were administered drinking water supplemented with 3% (wt/vol) dextran sodium sulfate (DSS; MP Biomedicals) for 7 days followed by a 13 day recovery period with unsupplemented drinking water. Compound 109 or compound 108 were suspended in vehicle (1% HPMC and 1% polysorbate 80 in water) and given daily by oral gavage (1 ug/mouse in 100 uL), starting at day 0. Control mice were administered 100 μL vehicle. Body weight and disease activity index (DAI) were recorded daily. DAI was determined by combining scores of weight loss, stool consistency, blood in stool, activity, and appearance.[1] Scores were determined as follows: change in weight (0: <1%, 1: 1-10%, 2: 10-18%, 3: 18-20%); stool consistency (0: normal, 1: loose stools, 2: diarrhea); stool blood (0: negative, 1: trace blood, 2: bloody stool, 3: gross bleeding), activity (0: normal, 1: low activity, 2: hiding, 3: no response to gentle stimuli) and appearance (0: normal, 1: rigor, 2: hunched posture). On day 7 and day 11, mice were euthanized and colon were removed for length measurement, histology, RNA isolation, and lamina propria mononuclear cell (LPMC) extraction as detailed below.

Histology

Dissected colon were cut longitudinally and rolled using the Swiss roll method with the distal side in the center.[2,3] Colons were fixed overnight in 10% neutral buffered formalin, processed for paraffin embedding and sectioned at 5 μm thickness. To visualize and quantify the inflammatory response and crypt loss, hematoxylin and eosin staining (H&E) was performed. Briefly, sections were cleared with xylene, rehydrated through alcohol gradient, stained by hematoxylin, washed by acid and ammonium alcohol, rinsed in water and exposed to Eosin followed by dehydrating through graded alcohols and cleared in xylene. All sections were mounted using Permount (Fisher Scientific) and visualized using a BX41 microscope (Olympus). For histological scoring, 3 transverse sections of Swiss roll were chosen and 9 (100×) images were captured for each section. Images were analyzed for inflammation and crypt structure and scored by a blind observer as follows: inflammation (0: rare inflammatory cells in the lamina propria; 1: increased numbers of inflammatory cells in the lamina propria; 2: confluence of inflammatory cells extending in to the submucosa; 3: transmural extension of the inflammatory infiltrate.); crypt loss (0: none; 1: basal 1/3 damaged; 2: basal 2/3 damaged; 3: only surface epithelium intact; 4: entire crypt and epithelium lost). Inflammation and crypt loss were scored separately and multiplied by a factor of 1-4 to adjust for impacted area of tissue section (1: 0-25%; 2: 25.1-50% affected; 3: 50.1-75% affected; 4: >75% affected).[1,4] To examine goblet cell number, sections were stained by a commercial periodic acid-Schiff (PAS) and Alcian blue kit (Fisher Scientific). For quantification, 3 transverse sections of Swiss roll were chosen per colon and 5 random images at 200× were taken per section in the distal region of the colon. Goblet cell number was counted per image and normalized to colon length by a blind observer using image J.[5]

Colonic Epithelium and Lamina Propria Cell Isolation

Colonic epithelium and lamina propria cells were isolated as previously described.[6,7] Briefly, colons were dissected and washed with HBSS to remove fecal contents. Colon were opened longitudinally and cut into 2 cm segments. Epithelium was isolated by incubation at 37° C. in RPMI medium supplemented with 5 mM EDTA and 1 mM DTT for 15 minutes with constant shaking. Crypt enriched supernatants were combined and allowed to sediment at 37° C. for 15 minutes. Settled crypts were washed once in HBSS and lysed in TRIzol for RNA isolation and q-PCR analysis of epithelial barrier gene expression. The remaining colon fragments were minced into 1 mm pieces and digested in RPMI medium containing 1 mg/ml collagenase (Sigma), 0.1 mg/ml DNase I (Sigma) at 37° C. under constant shaking for 45 minutes. Digested cell mixtures were filtered through a 70 μm cell strainer and lamina propria cells were purified by collecting at the interphase of 40% and 80% of Percoll (GE Healthcare) after a spin at 500×g for 20 minutes. Cells were washed and suspended at $10^6$/mL in RPMI medium with 10% FBS, 1× non-essential amino acids, 1× sodium pyruvate, 5 μM 2-mercaptoethanol and treated with Cell Stimulation Cocktail (00-4970-03, Thermo Fisher) containing PMA, ionomycin, and BFA for 8 hours.

Flow Cytometry

Cells were washed, blocked with anti-CD16/32 (2.4G2, eBioscience) and stained in permeabilization buffer (eBioscience) with antibody or isotype control, including: CD3 (17A2, BD Pharmingen), CD4 (RM4-5, eBioscience), RORγt (B2D, eBioscience), Foxp3 (FJK-16s, eBioscience), IL-22 (1H8PWSR, eBioscience), IL-17 (17A2, BD Pharmingen), IFN-γ (XMG1.2, BD Pharmingen), TNF-α (MP6-TX22, eBioscience). All analysis was performed on a LSRII flow cytometer (BD Bioscience). Lymphocytes were gated using forward scatter (FSC) and side scatter (SSC), within the lymphocyte gate, the populations were identified as T helper ($CD3^+CD4^+$), regulatory T cells ($CD3^+CD4^+Foxp3^+$) and innate lymphoid cell type 3 (ILC3, $CD3^-RORγt^+$). Cytokine expression levels were further quantified within defined populations.

q-PCR

RNA was extracted using TRIzol (Invitrogen) following manufacturer's instructions and 0.1 μg of RNA was converted to cDNA using a high capacity cDNA reverse transcription kit (Invitrogen). qPCR was performed on the Applied Biosystems 7900 using TaqMan® Universal PCR Master Mix (Life Technologies) with TaqMan® (Life Technologies) primers against cyp1a1 (Mm00487218_m1), AhR (Mm00478932_m1), IL-22 (Mm01226722_g1), Foxp3 (Mm00475162_m1), IL-10 (Mm01288386_m1), TNF-a (Mm00443258_m1), IFN-r (Mm01168134_m1). The fold increase from experimental groups to control was calculated using the delta-delta CT method with 18S (Mm00446186_m1) as an internal reference gene. In vitro and in vivo activation of the AhR singling pathway was confirmed by q-PCR characterization of cyp1a1. For in vitro induction, mouse Hepa-1c1c7 were cultured to confluence in 24 well plates in full DMEM followed by 24 hours incubation in tryptophan deficient media. Cells were treated with vehicle control (DMSO), ITE, compound 108, or compound 109 (10 nM-10 μM) for 8 hours in tryptophan deficient media. At the end of treatment, cells were lysed in TRIzol for RNA isolation. To monitor in vivo induction, (0.1-1000 μg) compound 109 was given per mouse via oral gavage in 100 μl of vehicle (1% HPMC, 1% polysorbate 80). After 12 hours, liver, colon, spleen and leukocytes from blood were collected and lysed in TRIzol (Invitrogen) for q-PCR analysis.

Primary Lymphocyte Culture and Treatment

To examine the role of lead compounds in IL-22 induction in spleen derived CD4+ T cells, whole spleens were isolated from C57BL/6 mice and broken to release cells. Red blood cells were lysed by osmotic shock and single cell suspensions were collected by filtering through 70 μm cell strainer. CD4+ T cells were isolated by negative selection using a T cell isolation kit (Miltenyi Biotech) and stimulated with plate bound CD3 and soluble CD28 antibody (5 μg/ml) in Th-17 polarization medium (20 ng/mL IL-6, 1 ng/mL TGF-β, 10 ng/mL IL-1, 10 μg/mL anti-IFN-γ in IMDM medium supplemented with 2 mM glutamine, 100 U penicillin, 100 U streptomycin, 50 μM 2-mercaptoethanol, and 5% FBS) for 5 days.[8] Cells were treated with vehicle (DMSO) or 1 μM of ITE, compound 108, or compound 109 from day 0. On day 5, to increase intracellular cytokine concentration, cells were re-stimulated with 500 ng/ml phorbol dibutyrate, 500 ng/mL ionomycin and 10 ug/ml Brefeldin for 4 hours before flow cytometry analysis of IL-22 production in $CD3^+$CD4+ T helper population. To examine the role of lead compounds in IL-22 induction in colonic lamina propria cells, lamina propria cells (LPCs) were isolated from C57BL/6 mice as described previously and treated with 10 μM of ITE, compound 108, or compound 109 from day 0 in RPMI medium supplemented with 10 ng/ml IL-23, 10 ng/ml IL-1β, 10% FBS, 1× non-essential amino acids, 1× sodium pyruvate, 50 μM 2-Mercaptoethanol for 3 days. On day 3, cells were treated with Cell Stimulation Cocktail (00-4970-03, Thermo Fisher) containing PMA, ionomycin, and BFA for 8 h. Flow cytometry was performed to study IL-22 production in $CD3^+$CD4+ T helper cells and CD3−RORγt+ TLCs.

Results

Nuclear Translocation and cyp1a1 Induction.

To verify on-target effects of lead compounds, the subcellular location of AhR with or without agonist activation in both human HepaG2 and mouse Hepa1c1c7 cells was studied. Consistent with literature reports, AhR largely resided in the cytoplasm without introduction of endogenous ligand. Compound 108, compound 109 and reference ligand, ITE, all induced rapid nuclear enrichment of AhR in both human and mouse cells (FIG. 2A-2B). After nuclear translocation, activated AhR is known to induce the expression of a battery of metabolic genes, among which is cyp1a1, a wildly used marker for AhR activation. Compounds 108 and 109 stimulated dose dependent induction of cyp1a1 expression in mouse Hepa-1c1c7 cells (FIG. 2C). Consistent with our observation that 109 demonstrates higher potency in mouse cells, we observed significantly increased cyp1a1 expression with 10 nM compound 109 relative to ITE and compound 108 (FIG. 2C).

Pharmacodynamic (PD) Profile.

Based on the favorable permeability profile and potency of compound 109 in both human and mouse cells, we choose to examine the PD profile of compound 109 with oral administration in a murine model. Compound 109 was suspended in vehicle (1% HPMC, 1% polysorbate 80) and administered to mice via oral gavage. For PD characterization, tissue cyp1a1 induction was selected as a surrogate marker of AhR agonist activity. Mice were administered 0.1-1000 μg compound 109 and tissue (liver, colon, spleen, blood) was collected at 12 hours for q-PCR. Robust, dose-dependent cyp1a1 induction was observed in liver and colon tissue while spleen and blood demonstrated cyp1a1 regulation only at the highest administered doses of compound 109 (FIGS. 2D-2E).

Compound 109 Attenuates DSS Induced Colitis.

Figure 3A:
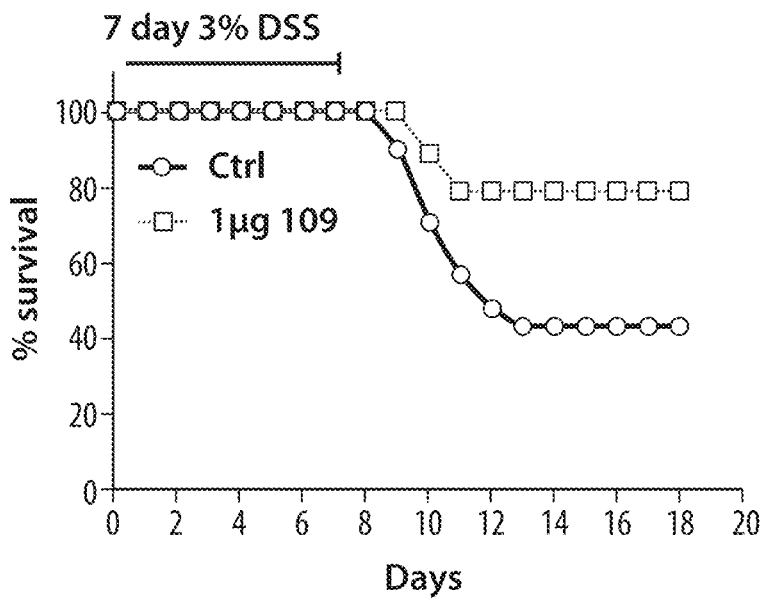
FIGS. 3A-3M show that compound 109 attenuates DSS induced colitis in mice. Mice were supplied with 3% DSS in drinking water for 7 days followed by 13 days of recovery. Compound 109 (1 μg) or vehicle control (Ctrl) were administered daily by oral gavage. Survival (FIG. 3A), body weight (FIG. 3B), and disease activity score (FIG. 3C) were recorded, data represent 3 independent trials with n=7/group/trial.
Figure 3B:
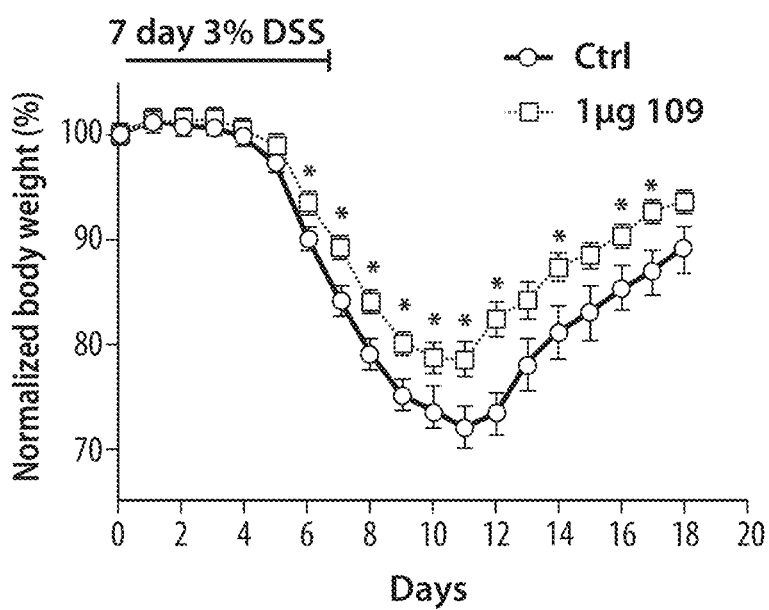
Figure 3C:
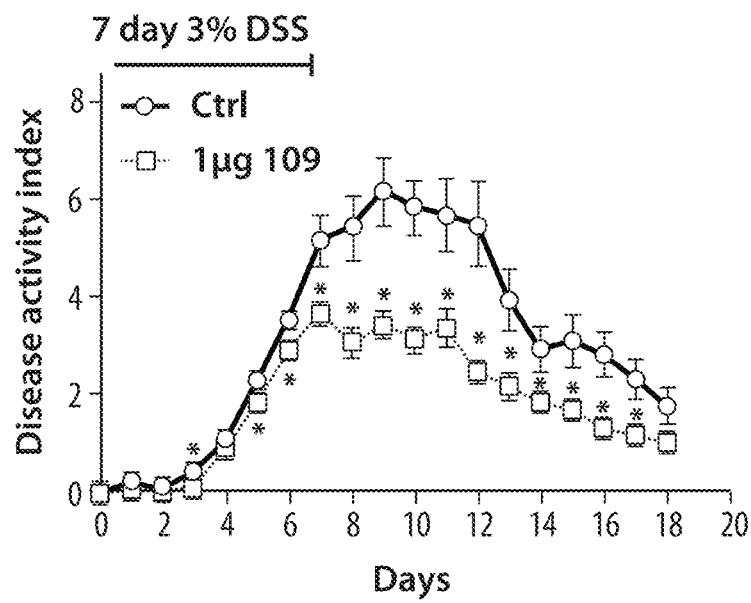
Figure 3D:
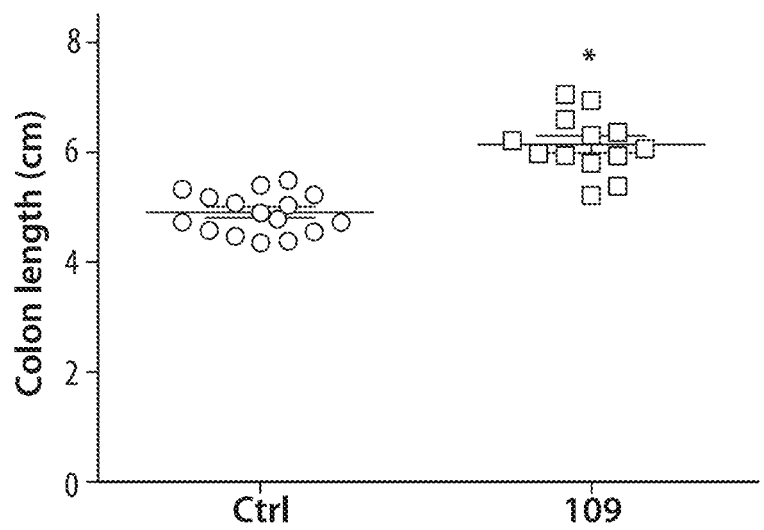
Figure 3E:
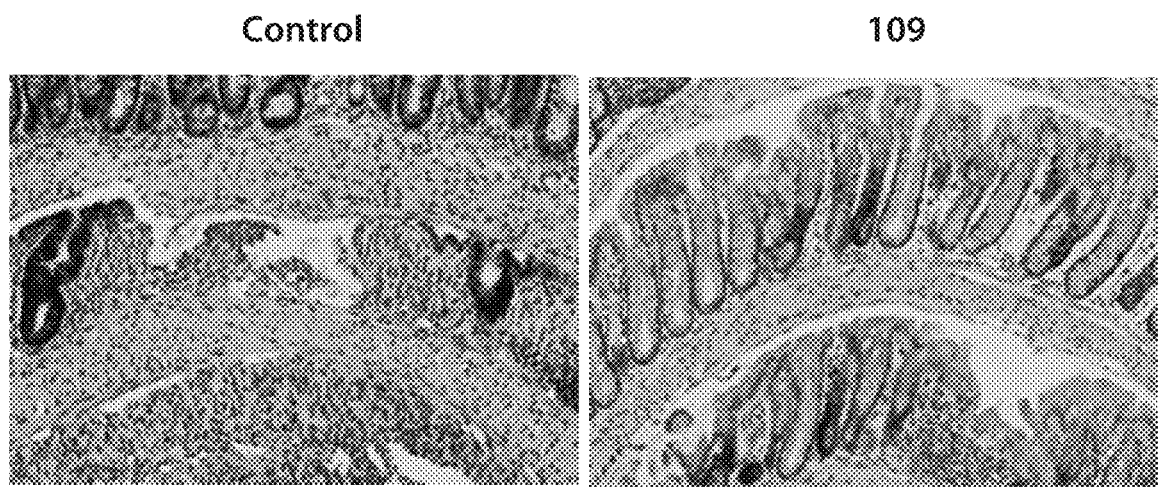
Figure 3F:
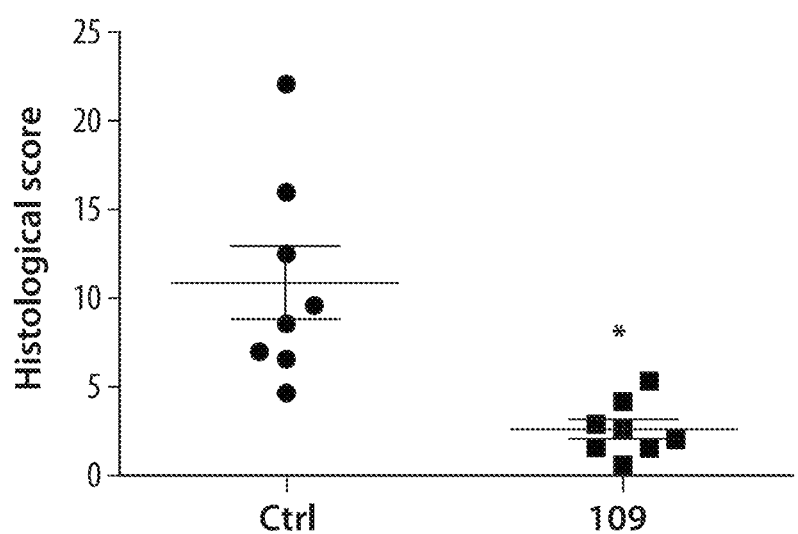
Figure 3G:
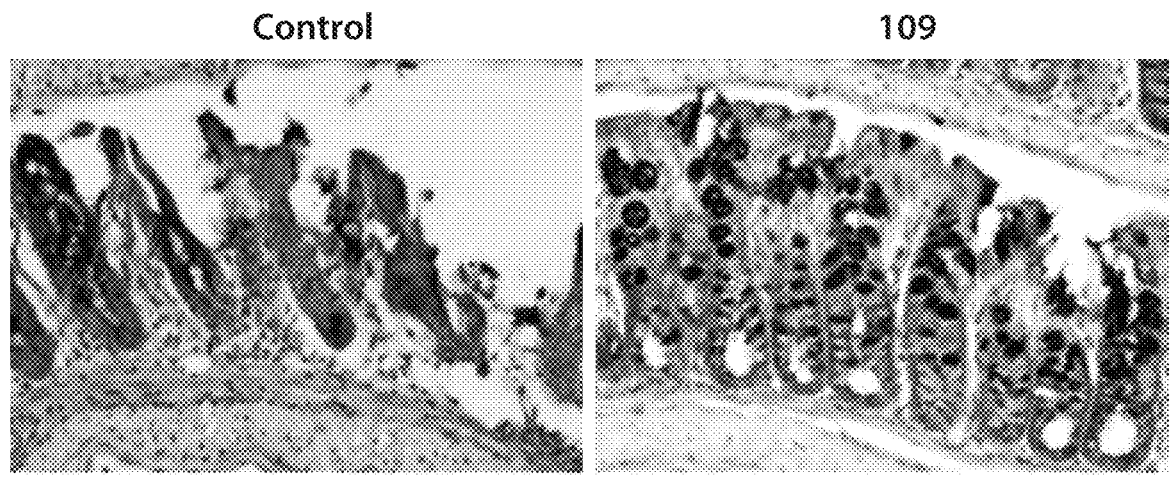
Figure 3H:
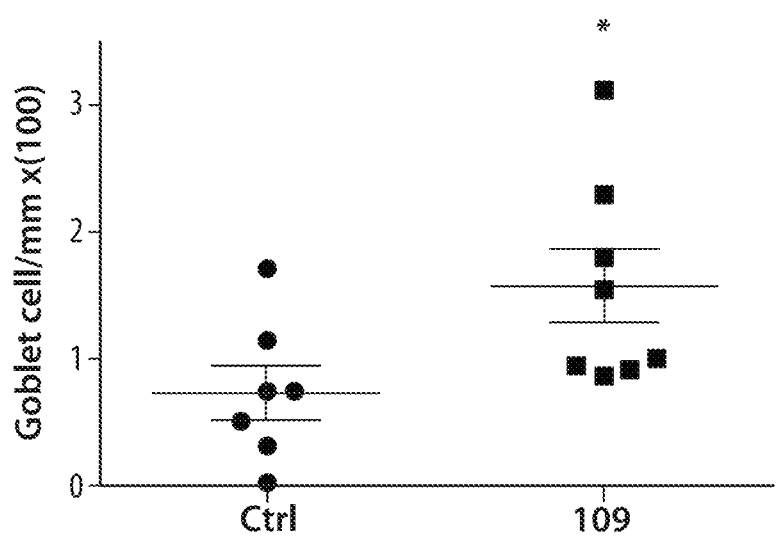
Figure 3I:
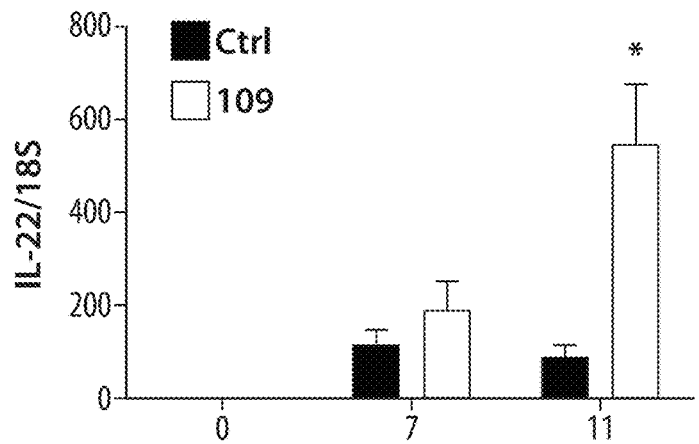
Figure 3J:
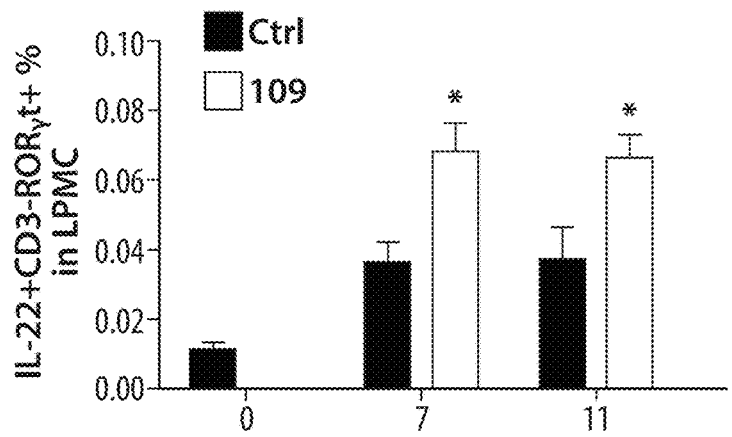
Figure 3K:
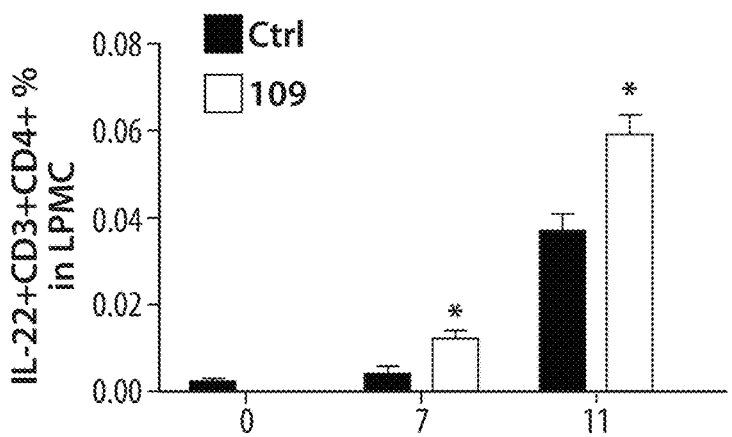
Figure 3L:
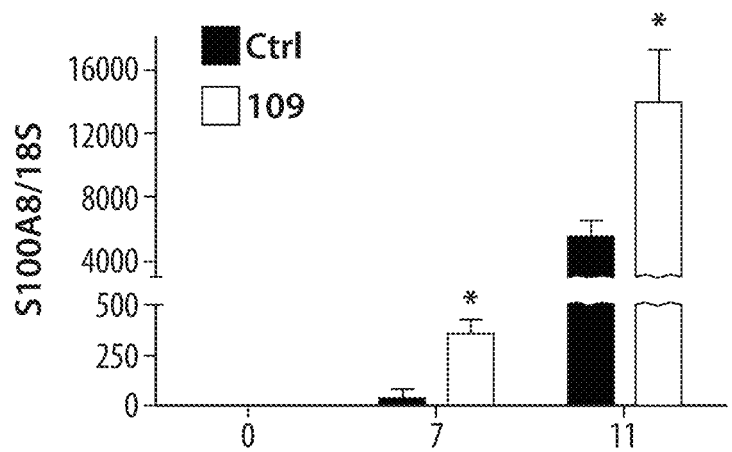
Figure 3M:
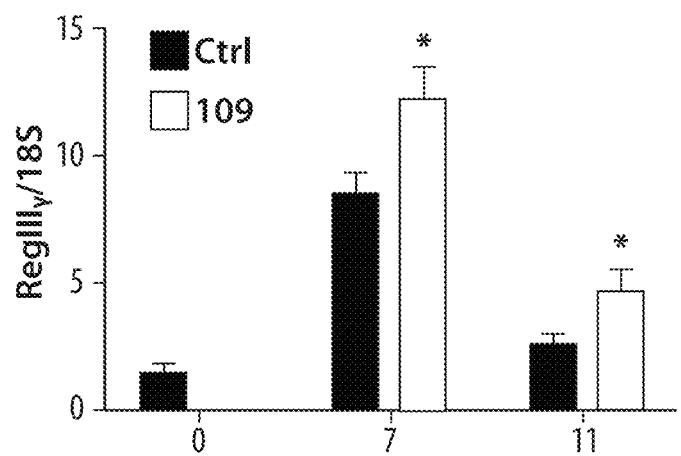
Figure 4A:
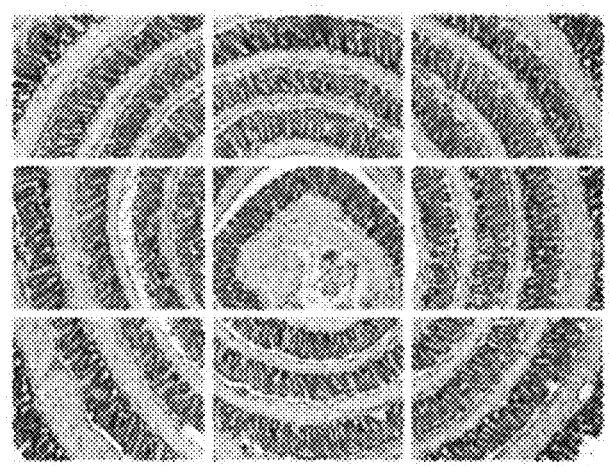
FIGS. 4A-4C show DSS colitis histological scoring. H&E staining was performed to characterize inflammation and crypt loss. For scoring, 3 transverse sections of swiss roll colon were selected and 9 (100×) images recorded (FIG. 4A, representative capture from healthy control colon). Images were analyzed and scored by a blind observer as follows. For inflammation scoring (FIG. 4B), 0: rare inflammatory cells in the lamina propria; 1: increased numbers of inflammatory cells in the lamina propria; 2: confluence of inflammatory cells extending in to the submucosa; 3: transmural extension of the inflammatory infiltrate. For crypt lost scoring (FIG. 4C), 0: none; 1: basal 1/3 damaged; 2: basal 2/3 damaged; 3: only surface epithelium intact; 4: entire crypt and epithelium lost. Inflammation and crypt loss were separately scored and then multiplied by affected area (1: 0-25%; 2: 25.1-50% affected; 3: 50.1-75% affected; 4: >75% affected). Data represent mean±s.e.m., $*p<0.05$ versus control.
Figure 4B:
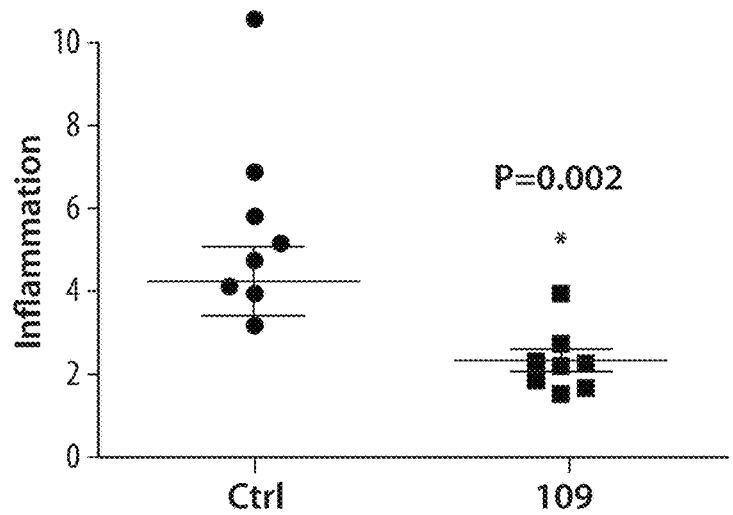
Figure 4C:
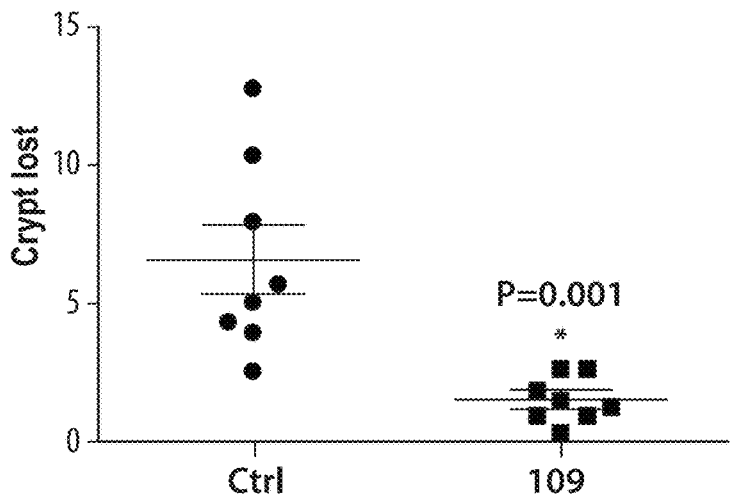
Figure 5A:
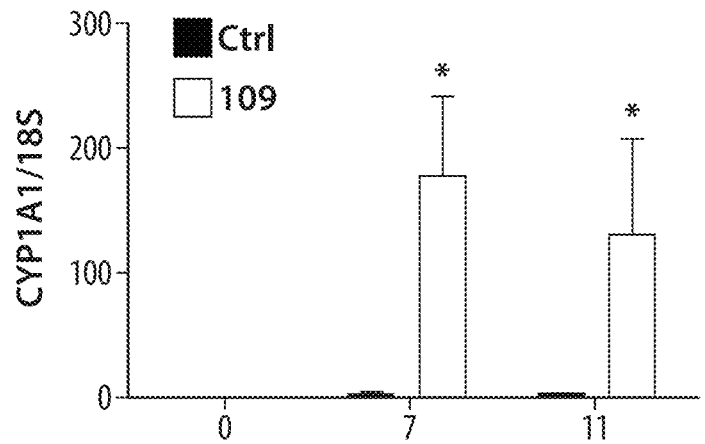
FIGS. 5A-5I show mRNA expression in DSS induced colitis. Mice were supplied with 3% DSS in drinking water for 7 days followed by 13 days of recovery. 109 (1 μg) or vehicle control (Ctrl) were administered daily by oral gavage.
Figure 5B:
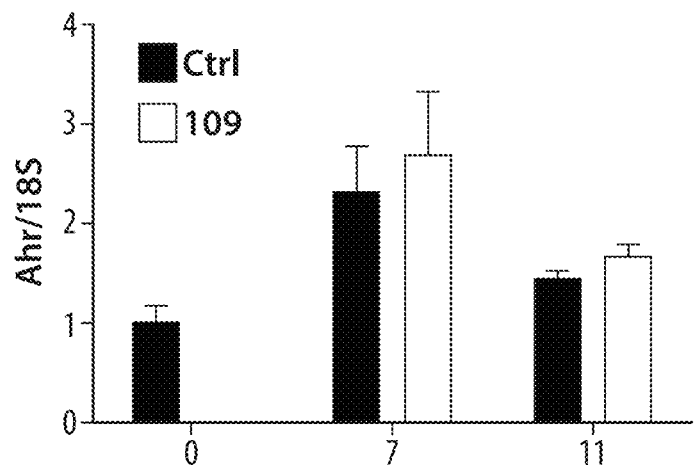
Figure 5C:
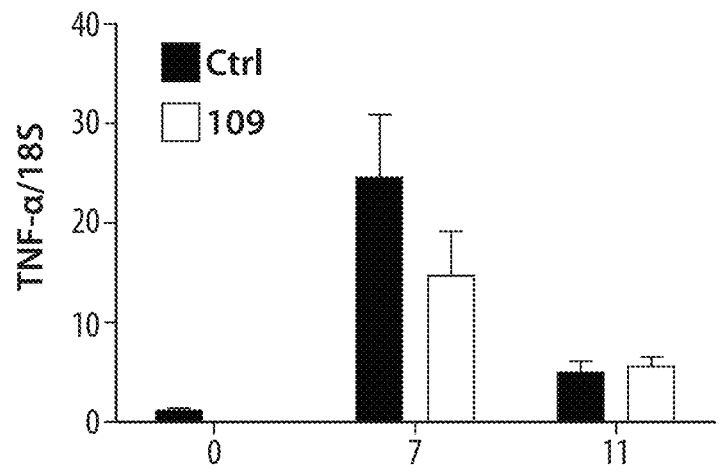
Figure 5D:
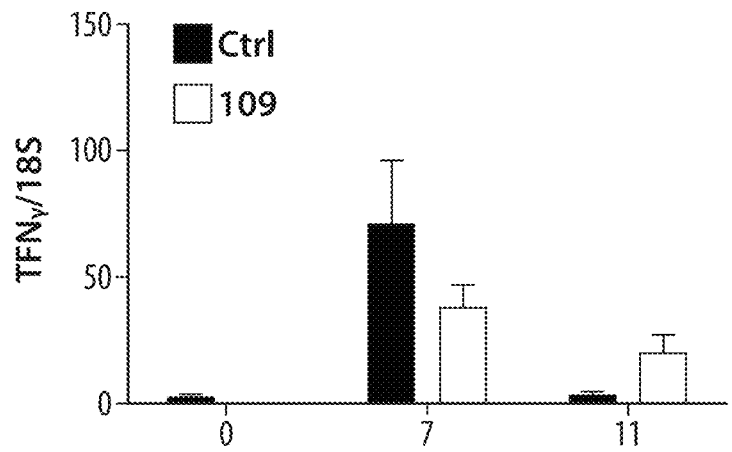
Figure 5E:
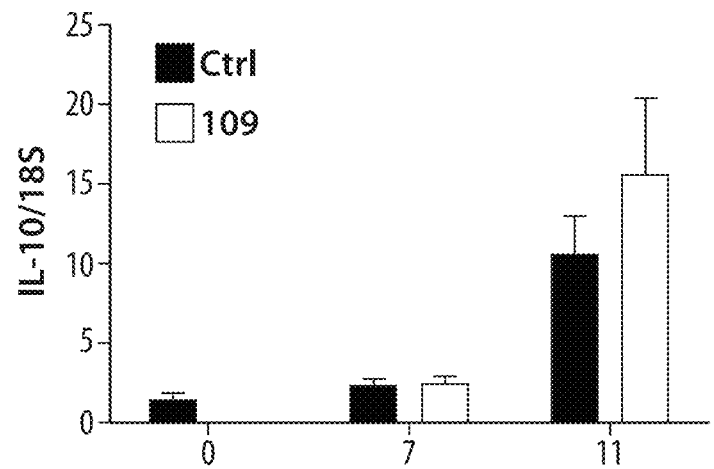
Figure 5F:
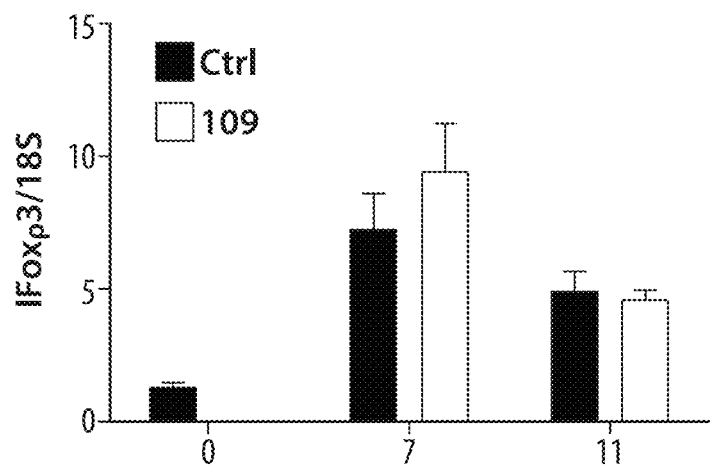
Figure 5G:
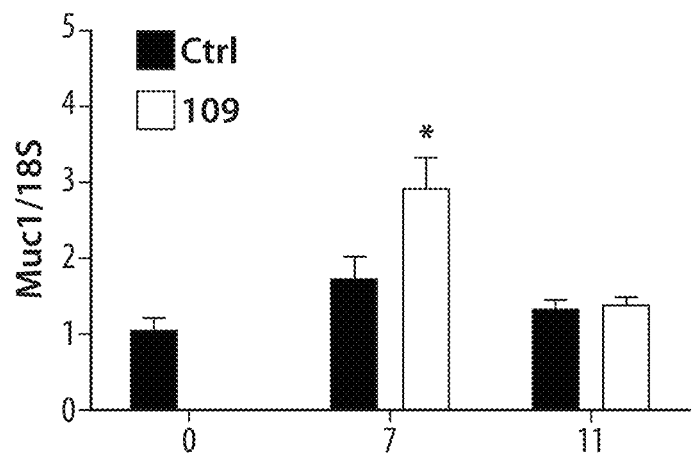
Figure 5H:
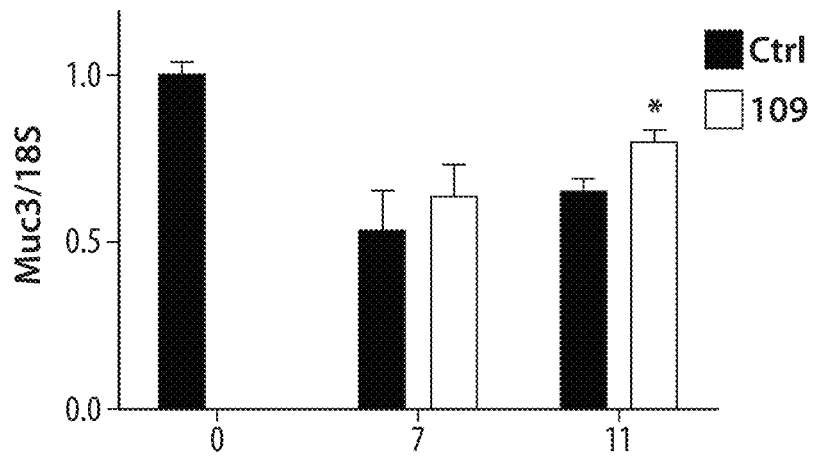
Figure 5I:
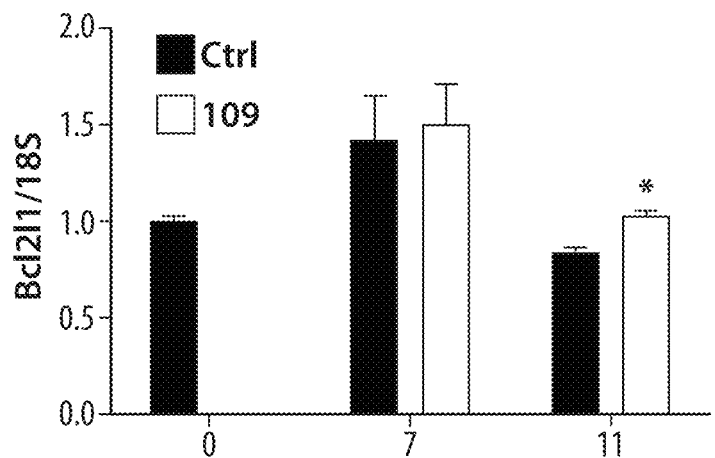

Acute murine colitis was induced with 3% dextran sodium sulfate (DSS) in drinking water for 7 days followed by a 13 day recovery period in vehicle control or 109 treatment groups (1 μg/day PO). Compound 109 significantly improved survival, reduced weight loss, and improved the overall disease score in DSS colitis (FIGS. 3A-3C). Colon length was significantly improved in compound 109 treated mice indicating reduced inflammation (FIG. 3D), this was further confirmed through histological examination of colon tissue at day 11. H&E-stained sections were subject to blind scoring for inflammation and crypt structure, compound 109 treatment mice displayed significant improvement in both colon inflammation and crypt loss (FIG. 4), with cumulative results captured in the histological score (FIGS. 3E and 3F). Mucin positive goblet cells, which are crucial for mucus secretion and barrier protection, were also characterized histologically with blind scoring. Consistent with reduced inflammation observed in H&E analysis, compound 109 treatment preserved goblet cell number, suggesting that compound 109 imparts significant protection to the colon epithelium (FIGS. 3G and 3H). Gene expression was examined at day 7 and 11, representing the acute and recovery phase of colitis. AhR activation marker cyp1a1 was significantly increased by compound 109 at both time points while AhR expression was consistent between groups (FIGS. 5A and 5B). Among immune mediators examined, barrier protective cytokine IL-22 was the only marker observed to demonstrate compound 109-dependent regulation with a trend toward increased expression at day 7 and significant (10-fold) upregulation of expression at day 11 (FIG. 3I and FIG. 5). Conflicting reports have suggested AhR regulation of Foxp3$^+$ regulatory T cells, however compound 109-dependent induction of Foxp3 was not observed (FIG. 5F). Single cell suspensions of colon tissue explants were subject to flow cytometry to confirm increased IL-22 production in compound 109 treatment mice. IL-22 secretion from both CD3+CD4+ T helper and CD3−RORrt (+) innate lymphoid cells was significantly elevated by compound 109 at day 7 and 11 (FIGS. 3J and 3K). IL-22 is reported to maintain colon epithelial integrity and mucosal immunity by action on colon epithelial cells, specifically, IL-22 is suggested to induce genes related to barrier function. Gene expression in the colon epithelial fraction was examined by q-PCR. Significant upregulation of antimicrobial peptides S100A8 and RegIIIγ was observed at day 7 and 11 (FIGS. 3L and 3M). Modest regulation of barrier protective genes Muc1, Muc3, and Bcl21 was also observed (FIGS. 5G-5I). Given the significant therapeutic effect of compound 109, we characterized alternate lead compound 108 in the same model of DSS induced colitis.

Compound 108 Attenuates DSS Induced Colitis.

Figure 6A:
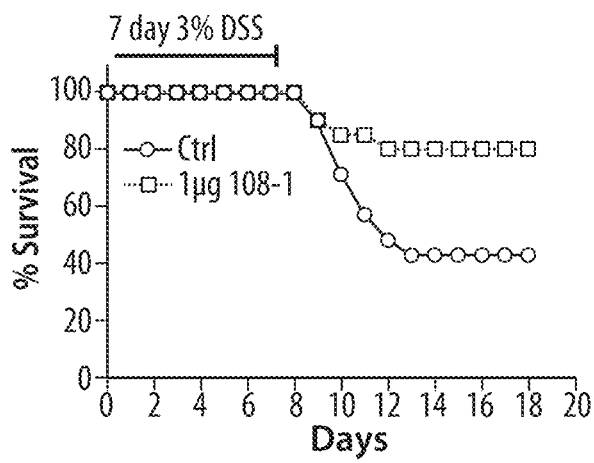
FIGS. 6A-6C show that compound 108 attenuates DSS induced colitis in mice. Mice were supplied with 3% DSS in drinking water for 7 days followed by 13 days of recovery. 108 (1 μg) or vehicle control (Ctrl) were administered daily by oral gavage. Survival (FIG. 6A), body weight (FIG. 6B) and disease activity score (FIG. 6C) were recorded, data represent 3 independent trials with n=7/group/trial. Data represent mean±s.e.m., $*p<0.05$ versus control.
Figure 6B:
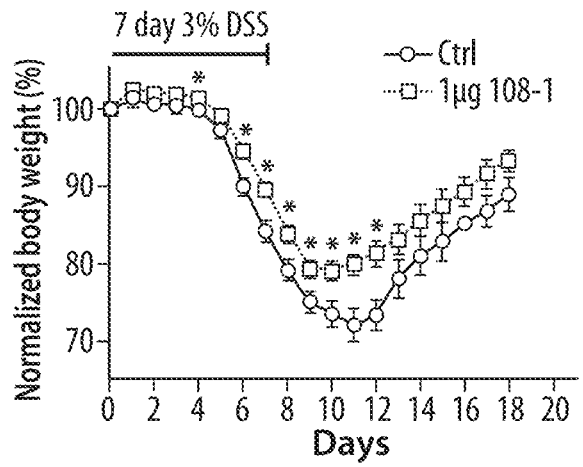
Figure 6C:
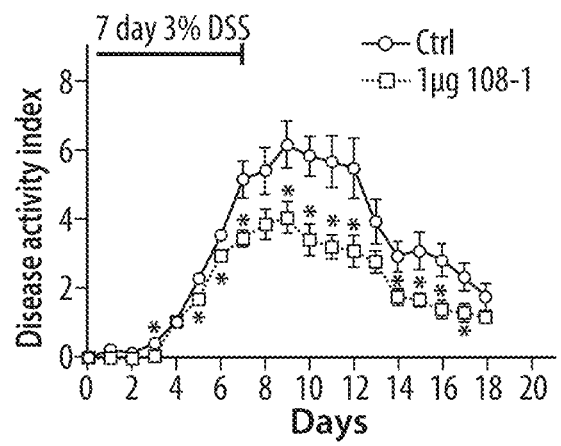

Acute murine colitis was induced with 3% dextran sodium sulfate (DSS) in drinking water for 7 days followed by a 13 day recovery period in vehicle control or compound 108 treatment in groups (1 μg/day PO). Compound 108 significantly improved survival, reduced weight loss, and improved the overall disease score in DSS colitis (FIGS. 6A-6C).

In vitro induction of T lymphocyte IL-22.

To confirm ability of compounds to promote T lymphocyte IL-22 production, spleen derived CD4+ or colonic lamina propria T cells were polarized in vitro to promote IL-22 production with addition of lead compound 109 or vehicle control. Significant increase in IL-22 production was observed in CD4+ T helper cells from both spleen and LPMC, CD3−RORrt(+) innate lymphoid cells also demonstrated compound 109 induced upregulation of IL-22 (FIGS. 7A-7D).

Collectively, these results indicate a promising chemical and biological platform to develop AhR based immune modulators to promote T lymphocyte IL-22 production and limit barrier mediated chronic inflammatory disease.

REFERENCES

1. Cooper, H. S., Murthy, S. N., Shah, R. S. & Sedergran, D. J. Clinicopathologic study of dextran sulfate sodium experimental murine colitis. Laboratory investigation; a journal of technical methods and pathology 69, 238-249 (1993).
2. Bialkowska, A. B., Ghaleb, A. M., Nandan, M. O. & Yang, V. W. Improved Swiss-rolling Technique for Intestinal Tissue Preparation for Immunohistochemical and Immunofluorescent Analyses. Journal of visualized experiments: JoVE, doi:10.3791/54161 (2016).
3. Kudelka, M. R. et al. Cosmc is an X-linked inflammatory bowel disease risk gene that spatially regulates gut microbiota and contributes to sex-specific risk. Proceedings of the National Academy of Sciences of the United States of America 113, 14787-14792, doi:10.1073/pnas.1612158114 (2016).
4. Klopfleisch, R. Multiparametric and semiquantitative scoring systems for the evaluation of mouse model histopathology-a systematic review. BMC veterinary research 9, 123, doi:10.1186/1746-6148-9-123 (2013).
5. Kober, O. I. et al. gammadelta T-cell-deficient mice show alterations in mucin expression, glycosylation, and goblet cells but maintain an intact mucus layer. American journal of physiology. Gastrointestinal and liver physiology 306, G582-593, doi:10.1152/ajpgi.00218.2013 (2014).
6. Nenci, A. et al. Epithelial NEMO links innate immunity to chronic intestinal inflammation. Nature 446, 557-561, doi:10.1038/nature05698 (2007).
7. Weigmann, B. et al. Isolation and subsequent analysis of murine lamina propria mononuclear cells from colonic tissue. Nature protocols 2, 2307-2311, doi:10.1038/nprot.2007.315 (2007).
8. Veldhoen, M. et al. The aryl hydrocarbon receptor links TH17-cell-mediated autoimmunity to environmental toxins. Nature 453, 106-109, doi:10.1038/nature06881 (2008).

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims.

Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula (II-b):

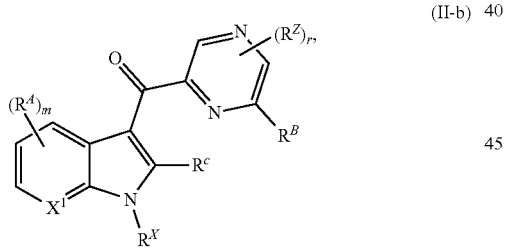

(II-b)

or a pharmaceutically acceptable salt, solvate, hydrate, stereoisomer, tautomer, isotopically labeled derivative, polymorph, or prodrug thereof; wherein:
$X^1$ is N or $CR^A$;
each instance of $R^A$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{A1}$, $-N(R^{A1})_2$, $-SR^{A1}$, $-CN$, $-C(R^{A1})_3$, $-SCN$, $-C(=NR^{A1})R^{A1}$, $-C(=NR^{A1})OR^{A1}$, $-C(=NR^{A1})N(R^{A1})_2$, $-C(=O)R^{A1}$, $-C(=O)OR^{A1}$, $-C(=O)N(R^{A1})_2$, $-NO_2$, $-NR^{A1}C(=O)R^{A1}$, $-NR^{A1}C(=O)OR^{A1}$, $-NR^{A1}C(=O)N(R^{A1})_2$, $-OC(=O)R^{A1}$, $-OC(=O)OR^{A1}$, or $-OC(=O)N(R^{A1})_2$, or two $R^A$ groups are joined to form a substituted or unsubstituted carbocyclic, substituted or unsubstituted heterocyclic, substituted or unsubstituted aryl, or substituted or unsubstituted heteroaryl ring;

each instance of $R^{A1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups attached to the same nitrogen atom are joined to form a substituted or unsubstituted heterocyclic or substituted or unsubstituted heteroaryl ring;

$R^B$ is hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{B1}$, $-N(R^{B1})_2$, $-SR^{B1}$, $-CN$, $-C(R^{B1})_3$, $-SCN$, $-C(=NR^{B1})R^{B1}$, $-C(=NR^{B1})OR^{B1}$, $-C(=NR^{B1})N(R^{B1})_2$, $-C(=O)R^{B1}$, $-C(=O)OR^{B1}$, $-C(=O)N(R^{B1})_2$, $-NO_2$, $-NR^{B1}C(=O)R^{B1}$, $-NR^{B1}C(=O)OR^{B1}$, $-NR^{B1}C(=O)N(R^{B1})_2$, $-OC(=O)R^{B1}$, $-OC(=O)OR^{B1}$, or $-OC(=O)N(R^{B1})_2$;

each instance of $R^{B1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{B1}$ groups attached to the same nitrogen atom are joined to form a substituted or unsubstituted carbocyclic, substituted or unsubstituted heterocyclic, substituted or unsubstituted aryl, or substituted or unsubstituted heteroaryl ring;

$R^C$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, $-OR^{C1}$, $-N(R^{C1})_2$, $-SR^{C1}$, $-CN$, $-C(R^{C1})_3$, $-SCN$, $-C(=NR^{C1})R^{C1}$, —C(=NR$^{C1}$)OR$^{C1}$, —C(=NR$^{C1}$)N(R$^{C1}$)$_2$, —C(=O)R$^{C1}$, —C(=O)OR$^{C1}$, —C(=O)N(R$^{C1}$)$_2$, —NO$_2$, —NR$^{C1}$C(=O)R$^{C1}$, —NR$^{C1}$C(=O)OR$^{C1}$, —NR$^{C1}$C(=O)N(R$^{C1}$)$_2$, —OC(=O)R$^{C1}$, —OC(=O)OR$^{C1}$, or —OC(=O)N(R$^{C1}$)$_2$;

each instance of R$^{C1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{C1}$ groups attached to the same nitrogen atom are joined to form a substituted or unsubstituted heterocyclic or substituted or unsubstituted heteroaryl ring;

R$^X$ is hydrogen, substituted or unsubstituted alkyl, substituted or unsubstituted alkenyl, substituted or unsubstituted alkynyl, substituted or unsubstituted acyl, or a nitrogen protecting group;

each instance of R$^Z$ is independently halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted carbocyclyl, substituted or unsubstituted heterocyclyl, substituted or unsubstituted aryl, substituted or unsubstituted heteroaryl, —OR$^{Z1}$, —N(R$^{Z1}$)$_2$, —SR$^{Z1}$, —CN, —C(R$^{Z1}$)$_3$, —SCN, —C(=NR$^{Z1}$)R$^{Z1}$, —C(=NR$^{Z1}$)OR$^{Z1}$, —C(=NR$^{Z1}$)N(R$^{Z1}$)$_2$, —C(=O)R$^{Z1}$, —C(=O)OR$^{Z1}$, —C(=O)N(R$^{Z1}$)$_2$, —NO$_2$, —NR$^{Z1}$C(=O)R$^{Z1}$, —NR$^{Z1}$C(=O)OR$^{Z1}$, —NR$^{Z1}$C(=O)N(R$^{Z1}$)$_2$, —OC(=O)R$^{Z1}$, —OC(=O)OR$^{Z1}$, or —OC(=O)N(R$^{Z1}$)$_2$;

each instance of R$^{Z1}$ is independently hydrogen, halogen, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted acyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{Z1}$ groups attached to the same nitrogen atom are joined to form a substituted or unsubstituted heterocyclic or substituted or unsubstituted heteroaryl ring;

m is 0, 1, 2, or 3; and r is 1 or 2.

2. The compound of claim 1, wherein the compound is of Formula (II-bi):

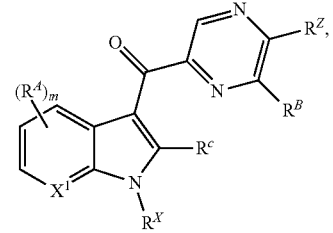

(II-bi)

or a pharmaceutically acceptable salt, solvate, hydrate, stereoisomer, tautomer, isotopically labeled derivative, polymorph, or prodrug thereof.

3. The compound of claim 1, wherein X$^1$ is CR$^A$.

4. The compound of claim 1, wherein X$^1$ is CH.

5. The compound of claim 1, wherein R$^X$ is hydrogen.

6. The compound of claim 1, wherein R$^C$ is hydrogen.

7. The compound of claim 1, wherein:
X$^1$ is CR$^A$;
R$^X$ is hydrogen; and
R$^C$ is hydrogen.

8. The compound of claim 1, wherein m is 0.

9. The compound of claim 1, wherein r is 1.

10. The compound of claim 1, wherein R$^B$ is hydrogen, halogen, substituted or unsubstituted alkyl, —OR$^{B1}$, —CN, —CF$_3$, or —C(=O)OR$^{B1}$.

11. The compound of claim 1, wherein at least one instance of R$^Z$ is halogen, substituted or unsubstituted alkyl, —OR$^{Z1}$, —CN, —CF$_3$, or —C(=O)OR$^{Z1}$.

12. The compound of claim 1, wherein at least one instance of R$^Z$ is —OR$^{Z1}$.

13. The compound of claim 1, wherein the compound is:

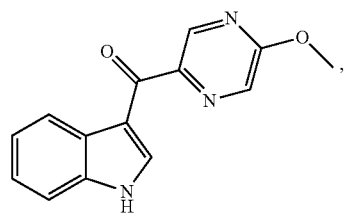 [SMILES: COc1cnc(C(=O)c2c[nH]c3ccccc23)cn1]

or a pharmaceutically acceptable salt thereof.

14. The compound of claim 1, wherein the compound is of Formula (II-b), or a pharmaceutically acceptable salt thereof.

15. A pharmaceutical composition comprising a compound of claim 1, or a pharmaceutically acceptable salt, solvate, hydrate, stereoisomer, tautomer, isotopically labeled derivative, polymorph, or prodrug thereof, and a pharmaceutically acceptable excipient.

16. A pharmaceutical composition comprising the compound of claim 13, or a pharmaceutically acceptable salt thereof, and a pharmaceutically acceptable excipient.

17. A method of modulating an aryl hydrocarbon receptor of a cell, the method comprising contacting the cell with a compound of claim 1, or a pharmaceutically acceptable salt, solvate, hydrate, stereoisomer, tautomer, isotopically labeled derivative, polymorph, or prodrug thereof, or a pharmaceutical composition thereof.

18. A method of increasing expression of a gene in a cell, regulating the expression of an interleukin in a cell, and/or regulating the secretion of an interleukin from a cell, the method comprising contacting the cell with a compound of claim 1, or a pharmaceutically acceptable salt, solvate, hydrate, stereoisomer, tautomer, isotopically labeled derivative, polymorph, or prodrug thereof, or a pharmaceutical composition thereof.

19. A method of modulating the function of an immune cell, the method comprising contacting the immune cell with a compound of claim 1, or a pharmaceutically acceptable salt, solvate, hydrate, stereoisomer, tautomer, isotopically labeled derivative, polymorph, or prodrug thereof, or a pharmaceutical composition thereof.

20. A method for therapeutic treatment of a disease or condition associated with activity of an aryl hydrocarbon receptor in a subject, the method comprising administering to the subject a compound of claim 1, or a pharmaceutically acceptable salt, solvate, hydrate, stereoisomer, tautomer, isotopically labeled derivative, polymorph, or prodrug thereof, or a pharmaceutical composition thereof, in an amount sufficient to modulate the activity of the aryl hydrocarbon receptor.

21. The method of claim 20, wherein the disease or condition is an inflammatory disease, an autoimmune disease, a metabolic disorder, or a proliferative disease.

22. The compound of claim 1, wherein at least one instance of $R^Z$ is —OMe.

23. The compound of claim 2, wherein $R^Z$ is —$OR^{Z1}$.

24. The compound of claim 2, wherein:
$X^1$ is CH;
m is 0;
$R^X$ is hydrogen;
$R^C$ is hydrogen;
$R^B$ is hydrogen;
$R^Z$ is —$OR^{Z1}$, wherein $R^{Z1}$ is unsubstituted $C_{1-6}$ alkyl.

* * * * *